United States Patent
Alailima et al.

(10) Patent No.: US 11,507,178 B2
(45) Date of Patent: Nov. 22, 2022

(54) COGNITIVE PLATFORM INCLUDING COMPUTERIZED ELEMENTS

(71) Applicant: Akili Interactive Labs, Inc., Boston, MA (US)

(72) Inventors: Titiimaea Alailima, Cambridge, MA (US); Jeffrey Bower, Norwood, MA (US); Jason Johnson, Novato, CA (US); Ashley Mateus, Cambridge, MA (US); Elena Cañadas Espinosa, Dorchester, MA (US); Adam Piper, Petaluma, CA (US); Matthew Omernick, Larkspur, CA (US); David Collins, Sherman Oaks, CA (US)

(73) Assignee: Akili Interactive Labs, Inc., Boston, MA (US)

( * ) Notice: Subject to any disclaimer, the term of this patent is extended or adjusted under 35 U.S.C. 154(b) by 0 days.

(21) Appl. No.: 16/793,977

(22) Filed: Feb. 18, 2020

(65) Prior Publication Data

US 2020/0174557 A1 Jun. 4, 2020

Related U.S. Application Data

(63) Continuation of application No. PCT/US2018/000179, filed on Aug. 15, 2018.
(Continued)

(51) Int. Cl.
*G06F 3/00* (2006.01)
*G06F 3/01* (2006.01)
(Continued)

(52) U.S. Cl.
CPC .......... *G06F 3/011* (2013.01); *G06F 3/0482* (2013.01); *G06F 9/542* (2013.01); *G06F 2203/011* (2013.01)

(58) Field of Classification Search
None
See application file for complete search history.

(56) References Cited

U.S. PATENT DOCUMENTS 5,377,100 A * 12/1994 Pope .................. A61B 5/0476
600/545
9,886,493 B2 2/2018 Coleman et al.
(Continued)

FOREIGN PATENT DOCUMENTS

CN 103561651 A 2/2014
CN 104717921 A 6/2015
(Continued)

OTHER PUBLICATIONS

Art Green; Temple Run 2 Walk-through; Jan. 21, 2013; https://www.gamezebo.com/2013/01/21/temple-run-2-walkthrough-cheats-strategy-guide/ (Year: 2013).*
(Continued)

*Primary Examiner* — Steve Rowland
(74) *Attorney, Agent, or Firm* — Gregory Finch; Finch Paolino, LLC

(57) ABSTRACT

Apparatus, systems, and methods are provided for generating a quantified indicator of cognitive skills in an individual. In certain configurations, the apparatus, systems, and methods can be implemented for enhancing cognitive skills in an individual.

16 Claims, 62 Drawing Sheets

Related U.S. Application Data

(60) Provisional application No. 62/545,968, filed on Aug. 15, 2017.

(51) Int. Cl.
*G06F 3/0482* (2013.01)
*G06F 9/54* (2006.01)

(56) References Cited

U.S. PATENT DOCUMENTS

| | | | |
|---|---|---|---|
| 10,311,744 B2 | 6/2019 | Zhang et al. | |
| 10,632,389 B1* | 4/2020 | Lu | A63F 13/69 |
| 10,953,280 B2* | 3/2021 | Kline | A63B 71/06 |
| 2002/0182574 A1* | 12/2002 | Freer | G09B 23/28 |
| | | | 434/236 |
| 2007/0017531 A1* | 1/2007 | Large | A61B 5/1116 |
| | | | 128/898 |
| 2009/0187844 A1* | 7/2009 | Dugan | G06F 16/9562 |
| | | | 715/771 |
| 2009/0258705 A1* | 10/2009 | Guinchard | A63F 13/245 |
| | | | 463/37 |
| 2010/0021873 A1* | 1/2010 | Stut | G16H 10/20 |
| | | | 434/236 |
| 2010/0094155 A1 | 4/2010 | Prichep | |
| 2010/0152249 A1 | 6/2010 | Rasgon | |
| 2010/0153869 A1* | 6/2010 | Dawson | H04L 67/38 |
| | | | 715/764 |
| 2010/0323846 A1* | 12/2010 | Komatsu | A63B 69/00 |
| | | | 482/9 |
| 2011/0105859 A1* | 5/2011 | Popovic | A61B 5/02405 |
| | | | 600/301 |
| 2011/0223995 A1* | 9/2011 | Geisner | G06F 3/011 |
| | | | 463/36 |
| 2012/0172100 A1* | 7/2012 | Colar | G09B 7/06 |
| | | | 463/9 |
| 2014/0107494 A1* | 4/2014 | Kato | A61B 5/4064 |
| | | | 600/473 |
| 2014/0121017 A1* | 5/2014 | Mandryk | A63F 13/352 |
| | | | 463/36 |
| 2014/0243154 A1* | 8/2014 | Park | A63B 24/0087 |
| | | | 482/8 |
| 2014/0370479 A1* | 12/2014 | Gazzaley | A61B 5/4884 |
| | | | 434/322 |
| 2015/0127404 A1* | 5/2015 | Laughter | G06Q 50/20 |
| | | | 705/7.19 |
| 2016/0196765 A1* | 7/2016 | Stauch | G09B 19/00 |
| | | | 434/236 |
| 2016/0210870 A1* | 7/2016 | Vyshedskiy | G09B 5/02 |
| 2016/0262680 A1* | 9/2016 | Martucci | A61B 5/4833 |
| 2016/0379175 A1* | 12/2016 | Bhattacharya | G06Q 10/1097 |
| | | | 705/7.21 |
| 2017/0270455 A1* | 9/2017 | Chi | G06Q 10/063112 |
| 2017/0357930 A1* | 12/2017 | Tani | G06Q 10/063114 |
| 2018/0001197 A1* | 1/2018 | Xu | G07F 17/3218 |
| 2018/0015373 A1* | 1/2018 | Greenberg | A63F 13/211 |
| 2018/0095429 A1* | 4/2018 | Weinstein | G06Q 10/06311 |
| 2018/0161678 A1* | 6/2018 | Snow | A63F 13/61 |
| 2018/0184936 A1* | 7/2018 | Han | A63F 13/28 |
| 2018/0286272 A1* | 10/2018 | McDermott | A63F 13/67 |
| 2018/0290060 A1* | 10/2018 | Noss | A63F 13/46 |
| 2019/0015751 A1* | 1/2019 | Kahn, II | A63F 13/85 |
| 2019/0054371 A1* | 2/2019 | Hamilton | A63F 13/49 |
| 2019/0320897 A1* | 10/2019 | Wu | G06K 9/00597 |
| 2020/0082735 A1* | 3/2020 | Nel | G06F 3/013 |
| 2021/0046373 A1* | 2/2021 | Smith | A63B 24/0062 |
| 2021/0158715 A1* | 5/2021 | Kim | G09B 9/00 |

FOREIGN PATENT DOCUMENTS

| | | | |
|---|---|---|---|
| CN | 104871160 A | 8/2015 | |
| EP | 2206464 A1 | 7/2010 | |
| WO | 2014191805 A1 | 12/2014 | |
| WO | 2015040532 A2 | 3/2015 | |
| WO | 2015179522 A1 | 11/2015 | |
| WO | WO-2015179522 A1 * | 11/2015 | ........... A61B 5/4088 |

OTHER PUBLICATIONS

International Search Report, International Application No. PCT/US2018/000179, dated Nov. 28, 2018. ISA/US, Alexandria, VA.
Written Opinion of the International Searching Authority, International Application No. PCT/US2018/000179, dated Nov. 28, 2018. ISA/US, Alexandria, VA.
Extended European Search Report, European Application No. 18846209.7, dated Feb. 16, 2021. European Patent Office, Munich, Germany.

* cited by examiner

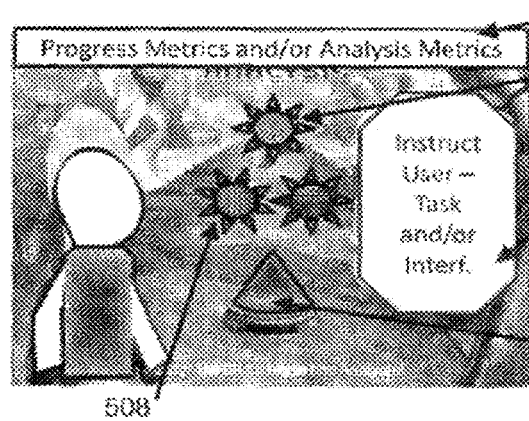
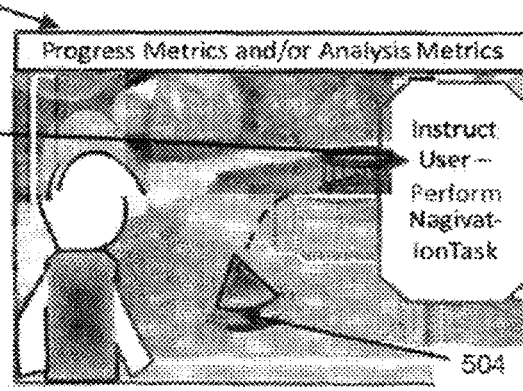
FIG. 5A  FIG. 5B
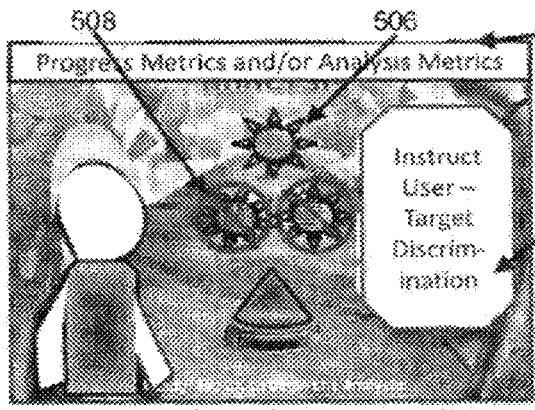
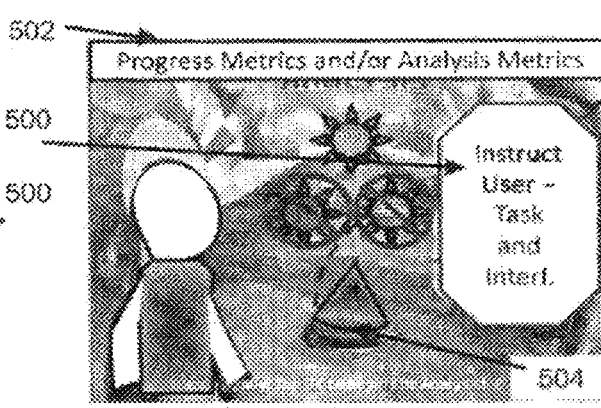
FIG. 5C  FIG. 5D

Present via the user interface a first instance of a task with an interference at the user interface, requiring a first response from the individual to the first instance of the task in the presence of the interference.
↘ 8142

Present via the user interface the first instance of the task, requiring a second response from the individual to the first instance of the task in the absence of the interference, where at least one of the first instance of the task and the interference comprises a computerized adjustable element that is adjusted in real time as an indication of a degree of success of the performance of at least one of the task or the interference.
↘ 8144

Measure substantially simultaneously the first response from the individual to the first instance of the task and the response from the individual to the interference.
↘ 8146

Receive data indicative of the first response and the second response.
↘ 8148

Analyze the data indicative of the first response and the second response to generate at least one performance metric comprising at least one quantified indicator of cognitive abilities of the individual.
↘ 8150

FIG. 12B

COGNITIVE PLATFORM INCLUDING COMPUTERIZED ELEMENTS

CROSS-REFERENCE TO RELATED APPLICATIONS

This application is a continuation of PCT Application No. PCT/US2018/000179, entitled "COGNITIVE PLATFORM INCLUDING COMPUTERIZED ELEMENTS" filed on Aug. 15, 2018, which claims priority to and benefit from U.S. Provisional Application No. 62/545,968, entitled "COGNITIVE PLATFORM INCLUDING COMPUTERIZED ELEMENTS" filed on Aug. 15, 2017, the contents of both applications hereby incorporated herein by reference in their entireties, including drawings.

BACKGROUND OF THE DISCLOSURE

In the normal course of aging, individuals can experience a certain amount of cognitive decline. This can cause an individual to experience increased difficulty in challenging situations, such as time-limited, attention-demanding conditions. In both older and younger individuals, certain cognitive conditions, diseases, or executive function disorders can result in compromised performance at tasks that require attention, memory, motor function, reaction, executive function, decision-making skills, problem-solving skills, language processing, or comprehension.

SUMMARY OF THE DISCLOSURE

In view of the foregoing, apparatus, systems and methods are provided for quantifying aspects of cognition (including cognitive abilities). In certain configurations, the apparatus, systems and methods can be implemented for enhancing certain cognitive abilities.

In an aspect, embodiments relate to a system for generating a quantified indicator of cognitive skills in an individual. The system includes one or more processors, and a memory to store processor-executable instructions and communicatively coupled with the one or more processors. Upon execution of the processor-executable instructions by the one or more processors, the one or more processors are configured to generate a user interface, and to present via the user interface a first instance of a task with an interference at the user interface, requiring a first response from the individual to the first instance of the task in the presence of the interference. The first instance of a task, requiring a second response from the individual to the first instance of the task in the absence of the interference, is presented via the user interface. At least one of the first instance of the task and the interference includes a computerized adjustable element that is adjusted in real time as an indication of a degree of success of a performance by the individual of at least one of the task or the interference. The first response from the individual to the first instance of the task and the response from the individual to the interference are measured substantially simultaneously. Data indicative of physical actions of the individual to cause a guide to avoid the at least one first type of milestone object and to cause the guide to not avoid the at least one second type of milestone object is measured. Data indicative of the first response and the second response is received. The data indicative of the first response and the second response is analyzed to generate at least one performance metric including at least one quantified indicator of cognitive abilities of the individual.

In another aspect, embodiments relate to a system for enhancing cognitive skills in an individual. The system includes one or more processors, and a memory to store processor-executable instructions and communicatively coupled with the one or more processors. Upon execution of the processor-executable instructions by the one or more processors, the one or more processors are configured to generate a user interface, and to present via the user interface a first instance of a task with an interference at a first difficulty level, requiring a first response from the individual to the first instance of the task in the presence of the interference. The first instance of the task, requiring a second response from the individual to the first instance of the task in the absence of the interference, is presented via the user interface. At least one of the first instance of the task and the interference includes a computerized adjustable element that is adjusted in real time as an indication of a degree of success of a performance by the individual of at least one of the task or the interference. The first response from the individual to the first instance of the task and the response from the individual to the interference are measured substantially simultaneously. Data indicative of the physical actions of the individual to cause a guide to avoid the at least one first type of milestone object and to cause the guide to not avoid the at least one second type of milestone object are measured. Data indicative of the first response and the second response is received. Data indicative of the first response and the second response is analyzed to generate at least one first performance metric representative of cognitive abilities of the individual based at least in part on the data indicative of the first and the second response. A difficulty of one or more of the task and the interference is adjusted based on the at least one first performance metric such that the user interface presents at least one of a second instance of the task or the interference at a second difficulty level. The second instance of the task with the interference and in the absence of the interference is presented in an iterative manner. The first response to the second instance of the task with the interference and the second response to the second instance of the task in the absence of the interference are measured. A second performance metric representative of cognitive abilities of the individual is generated, based at least in part on the data indicative of the first and second responses to the second instance of the task.

One or more of the following features may be included with any aspect of any embodiment. The one or more processors may be configured to (i) generate an output representing the at least one performance metric and/or (ii) transmit to a computing device the at least one performance metric.

The one or more processors may be further configured to present via the user interface a second instance of the task, requiring a second response from the individual to the second instance of the task, and analyze a difference between the data indicative of the first response and the second response to compute an interference cost as a measure of at least one additional indication of cognitive abilities of the individual. The first instance of the task may be a continuous task. The first instance of the task may be the task presented over a first time interval, the second instance of the task may the task presented over a second time interval, and the first time interval may be different from the second time interval. The at least one measure of cognitive capabilities of the individual may be computed based on at least one of a measure of the individual's capability to distinguish among differing types of computerized adjustable elements, and a measure of the individual's capability to distinguish among computerized adjustable elements having differing valence.

The one or more processors may configure the at least one computerized adjustable element as a temporally overlapping task with at least one of the first instance of the task or the interference.

The one or more processors may configure the at least one computerized adjustable element as at least one of a sound, an image, or a word.

The system may further include at least one actuating component, with the one or more processors being further configured to control the at least one actuating component to effect at least one of an auditory stimulus, a tactile stimulus, or a vibrational stimulus, and with the computerized adjustable element including at least one of the auditory stimulus, the tactile stimulus, or the vibrational stimulus.

The at least one performance metric may include data indicative of at least one of: (i) a projected performance of the individual at one or more of a cognitive test or a behavioral test, and/or (ii) a diagnosis of a status or progression of a cognitive condition, a disease or an executive function disorder of the individual. The at least one performance metric may be used for monitoring at least one of the cognitive condition, the disease, and/or the executive function disorder. The at least one performance metric may be used for monitoring of the individual's treatment regimen for at least one of the cognitive condition, the disease, or the executive function disorder.

The cognitive condition, disease, or executive function disorder may be anxiety (including social anxiety), depression, bipolar disorder, post-traumatic stress disorder, schizophrenia, autism spectrum disorder, attention deficit hyperactivity disorder, dementia, Parkinson's disease, Huntington's disease, cerebral amyloid angiopathy, familial amyloid neuropathy, Alzheimer's disease, multiple sclerosis, presence of the 16p11.2 duplication, attention deficit hyperactivity disorder (ADHD), sensory-processing disorder (SPD), mild cognitive impairment (MCI), and/or major depressive disorder (MDD).

The one or more processors may be further configured to use the at least one performance metric to at least one of: (i) recommend a change of at least one of an amount, concentration, or dose titration of a pharmaceutical agent, drug, or biologic, (ii) identifying a likelihood of the individual experiencing an adverse event in response to administration of the pharmaceutical agent, drug, or biologic, (iii) identify a change in the individual's cognitive response capabilities, (iv) recommend a treatment regimen, and/or (v) recommend or determine a degree of effectiveness of at least one of a behavioral therapy, counseling, or physical exercise.

The one or more processors may be configured to present via the user interface the first instance of the task as a continuous visuomotor tracking task, and with a duration of the first instance of the task being a first time interval of the continuous visuomotor task.

The one or more processors may be configured to present via the user interface the interference as a target discrimination interference.

The one or more processors may be configured to present via the user interface the first instance of the task with the interference by presenting the first instance of the task in the presence of the interference such that the interference diverts the individual's attention from the task, the interference being a distraction and/or an interruptor.

The one or more processors may be configured to receive a secondary response to the interference at substantially the same time as the first response to the first instance of the task is received, or receive a secondary response to the interference that is an interruptor at substantially the same time as the user interface receives the first response to the first instance of the task and not receive the secondary response to the interference that is a distraction at substantially the same time that the one or more processors receive the first response to the first instance of the task.

The one or more processors may be further configured to compute a psychometric curve of the individual's performance using the generated performance metric.

The one or more processors may be configured to present the at least one computerized adjustable element in a time-limited task or interference.

The one or more processors may be configured to modulate a time limit of the time-limited task or interference.

At least one of the task or interference may include a targeting task, such as a target discriminating task.

The one or more processors may be further configured to compute an interference cost based on the data indicative of the first response and the second response, with the performance metric including the computed interference cost.

The one or more processors may be further configured to present a predictive model based on the generated values of the performance metric, to generate a classifier output indicative of a measure of cognition, a mood, a level of cognitive bias, or an affective bias of the individual. The predictive model may include at least one of a linear/logistic regression, principal component analysis, generalized linear mixed models, random decision forests, support vector machines, and/or artificial neural networks.

The at least one computerized adjustable element may include at least one of a facial expression and/or a vocal expression.

The at least one computerized adjustable element may include an image of a face that represents or correlates with an expression of a specific emotion or a combination of emotions.

The generated performance metric may include an indicator of a projected response of the individual to a cognitive treatment.

The generated performance metric may include a quantitative indicator of at least one of a mood, a cognitive bias, or an affective bias of the individual.

The one or more processors may be further configured to use the performance metric to at least one of (i) recommend a change of at least one of an amount, concentration, or dose titration of a pharmaceutical agent, drug, or biologic, (ii) identify a likelihood of the individual experiencing an adverse event in response to administration of the pharmaceutical agent, drug, or biologic, (iii) identify a change in the individual's cognitive response capabilities, (iv) recommend a treatment regimen, and/or (v) recommend or determine a degree of effectiveness of at least one of a behavioral therapy, counseling, and/or physical exercise.

The one or more processors may be further configured to present the first instance of the task and the interference to obtain the first and second responses in an iterative manner, with the difficulty level being adjusted between two or more of the iterations. The at least one evocative element may include an image of a face that represents or correlates with an expression of a specific emotion or a combination of emotions. Adjusting the difficulty level may include modifying a time-varying aspect of at least one of the first instance of the task or the interference.

Modifying the time-varying aspect of the task or the interference may include adjusting a temporal length of the presenting of the task or interference via the user interface between two or more sessions of interactions of the individual.

The task or the interference may include an adaptive response-deadline procedure having a response-deadline, and the one or more processors may modify the response-deadline of the at least one adaptive response-deadline procedure to adjust the difficulty level.

The one or more processors may modify, via the user interface, a temporal length of the response window associated with the response-deadline procedure.

Adjusting the difficulty level may include applying an adaptive algorithm to progressively adjust a level of valence of the at least one evocative element.

The one or more processors may be further configured to analyze data indicative of the first response and the second response at the second difficulty level to generate at least one second performance metric representative of a performance of the individual of interference processing.

At least one of the first instance of the task and the interference may include two or more differing types of milestone objects, including at least one first type of milestone object that is to be avoided and at least one second type of milestone object that is not to be avoided. The one or more processors may be further configured to measure data indicative of physical actions of the individual to cause a guide to avoid the at least one first type of milestone object and to cause the guide to not avoid the at least one second type of milestone object.

The task may include an adjustable element adjusted in real time as an indication of a degree of success of the performance of at least one of the task or the interference. The adjustable element may include a time-varying assembly of component objects, with one or more component objects being added to the adjustable element to indicate success and one or more component objects being removed from the adjustable element to indicate an error in the performance of at least one of the task, or the interference. The component objects may include avatars.

The system may further include an input device such as a controller including a sensor, a keyboard, a computer mouse, a joystick, a handheld console, and/or a wearable device including a sensor, with the input device being configured to transmit an input from the individual to the one or more processors.

The one or more processors may be further configured to modulate one or more parameters a sound or music that accompanies at least a portion of the presentation of the tasks and/or interference.

The one or more processors may be further configured to modulate the sound or the music based on the individual's degree of success in responding to the task and/or the interference, as an additional indication of success in performance of the task and/or the interference in a trial and/or over a session.

The one or more processors may be further configured to modulate the one or more parameters of the sound or the music by gradually or discretely modifying or otherwise controlling one or more of the volume, the frequency, the beat, the tempo, the pitch, the melody, the harmony, the rhythm, the pattern, the spectrum, the envelope, the energy, or the overtones of the sound or the music.

The one or more processors may be further configured to measure substantially simultaneously the first response from the individual to the first instance of the task, a secondary response of the individual to the interference, and the response to the at least one computerized adjustable element; and generate the performance metric based on the first response, secondary response, and the response to the at least one computerized adjustable element.

The system may be a virtual reality system, an augmented reality system, and/or a mixed reality system. The system may further include one or more physiological components, wherein upon execution of the processor-executable instructions by the one or more processors, the one or more processors receive data indicative of one or more measurements of the physiological component, and analyze the data indicative of the first response and the response of the individual to the at least one computerized adjustable element, and the data indicative of one or more measurements of the physiological component to generate the at least one performance metric.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 5A-5D show exemplary user interfaces with instructions to a user that can be presented via an exemplary user interface, according to the principles herein.

FIGS. 12A-12C are flowcharts of exemplary methods, according to the principles herein.

DETAILED DESCRIPTION

Figure 1:
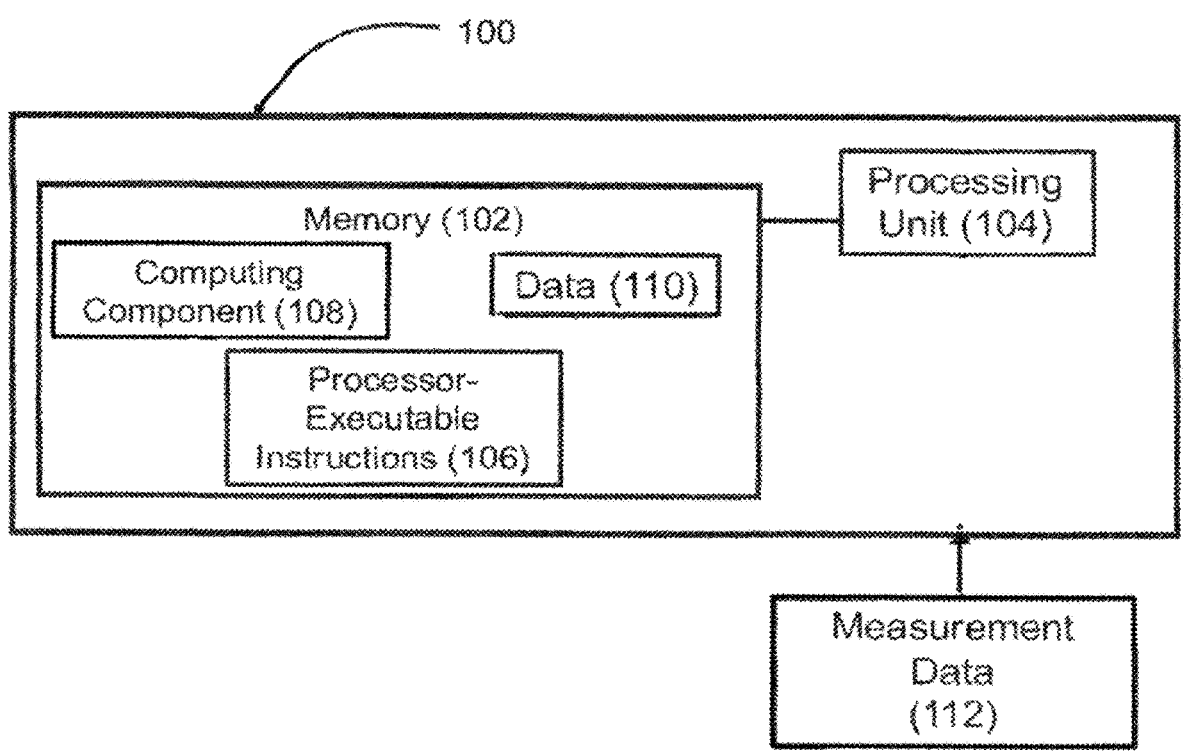
FIG. 1 is a block diagram of an exemplary system, according to the principles herein.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems comprising a cognitive platform configured for using computerized adjustable elements (i.e., emotional or affective elements) in computerized tasks (including computerized tasks that appear to a user as platform interactions) that employ one or more interactive user elements to provide cognitive assessment or deliver a cognitive treatment. The exemplary cognitive platform can be associated with a computer-implemented device platform that implements processor-executable instructions (including software programs) to provide an indication of the individual's performance, and/or for cognitive assessment, and/or to deliver a cognitive treatment. In the various examples, the computer-implemented device can be configured as a computer-implemented medical device or other type of computer-implemented device.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

As used herein, "exemplary" means serving as an example or illustration, and does not necessarily denote ideal or best.

As used herein, the term "includes" means includes but is not limited to, the term "including" means including but not limited to. The term "based on" means based at least in part on.

As used herein, the term "target" refers to a type of stimulus that is specified to an individual (e.g., in instructions) to be the focus for an interaction. A target differs from a non-target in at least one characteristic or feature. Two targets may differ from each other by at least one characteristic or feature, but overall are still instructed to an individual as a target, in an example where the individual is instructed/required to make a choice (e.g., between two different degrees of a facial expression or other characteristic/feature difference, such as but not limited to between a happy face and a happier face or between an angry face and an angrier face).

As used herein, the term "non-target" refers to a type of stimulus that is not to be the focus for an interaction, whether indicated explicitly or implicitly to the individual.

As used herein, the term "task" refers to a goal and/or objective to be accomplished by an individual. Using the exemplary systems, methods, and apparatus described herein, the computerized task is rendered using programmed computerized components, and the individual is instructed (e.g., using a computing device) as to the intended goal or objective from the individual for performing the computerized task. The task may require the individual to provide or withhold a response to a particular stimulus, using at least one component of the computing device (e.g., one or more sensor components of the computing device). The "task" can be configured as a baseline cognitive function that is being measured.

As used herein, the term "interference" refers to a type of stimulus presented to the individual such that it interferes with the individual's performance of a primary task. In any example herein, an interference is a type of task that is presented/rendered in such a manner that it diverts or interferes with an individual's attention in performing another task (including the primary task). In some examples herein, the interference is configured as a secondary task that is presented simultaneously with a primary task, either over a short, discrete time period or over an extended time period (less than the time frame over which the primary task is presented), or over the entire period of time of the primary task. In any example herein, the interference can be presented/rendered continuously, or continually (i.e., repeated in a certain frequency, irregularly, or somewhat randomly). For example, the interference can be presented at the end of the primary task or at discrete, interim periods during presentation of the primary task. The degree of interference can be modulated based on the type, amount, and/or temporal length of presentation of the interference relative to the primary task.

As used herein, the term "stimulus," refers to a sensory event configured to evoke a specified functional response from an individual. The degree and type of response can be quantified based on the individual's interactions with a measuring component (including using sensor devices or other measuring components). Non-limiting examples of a stimulus include a navigation path (with an individual being instructed to control an avatar or other processor-rendered guide to navigate the path), or a discrete object, whether a target or a non-target, rendered to a user interface (with an individual being instructed to control a computing component to provide input or other indication relative to the discrete object). In any example herein, the task and/or interference includes a stimulus, which can be a computerized adjustable element as described hereinbelow.

As used herein, a "trial" includes at least one iteration of presenting of a task and/or interference (either or both including a computerized adjustable element) and at least one receiving of the individual's response(s) to the task and/or interference (either or both including a computerized adjustable element). As non-limiting examples, a trial can include at least a portion of a single-tasking task and/or at least a portion of a multi-tasking task. For example, a trial can be a period of time during a navigation task (including a visuomotor navigation task) in which the individual's performance is assessed, such as but not limited to, assessing whether or the degree of success to which an individual's actions in interacting with the platform result in a guide (including a computerized avatar) navigating along at least a portion of a certain path or in an environment for a time interval (such as but not limited to, fractions of a second, a second, several seconds, or more) and/or causes the guide (including computerized avatar) to cross (or avoid crossing) performance thresholds along the path or in the environment. In another example, a trial can be a period of time during a targeting task in which the individual's performance is assessed, such as but not limited to, assessing whether or the degree of success to which an individual's actions in interacting with the platform result in identification/selection of a target versus a non-target (e.g., red object versus yellow object), or discriminates between two different types of targets (a happy face versus a happier face). In these examples, the segment of the individual's performance that is designated as a trial for the navigation task does not need to be co-extensive or aligned with the segment of the individual's performance that is designated as a trial for the targeting task.

In any example herein, an object may be rendered as a depiction of a physical object (including a polygonal or other object), a face (human or non-human), a caricature, or another type of object.

In any of the examples herein, instructions can be provided to the individual to specify how the individual is expected to perform the task and/or interference (either or both including a computerized adjustable element) in a trial and/or a session. In non-limiting examples, the instructions can inform the individual of the expected performance of a navigation task (e.g., stay on this path, go to these parts of the environment, cross or avoid certain milestone objects in the path or environment), a targeting task (e.g., describe or show the type of object that is the target object versus the non-target object, or describe or show the type of object that is the target object versus the non-target object, or two different types of target object that the individual is expected to choose between (e.g., happy face versus happier face)), and/or describe how the individual's performance is to be scored. In examples, the instructions may be provided visually (e.g., based on a rendered user interface) or via sound. In various examples, the instructions may be provided once prior to the performance two or more trials or sessions, or repeated each time prior to the performance of a trial or a session, or some combination thereof.

While some exemplary systems, methods, and apparatus described herein are based on an individual being instructed/required to decide/select between a target versus a non-target may, in other embodiments, the exemplary systems, methods, and apparatus can be configured such that the individual is instructed/required to decide/choose between two different types of targets (such as but not limited to between two different degrees of a facial expression or other characteristic/feature difference).

In addition, while exemplary systems, methods, and apparatus may be described herein relative to an individual, in other embodiments, the systems, methods, and apparatus can be configured such that two or more individuals, or members of a group (including a clinical population), perform the tasks and/or interference (either or both including a computerized adjustable element), either individually or concurrently.

The platform products and cognitive platforms according to the principles described herein can be applicable to many different types of cognitive conditions, disease, or executive function disorders such as but not limited to anxiety (including social anxiety), depression, bipolar disorder, post-traumatic stress disorder, schizophrenia, autism spectrum disorder, attention deficit hyperactivity disorder, dementia, Parkinson's disease, Huntington's disease, cerebral amyloid angiopathy, familial amyloid neuropathy, Alzheimer's disease, multiple sclerosis, presence of the 16p11.2 duplication, attention deficit hyperactivity disorder (ADHD), sensory-processing disorder (SPD), mild cognitive impairment (MCI), major depressive disorder (MDD), and/or other neurodegenerative conditions.

The instant disclosure is directed to computer-implemented devices formed as exemplary platform products configured to implement software or other processor-executable instructions for the purpose of measuring data indicative of a user's performance at one or more tasks, to provide a user performance metric. The performance metric can be used to derive an assessment of a user's cognitive abilities and/or to measure a user's response to a cognitive treatment, and/or to provide data or other quantitative indicia of a user's mood or cognitive or affective bias. As used herein, indicia of cognitive or affective bias include data indicating a user's preference for a negative emotion, perspective, or outcome as compared to a positive emotion, perspective, or outcome.

In a non-limiting exemplary implementation, the example platform product herein may be formed as, be based on, or be integrated with, an AKILI™ platform product (also referred to herein as an "APP") by Akili Interactive Labs, Inc., Boston, Mass.

As described in greater detail below, the computing device can include an application (an "App program") to perform such functionalities as analyzing the data. For example, the data from the at least one sensor component can be analyzed as described herein by a processor executing the App program on an example computing device to receive (including to measure) substantially simultaneously two or more of: (i) the response from the individual to a task, (i) a secondary response of the individual to an interference, and (iii) a response of the individual to at least one computerized adjustable element. As another example, the data from the at least one sensor component can be analyzed as described herein by a processor executing the App program on an exemplary computing device to analyze the data indicative of the first response and the response of the individual to the at least one computerized adjustable element to compute at least one performance metric comprising at least one quantified indicator of cognitive abilities.

A system according to the principles herein provides for generating a quantifier of cognitive skills in an individual (including using a machine learning classifier) and/or enhancing cognitive skills in an individual. In an embodiment, the system employs an App program running on a mobile communication device or other hand-held devices. Non-limiting examples of such mobile communication devices or hand-held device include a smartphone, such as but not limited to an iPhone®, a BlackBerry®, or an Android-based smartphone, a tablet, a slate, an electronic-reader (e-reader), a digital assistant, or other electronic reader or hand-held, portable, or wearable computing device, or any other equivalent device, an Xbox®, a Wii®, or other computing system that can be used to render game-like elements. In some embodiments, the system can include a head-mounted device, such as smart eyeglasses with built-in displays, a smart goggle with built-in displays, or a smart helmet with built-in displays, and the user can hold a controller or an input device having one or more sensors in which the controller or the input device communicates wirelessly with the head-mounted device. In some embodiments, the computing system may be stationary, such as a desktop computing system that includes a main computer and a desktop display (or a projector display), in which the user provides inputs to the App program using a keyboard, a computer mouse, a joystick, handheld consoles, wristbands, or other wearable devices having sensors that communicate with the main computer using wired or wireless communication. In other examples herein, the exemplary system may be a virtual reality system, an augmented reality system, or a mixed reality system. In examples herein, the sensors can be configured to measure movements of the user's hands, feet, and/or any other part of the body. In some embodiments, the exemplary system can be configured as a virtual reality (VR) system (a simulated environment including as an immersive, interactive 3-D experience for a user), an augmented reality (AR) system (including a live direct or indirect view of a physical, real-world environment whose elements are augmented by computer-generated sensory input such as but not limited to sound, video, graphics and/or GPS data), or a mixed reality (MR) system (also referred to as a hybrid reality which merges the real and virtual worlds to produce new environments and visualizations where physical and digital objects co-exist and interact substantially in real time).

As used herein, the term "cData" refers to data collected from measures of an interaction of a user with a computer-implemented device formed as a platform product.

As used herein, the term "computerized stimuli or interaction" or "CSI" refers to a computerized element that is presented to a user to facilitate the user's interaction with a stimulus or other interaction. As non-limiting examples, the computing device can be configured to present auditory stimulus (presented, e.g., as an auditory computerized adjustable element or an element of a computerized auditory task) or initiate other auditory-based interaction with the user, and/or to present vibrational stimuli (presented, e.g., as a vibrational computerized adjustable element or an element of a computerized vibrational task) or initiate other vibrational-based interaction with the user, and/or to present tactile stimuli (presented, e.g., as a tactile computerized adjustable element or an element of a computerized tactile task) or initiate other tactile-based interaction with the user, and/or to present visual stimuli or initiate other visual-based interaction with the user.

In an example where the computing device is configured to present visual CSI, the CSI can be rendered as at least one user interface to be presented to a user. In some examples, the at least one user interface is configured for measuring responses as the user interacts with a CSI computerized element rendered at the at least one user interface. In a non-limiting example, the user interface can be configured such that the CSI computerized element(s) are active, and may require at least one response from a user, such that the user interface is configured to measure data indicative of the type or degree of interaction of the user with the platform product. In another example, the user interface can be configured such that the CSI computerized element(s) are a passive and are presented to the user using the at least one user interface but may not require a response from the user. In this example, the at least one user interface can be configured to exclude the recorded response of an interaction of the user, to apply a weighting factor to the data indicative of the response (e.g., to weight the response to lower or higher values), or to measure data indicative of the response of the user with the platform product as a measure of a misdirected response of the user (e.g., to issue a notification or other feedback to the user of the misdirected response).

In an example, the platform product can be configured as a processor-implemented system, method or apparatus that includes a display component, an input device, and one or more processors. In an example, the one or more processors can be programmed to generate at least one user interface, for display at the display component, to present the computerized stimuli or interaction (CSI) or other interactive elements to the user for interaction. In other examples, one or more processors, e.g., at least one processing unit, can be programmed to cause an actuating component of the platform product to effect auditory, tactile, or vibrational computerized elements (including CSIs) to effect the stimulus or other interaction with the user. The at least one processing unit can be programmed to cause a component of the program product to receive data indicative of at least one user response based on the user interaction with the CSI or other interactive element (such as but not limited to cData), including responses provided using the input device. In an example where at least one user interface is generated to present the computerized stimuli or interaction (CSI) or other interactive elements to the user, the at least one processing unit can be programmed to cause the user interface to receive the data indicative of at least one user response. The at least one processing unit also can be programmed to: analyze the differences in the individual's performance based on determining the differences between the user's responses, and/or adjust the difficulty level of the CSI or other interactive elements based on the individual's performance determined in the analysis, and/or provide an output or other feedback from the platform product indicative of the individual's performance, and/or cognitive assessment, and/or response to cognitive treatment. In some examples, the results of the analysis may be used to modify the difficulty level or other property of the CSI or other interactive elements.

In a non-limiting example, the computerized element includes at least one task presented via a user interface as a visual task or presented as an auditory, tactile, or vibrational task. Each task can be rendered as interactive mechanics that are designed to elicit a response from a user after the user is exposed to stimuli for the purpose of cData collection.

In a non-limiting example of a computerized auditory task, the individual may be required to follow a certain computer-rendered path or navigate another environment based on auditory cues emitted to the individual. The processing unit may be configured to cause an auditory component to emit the auditory cues (e.g., sounds or human voices or music) to provide the individual with performance progress indicators to maintain or modify the path of a computerized avatar in the computer environment, and/or to indicate to the individual their degree of success in performing the physical actions measured by the sensors of the computing device to cause the computerized avatar to maintain the expected course or path.

In a non-limiting example of a computerized vibrational task, the individual may be required to follow a certain computer-rendered path or navigate another environment based on vibrational cues emitted to the individual. The processing unit may be configured to control an actuating component to vibrate (including causing a component of the computing device to vibrate) to provide the individual with the performance progress indicators to maintain or modify the path of a computerized avatar in the computer environment, and/or to indicate to the individual their degree of success in performing the physical actions measured by the sensors of the computing device to cause the computerized avatar to maintain the expected course or path.

In a non-limiting example of a computerized auditory task, the individual may be required to interact with one or more sensations perceived through the sense of touch. In a non-limiting example, a computerized adjustable element may be controlled by one or more processors to actuate an actuating component to present differing types of tactile stimuli (e.g., sensation of touch, textured surfaces or temperatures) for interaction with an individual. For example, an individual with an autism spectrum disorder (ASD) may be sensitive to (including having an aversion to) certain tactile sensory sensations (including being touched as they dress or groom themselves); individuals with Alzheimer's disease and other dementias may benefit through the sense of touch or other tactile sensation. An example tactile task may engage a tactile-sensitive individual in physical actions that causes them to interact with textures and touch sensations.

In a non-limiting example, the computerized element includes at least one platform interaction (gameplay) element of the platform rendered at a user interface, or as auditory, tactile, or vibrational element of a program product. Each platform interaction (gameplay) element of the platform product can include interactive mechanics (including in the form of videogame-like mechanics) or visual (or cosmetic) features that may or may not be targets for cData collection.

As used herein, the term "gameplay" encompasses a user interaction (including other user experience) with aspects of the platform product.

In a non-limiting example, the computerized element includes at least one element to indicate positive feedback to a user. Each such element can include an auditory signal and/or a visual signal emitted to the user that indicates success at a task or other platform interaction element, i.e., that the user responses at the platform product has exceeded a threshold success measure on a task or platform interaction (gameplay) element.

In a non-limiting example, the computerized element includes at least one element to indicate negative feedback to a user. Each such element can include an auditory signal and/or a visual signal emitted to the user that indicates failure at a task or platform interaction (gameplay) element, i.e., that the user responses at the platform product has not met a threshold success measure on a task or platform interaction element.

In a non-limiting example, the computerized element includes at least one element for messaging, i.e., a communication to the user that is different from positive feedback or negative feedback.

In a non-limiting example, the computerized element includes at least one element for indicating a reward. A reward computer element can be a computer generated feature that is delivered to a user to promote user satisfaction with the CSIs and as a result, increase positive user interaction (and hence enjoyment of the user experience).

In a non-limiting example, the cognitive platform can be configured to render at least one computerized adjustable element. As used herein, a "computerized adjustable element" is a computerized element that is configured to be change or otherwise modulate in content and/or appearance using the computing system based on the individual's performance in providing response(s) to the task and/or the interference. The exemplary system, apparatus, and method may be configured to adjust the computerized adjustable element on a real-time basis or near real-time basis as the individual(s) performs a task and/or interference (including a task with or without interference) to indicate to the individual(s) whether the individual's performance has been achieving certain performance thresholds within a given trial or session, how the individual's performance in a given trial or session compares to other or previous performances, and/or whether the individual has achieved a particular achievement level in a given trial or session. For example, the computerized adjustable element based on the degree of success of the individual in performing a portion of a task, the computerized adjustable element may be modified in a manner that represents or otherwise embodies that success. In an example, the content and/or appearance of the computerized adjustable element may be configured to evoke an emotion, an affect, a mood, a parasympathetic arousal and/or other type of response from the individual.

In the various examples herein, the computerized adjustable elements (i.e., emotional elements and/or affective elements) can be rendered as CSIs including images (including images of faces), sounds (including voices), and/or objects that increase or decrease in number and/or complexity based on the performance of the individual. For example, the change or modulation in content and/or appearance of the computerized adjustable elements based on the individual's performance in providing response(s) to the task and/or the interference may be one or more of an increase or decrease in the number of features included in the computerized adjustable element, the types of features included in the computerized adjustable element, and/or the speed or trajectory of movement of the features included in the computerized adjustable element.

In a non-limiting example, the cognitive platform can be configured to render multi-task interactive elements. In some examples, the multi-task interactive elements are referred to as multi-task gameplay (MTG). The multi-task interactive elements include interactive mechanics configured to engage the user in multiple temporally overlapping tasks, i.e., tasks that may require multiple, substantially simultaneous responses from a user.

In any example herein, the multi-tasking tasks can include any combination of two or more tasks. The multi-task interactive elements of an implementation include interactive mechanics configured to engage the individual in multiple temporally overlapping tasks, i.e., tasks that may require multiple, substantially simultaneous responses from an individual. In non-limiting examples herein, in an individual's performance of at least a portion of a multi-tasking task, the system, method, and apparatus are configured to measure data indicative of the individual's multiple responses in real-time, and also to measure a first response from the individual to a task (as a primary task) substantially simultaneously with measuring a second response from the individual to an interference (as a secondary task).

In an embodiment involving multi-tasking tasks, the computer device is configured (such as using at least one specially programmed processing unit) to cause the cognitive platform to present to a user two or more different types of tasks, such as but not limited to, target discrimination and/or navigation and/or facial expression recognition or object recognition tasks, during a short time frame (including in real-time and/or substantially simultaneously). The computer device is also configured (such as using at least one specially programmed processing unit) to collect data indicative of the type of user response received for the multi-tasking tasks, within the short time frame (including in real-time and/or substantially simultaneously). In these examples, the two or more different types of tasks can be presented to the individual within the short time frame (including in real-time and/or substantially simultaneously), and the computing device can be configured to receive data indicative of the user response(s) relative to the two or more different types of tasks within the short time frame (including in real-time and/or substantially simultaneously).

Based on the type of computerized task presented to an individual using the cognitive platform, the types of response(s) expected as a result of the individual interacting with the cognitive platform to perform the task(s), and types of data expected to be received (including being measured) using the cognitive platform, depends on the type of the task(s). For a target discrimination task, the cognitive platform may require a temporally specific and/or a position-specific response from an individual, including to select between a target and a non-target (e.g., in a GO/NO-GO task) or to select between two differing types of targets, e.g., in a two-alternative forced choice (2AFC) task (including choosing between two differing degrees of a facial expression or other characteristic/feature difference). For a navigation task, the cognitive platform may require a position-specific and/or a motion-specific response from the user. For a facial expression recognition or object recognition task, the cognitive platform may require temporally specific and/or position-specific responses from the user. In non-limiting examples, the user response to tasks, such as but not limited to targeting and/or navigation and/or facial expression recognition or object recognition task(s), can be recorded using an input device of the cognitive platform. Non-limiting examples of such input devices can include a device for capturing a touch, swipe or other gesture relative to a user interface, an audio capture device (e.g., a microphone input), or an image capture device (such as but not limited to a touch-screen or other pressure-sensitive or touch-sensitive surface, or a camera), including any form of user interface configured for recording a user interaction. In other non-limiting examples, the user response recorded using the cognitive platform for tasks, such as but not limited to targeting and/or navigation and/or facial expression recognition or object recognition task(s), can include user actions that cause changes in a position, orientation, or movement of a computing device including the cognitive platform. Such changes in a position, orientation, or movement of a computing device can be recorded using an input device disposed in or otherwise coupled to the computing device, such as but not limited to a sensor. Non-limiting examples of sensors include a motion sensor, position sensor, and/or an image capture device (such as but not limited to a camera).

In the example herein, "substantially simultaneously" means tasks are rendered, or response measurements are performed, within less than about 5 milliseconds of each other, or within about 10 milliseconds, about 20 milliseconds, about 50 milliseconds, about 75 milliseconds, about 100 milliseconds, or about 150 milliseconds or less, about 200 milliseconds or less, about 250 milliseconds or less, of each other. In any example herein, "substantially simultaneously" is a period of time less than the average human reaction time. In another example, two tasks may be substantially simultaneous if the individual switches between the two tasks within a pre-set amount of time. The set amount of time for switching considered "substantially simultaneously" can be about 1 tenth of a second, 1 second, about 5 seconds, about 10 seconds, about 30 seconds, or greater.

In some examples, the short time frame can be any time interval at a resolution of up to about 1.0 millisecond or greater. The time intervals can be, but are not limited to, durations of time of any division of a periodicity of about 2.0 milliseconds or greater, up to any reasonable end time. The time intervals can be, but are not limited to, about 3.0 milliseconds, about 5.0 milliseconds, about 10 milliseconds, about 25 milliseconds, about 40 milliseconds, about 50 milliseconds, about 60 milliseconds, about 70 milliseconds, about 100 milliseconds, or greater. In other examples, the short time frame can be, but is not limited to, fractions of a second, about a second, between about 1.0 and about 2.0 seconds, or up to about 2.0 seconds, or more.

In any example herein, the cognitive platform can be configured to collect data indicative of a reaction time of a user's response relative to the time of presentation of the tasks (including an interference with a task). For example, the computing device can be configured to cause the platform product or cognitive platform to provide smaller or larger reaction time window for a user to provide a response to the tasks as an example way of adjusting the difficulty level.

In a non-limiting example, the cognitive platform can be configured to render single-task interactive elements. In some examples, the single-task interactive elements are referred to as single-task gameplay (STG). The single-task interactive elements include interactive mechanics configured to engage the user in a single task in a given time interval.

According to the principles herein, the term "cognition" refers to the mental action or process of acquiring knowledge and understanding through thought, experience, and the senses. This includes, but is not limited to, psychological concepts/domains such as, executive function, memory, perception, attention, emotion, motor control, and interference processing. An example computer-implemented device according to the principles herein can be configured to collect data indicative of user interaction with a platform product, and to compute metrics that quantify user performance. The quantifiers of user performance can be used to provide measures of cognition (for cognitive assessment) or to provide measures of status or progress of a cognitive treatment.

According to the principles herein, the term "treatment" refers to any manipulation of CSI in a platform product (including in the form of an APP) that results in a measurable improvement of the abilities of a user, such as but not limited to improvements related to cognition, a user's mood or level of cognitive or affective bias. The degree or level of improvement can be quantified based on user performance measures as describe herein.

According to the principles herein, the term "session" refers to a discrete time period, with a clear start and finish, during which a user interacts with a platform product to receive assessment or treatment from the platform product (including in the form of an APP). In examples herein, a session can refer to at least one trial or can include at least one trial and at least one other type of measurement and/or other user interaction. As a non-limiting example, a session can include at least one trial and one or more of a measurement using a physiological or monitoring component and/or a cognitive testing component. As another non-limiting example, a session can include at least one trial and receipt of data indicative of one or more measures of an individual's condition, including physiological condition and/or cognitive condition.

According to the principles herein, the term "assessment" refers to at least one session of user interaction with CSIs or other feature or element of a platform product. The data collected from one or more assessments performed by a user using a platform product (including in the form of an APP) can be used as to derive measures or other quantifiers of cognition, or other aspects of a user's abilities.

According to the principles herein, the term "cognitive load" refers to the amount of mental resources that a user may need to expend to complete a task. This term also can be used to refer to the challenge or difficulty level of a task or gameplay.

According to the principles herein, the term "emotional load" refers to cognitive load that is specifically associated with processing emotional information or regulating emotions or with affective bias in an individual's preference for a negative emotion, perspective, or outcome as compared to a positive emotion, perspective, or outcome. The emotional load may be modified (i.e., increased or decreased) by using an example apparatus, system or method to configure a computerized adjustable element to indicate to the individual(s) their degree of success in performing a portion of a task and/or an interference (including a task with or without an interference).

According to the principles herein, the term "ego depletion" refers to a state reached by a user after a period of effortful exertion of self-control, characterized by diminished capacity to exert further self-control. The state of ego-depletion may be measured based on data collected for a user's responses to the interactive elements rendered at user interfaces, or as auditory, tactile, or vibrational elements, of a platform product described hereinabove.

According to the principles herein, the term "emotional processing" refers to a component of cognition specific to cognitive and/or neurologic processing of emotion/affect/mood or parasympathetic arousal. The degree of emotional processing may be measured based on data collected for a user's responses to the interactive computerized adjustable elements rendered at user interfaces (including as an auditory, tactile, or vibrational element), of a platform product described hereinabove.

An exemplary system, method, and apparatus according to the principles herein includes a platform product (including using an APP) that uses a cognitive platform configured to render at least one computerized adjustable element, to provide additional control of cognitive load as an overt component for tasks in MTG or STG. In one example, the computerized adjustable element is used in the tasks configured to assess cognition or improve cognition related to emotions, and the data (including cData) collected as a measure of user interaction with the rendered computerized adjustable element in the platform product is used to determine the measures of the assessment of cognition or the improvement to measures of cognition after a treatment configured for interaction using the user interface, or as auditory, tactile, or vibrational elements, of the platform product. The computerized adjustable element can be configured to collect data to measure the impact of emotions on non-emotional cognition, such as by causing the user interface to render spatial tasks for the user to perform, and/or to collect data to measure the impact of non-emotional cognition on emotions, such as by causing the user interface to render features that employ measures of executive function to regulate emotions. In one embodiment, the user interface can be configured to render tasks for identifying the emotion indicated by the CSI (based on measurement data), maintaining that identification in working memory, and comparing it with the measures of emotion indicated by subsequent CSI, while under cognitive load due to MTG.

In one example, the user interface may be configured to present to a user a program platform based on a cognitive platform based on interference processing. In an exemplary system, method and apparatus that implements interference processing, the at least one processing unit is programmed to generate at least one first user interface, or auditory, tactile, or vibrational signal, to present a first task that requires a first type of response from a user, and to render at least one second user interface, or auditory, tactile, or vibrational signal, to present a first interference with the first task, requiring a second type of response from the user to the first task in the presence of the first interference. In a non-limiting example, the second type of response can include the first type of response to the first task and a secondary response to the first interference. In another non-limiting example, the second type of response may not include, and be quite different from, the first type of response. The at least one processing unit is also programmed to receive data indicative of the first type of response and the second type of response based on the user interaction with the platform product (such as but not limited to cData), such as but not limited to by rendering the at least one user interface to receive the data. The at least one processing unit also can be programmed to: analyze the differences in the individual's performance based on determining the differences between the measures of the user's first type and second type of responses, and/or adjust the difficulty level of the first task and/or the first interference based on the individual's performance determined in the analysis, and/or provide an output or other feedback from the platform product that can be indicative of the individual's performance, and/or cognitive assessment, and/or response to cognitive treatment, and/or assessed measures of cognition. As a non-limiting example, the cognitive platform based on interference processing can be the Project:EVO™ platform by Akili Interactive Labs, Inc., Boston, Mass.

In an exemplary system, method and apparatus according to the principles herein that is based on interference processing, the user interface is configured such that, as a component of the interference processing, one of the discriminating features of the targeting task that the user responds to is a feature in the platform that displays an emotion, similar to the way that shape, color, and/or position may be used in an interference element in interference processing.

In another exemplary system, method and apparatus according to the principles herein that is based on interference processing, a platform product may include a working-memory task such as cognitive tasks that employs computerized adjustable element, where the affective content is either a basis for matching or a distractive element as part of the user interaction, within a MTG or a STG.

An exemplary system, method, and apparatus according to the principles herein includes a platform product (including using an APP) that uses a cognitive platform configured to render at least one integrating computerized adjustable element in a MTG or a STG, where the user interface is configured to not explicitly call attention to the computerized adjustable element. The user interface of the platform product may be configured to render computerized adjustable element for the purpose of assessing or adjusting emotional biases in attention, interpretation, or memory, and to collected data indicative of the user interaction with the platform product.

An exemplary system, method, and apparatus according to the principles herein includes a platform product (including using an APP) that uses a cognitive platform configured to render at least one computerized adjustable element that reinforces positive or negative feedback provided within the one or more tasks.

An exemplary system, method, and apparatus according to the principles herein includes a platform product (including using an APP) that uses a cognitive platform configured to render at least one computerized adjustable element that introduces fixed or adjustable levels of cognitive or emotional load to the user interaction (including to gameplay). This could be used for the purposes of modulating the difficulty of an MTG or a STG. This includes using computerized adjustable element(s) that conflict with the positive feedback or negative feedback provided within the one or more tasks or using computerized adjustable element(s) to induce ego depletion to impact the user's cognitive control capabilities.

An exemplary system, method, and apparatus according to the principles herein includes a platform product (including using an APP) that uses a cognitive platform configured to render and integrate at least one simultaneous conflicting computerized adjustable element(s) into different tasks during a MTG. This could be used for the purpose of assessing or improving measures of cognition related to the user interaction with the platform product indicating the user's handling of conflicting emotional information.

An exemplary system, method, and apparatus according to the principles herein includes a platform product (including using an APP) that uses video or audio sensors to detect the performance of physical or vocal actions by the user, as a means of response to CSI within a task. These actions may be representations of emotions, such as facial or vocal expressions, or words.

An exemplary system, method, and apparatus according to the principles herein includes a platform product (including using an APP) that uses a cognitive platform configured to render at least one computerized adjustable element as part of an emotional regulation strategy to enable better user engagement with the platform product when the analysis of the collected data indicates that the user is in a non-optimal emotional state. For example, if the data analysis of the performance measures of the platform product determines that the user is frustrated and unable to properly engage in treatment or assessment, the platform product could be configured to introduce some sort of break in the normal interaction sequence that employs computerized adjustable elements until after a time interval that the user is deemed ready to engage sufficiently again. This can be a fixed interval of time or an interval of time computed based on the user's previous performance data.

An exemplary system, method, and apparatus according to the principles herein includes a platform product (including using an APP) that uses a cognitive platform configured to render at least one computerized adjustable element in the interaction sequence, measure user responses, and adjust the CSI accordingly. These measurements may be compared with the user responses to interaction sequences in the platform that do not present computerized adjustable elements, in order to determine measures of the user's emotional reactivity. This measurement, with or without comparison to measurements made during interaction sequences that do not present computerized adjustable elements, may be for the purpose of assessing the user's emotional state. The CSI adjustments might be initiating an emotional regulation strategy to enable better engagement with the platform product or initiating certain interactive elements, such as but not limited to tasks or rewards, only under certain emotional conditions. The user response measurement may employ use of inputs such as touchscreens, keyboards, or accelerometers, or passive external sensors such as video cameras, microphones, eye-tracking software/devices, bio-sensors, and/or neural recording (e.g., electroencephalogram), and may include responses that are not directly related to interactions with the platform product, as well as responses based on user interactions with the platform product. The platform product can present measures of a user's emotional state that include a measure of specific moods and/or a measure of general state of ego depletion that impacts emotional reactivity.

An exemplary system, method, and apparatus according to the principles herein includes a platform product (including using an APP) that uses a cognitive platform configured to render at least one computerized adjustable element to suggest possible appropriate task responses. This may be used to evaluate the user's ability to discern emotional cues, or to choose appropriate emotional responses.

An exemplary system, method, and apparatus according to the principles herein includes a platform product (including using an APP) that uses a cognitive platform configured to render at least one computerized adjustable element in time-limited tasks, where the time limits may be modulated. This may be for the purposes of measuring user responses via different cognitive processes, such as top-down conscious control vs. bottom-up reflexive response.

An exemplary system, method, and apparatus according to the principles herein includes a platform product (including using an APP) that uses a cognitive platform configured to render at least one computerized adjustable element with levels of valence determined based on previous user responses to computerized adjustable element at one or more level of valence. This may include applying an adaptive algorithm to progressively adjust the level of valence to achieve specific goals, such as creating a psychometric curve of expected user performance on a task across stimulus or difficulty levels, or determining the specific level at which a user's task performance would meet a specific criterion like 50% accuracy in a Go/No-Go task.

As described hereinabove, the exemplary systems, methods, and apparatus according to the principles herein can be implemented, using at least one processing unit of a programmed computing device, to provide the cognitive platform. FIG. 1 shows an exemplary system or apparatus 100 according to the principles herein that can be used to implement the cognitive platform described hereinabove herein. The exemplary system or apparatus 100 includes at least one memory 102 and one or more processors, e.g., at least one processing unit 104. The at least one processing unit 104 is communicatively coupled to the at least one memory 102.

Exemplary memory 102 can include, but is not limited to, hardware memory, non-transitory tangible media, magnetic storage disks, optical disks, flash drives, computational device memory, random access memory, such as but not limited to DRAM, SRAM, EDO RAM, any other type of memory, or combinations thereof. Example processing unit 104 can include, but is not limited to, a microchip, a processor, a microprocessor, a special purpose processor, an application specific integrated circuit, a microcontroller, a field programmable gate array, any other suitable processor, or combinations thereof.

The at least one memory 102 is configured to store processor-executable instructions 106 and a computing component 108. In a non-limiting example, the computing component 108 can be used to receive (including to measure) substantially simultaneously two or more of: (i) the response from the individual to a task, (i) a secondary response of the individual to an interference, and (iii) a response of the individual to at least one computerized adjustable element. In another non-limiting example, the computing component 108 can be used to analyze the data from the at least one sensor component as described herein and/or to analyze the data indicative of the first response and the response of the individual to the at least one computerized adjustable element to compute at least one performance metric comprising at least one quantified indicator of cognitive abilities. In another non-limiting example, the computing component 108 can be used to compute signal detection metrics in computer-implemented adaptive response-deadline procedures. As shown in FIG. 1, the memory 102 also can be used to store data 110, such as but not limited to the measurement data 112. In various examples, the measurement data 112 can include physiological measurement data (including data collected based on one or more measurements) of an individual received from a physiological component (not shown) and/or data indicative of the response of an individual to a task and/or an interference rendered at a user interface of the apparatus 100 (as described in greater detail below), or using an auditory, tactile, or vibrational signal from an actuating component of the apparatus 100, and/or data indicative of one or more of an amount, concentration, or dose titration, or other treatment regimen of a drug, pharmaceutical agent, biologic, or other medication being or to be administered to an individual.

In a non-limiting example, the at least one processing unit 104 executes the processor-executable instructions 106 stored in the memory 102 at least to measure substantially simultaneously two or more of: (i) the response from the individual to a task, (i) a secondary response of the individual to an interference, and (iii) a response of the individual to at least one computerized adjustable element. The at least one processing unit 104 also executes the processor-executable instructions 106 stored in the memory 102 at least to analyze the data collected using a measurement component (including the data indicative of the first response and the response of the individual to the at least one computerized adjustable element) to compute at least one performance metric comprising at least one quantified indicator of cognitive abilities using the computing component 108. The at least one processing unit 104 also may be programmed to execute processor-executable instructions 106 to control a transmission unit to transmit values indicative of the computed signal detection metrics and/or controls the memory 102 to store values indicative of the signal detection metrics.

In a non-limiting example, the at least one processing unit 104 also executes processor-executable instructions 106 to control a transmission unit to transmit values indicative of the generated performance metric and/or controls the memory 102 to store values indicative of the generated performance metric.

In another non-limiting example, the at least one processing unit 104 executes the processor-executable instructions 106 stored in the memory 102 at least to apply signal detection metrics in computer-implemented adaptive response-deadline procedures.

In any example herein, the user interface may be a graphical user interface.

In another non-limiting example, the measurement data 112 can be collected from measurements using one or more physiological or monitoring components and/or cognitive testing components. In any example herein, the one or more physiological components are configured for performing physiological measurements. The physiological measurements provide quantitative measurement data of physiological parameters and/or data that can be used for visualization of physiological structure and/or functions.

In any example herein, the measurement data 112 can include reaction time, response variance, correct hits, omission errors, number of false alarms (such as but not limited to a response to a non-target), learning rate, spatial deviance, subjective ratings, and/or performance threshold, or data from an analysis, including percent accuracy, hits, and/or misses in the latest completed trial or session. Other non-limiting examples of measurement data 112 include response time, task completion time, number of tasks completed in a set amount of time, preparation time for task, accuracy of responses, accuracy of responses under set conditions (e.g., stimulus difficulty or magnitude level and association of multiple stimuli), number of responses a participant can register in a set time limit number of responses a participant can make with no time limit, number of attempts at a task needed to complete a task, movement stability, accelerometer and gyroscope data, and/or self-rating.

In any example herein, the one or more physiological components can include any means of measuring physical characteristics of the body and nervous system, including electrical activity, heart rate, blood flow, and oxygenation levels, to provide the measurement data 112. This can include camera-based heart rate detection, measurement of galvanic skin response, blood pressure measurement, electroencephalogram, electrocardiogram, magnetic resonance imaging, near-infrared spectroscopy, and/or pupil dilation measures, to provide the measurement data 112. The one or more physiological components can include one or more sensors for measuring parameter values of the physical characteristics of the body and nervous system, and one or more signal processors for processing signals detected by the one or more sensors.

Other examples of physiological measurements to provide measurement data 112 include, but are not limited to, the measurement of body temperature, heart or other cardiac-related functioning using an electrocardiograph (ECG), electrical activity using an electroencephalogram (EEG), event-related potentials (ERPs), functional magnetic resonance imaging (fMRI), blood pressure, electrical potential at a portion of the skin, galvanic skin response (GSR), magneto-encephalogram (MEG), eye-tracking device or other optical detection device including processing units programmed to determine degree of pupillary dilation, functional near-infrared spectroscopy (fNIRS), and/or a positron emission tomography (PET) scanner. An EEG-fMRI or MEG-fMRI measurement allows for simultaneous acquisition of electrophysiology (EEG/MEG) data and hemodynamic (fMRI) data.

The exemplary system or apparatus of FIG. 1 can be configured as a computing device for performing any of the exemplary methods described herein. The computing device can include an App program for performing some of the functionality of the example methods described herein.

In any example herein, the exemplary apparatus can be configured to communicate with one or more of a cognitive monitoring component, a disease monitoring component, and a physiological measurement component, to provide for biofeedback and/or neurofeedback of data to the computing device, for adjusting a type or a difficulty level of one or more of the task, the interference, and the computerized adjustable element, to achieve the desired performance level of the individual. As a non-limiting example, the biofeedback can be based on physiological measurements of the individual as they interact with the apparatus, to modify the type or a difficulty level of one or more of the task, the interference, and the computerized adjustable element based on the measurement data indicating, e.g., the individual's attention, mood, or emotional state. As a non-limiting example, the neurofeedback can be based on measurement and monitoring of the individual using a cognitive and/or a disease monitoring component as the individual interacts with the apparatus, to modify the type or a difficulty level of one or more of the task, the interference, and the computerized adjustable element based on the measurement data indicating, e.g., the individual's cognitive state, disease state (including based on data from monitoring systems or behaviors related to the disease state).

Figure 2:
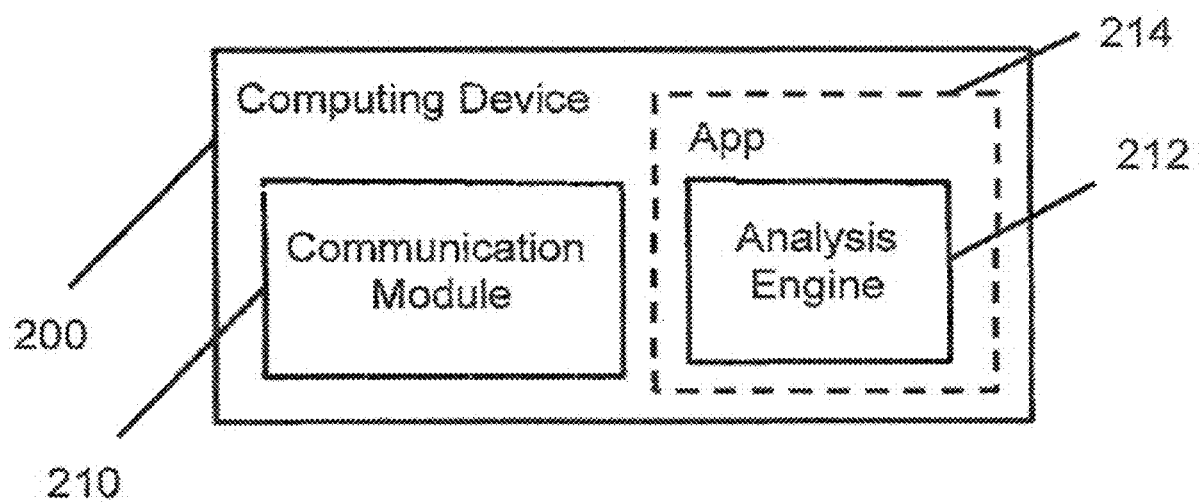
FIG. 2 is a block diagram of an exemplary computing device, according to the principles herein.

FIG. 2 shows another exemplary system according to the principles herein, configured as a computing device 200 that can be used to implement the cognitive platform according to the principles herein. The exemplary computing device 200 can include a communication module 210 and an analysis engine 212. The communication module 210 can be implemented to receive data indicative of at least one response of an individual to the task in the absence of an interference, and/or at least one response of an individual to the task that is being rendered in the presence of the interference. In an example, the communication module 210 can be implemented to receive substantially simultaneously two or more of: (i) the response from the individual to a task, (ii) a secondary response of the individual to an interference, and (iii) a response of the individual to at least one computerized adjustable element. The analysis engine 212 can be implemented to analyze the data from the at least one sensor component as described herein and/or to analyze the data indicative of the first response and the response of the individual to the at least one computerized adjustable element to compute at least one performance metric comprising at least one quantified indicator of cognitive abilities. In another example, the analysis engine 212 can be implemented to analyze data to generate a response profile, decision boundary metric (such as but not limited to response criteria), a classifier, and/or other metrics and analyses described herein. As shown in the example of FIG. 2, the computing device 200 can include processor-executable instructions such that a processor unit can execute an application program (App 214) that a user can implement to initiate the analysis engine 212. In an example, the processor-executable instructions can include software, firmware, or other instructions.

The exemplary communication module 210 can be configured to implement any wired and/or wireless communication interface by which information may be exchanged between the computing device 200 and another computing device or computing system. Non-limiting examples of wired communication interfaces include, but are not limited to, USB ports, RS232 connectors, RJ45 connectors, and Ethernet connectors, and any appropriate circuitry associated therewith. Non-limiting examples of wireless communication interfaces may include, but are not limited to, interfaces implementing Bluetooth® technology, Wi-Fi, Wi-Max, IEEE 802.11 technology, radio frequency (RF) communications, Infrared Data Association (IrDA) compatible protocols, Local Area Networks (LAN), Wide Area Networks (WAN), and Shared Wireless Access Protocol (SWAP).

In an exemplary implementation, the example computing device 200 includes at least one other component that is configured to transmit a signal from the apparatus to a second computing device. For example, the at least one component can include a transmitter or a transceiver configured to transmit a signal including data indicative of a measurement by at least one sensor component to the second computing device.

In any example herein, the App 214 on the computing device 200 can include processor-executable instructions such that a processor unit of the computing device implements an analysis engine to analyze data indicative of the individual's response to the rendered tasks and/or interference (either or both with computerized adjustable element) and the response of the individual to the at least one computerized adjustable element to compute at least one performance metric comprising at least one quantified indicator of cognitive abilities. In another example, the App 214 on the computing device 200 can include processor-executable instructions such that a processor unit of the computing device implements an analysis engine to analyze the data indicative of the individual's response to the rendered tasks and/or interference (either or both with computerized adjustable element) and the response of the individual to the at least one computerized adjustable element to provide a classifier based on the computed values of the performance metric, to generate a classifier output indicative of a measure of cognition, a mood, a level of cognitive bias, or an affective bias of the individual. In some examples, the App 214 can include processor-executable instructions such that the processing unit of the computing device implements the analysis engine to provide a classifier as to response profile, decision boundary metric (such as but not limited to response criteria), a classifier, and other metrics and analyses described herein. In some example, the App 214 can include processor-executable instructions to provide one or more of: (i) a classifier output indicative of the cognitive capabilities of the individual, (ii) a likelihood of the individual experiencing an adverse event in response to administration of the pharmaceutical agent, drug, or biologic, (iii) a change in one or more of the amount, concentration, or dose titration of the pharmaceutical agent, drug, or biologic, and (iv) a change in the individual's cognitive capabilities, a recommended treatment regimen, or recommending or determining a degree of effectiveness of at least one of a behavioral therapy, counseling, or physical exercise.

In any example herein, the App 214 can be configured to receive measurement data including physiological measurement data of an individual received from a physiological component, and/or data indicative of the response of an individual to a task and/or an interference rendered at a user interface of the apparatus 100 (as described in greater detail below), and/or data indicative of one or more of an amount, concentration, or dose titration, or other treatment regimen of a drug, pharmaceutical agent, biologic, or other medication being or to be administered to an individual.

Non-limiting examples of the computing device include a smartphone, a tablet, a slate, an e-reader, a digital assistant, or any other equivalent device, including any of the mobile communication devices described hereinabove. As an example, the computing device can include a processor unit that is configured to execute an application that includes an analysis module for analyzing the data indicative of the individual's response to the rendered tasks and/or interference (either or both with computerized adjustable element).

The exemplary systems, methods, and apparatus can be implemented as a component in a product comprising a computing device that uses computer-implemented adaptive psychophysical procedures to assess human performance or delivers psychological/perceptual therapy.

A non-limiting example characteristic of a type of decision boundary metric that can be computed based on the response profile is the response criterion (a time-point measure), calculated using the standard procedure to calculate response criterion for a signal detection psychophysics assessment. See, e.g., Macmillan and Creelman (2004), "Signal Detection: A Users Guide" 2nd edition, Lawrence Erlbaum USA.

In other non-limiting examples, the decision boundary metric may be more than a single quantitative measure but rather a curve defined by quantitative parameters based on which decision boundary metrics can be computed, such as but not limited to an area to one side or the other of the response profile curve. Other non-limiting example types of decision boundary metrics that can be computed to characterize the decision boundary curves for evaluating the time-varying characteristics of the decision process include a distance between the initial bias point (the starting point of the belief accumulation trajectory) and the criterion, a distance to the decision boundary, a "waiting cost" (e.g., the distance from the initial decision boundary and the maximum decision boundary, or the total area of the curve to that point), or the area between the decision boundary and the criterion line (including the area normalized to the response deadline to yield a measure of an "average decision boundary" or an "average criterion"). While examples herein may be described based on computation of a response criterion, other types of decision boundary metrics are applicable.

Following is a description of a non-limiting example use of a computational model of human decision-making (based on a drift diffusion model). While the drift diffusion model is used as the example, other types of models apply, including a Bayesian model. The drift-diffusion model (DDM) can be applied for systems with two-choice decision making See, e.g., Ratcliff, R. (1978), "A theory of memory retrieval." Psychological Review, 85, 59-108; Ratcliff, R., & Tuerlinckx, F. (2002), "Estimating parameters of the diffusion model: Approaches to dealing with contaminant reaction times and parameter variability," Psychonomic Bulletin & Review, 9, 438-481. The diffusion model is based on an assumption that binary decision processes are driven by systematic and random influences.

Figure 3A:
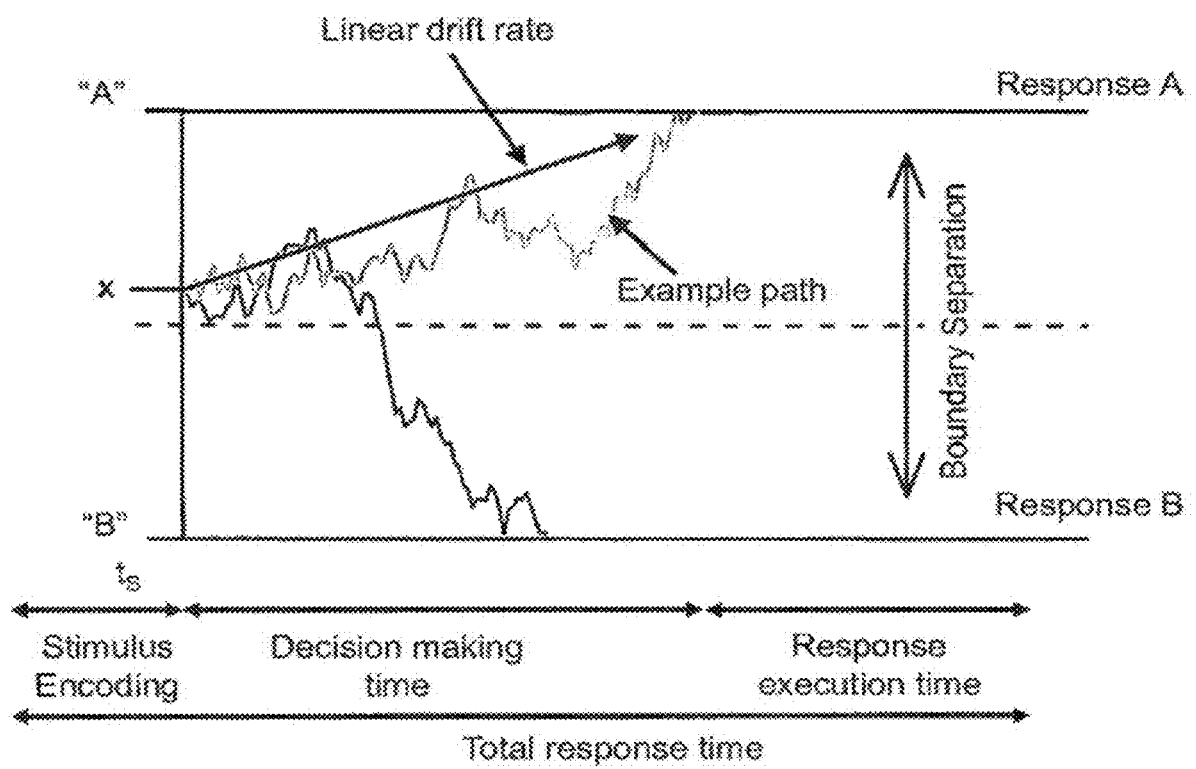
FIG. 3A is an exemplary graphical depiction of a drift-diffusion model for linear belief accumulation, according to the principles herein.

FIG. 3A shows an example plot of the diffusion model with a stimulus that results in a linear drift rate, showing example paths of the accumulation of belief from a stimulus. It shows the distributions of drift rates across trials for targets (signal) and non-targets (noise). The vertical line is the response criterion. The drift rate on each trial is determined by the distance between the drift criterion and a sample from the drift distribution. The process starts at point x, and moves over time until it reaches the lower threshold at "A" or the upper threshold at "B". The DDM assumes that an individual is accumulating evidence for one or other of the alternative thresholds at each time step, and integrating that evidence to develop a belief, until a decision threshold is reached. Depending on which threshold is reached, different responses (i.e., Response A or Response B) are initiated by the individual. In a psychological application, this means that the decision process is finished and the response system is being activated, in which the individual initiates the corresponding response. As described in non-limiting examples below, this can require a physical action of the individual to actuate a component of the system or apparatus to provide the response (such as but not limited to tapping on the user interface in response to a target). The systematic influences are called the drift rate, and they drive the process in a given direction. The random influences add an erratic fluctuation to the constant path. With a given set of parameters, the model predicts distributions of process durations (i.e., response times) for the two possible outcomes of the process.

FIG. 3A also shows an example drift-diffusion path of the process, illustrating that the path is not straight but rather oscillates between the two boundaries, due to random influences. In a situation in which individuals are required to categorize stimuli, the process describes the ratio of information gathered over time that causes an individual to foster each of the two possible stimulus interpretations. Once belief points with sufficient clarity is reached, the individual initiates a response. In the example of FIG. 3A, processes reaching the upper threshold are indicative of a positive drift rate. In some trials, the random influences can outweigh the drift, and the process terminates at the lower threshold.

Exemplary parameters of the drift diffusion model include quantifiers of the thresholds ("A" or "B"), the starting point (x), the drift rate, and a response time constant (t0). The DDM can provide a measure of conservatism, an indication that the process takes more time to reach one threshold and that it will reach the other threshold (opposite to the drift) less frequently. The starting point (x) provides an indicator of bias (reflecting differences in the amount of information that is required before the alternative responses are initiated). If x is closer to "A", an individual requires a smaller (relative) amount of information to develop a belief to execute Response A, as compared with a larger (relative) amount of information that the individual would need to execute Response B. The smaller the distance between the starting point (x) and a threshold, the shorter the process durations would be for the individual to execute the corresponding response. A positive value of drift rate (v) serves as a measure of the mean rate of approach to the upper threshold ("A"). The drift rate indicates the relative amount of information per time unit that the individual absorbs information on a stimulus to develop a belief in order to initiate and execute a response. In an example, comparison of the drift rates computed from data of one individual to data from another can provide a measure of relative perceptual sensitivity of the individuals. In another example, comparison of the drift rates can provide a relative measure of task difficulty. For computation of the response time, the DDM allows for estimating their total duration, and the response time constant (t0) indicates the duration of extra-decisional processes. The DDM has been shown to describe accuracy and reaction times in human data for tasks. In the non-limiting example of FIG. 3A, the total response time is computed as a sum of the magnitude of time for stimulus encoding (tS), the time the individual takes for the decision, and the time for response execution.

As compared to the traditional drift diffusion model that is based on stimuli that result in linear drift rates, the exemplary systems, methods, and apparatus according to the principles herein are configured to render stimuli that result in non-linear drift rates, stimuli being based on tasks and/or interference (either or both with computerized adjustable element) that are time-varying and have specified response deadlines. As a result, the exemplary systems, methods, and apparatus according to the principles herein are configured to apply a modified diffusion model (modified DDM) based on these stimuli that result in non-linear drift rates.

Figure 3B:
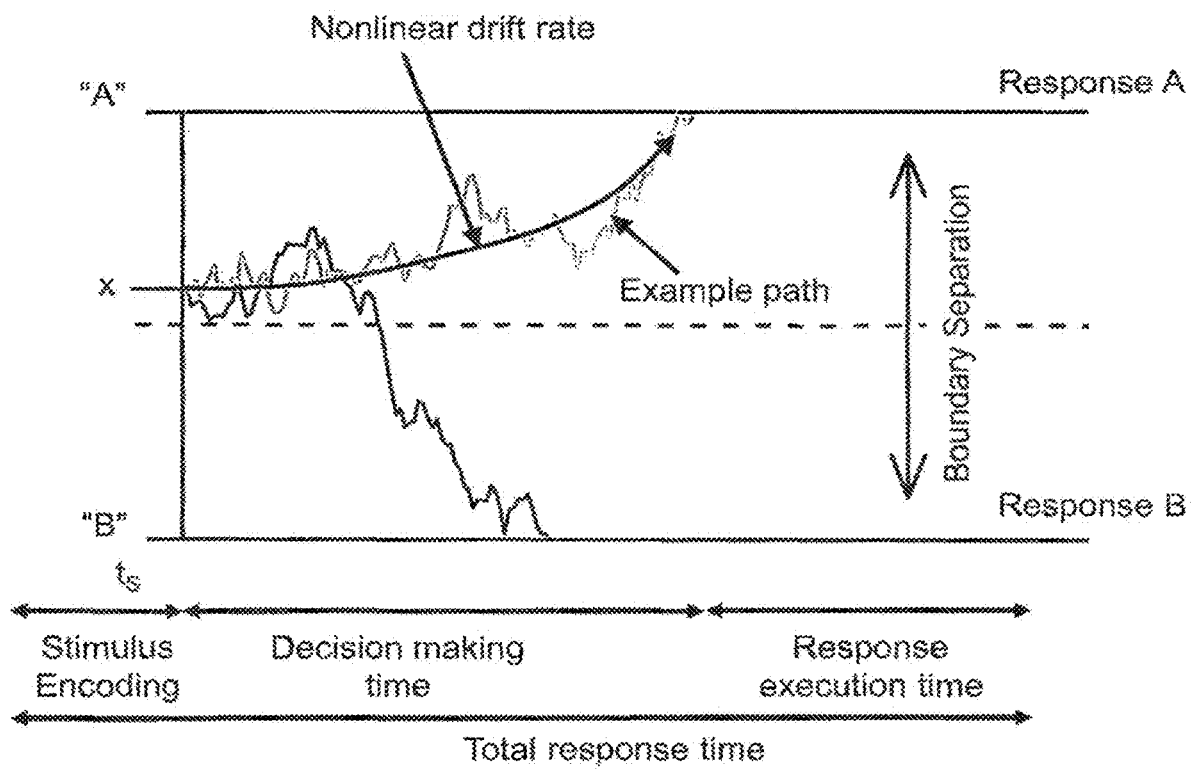
FIG. 3B is an exemplary graphical depiction of a drift-diffusion model for non-linear belief accumulation, according to the principles herein.

FIG. 3B shows an example plot of a non-linear drift rate in a drift diffusion computation. Example parameters of the modified DDM also include quantifiers of the thresholds ("A" or "B"), the starting point (x), the drift rate, and a response time constant (t0). Based on data collected from user interaction with the exemplary systems, methods, and apparatus herein, the systems, methods, and apparatus are configured to apply the modified DDM with the non-linear drift rates to provide a measure of the conservatism or impulsivity of the strategy employed in the user interaction with the example platforms herein. The exemplary systems, methods, and apparatus are configured to compute a measure of the conservatism or impulsivity of the strategy used by an individual based on the modified DDM model, to provide an indication of the time the process takes for a given individual to reach one threshold and as compared to reaching the other threshold (opposite to the drift). The starting point (x) in FIG. 3B also provides an indicator of bias (reflecting differences in the amount of information that is required before the alternative responses are initiated). For computation of the response time, the DDM allows for estimating their total duration, and the response time constant (t0) indicates the duration of extra-decisional processes.

In the exemplary systems, methods, and apparatus according to the principles herein, the non-linear drift rate results from the time-varying nature of the stimuli, including (i) the time-varying feature of portions of the task and/or interference (either or both with computerized adjustable element) rendered to the user interface for user response (as a result of which the amount of information available for an individual to develop a belief is presented in a temporally non-linear manner), and (ii) the time limit of the response deadlines of the task and/or interference (either or both with computerized adjustable element), which can influence an individual's sense of timing to develop a belief in order to initiate a response. In this example as well, a positive value of drift rate (v) serves as a measure of the mean rate of approach to the upper threshold ("A"). The non-linear drift rate indicates the relative amount of information per time unit that the individual absorbs to develop a belief in order to initiate and execute a response. In an example, comparison of the drift rate computed from response data collected from one individual to the drift rate computed from response data collected from another individual can be used to provide a measure of relative perceptual sensitivity of the individuals. In another example, comparison of the drift rate computed from response data collected from a given individual from two or more different interaction sessions can be used to provide a relative measure of task difficulty. For computation of the response time of the individual's responses, the modified DDM also allows for estimating the total duration of the response time, and the response time constant (t0) indicates the duration of extra-decisional processes. In the non-limiting example of FIG. 3A, the total response time is computed as a sum of the magnitude of time for stimulus encoding (tS), the time the individual takes for the decision, and the time for response execution.

For the modified DDM, the distance between the thresholds (i.e., between "A" and "B") provides a measure of conservatism—that is, the larger the separation, the more information is collected prior to an individual executing a response. The starting point (x) also provides an estimate of relative conservatism: if the process starts above or below the midpoint between the two thresholds, different amounts of information are required for both responses; that is, a more conservative decision criterion is applied for one response, and a more liberal criterion (i.e., impulsive) for the opposite response. The drift rate (v) indicates the (relative) amount of information gathered per time, denoting either perceptual sensitivity or task difficulty.

Figure 4:
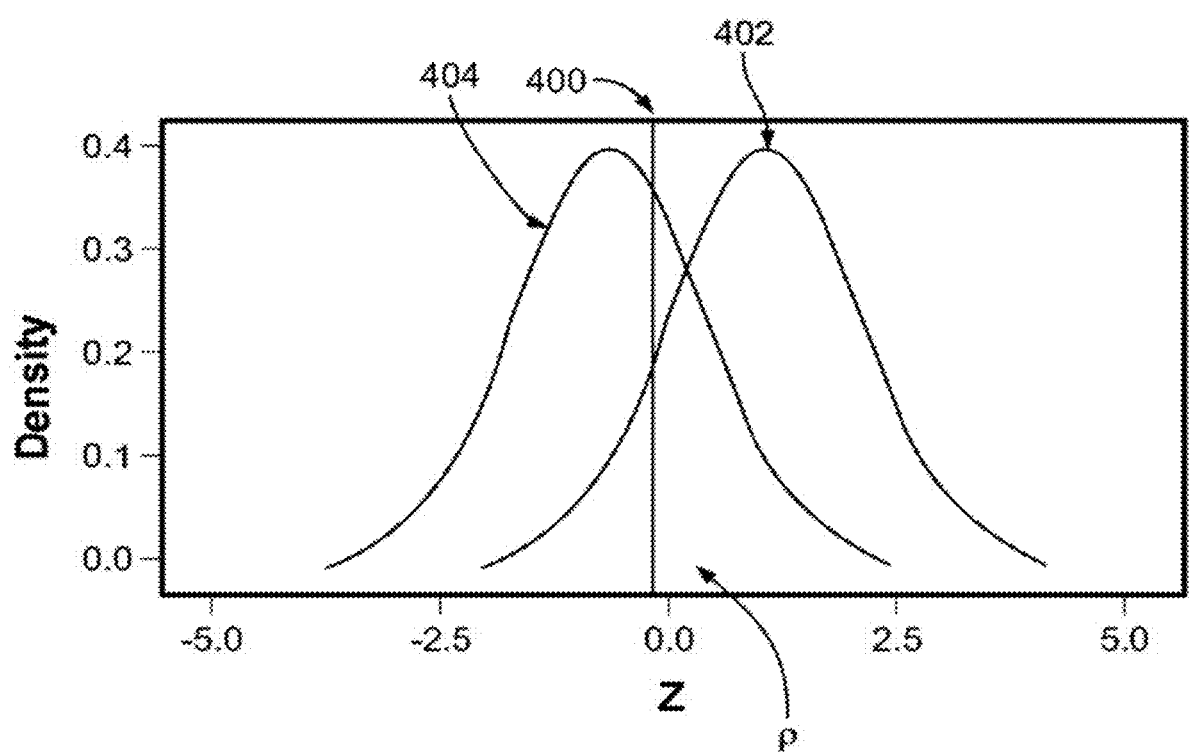
FIG. 4 is an exemplary plot of signal and noise based on an exemplary cognitive platform, according to the principles herein.

FIG. 4 shows an example plot of the signal (right curve 402) and noise (left curve 404) distributions of an individual or group psychophysical data, and the computed response criterion 400, based on data collected from an individual's responses with the tasks and/or interference rendered at a user interface of a computing device according to the principles herein (as described in greater detail hereinbelow). The intercept of the criterion line on the X axis (in Z units) can be used to provide an indication of the tendency of an individual to respond 'yes' (further right) or 'no' (further left). The response criterion 400 is left of the zero-bias decision point (p) and where the signal and noise distributions intersect. In the non-limiting example of FIG. 4, p is the location of the zero-bias decision on the decision axis in Z-units, and response criterion values to the left of p indicate an impulsive strategy and response criterion values to the right of p indicate a conservative strategy, with intercepts on the zero-bias point indicating a balanced strategy.

The exemplary systems, methods, and apparatus according to the principles herein can be configured to compute a response criterion based on the detection or classification task(s) described herein that are composed of signal and non-signal response targets (as stimuli), in which a user indicates a response that indicates a feature, or multiple features, are present in a series of sequential presentations of stimuli or simultaneous presentation of stimuli.

The data indicative of the results of the classification of an individual according to the principles herein (including a classifier output) can be transmitted (with the pertinent consent) as a signal to one or more of a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in one or more of an amount, concentration, or dose titration of a drug, biologic or other pharmaceutical agent being or to be administered to the individual and/or to determine an optimal type or combination of drug, biologic or other pharmaceutical agent to be administered to the individual.

The exemplary systems, methods, and apparatus herein provide computerized classifiers, treatment tools, and other tools that can be used by a medical, behavioral, healthcare, or other professional as an aid in an assessment and/or enhancement of an individual's attention, working memory, and goal management. In an embodiment, the exemplary systems, methods, and apparatus herein apply the modified DDM to the collected data to provide measures of conservatism or impulsivity. The example analysis performed using the exemplary systems, methods, and apparatus according to the principles herein can be used to provide measures of attention deficits and impulsivity (including ADHD). The exemplary systems, methods, and apparatus herein provide computerized classifiers, treatment tools, and other tools that can be used as aids in assessment and/or enhancement in other cognitive domains, such as but not limited to attention, memory, motor, reaction, executive function, decision-making, problem-solving, language processing, and comprehension. In some examples, the systems, methods, and apparatus can be used to compute measures for use for cognitive monitoring and/or disease monitoring. In some examples, the systems, methods, and apparatus can be used to compute measures for use for cognitive monitoring and/or disease monitoring during treatment of one or more cognitive conditions and/or diseases and/or executive function disorders.

An exemplary system, method, and apparatus according to the principles herein can be configured to execute an example classifier to generate a quantifier of the cognitive skills in an individual. The example classifier can be built using a machine learning tool, such as but not limited to linear/logistic regression, principal component analysis, generalized linear mixed models, random decision forests, support vector machines, and/or artificial neural networks. In a non-limiting example, classification techniques that may be used to train a classifier using the performance measures of a labeled population of individuals (e.g., individuals with known cognitive disorders, executive function disorder, disease or other cognitive condition). The trained classifier can be applied to the computed values of the performance metric, to generate a classifier output indicative of a measure of cognition, a mood, a level of cognitive bias, or an affective bias of the individual. The trained classifier can be applied to measures of the responses of the individual to the tasks and/or interference (either or both with computerized adjustable element) to classify the individual as to a population label (e.g., cognitive disorder, executive function disorder, disease or other cognitive condition). In an example, machine learning may be implemented using cluster analysis. Each measurement of the cognitive response capabilities of participating individuals can be used as the parameter that groups the individuals to subsets or clusters. For example, the subset or cluster labels may be a diagnosis of a cognitive disorder, cognitive disorder, executive function disorder, disease or other cognitive condition. Using a cluster analysis, a similarity metric of each subset and the separation between different subsets can be computed, and these similarity metrics may be applied to data indicative of an individual's responses to a task and/or interference (either or both with computerized adjustable element) to classify that individual to a subset. In another example, the classifier may be a supervised machine learning tool based on artificial neural networks. In such a case, the performance measures of individuals with known cognitive abilities may be used to train the neural network algorithm to model the complex relationships among the different performance measures. A trained classifier can be applied to the performance/response measures of a given individual to generate a classifier output indicative of the cognitive response capabilities of the individual. Other applicable techniques for generating a classifier include a regression or Monte Carlo technique for projecting cognitive abilities based on his/her cognitive performance. The classifier may be built using other data, including a physiological measure (e.g., EEG) and demographic measures.

In a non-limiting example, classification techniques that may be used to train a classifier using the performance measures of a labeled population of individuals, based on each individual's generated performance metrics, and other known outcome data on the individual, such as but not limited to outcome in the following categories: (i) an adverse event each individual experience in response to administration of a particular pharmaceutical agent, drug, or biologic; (ii) the amount, concentration, or dose titration of a pharmaceutical agent, drug, or biologic, administered to the individuals that resulted in a measurable or characterizable outcome for the individual (whether positive or negative); (iii) any change in the individual's cognitive capabilities based on one or more interactions with the single-tasking and multi-tasking tasks rendered using the computing devices herein; (iv) a recommended treatment regimen, or recommending or determining a degree of effectiveness of at least one of a behavioral therapy, counseling, or physical exercise that resulted in a measurable or characterizable outcome for the individual (whether positive or negative); (v) the performance score of the individual at one or more of a cognitive test or a behavioral test, and (vi) the status or degree of progression of a cognitive condition, a disease or an executive function disorder of the individual. The example classifier can be trained based on the computed values of performance metrics of the known individuals, to be able to classify other yet-to-be classified individuals as to potential outcome in any of the possible categories.

In an embodiment, a programmed processing unit is configured to execute processor-executable instructions to render a task with an interference at a user interface. As described in greater detail herein, one or more of the task and the interference can be time-varying and have a response deadline, such that the user interface imposes a limited time period for receiving at least one type of response from the individual interacting with the apparatus or system. The processing unit is configured to control the user interface to measure data indicative of two or more differing types of responses to the task or to the interference. The programmed processing unit is further configured to execute processor-executable instructions to cause the exemplary system or apparatus to receive data indicative of a first response of the individual to the task and a second response of the individual to the interference, analyze at least some portion of the data to compute at least one response profile representative of the performance of the individual, and determine a decision boundary metric (such as but not limited to the response criterion) from the response profile. The decision boundary metric (such as but not limited to the response criterion) can give a quantitative measure of a tendency of the individual to provide at least one type of response of the two or more differing types of responses (Response A vs. Response B) to the task or the interference. The programmed processing unit is further configured to execute processor-executable instructions to execute a classifier based on the computed values of the decision boundary metric (such as but not limited to the response criterion), to generate a classifier output indicative of the cognitive response capabilities of the individual.

In an example, the processing unit further uses the classifier output for one or more of changing one or more of the amount, concentration, or dose titration of the pharmaceutical agent, drug, biologic or other medication, identifying a likelihood of the individual experiencing an adverse event in response to administration of the pharmaceutical agent, drug, biologic or other medication, identifying a change in the individual's cognitive response capabilities, recommending a treatment regimen, or recommending or determining a degree of effectiveness of at least one of a behavioral therapy, counseling, or physical exercise.

In any example herein, the example classifier can be used as an intelligent proxy for quantifiable assessments of an individual's cognitive abilities. That is, once a classifier is trained, the classifier output can be used to provide the indication of the cognitive response capabilities of multiple individuals without use of other cognitive or behavioral assessment tests.

Monitoring cognitive deficits allows individuals, and/or medical, healthcare, behavioral, or other professional (with consent) to monitor the status or progression of a cognitive condition, a disease, or an executive function disorder. For example, individuals with Alzheimer's disease may shows mild symptoms initially, but others have more debilitating symptoms. If the status or progression of the cognitive symptoms can be regularly or periodically quantified, it can provide an indication of when a form of pharmaceutical agent or other drug may be administered or to indicate when quality of life might be compromised (such as the need for assisted living). Monitoring cognitive deficits also allows individuals, and/or medical, healthcare, behavioral, or other professional (with consent) to monitor the response of the individual to any treatment or intervention, particularly in cases where the intervention is known to be selectively effective for certain individuals. In an example, a cognitive assessment tool based on the classifiers herein can be an individual patient with attention deficit hyperactivity disorder (ADHD). In another example, the classifiers and other tools herein can be used as a monitor of the presence and/or severity of any cognitive side effects from therapies with known cognitive impact, such as but not limited to chemotherapy, or that involve uncharacterized or poorly characterized pharmacodynamics In any example herein, the cognitive performance measurements and/or classifier analysis of the data may be performed every 30 minutes, each few hours, daily, two or more times per week, weekly, bi-weekly, each month, or once per year.

In an example, classifier can be used as an intelligent proxy for quantifiable measures of the performance of the individual.

In a non-limiting example, the task and the interference can be rendered at the user interface such that the individual is required to provide the first response and the second response within a limited period of time. In an example, the individual is required to provide the first response and the second response substantially simultaneously.

In an example, the processing unit executes further instructions including applying at least one adaptive procedure to modify the task and/or the interference, such that analysis of the data indicative of the first response and/or the second response indicates a modification of the first response profile.

In an example, the processing unit controls the user interface to modify a temporal length of the response window associated with the response-deadline procedure.

In an example, the processing unit controls the user interface to modify a time-varying characteristic of an aspect of the task or the interference rendered to the user interface.

As described in connection with FIGS. 3A and 3B, the time-varying characteristics of the task and/or interference results in the time-varying availability of information about the target, such that that a linear drift-rate is no longer sufficient to capture development of belief over time (rather, requiring a nonlinear drift rate). A time-varying characteristic can be a feature such as, but not limited to, color, shape, type of creature, facial expression, or other feature that an individual requires in order to discriminate between a target and a non-target, resulting in differing time-characteristics of availability. The trial-by-trial adjustment of the response window length also can be a time-varying characteristic that alters the individual's perception of where the decision criteria needs to be in order to respond successfully to a task and/or an interference. Another time-varying characteristic that can be modified is the degree that an interference interferes with a parallel task which can introduce interruptions in belief accumulation and/or response selection and execution.

In an example, modifying the time-varying characteristics of an aspect of the task or the interference includes adjusting a temporal length of the rendering of the task or interference at the user interface between two or more sessions of interactions of the individual.

In an example, the time-varying characteristics can be one or more of a speed of an object, a rate of change of a facial expression, a direction of trajectory of an object, a change of orientation of an object, at least one color of an object, a type of an object, or a size of an object.

In an example, the time-varying characteristics can be the rate of change or modulation in content and/or appearance of the computerized adjustable elements, including one or more of a rate of change of the increase or decrease in the number of features included in the computerized adjustable element, a rate of change of the types of features included in the computerized adjustable element, and/or a rate of change of the speed or trajectory of movement of the features included in the computerized adjustable element.

In an example, the change in type of object is effected using morphing from a first type of object to a second type of object or rendering a blendshape as a proportionate combination of the first type of object and the second type of object.

In a non-limiting example, the processing unit can be configured to render a user interface or cause another component to execute least one element for indicating a reward to the individual for a degree of success in interacting with a task and/or interference, or another feature or other element of a system or apparatus. A reward computer element can be a computer-generated feature that is delivered to a user to promote user satisfaction with the exemplary system, method or apparatus, and as a result, increase positive user interaction and hence enjoyment of the experience of the individual.

In an example, the processing unit further computes as the classifier output parameters indicative of one or more of a bias sensitivity derived from the data indicative of the first response and the second response, a non-decision time sensitivity to parallel tasks, a belief accumulation sensitivity to parallel task demands, a reward rate sensitivity, or a response window estimation efficiency. Bias sensitivity can be a measure of how sensitive an individual is to certain of the tasks based on their bias (tendency to one type of response versus another (e.g., Response A vs. Response B)). Non-decision time sensitivity to parallel tasks can be a measure of how much the interference interferes with the individual's performance of the primary task. Belief accumulation sensitivity to parallel task demands can be a measure of the rate of the individual to develop/accumulate belief for responding to the interference during the individual's performance of the primary task. Reward rate sensitivity can be used to measure how an individual's response changes based on the temporal length of the response deadline window. When near the end of a response deadline window (e.g., as individual sees interference about to move off the field of view), the individual realizes that he is running out of time to make a decision. This measures how the individual's responses change accordingly. Response window estimation efficiency is explained as follows. When the individual is making a decision to act/respond or not act/no response, the decision needs to be based on when the individual thinks his time to respond is running out. For a varying window, the individual will not be able to measure that window perfectly, but with enough trials/session, based the response data, it may be possible to infer how good the individual is at making that estimation based on the time-varying aspect (e.g., trajectory) of the objects in the task or interference.

An exemplary system, method, and apparatus according to the principles herein can be configured to train a predictive model of a measure of the cognitive capabilities of individuals based on feedback data from the output of the computational model of human decision-making for individuals that are previously classified as to the measure of cognitive abilities of interest. As used herein, the term "predictive model" encompasses models trained and developed based on models providing continuous output values and/or models based on discrete labels. In any example herein, the predictive model encompasses a classifier model. For example, the classifier can be trained using a plurality of training datasets, where each training dataset is associated with a previously classified individual from a group of individuals. Each of the training dataset includes data indicative of the first response of the classified individual to the task and data indicative of the second response of the classified individual to the interference, based on the classified individual's interaction with an example apparatus, system, or computing device described herein. The example classifier also can take as input data indicative of the performance of the classified individual at a cognitive test, and/or a behavioral test, and/or data indicative of a diagnosis of a status or progression of a cognitive condition, a disease, or a disorder (including an executive function disorder) of the classified individual.

In any example herein, the at least one processing unit can be programmed to cause an actuating component of the apparatus (including the cognitive platform) to effect auditory, tactile, or vibrational computerized elements to effect the stimulus or other interaction with the individual. In a non-limiting example, the at least one processing unit can be programmed to cause a component of the cognitive platform to receive data indicative of at least one response from the individual based on the user interaction with the task and/or interference, including responses provided using an input device. In an example where at least one graphical user interface is rendered to present the computerized stimulus to the individual, the at least one processing unit can be programmed to cause the graphical user interface to receive the data indicative of at least one response from the individual.

In any example herein, the data indicative of the response of the individual to a task and/or an interference can be measured using at least one sensor device contained in and/or coupled to an exemplary system or apparatus herein, such as but not limited to a gyroscope, an accelerometer, a motion sensor, a position sensor, a pressure sensor, an optical sensor, an auditory sensor, a vibrational sensor, a video camera, a pressure-sensitive surface, a touch-sensitive surface, or other type of sensor. In other examples, the data indicative of the response of the individual to the task and/or an interference can be measured using other types of sensor devices, including a video camera, a microphone, joystick, keyboard, a mouse, a treadmill, elliptical, bicycle, steppers, or a gaming system (including a Wii®, a Playstation®, or an Xbox® or other gaming system). The data can be generated based on physical actions of the individual that are detected and/or measured using the at least one sensor device, as the individual executed a response to the stimuli presented with the task and/or interference.

The user may respond to tasks by interacting with the computer device. In an example, the user may execute a response using a keyboard for alpha-numeric or directional inputs; a mouse for GO/NO-GO clicking, screen location inputs, and movement inputs; a joystick for movement inputs, screen location inputs, and clicking inputs; a microphone for audio inputs; a camera for still or motion optical inputs; sensors such as accelerometer and gyroscopes for device movement inputs; among others. Non-limiting example inputs for a game system include but are not limited to a game controller for navigation and clicking inputs, a game controller with accelerometer and gyroscope inputs, and a camera for motion optical inputs. Example inputs for a mobile device or tablet include a touch screen for screen location information inputs, virtual keyboard alpha-numeric inputs, go/no go tapping inputs, and touch screen movement inputs; accelerometer and gyroscope motion inputs; a microphone for audio inputs; and a camera for still or motion optical inputs, among others. In other examples, data indicative of the individual's response can include physiological sensors/measures to incorporate inputs from the user's physical state, such as but not limited to electroencephalogram (EEG), magnetoencephalography (MEG), heart rate, heart rate variability, blood pressure, weight, eye movements, pupil dilation, electrodermal responses such as the galvanic skin response, blood glucose level, respiratory rate, and blood oxygenation.

In any example herein, the individual may be instructed to provide a response via a physical action of clicking a button and/or moving a cursor to a correct location on a screen, head movement, finger or hand movement, vocal response, eye movement, or other action of the individual.

As a non-limiting example, an individual's response to a task or interference rendered at the user interface that requires a user to navigate a course or environment or perform other visuomotor activity may require the individual to make movements (such as but not limited to steering) that are detected and/or measured using at least one type of the sensor device. The data from the detection or measurement provides the response to the data indicative of the response.

As a non-limiting example, an individual's response to a task or interference rendered at the user interface that requires a user to discriminate between a target and a non-target may require the individual to make movements (such as but not limited to tapping or other spatially or temporally discriminating indication) that are detected and/or or measured using at least one type of the sensor device. The data that is collected by a component of the system or apparatus based on the detection or other measurement of the individual's movements (such as but not limited to at least one sensor or other device or component described herein) provides the data indicative of the individual's responses.

The exemplary system, method, and apparatus can be configured to apply the predictive model, using computational techniques and machine learning tools, such as but not limited to linear/logistic regression, principal component analysis, generalized linear mixed models, random decision forests, support vector machines, or artificial neural networks, to the data indicative of the individual's response to the tasks and/or interference, and/or data from one or more physiological measures, to create composite variables or profiles that are more sensitive than each measurement alone for generating a classifier output indicative of the cognitive response capabilities of the individual. In an example, the classifier output can be configured for other indications such as but not limited to detecting an indication of a disease, disorder or cognitive condition, or assessing cognitive health.

The exemplary classifiers herein can be trained to be applied to data collected from interaction sessions of individuals with the cognitive platform to provide the output. In a non-limiting example, the predictive model can be used to generate a standards table, which can be applied to the data collected from the individual's response to task and/or interference to classify the individual's cognitive response capabilities.

Non-limiting examples of assessment of cognitive abilities include assessment scales or surveys such as the Mini Mental State Exam, CANTAB cognitive battery, Test of Variables of Attention (TOVA), Repeatable Battery for the Assessment of Neuropsychological Status, Clinical Global Impression scales relevant to specific conditions, Clinician's Interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities for Daily Living scales, ADHD self-report scale, Positive and Negative Affect Schedule, Depression Anxiety Stress Scales, Quick Inventory of Depressive Symptomatology, and PTSD Checklist.

In other examples, the assessment may test specific functions of a range of cognitions in cognitive or behavioral studies, including tests for perceptive abilities, reaction and other motor functions, visual acuity, long-term memory, working memory, short-term memory, logic, and decision-making, and other specific example measurements, including but are not limited to TOVA, MOT (motion-object tracking), SART, CDT (Change detection task), UFOV (useful Field of view), Filter task, WAIS digit symbol, Troop, Simon task, Attentional Blink, N-back task, PRP task, task-switching test, and Flanker task.

In non-limiting examples, the exemplary systems, methods, and apparatus according to the principles described herein can be applicable to many different types of neuropsychological conditions, such as but not limited to dementia, Parkinson's disease, cerebral amyloid angiopathy, familial amyloid neuropathy, Huntington's disease, or other neurodegenerative condition, autism spectrum disorder (ASD), presence of the 16p11.2 duplication, and/or an executive function disorder, such as but not limited to attention deficit hyperactivity disorder (ADHD), sensory-processing disorder (SPD), mild cognitive impairment (MCI), schizophrenia, major depressive disorder (MDD), or anxiety (including social anxiety), bipolar disorder, post-traumatic stress disorder, schizophrenia, dementia, Alzheimer's disease, and/or multiple sclerosis.

Embodiments of the instant disclosure are directed to computer-implemented devices formed as cognitive platforms configured to implement software and/or other processor-executable instructions for the purpose of measuring data indicative of a user's performance at one or more tasks, to provide a user performance metric. The example performance metric can be used to derive an assessment of a user's cognitive abilities and/or to measure a user's response to a cognitive treatment, and/or to provide data or other quantitative indicia of a user's condition (including physiological condition and/or cognitive condition). Non-limiting example cognitive platforms according to the principles herein can be configured to classify an individual as to a neuropsychological condition, autism spectrum disorder (ASD), presence of the 16p11.2 duplication, and/or an executive function disorder, and/or potential efficacy of use of the cognitive platform when the individual is being administered (or about to be administered) a drug, biologic or other pharmaceutical agent, based on the data collected from the individual's interaction with the cognitive platform and/or metrics computed based on the analysis (and associated computations) of that data. Yet other non-limiting example cognitive platforms according to the principles herein can be configured to classify an individual as to likelihood of onset and/or stage of progression of a neuropsychological condition, including as to a neurodegenerative condition, based on the data collected from the individual's interaction with the cognitive platform and/or metrics computed based on the analysis (and associated computations) of that data. The neurodegenerative condition can be, but is not limited to, Alzheimer's disease, dementia, Parkinson's disease, cerebral amyloid angiopathy, familial amyloid neuropathy, and/or Huntington's disease.

Any classification of an individual as to likelihood of onset and/or stage of progression of a neurodegenerative condition according to the principles herein can be transmitted as a signal to a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in dosage of a drug, biologic or other pharmaceutical agent to the individual or to determine an optimal type or combination of drug, biologic or other pharmaceutical agent to the individual.

In any example herein, the cognitive platform can be configured as any combination of a medical device platform, a monitoring device platform, a screening device platform, or other device platform.

The instant disclosure is also directed to exemplary systems that include cognitive platforms that are configured for coupling with one or more physiological or monitoring component and/or cognitive testing component. In some examples, the systems include cognitive platforms that are integrated with the one or more other physiological or monitoring component and/or cognitive testing component. In other examples, the systems include cognitive platforms that are separately housed from and configured for communicating with the one or more physiological or monitoring component and/or cognitive testing component, to receive data indicative of measurements made using such one or more components.

In an embodiment, the processing unit can be programmed to control the user interface to modify a temporal length of the response window associated with a response-deadline procedure.

In an embodiment, the processing unit can be configured to control the user interface to modify a time-varying characteristic of an aspect of the task or the interference rendered to the user interface. For example, modifying the time-varying characteristics of an aspect of the task or the interference can include adjusting a temporal length of the rendering of the task or interference at the user interface between two or more sessions of interactions of the individual. As another example, the time-varying characteristics is one or more of a speed of an object, a rate of change of a facial expression, a direction of trajectory of an object, a change of orientation of an object, at least one color of an object, a type of an object, or a size of an object. In any example herein, the foregoing time-varying characteristic can be applied to an object that includes the computerized adjustable element to modify a cognitive or emotional load of the individual's interaction with the apparatus (e.g., computing device or cognitive platform).

In an exemplary system, method, and apparatus, the change in type of object is effected using morphing from a first type of object to a second type of object or rendering a blendshape as a proportionate combination of the first type of object and the second type of object.

In an exemplary system, method, and apparatus, the processing unit can be further programmed to compute as the classifier output parameters indicative of one or more of a bias sensitivity derived from the data indicative of the first response and the second response, a non-decision time sensitivity to parallel tasks, a belief accumulation sensitivity to parallel task demands, a reward rate sensitivity, or a response window estimation efficiency.

In an exemplary system, method, and apparatus, the processing unit can be further programmed to control the user interface to render the task as a continuous visuomotor tracking task.

In an exemplary system, method, and apparatus, the processing unit controls the user interface to render the interference as a target discrimination task.

As used herein, a target discrimination task may also be referred to as a perceptual reaction task, in which the individual is instructed to perform a two-feature reaction task including target stimuli and non-target stimuli through a specified form of response. As a non-limiting example, that specified type of response can be for the individual to make a specified physical action in response to a target stimulus (e.g., move or change the orientation of a device, tap on a sensor-coupled surface such as a screen, move relative to an optical sensor, make a sound, or other physical action that activates a sensor device) and refrain from making such specified physical action in response to a non-target stimulus.

In a non-limiting example, the individual is required to perform a visuomotor task (as a primary task) with a target discrimination task as an interference (secondary task) (either or both including a computerized adjustable element). To effect the visuomotor task, a programmed processing unit renders visual stimuli that require fine motor movement as reaction of the individual to the stimuli. In some examples, the visuomotor task is a continuous visuomotor task. The processing unit is programmed to alter the visual stimuli and recording data indicative of the motor movements of the individual over time (e.g., at regular intervals including 1, 5, 10, or 30 times per second). Example stimuli rendered using the programmed processing unit for a visuomotor task requiring fine motor movement may be a visual presentation of a path that an avatar is required to remain within. The programmed processing unit may render the path with certain types of obstacles that the individual is either required to avoid or to navigate towards. In an example, the fine motor movements effect by the individual, such as but not limited to tilting or rotating a device, are measured using an accelerometer and/or a gyroscope (e.g., to steer or otherwise guide the avatar on the path while avoiding or crossing the obstacles as specified). The target discrimination task (serving as the interference), can be based on targets and non-targets that differ in shape and/or color.

In any example, the apparatus may be configured to instruct the individual to provide the response to the computerized adjustable element as an action that is read by one or more sensors (such as a movement that is sensed using a gyroscope or accelerometer or a motion or position sensor, or a touch that is sensed using a touch-sensitive, pressure sensitive or capacitance-sensitive sensor.

In some examples, the task and/or interference can be a visuomotor task, a target discrimination task, and/or a memory task.

Within the context of a computer-implemented adaptive response-deadline procedure, the response-deadline can be adjusted between trials or blocks of trials to manipulate the individual's performance characteristics towards certain goals. A common goal is driving the individual's average response accuracy towards a certain value by controlling the response deadline.

In a non-limiting example, the hit rate may be defined as the number of correct responses to a target stimuli divided by the total number of target stimuli presented, or the false alarm rate (e.g., the number of responses to a distractor stimuli divided by the number of distractor stimuli presented), the miss rate (e.g., the number of nonresponses to a target stimuli divided by the number of incorrect responses, including the nonresponses to a target stimuli added to the number of responses to a distractor stimuli), the correct response rate (the proportion of correct responses not containing signal). In an example, the correct response rate may be calculated as the number of non-responses to the distractor stimuli divided by the number of non-responses to the distractor stimuli plus the number of responses to the target stimuli.

An exemplary system, method, and apparatus according to the principles herein can be configured to apply adaptive performance procedures to modify measures of performance to a specific stimulus intensity. The procedure can be adapted based on a percent correct (PC) signal detection metric of sensitivity to a target. In an example system, the value of percent correct (i.e., percent of correct responses of the individual to a task or computerized adjustable element) may be used in the adaptive algorithms as the basis for adapting the stimulus level of tasks and/or interferences rendered at the user interface for user interaction from one trial to another. An adaptive procedure based on a computational model of human decision-making (such as but not limited to the modified DDM), classifiers built from outputs of such models, and the analysis described herein based on the output of the computational model, can be more quantitatively informative on individual differences or on changes in sensitivity to a specific stimulus level. The performance metric provides a flexible tool for determining a performance of the individual. Accordingly, an adaptation procedure based on performance metric measurements at the individual or group level become a desirable source of information about the changes in performance at the individual or group level over time with repeated interactions with the tasks and computerized adjustable elements described herein, and measurements of the individual's responses with the interactions.

Executive function training, such as that delivered by the exemplary systems, methods, and apparatus described herein can be configured to apply an adaptive algorithm to modify the stimulus levels (including cognitive or emotional load based on the computerized adjustable element(s) implemented) between trials, to move a user's performance metric to the desired level (value), depending on the needs or preference of the individual or based on the clinical population receiving the treatment.

The exemplary systems, methods, and apparatus described herein can be configured to apply an adaptive algorithm that is adapted based on the generated performance metric as described herein to modify the difficulty levels of the tasks and/or interference (either or both including a computerized adjustable element) rendered at the user interface for user interaction from one trial to another.

In an example, the task and/or interference (either or both including a computerized adjustable element) can be modified/adjusted/adapted based on an iterative estimation of metrics by tracking current estimates and selecting the features, trajectory, and response window of the targeting task, and level/type of parallel task interference for the next trial in order to maximize information the trial can provide.

In some examples, the task and/or interference (either or both including a computerized adjustable element) are adaptive tasks. The task and/or interference can be adapted or modified in difficulty level based on the performance metric, as described hereinabove. Such difficulty adaptation may be used to determine the ability of the participant.

In an example, the difficulty of the task (potentially including a computerized adjustable element) adapts with every stimuli that is presented, which could occur more often than once at regular time intervals (e.g., every 5 seconds, every 10 seconds, every 20 seconds or other regular schedule).

In another example, the difficulty of a continuous task (potentially including a computerized adjustable element) can be adapted on a set schedule, such as but not limited to every 30 seconds, 10 seconds, 1 second, 2 times per second, or 30 times per second.

In an example, the length of time of a trial depends on the number of iterations of rendering (of the tasks/interference) and receiving (of the individual's responses) and can vary in time. In an example, a trial can be on the order of about 500 milliseconds, about 1 second (s), about 10 s, about 20 s, about 25 s, about 30 s, about 45 s, about 60 s, about 2 minutes, about 3 minutes, about 4 minutes, about 5 minutes, or greater. Each trial may have a pre-set length or may be dynamically set by the processing unit (e.g., dependent on an individual's performance level or a requirement of the adapting from one level to another).

In an example, the task and/or interference (either or both including a computerized adjustable element) can be modified based on targeting changes in one or more specific metrics by selecting features, trajectory, and response window of the targeting task, and level/type of parallel task interference to progressively require improvements in those metrics in order for the apparatus to indicate to an individual that they have successfully performed the task. This could include specific reinforcement, including explicit messaging, to guide the individual to modify performance according to the desired goals.

In an example, the task and/or interference (either or both including a computerized adjustable element) can be modified based on a comparison of an individual's performance with normative data or a computer model or taking user input (the individual performing the task/interference or another individual such as a clinician) to select a set of metrics to target for changing in a specific order, and iteratively modifying this procedure based on the subject's response to treatment. This could include feedback to the individual performing the task/interference or another individual to serve as notification of changes to the procedure, potentially enabling them to approve or modify these changes before they take effect.

In various examples, the difficulty level may be kept constant or may be varied over at least a portion of a session in an adaptive implementation, where the adaptive task (primary task or secondary task) increases or decreases in difficulty based on the performance metric.

An exemplary system, method, and apparatus according to the principles herein can be configured to enhance the cognitive skills in an individual. In an embodiment, a programmed processing unit is configured to execute processor-executable instructions to render a task with an interference at a user interface. As described in greater detail herein, one or more of the task and the interference (either or both including a computerized adjustable element) can be time-varying and have a response deadline, such that the user interface imposes a limited time period for receiving at least one type of response from the individual interacting with the apparatus or system.

One or more processors may be configured to present via the user interface a first instance of a task with an interference at the user interface, requiring a first response from the individual to the first instance of the task in the presence of the interference and a response from the individual to at least one computerized adjustable element. Either or both of the first instance of the task and the interference includes at least one a computerized adjustable element. The user interface can be configured to measure data indicative of the response of the individual to the at least one computerized adjustable element, the data including at least one measure of cognitive capabilities of the individual. The one or more processors may be configured to measure substantially simultaneously the first response from the individual to the first instance of the task and the response from the individual to the at least one computerized adjustable element, and to receive data indicative of the first response and the response of the individual to the at least one computerized adjustable element. The one or more processors may also be configured to analyze the data indicative of the first response and the response of the individual to the at least one computerized adjustable element to generate at least one performance metric comprising at least one quantified indicator of cognitive abilities of the individual.

In an example, the indication of the modification of the cognitive response capabilities can be based on observation of a change in a measure of a degree of impulsiveness or conservativeness of the individual's cognitive response capabilities.

In an example, the indication of the modification of the cognitive abilities can include a change in a measure of one or more of affective bias, mood, level of cognitive bias, sustained attention, selective attention, attention deficit, impulsivity, inhibition, perceptive abilities, reaction and other motor functions, visual acuity, long-term memory, working memory, short-term memory, logic, and decision-making.

In an example, adapting the task and/or interference based on the first performance metric includes one or more of modifying the temporal length of the response window, modifying a type of reward or rate of presentation of rewards to the individual, and modifying a time-varying characteristic of the task and/or interference (including the computerized adjustable element).

In an example, modifying the time-varying characteristics of an aspect of the task or the interference (including the computerized adjustable element) can include adjusting a temporal length of the rendering of the task or interference at the user interface between two or more sessions of interactions of the individual.

In an example, the time-varying characteristics can include one or more of a speed of an object, a rate of change of a facial expression, a direction of trajectory of an object, a change of orientation of an object, at least one color of an object, a type of an object, or a size of an object, or modifying a sequence or balance of rendering of targets versus non-targets at the user interface.

In an example, the change in type of object is effected using morphing from a first type of object to a second type of object or rendering a blendshape as a proportionate combination of the first type of object and the second type of object.

Designing the computer-implemented adaptive procedure using a goal of explicitly measuring the shape and/or area of the decision boundary, the response deadlines can be adjusted to points where measurements produce maximal information of use for defining this boundary. These optimal deadlines may be determined using an information theoretic approach to minimize the expected information entropy.

Exemplary systems, methods and apparatus according to the principles herein can be implemented using a programmed computing device including at least one processing unit, to determine a potential biomarker for clinical populations.

Exemplary systems, methods and apparatus according to the principles herein can be implemented using a programmed computing device including at least one processing unit to measure change in response profile in individuals or groups after use of an intervention.

Exemplary systems, methods and apparatus according to the principles herein can be implemented using a programmed computing device including at least one processing unit to apply the example metrics herein, to add another measurable characteristic of individual or group data that can be implemented for greater measurement of psycho-physical-threshold accuracy and assessment of response profile to computer-implemented adaptive psychophysical procedures.

Exemplary systems, methods and apparatus according to the principles herein can be implemented using a programmed computing device including at least one processing unit to apply the example metrics herein to add a new dimension to available data that can be used to increase the amount of information harvested from psychophysical testing.

An exemplary system, method, and apparatus according to the principles herein can be configured to enhance the cognitive skills in an individual. In an embodiment, a programmed processing unit is configured to execute processor-executable instructions to render a task with an interference at a user interface. As described in greater detail herein, one or more of the task and the interference can be time-varying and have a response deadline, such that the user interface imposes a limited time period for receiving at least one type of response from the individual interacting with the apparatus or system. An example processing unit is configured to control the user interface to render a first instance of a task with an interference at the user interface, requiring a first response from the individual to the first instance of the task in the presence of the interference and a response from the individual to at least one computerized adjustable element. Either or both of the first instance of the task and the interference includes at least one a computerized adjustable element. The user interface can be configured to measure data indicative of the response of the individual to the at least one computerized adjustable element, the data including at least one measure of cognitive capabilities of the individual. The example processing unit is configured to measure substantially simultaneously the first response from the individual to the first instance of the task and the response from the individual to the at least one computerized adjustable element, and to receive data indicative of the first response and the response of the individual to the at least one computerized adjustable element. The example processing unit is also configured to analyze the data indicative of the first response and the response of the individual to the at least one computerized adjustable element to compute a first performance metric comprising at least one quantified indicator of cognitive abilities of the individual. The programmed processing unit is further configured to adjust a difficulty of one or more of the task and the interference based on the computed at least one first performance metric such that the apparatus renders the task with the interference at a second difficulty level, and compute a second performance metric representative of cognitive abilities of the individual based at least in part on the data indicative of the first response and the response of the individual to the at least one computerized adjustable element.

Another exemplary system, method, and apparatus according to the principles herein can be configured to enhance the cognitive skills in an individual. In an embodiment, a programmed processing unit is configured to execute processor-executable instructions to render a task with an interference at a user interface. As described in greater detail herein, one or more of the task and the interference can be time-varying and have a response deadline, such that the user interface imposes a limited time period for receiving at least one type of response from the individual interacting with the apparatus or system. An example processing unit is configured to control the user interface to render a first instance of a task with an interference at the user interface, requiring a first response from the individual to the first instance of the task in the presence of the interference and a response from the individual to at least one computerized adjustable element. Either or both of the first instance of the task and the interference includes at least one a computerized adjustable element. The user interface can be configured to measure data indicative of the response of the individual to the at least one computerized adjustable element, the data including at least one measure of cognitive capabilities of the individual. The example processing unit is configured to measure substantially simultaneously the first response from the individual to the first instance of the task and the response from the individual to the at least one computerized adjustable element, and to receive data indicative of the first response and the response of the individual to the at least one computerized adjustable element. The example processing unit is also configured to analyze the data indicative of the first response and the response of the individual to the at least one computerized adjustable element to compute at least one performance metric comprising at least one quantified indicator of cognitive abilities of the individual. Based at least in part on the at least one performance metric, the example processing unit is also configured to generate an output to the user interface indicative of at least one of: (i) a likelihood of the individual experiencing an adverse event in response to administration of the pharmaceutical agent, drug, or biologic, (ii) a recommended change in one or more of the amount, concentration, or dose titration of the pharmaceutical agent, drug, or biologic, (iii) a change in the individual's cognitive response capabilities, (iv) a recommended treatment regimen, or (v) a recommended or determined degree of effectiveness of at least one of a behavioral therapy, counseling, or physical exercise.

In a non-limiting example, the one or more processors may be further configured to measure substantially simultaneously the first response from the individual to the first instance of the task, a secondary response of the individual to the interference, and the response to the at least one computerized adjustable element.

In a non-limiting example, the one or more processors may be further configured to output to the individual or transmit to a computing device the computed at least one performance metric.

In a non-limiting example, the one or more processors may be further configured to present via the user interface a second instance of the task, requiring a second response from the individual to the second instance of the task, and analyze a difference between the data indicative of the first response and the second response to compute an interference cost as a measure of at least one additional indication of cognitive abilities of the individual.

In a non-limiting example, based on the results of the analysis of the performance metrics, a medical, healthcare, or other professional (with consent of the individual) can gain a better understanding of potential adverse events which may occur (or potentially are occurring) if the individual is administered a particular type of, amount, concentration, or dose titration of a pharmaceutical agent, drug, biologic, or other medication, including potentially affecting cognition.

In a non-limiting example, a searchable database is provided herein that includes data indicative of the results of the analysis of the performance metrics for particular individuals, along with known levels of efficacy of at least one types of pharmaceutical agent, drug, biologic, or other medication experiences by the individuals, and/or quantifiable information on one or more adverse events experienced by the individual with administration of the at least one types of pharmaceutical agent, drug, biologic, or other medication. The searchable database can be configured to provide metrics for use to determine whether a given individual is a candidate for benefiting from a particular type of pharmaceutical agent, drug, biologic, or other medication based on the performance metrics, response measures, response profiles, and/or decision boundary metric (such as but not limited to response criteria) obtained for the individual in interacting with the task and/or interference rendered at the computing device.

As a non-limiting example, performance metrics can assist with identifying whether the individual is a candidate for a particular type of drug (such as but not limited to a stimulant, e.g., methylphenidate or amphetamine) or whether it might be beneficial for the individual to have the drug administered in conjunction with a regiment of specified repeated interactions with the tasks and/or interference rendered to the computing device. Other non-limiting examples of a biologic, drug or other pharmaceutical agent applicable to any example described herein include methylphenidate (MPH), scopolamine, donepezil hydrochloride, rivastigmine tartrate, memantine HCl, solanezumab, aducanumab, and crenezumab.

In a non-limiting example, based on the results of the analysis of the performance metric, a medical, healthcare, or other professional (with consent of the individual) can gain a better understanding of potential adverse events which may occur (or potentially are occurring) if the individual is administered a different amount, concentration, or dose titration of a pharmaceutical agent, drug, biologic, or other medication, including potentially affecting cognition.

In a non-limiting example, a searchable database is provided herein that includes data indicative of the results of the analysis of the performance metrics for particular individuals, along with known levels of efficacy of at least one types of pharmaceutical agent, drug, biologic, or other medication experiences by the individuals, and/or quantifiable information on one or more adverse events experienced by the individual with administration of the at least one types of pharmaceutical agent, drug, biologic, or other medication. The searchable database can be configured to provide metrics for use to determine whether a given individual is a candidate for benefiting from a particular type of pharmaceutical agent, drug, biologic, or other medication based on the response measures, response profiles, and/or decision boundary metric (such as but not limited to response criteria) obtained for the individual in interacting with the task and/or interference rendered at the computing device. As a non-limiting example, based on data indicative of a user interaction with the tasks and/or interference (including the computerized adjustable element) rendered at a user interface of a computing device, the performance metrics could provide information on the individual, based on the cognitive capabilities of the individual. This data can assist with identifying whether the individual is a candidate for a particular type of drug (such as but not limited to a stimulant, e.g., methylphenidate or amphetamine) or whether it might be beneficial for the individual to have the drug administered in conjunction with a regiment of specified repeated interactions with the tasks and/or interference rendered to the computing device. Other non-limiting examples of a biologic, drug or other pharmaceutical agent applicable to any example described herein include methylphenidate (MPH), scopolamine, donepezil hydrochloride, rivastigmine tartrate, memantine HCl, solanezumab, aducanumab, and crenezumab.

In an example, the change in the individual's cognitive response capabilities comprises an indication of a change in degree of impulsiveness or conservativeness of the individual's cognitive response strategy.

As a non-limiting example, given that impulsive behavior is attendant with ADHD, an example cognitive platform that is configured for delivering treatment (including of executive function) may promote less impulsive behavior in a regimen. This may target dopamine systems in the brain, increasing normal regulation, which may result in a transfer of benefits of the reduction of impulsive behavior to the everyday life of an individual.

Stimulants such as methylphenidate and amphetamine are also administered to individuals with ADHD, to increase levels of norepinephrine and dopamine in the brain. Their cognitive effects may be attributed to their actions at the prefrontal cortex, however, there may not be remediation of cognitive control deficits or other cognitive abilities. An embodiment of a cognitive platform herein can be configured for delivering treatment (including of executive function) to remediate an individual's cognitive control deficit.

The use of the exemplary systems, methods, and apparatus according to the principles described herein can be applicable to many different types of neuropsychological conditions, such as but not limited to dementia, Parkinson's disease, cerebral amyloid angiopathy, familial amyloid neuropathy, Huntington's disease, or other neurodegenerative condition, autism spectrum disorder (ASD), presence of the 16p11.2 duplication, and/or an executive function disorder, such as but not limited to attention deficit hyperactivity disorder (ADHD), sensory-processing disorder (SPD), mild cognitive impairment (MCI), Alzheimer's disease, multiple sclerosis, schizophrenia, depression, bipolar disorder, post-traumatic stress disorder, major depressive disorder (MDD), and/or anxiety (including social anxiety).

In any embodiment, data and other information from an individual is collected, transmitted, and analyzed with his or her consent.

As a non-limiting example, the cognitive platform described in connection with any exemplary system, method and apparatus herein, including a cognitive platform based on interference processing, can be based on or include the Project: EVO™ platform by Akili Interactive Labs, Inc., Boston, Mass.

Non-Limiting Exemplary Tasks and Interference

Following is a summary of reported results showing the extensive physiological, behavioral, and cognitive measurements data and analysis of the regions of the brain, neural activity, and/or neural pathways mechanisms involved (e.g., activated or suppressed) as an individual interact with stimuli under differing cognitive or emotional load. The articles also describe the differences that can be sensed and quantifiably measured based on the individual's performance at cognitive tasks versus stimuli with computerized adjustable elements.

Based on physiological and other measurements, regions of the brain implicated in emotional processing, cognitive tasks, and tasks, are reported. For example, in the review article by Pourtois et al., 2013, "Brain mechanisms for emotional influences on perception and attention: What is magic and what is not," Biological Psychology, 92, 492-512, it is reported that the amygdala monitors the emotional value of stimuli, projects to several other areas of the brain, and sends feedback to sensory pathways (including striate and extrastriate visual cortex). It is also reported that, due to an individual's limited processing capacity, the individual cannot fully analyze simultaneous stimuli in parallel, and these stimuli compete for processing resources in order to gain access to higher cognitive stages and awareness of the individual. With an individual having to direct attention to the location or features of a given stimulus, neural activity in brain regions representing this stimulus increases, at the expense of other concurrent stimuli. Pourtois et al. indicates that this phenomenon has been extensively demonstrated by neuronal recordings as well as imaging methods (EEG, PET, fMRI), and attributed to a gain control. Pourtois et al. concludes that emotion signals may enhance processing efficiency and competitive strength of emotionally significant events through gain control mechanisms similar to those of other attentional systems, but mediated by distinct neural mechanisms in the amygdala and interconnected prefrontal areas, and indicate that alterations in these brain mechanisms might be associated with psychopathological conditions, such as anxiety or phobia. It is also reported that anxious or depressed patients can show maladaptive attentional biases towards negative information. Pourtois et al. also reports that imaging results from EEG and fMRI support a conclusion that the processing of emotional (such as fearful or threat-related) stimuli yields a gain control effect in the visual cortex and the emotional gain control effect can account for the more efficient processing of threat-related stimuli, in addition to or in parallel with any concurrent modulation by other task-dependent or exogenous stimulus-driven mechanisms of attention (see also Brosch et al., 2011, "Additive effects of emotional, endogenous, and exogenous attention: behavioral and electrophysiological evidence," Neuropsychologia 49, 1779-1787).

As described hereinabove, emotional processing and cognitive processing each require interactions within and among specific brain networks. Major depressive disorder and other similar or related disorders can be associated with changes to cognitive capabilities in multiple cognitive domains including attention (concentration), memory (learning), decision making (judgment), comprehension, judgment, reasoning, understanding, learning, and remembering. The cognitive changes associated with depression can contribute to some of the disabilities experienced by individuals with this disorder.

Individuals with major depressive disorder may respond to some treatment, such as antidepressants, to diminish the non-cognitive symptoms of depression. However, such treatments do not provide objective assessments of the individual's cognitive deficits or decline, and existing clinical examinations provide few useful tools to assess changes in cognition. Individuals who have resolution of mood symptoms but not cognitive symptoms could be at risk for relapse, particularly when they are trying to function in complex work and social environments where cognitive defects could impact performance.

Shilyansky et al., 2016, "Effect of antidepressant treatment on cognitive impairments associated with depression: a randomized longitudinal study," The Lancet Psychiatry, 3, 425-435, reports on the influence of antidepressant treatment on the cognitive deficits associated with major depression. Shilyansky et al. described a study of over 1,000 adults between the ages 18 and 65 suffering from major depressive disorder, none of whom was taking antidepressant medication at the start of the study. Various aspects of cognition were measured in the individuals before and after treatment with one of three antidepressants, using a variety of neuropsychological tests. The test results were compared to the results derived from administering these neuropsychological tests to a group of age- and education-matched individuals not diagnosed as suffering from major depressive disorder.

Shilyansky et al. discloses that, prior to treatment, the study individuals demonstrated diminished abilities in seven cognitive domains: attention, response inhibition, verbal memory, executive function, cognitive flexibility, decision speed, and information processing. Following treatment and remission of clinical symptoms, the neuropsychological test results showed that five of the seven cognitive domains remained compromised after the non-cognitive symptoms of depression improved in the study individuals. Executive function and cognitive flexibility showed some change with antidepressant treatment. The results indicated that individuals with a history of depression may still be handicapped by the cognitive deficits of this illness even after other depressive symptoms improve (independent of the type of antidepressants used).

Shilyansky et al. demonstrates major depressive disorder is associated with cognitive impairment, which may persist even after other symptoms of the disorder are managed. Unless this cognitive impairment is addressed, individuals with depression may not be able to function in complex environments, even if mood symptoms are under control. The systems, methods, and apparatus described herein are configured to provide an indication of the individual's performance, and/or for cognitive assessment, (e.g., to determine the degree of cognitive impairment), and/or to deliver a cognitive treatment (i.e., through enhancing cognitive capabilities using adaptive application of tasks and/or interference through interference processing).

As described hereinabove, the individual's response to a stimulus can vary depending on the state of the individual, including based on the individual's cognitive condition, disease, or executive function disorder. Measurements of the individual's performance can provide insight into the individual's status relative to a cognitive condition, disease, or executive function disorder, including the likelihood of onset and/or stage of progression of the cognitive condition, disease, or executive function disorder.

The foregoing non-limiting examples of physiological measurement data, behavioral data, and other cognitive data show that the responses of an individual to tasks can differ based on the type of stimuli. Furthermore, the foregoing examples indicate that the degree to which an individual is affected by a computerized adjustable element, and the degree to which the performance of the individual at a task is affected in the presence of the computerized adjustable element, is dependent on the degree to which the individual exhibits a form of emotional or affective bias. As described herein, the differences in the individual's performance may be quantifiably sensed and measured based on the performance of the individual at cognitive tasks versus stimuli with computerized adjustable elements (e.g., emotional or affective elements). The reported physiological measurement data, behavioral data, and other cognitive data, also show that the cognitive or emotional load evoked by a stimulus can vary depending on the state of an individual, including based on the individual's cognitive condition, disease state, or presence or absence of executive function disorder. As described herein, measurements of the differences in the individual's performance at cognitive tasks versus stimuli with computerized adjustable elements can provide quantifiable insight into the likelihood of onset and/or stage of progression of a cognitive condition, disease, and/or executive function disorder, in the individual, such as but not limited to, anxiety, depression, bipolar disorder, major depressive disorder, post-traumatic stress disorder, schizophrenia, autism spectrum disorder, attention deficit hyperactivity disorder, dementia, Parkinson's disease, Huntington's disease, or other neurodegenerative condition, cerebral amyloid angiopathy, familial amyloid neuropathy, Alzheimer's disease, multiple sclerosis, presence of the 16p11.2 duplication, attention deficit hyperactivity disorder (ADHD), sensory-processing disorder (SPD), and/or mild cognitive impairment (MCI).

The effects of interference processing on the cognitive control abilities of individuals has been reported. See, e.g., A. Anguera, Nature 501, p. 97 (Sep. 5, 2013) (the "Nature article"). See, also, U.S. Publication No. 20140370479A1 (U.S. application Ser. No. 13/879,589), filed on Nov. 10, 2011, which is incorporated herein by reference. Some of those cognitive abilities include cognitive control abilities in the areas of attention (selectivity, sustainability, etc.), working memory (capacity and the quality of information maintenance in working memory) and goal management (ability to effectively parallel process two attention-demanding tasks or to switch tasks). As an example, children diagnosed with ADHD (attention deficit hyperactivity disorder) exhibit difficulties in sustaining attention. Attention selectivity was found to depend on neural processes involved in ignoring goal-irrelevant information and on processes that facilitate the focus on goal-relevant information. The publications report neural data showing that when two objects are simultaneously placed in view, focusing attention on one can pull visual processing resources away from the other. Studies were also reported showing that memory depended more on effectively ignoring distractions, and the ability to maintain information in mind is vulnerable to interference by both distraction and interruption. Interference by distraction can be, e.g., an interference that is a non-target, that distracts the individual's attention from the primary task, but that the instructions indicate the individual is not to respond to. Interference by interruption/interruptor can be, e.g., an interference that is a target or two or more targets, that also distracts the individual's attention from the primary task, but that the instructions indicate the individual is to respond to (e.g., for a single target) or choose between/among (e.g., a forced-choose situation where the individual decides between differing degrees of a feature).

There were also fMRI results reported showing that diminished memory recall in the presence of a distraction can be associated with a disruption of a neural network involving the prefrontal cortex, the visual cortex, and the hippocampus (involved in memory consolidation). Prefrontal cortex networks (which play a role in selective attention) can be vulnerable to disruption by distraction. The publications also report that goal management, which requires cognitive control in the areas of working memory or selective attention, can be impacted by a secondary goal that also demands cognitive control. The publications also reported data indicating beneficial effects of interference processing as an intervention with effects on an individual's cognitive abilities, including to diminish the detrimental effects of distractions and interruptions. The publications described cost measures that can be computed (including an interference cost) to quantify the individual's performance, including to assess single-tasking or multitasking performance.

An exemplary cost measure disclosed in the publications is the percentage change in an individual's performance at a single-tasking task as compared to a multi-tasking task, such that greater cost (that is, a more negative percentage cost) indicates increased interference when an individual is engaged in single-tasking vs multi-tasking. The publications describe an interference cost determined as the difference between an individual's performance on a task in isolation versus a task with one or more interference applied, where the interference cost provide an assessment of the individual's susceptibility to interference.

The tangible benefits of computer-implemented interference processing are also reported. For example, the Nature paper states that multi-tasking performance assessed using computer-implemented interference processing was able to quantify a linear age-related decline in performance in adults from 20 to 79 years of age. The Nature paper also reports that older adults (60 to 85 years old) who interacted with an adaptive form of the computer-implemented interference processing exhibited reduced multitasking costs, with the gains persisting for six (6) months. The Nature paper also reported that age-related deficits in neural signatures of cognitive control, as measured with electroencephalography, were remediated by the multitasking training (using the computer-implemented interference processing), with enhanced midline frontal theta power and frontal-posterior theta coherence. Interacting with the computer-implemented interference processing resulted in performance benefits that extended to untrained cognitive control abilities (enhanced sustained attention and working memory), with an increase in midline frontal theta power predicting a boost in sustained attention and preservation of multitasking improvement six (6) months later.

The exemplary systems, methods, and apparatus according to the principles herein are configured to classify an individual as to cognitive abilities and/or to enhance those cognitive abilities based on implementation of interference processing using a computerized cognitive platform. The exemplary systems, methods, and apparatus are configured to implement a form of multi-tasking using the capabilities of a programmed computing device, where an individual is required to perform a task and an interference substantially simultaneously, where the task and/or the interference includes a computerized adjustable element, and the individual is required to respond to the computerized adjustable element. The sensing and measurement capabilities of the computing device are configured to collect data indicative of the physical actions taken by the individual during the response execution time to respond to the task at substantially the same time as the computing device collects the data indicative of the physical actions taken by the individual to respond to the computerized adjustable element. The capabilities of the computing devices and programmed processing units present via a user interface the task and/or the interference in real time, and to measure the data indicative of the individual's responses to the task and/or the interference and the computerized adjustable element in real time and substantially simultaneously can provide quantifiable measures of an individual's cognitive capabilities, to rapidly switch to and from different tasks and interferences, or to perform multiple, different, tasks or interferences in a row (including for single-tasking, where the individual is required to perform a single type of task for a set period of time).

In any example herein, the one or more processors may configure the at least one computerized adjustable element to be adjusted in real time as an indication of a degree of success of the performance of at least one of the task or the interference. In any example herein, the timescale of real time can relate to a system or apparatus in which the one or more processors process measurement data and present the adjustment of the adjustable element within a time period for the user to respond to the task and/or the interference within a predetermined amount of time, such as but not limited to, within milliseconds, or within tens of milliseconds, or within about 1 second, or within about 5 seconds, or within about 10 seconds, or within about 20 seconds, or greater (or other similar timescales).

In any example herein, the task and/or interference includes a response deadline, such that the user interface imposes a limited time period for receiving at least one type of response from the individual interacting with the apparatus or computing device. For example, the period of time that an individual is required to interact with a computing device or other apparatus to perform a task and/or an interference can be a predetermined amount of time, such as but not limited to about 30 seconds, about 1 minute, about 4 minutes, about 7 minutes, about 10 minutes, or greater than 10 minutes.

The exemplary systems, methods, and apparatus can be configured to implement a form of multi-tasking to provide measures of the individual's capabilities in deciding whether to perform one action instead of another and to activate the rules of the current task in the presence of an interference such that the interference diverts the individual's attention from the task, as a measure of an individual's cognitive abilities in executive function control.

The exemplary systems, methods, and apparatus can be configured to implement a form of single-tasking, where measures of the individual's performance at interacting with a single type of task (i.e., with no interference) for a set period of time (such as but not limited to navigation task only or a target discriminating task only) can also be used to provide measure of an individual's cognitive abilities.

The exemplary systems, methods, and apparatus can be configured to implement sessions that involve differing sequences and combinations of single-tasking and multi-tasking trials. In a first exemplary implementation, a session can include a first single-tasking trial (with a first type of task), a second single-tasking trial (with a second type of task), and a multi-tasking trial (a primary task rendered with an interference). In a second exemplary implementation, a session can include two or more multi-tasking trials (a primary task rendered with an interference). In a third exemplary implementation, a session can include two or more single-tasking trials (all based on the same type of tasks or at least one being based on a different type of task).

The performance can be further analyzed by comparing the effects of two different types of interference (e.g. distraction or interruptor) on the performances of the various tasks. Some comparisons can include performance without interference, performance with distraction, and performance with interruption. The cost of each type of interference (e.g. distraction cost and interruptor/multi-tasking cost) on the performance level of a task is analyzed and reported to the individual.

In any example herein, the interference can a secondary task that includes a stimulus that is either a non-target (as a distraction) or a target (as an interruptor), or a stimulus that is differing types of targets (e.g., differing degrees of a facial expression or other characteristic/feature difference).

Based on the capability of a programmed processing unit to control the effecting of multiple separate sources (including sensors and other measurement components) and the receiving of data selectively from these multiple different sources at substantially simultaneously (i.e., at roughly the same time or within a short time interval) and in real-time, the exemplary systems, methods, and apparatus herein can be used to collect quantitative measures of the responses form an individual to the task and/or interference, which could not be achieved using normal human capabilities. As a result, the exemplary systems, methods, and apparatus herein can be configured to implement a programmed processing unit to render the interference substantially simultaneously with the task over certain time periods.

In some exemplary implementations, the exemplary systems, methods, and apparatus herein also can be configured to receive the data indicative of the measure of the degree and type of the individual's response to the task substantially simultaneously as the data indicative of the measure of the degree and type of the individual's response to the interference is collected (whether the interference includes a target or a non-target). In some examples, the exemplary systems, methods, and apparatus are configured to perform the analysis by applying scoring or weighting factors to the measured data indicative of the individual's response to a non-target that differ from the scoring or weighting factors applied to the measured data indicative of the individual's response to a target, in order to compute a cost measure (including an interference cost).

In the exemplary systems, methods, and apparatus herein, the cost measure can be computed based on the difference in measures of the performance of the individual at one or more tasks in the absence of interference as compared to the measures of the performance of the individual at the one or more tasks in the presence of interference, where the one or more tasks and/or the interference includes one or more computerized adjustable elements. As described herein, the requirement of the individual to interact with (and provide a response to) the computerized adjustable element(s) can introduce cognitive or emotional load that quantifiably affects the individuals capability at performing the task(s) and/or interference due to the requirement for emotional processing to respond to the computerized adjustable element. In an example, the interference cost computed based on the data collected herein can provide a quantifiable assessment of the individual's susceptibility to interference. The determination the difference between an individual's performance on a task in isolation versus a task in the presence of one or more interference (the task and/or interference including the computerized adjustable element) provides an interference cost metric that can be used to assess and classify cognitive capabilities of the individual. The interference cost computed based on the individuals performance of tasks and/or interference performed can also provide a quantifiable measure of the individual's cognitive condition, disease state, or presence or stage of an executive function disorder, such as but not limited to, anxiety (including social anxiety), depression, bipolar disorder, post-traumatic stress disorder, schizophrenia, autism spectrum disorder, attention deficit hyperactivity disorder, dementia, Parkinson's disease, Huntington's disease, or other neurodegenerative condition, Alzheimer's disease, multiple sclerosis, presence of the 16p11.2 duplication, attention deficit hyperactivity disorder (ADHD), sensory-processing disorder (SPD), mild cognitive impairment (MCI), and major depressive disorder (MDD).

The exemplary systems, methods, and apparatus herein can be configured to perform the analysis of the individual's susceptibility to interference (including as a cost measure such as the interference cost), as a reiterating, cyclical process. For example, where an individual is determined to have minimized interference cost for a given task and/or interference, the exemplary systems, methods, and apparatus can be configured to require the individual to perform a more challenging task and/or interference (i.e., having a higher difficulty level) until the individual's performance metric indicates a minimized interference cost in that given condition, at which point exemplary systems, methods, and apparatus can be configured to present the individual with an even more challenging task and/or interference until the individual's performance metric once again indicates a minimized interference cost for that condition. This can be repeated any number of times until a desired end-point of the individual's performance is obtained.

As a non-limiting example, the interference cost can be computed based on measurements of the individual's performance at a single-tasking task (without an interference) as compared to a multi-tasking task (with interference), to provide an assessment. For example, an individual's performance at a multi-tasking task (e.g., targeting task with interference) can be compared to their performance at a single-tasking targeting task without interference to provide the interference cost.

Exemplary systems, apparatus and methods herein are configured to analyze data indicative of the degree to which an individual is affected by a computerized adjustable element, and/or the degree to which the performance of the individual at a task is affected in the presence of the computerized adjustable element, to provide performance metric including a quantified indicator of cognitive abilities of the individual. The performance metric can be used as an indicator of the degree to which the individual exhibits a form of emotional or affective bias.

In some exemplary implementations, the exemplary systems, methods, and apparatus herein also can be configured to selectively receive data indicative of the measure of the degree and type of the individual's response to an interference that includes a target stimulus (i.e., an interruptor) substantially simultaneously (i.e., at substantially the same time) as the data indicative of the measure of the degree and type of the individual's response to the task is collected and to selectively not collect the measure of the degree and type of the individual's response to an interference that includes a non-target stimulus (i.e., a distraction) substantially simultaneously (i.e., at substantially the same time) as the data indicative of the measure of the degree and type of the individual's response to the task is collected. That is, the exemplary systems, methods, and apparatus are configured to discriminate between the windows of response of the individual to the target versus non-target by selectively controlling the state of the sensing/measurement components for measuring the response either temporally and/or spatially. This can be achieved by selectively activating or de-activating sensing/measurement components based on the presentation of a target or non-target, or by receiving the data measured for the individual's response to a target and selectively not receiving (e.g., disregarding, denying, or rejecting) the data measured for the individual's response to a non-target.

As described herein, using the exemplary systems, methods, and apparatus herein can be implemented to provide a measure of the cognitive abilities of an individual in the area of attention, including based on capabilities for sustainability of attention over time, selectivity of attention, and reduction of attention deficit. Other areas of an individual's cognitive abilities that can be measured using the exemplary systems, methods, and apparatus herein include affective bias, mood, level of cognitive bias, impulsivity, inhibition, perceptive abilities, reaction and other motor functions, visual acuity, long-term memory, working memory, short-term memory, logic, and decision-making.

As described herein, using the exemplary systems, methods, and apparatus herein can be implemented to adapt the tasks and/or interference (at least one including a computerized adjustable element) from one user session to another (or even from one user trial to another) to enhance the cognitive skills of an individual based on the science of brain plasticity. Adaptivity is a beneficial design element for any effective plasticity-harnessing tool. In exemplary systems, methods, and apparatus, the processing unit is configured to control parameters of the tasks and/or interference, such as but not limited to the timing, positioning, and nature of the stimuli, so that the physical actions of the individual can be recorded during the interaction(s). As described hereinabove, the individual's physical actions are affected by their neural activity during the interactions with the computing device to perform single-tasking and multi-tasking tasks. The science of interference processing shows (based on the results from physiological and behavioral measurements) that the aspect of adaptivity can result in changes in the brain of an individual in response to the training from multiple sessions (or trials) based on neuroplasticity, thereby enhancing the cognitive skills of the individual. The exemplary systems, methods, and apparatus are configured to implement tasks and/or interference with at least one computerized adjustable element, where the individual performs the interference processing. As supported in the published research results described hereinabove, the effect on an individual of performing tasks can tap into novel aspects of cognitive training to enhance the cognitive abilities of the individual.

FIGS. 5A-11H show non-limiting exemplary user interfaces that can be generated using exemplary systems, methods, and apparatus herein to render the tasks and/or interferences (either or both with computerized adjustable element) for user interactions. The non-limiting example user interfaces of FIGS. 5A-11H also can be used for one or more of: to display instructions to the individual for performing the tasks and/or interferences, interact with the computerized adjustable element, to collect the data indicative of the individual's responses to the tasks and/or the interferences and the computerized adjustable element, to show progress metrics, and to provide the analysis metrics.

FIGS. 5A-5D show non-limiting exemplary user interfaces rendered using example systems, methods, and apparatus herein. As shown in FIGS. 5A-5B, an exemplary programmed processing unit can be used to render to the user interfaces (including graphical user interfaces) display features 500 for displaying instructions to the individual for performing the tasks and/or interferences and to interact with the computerized adjustable element, and metric features 502 to show status indicators from progress metrics and/or results from application of analytics to the data collected from the individual's interactions (including the responses to tasks/interferences) to provide the analysis metrics. In any example systems, methods, and apparatus herein, the classifier can be used to provide the analysis metrics provided as a response output. In any example systems, methods, and apparatus herein, the data collected from the user interactions can be used as input to train the classifier. As shown in FIGS. 5A-5B, an example programmed processing unit also may be used to render to the user interfaces (including graphical user interfaces) an avatar or other processor-rendered guide 504 that an individual is required to control (such as but not limited to navigate a path or other environment in a visuomotor task, and/or to select an object in a target discrimination task). In an example, the computerized adjustable element may be includes as a component of the visuomotor task (e.g., as a milestone object along the path) or as a component of the target discrimination task, e.g., where a specific type of computerized adjustable element (such as but not limited to an angry or happy face, loud or angry voice or a threat or fear-inducing word) is the target, and other types of the computerized adjustable element are not (such as but not limited to a neutral face, a happy voice, or a neutral word). As shown in FIG. 5B, the display features 500 can be used to instruct the individual what is expected to perform a navigation task while the user interface depicts (using the dashed line) the type of movement of the avatar or other processor-rendered guide 504 required for performing the navigation task. In an example, the navigation task may include milestone objects (possibly including computerized adjustable elements) that the individual is required to steer an avatar to cross or avoid, in order to determine the scoring. As shown in FIG. 5C, the display features 500 can be used to instruct the individual what is expected to perform a target discrimination task while the user interface depicts the type of object(s) 506 and 508 that may be rendered to the user interface, with one type of object 506 (possibly including a target computerized adjustable element) designated as a target while the other type of object 508 that may be rendered to the user interface is designated as a non-target (possibly including a non-target computerized adjustable element), e.g., by being crossed out in this example. As shown in FIG. 5D, the display features 500 can be used to instruct the individual what is expected to perform both a navigation task as a primary task and a target discrimination as a secondary task (i.e., an interference) while the user interface depicts (using the dashed line) the type of movement of the avatar or other processor-rendered guide 504 required for performing the navigation task, and the user interface renders the object type designated as a target object 506 and the object type designated as a non-target object 508.

Figure 6A:
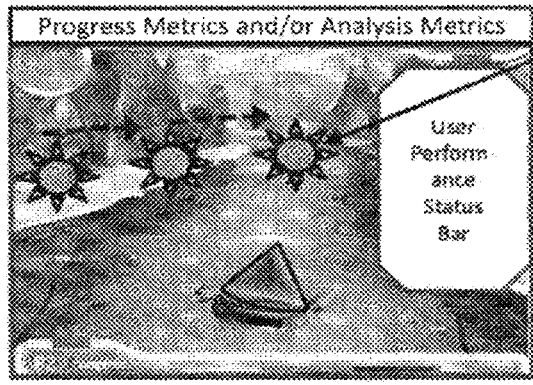
FIGS. 6A-6D show examples of the time-varying features of exemplary objects (targets or non-targets) that can be presented via an exemplary user interface, according to the principles herein.
Figure 6B:
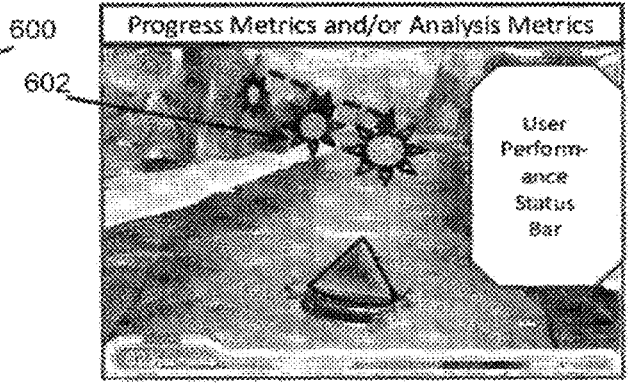
Figure 6C:
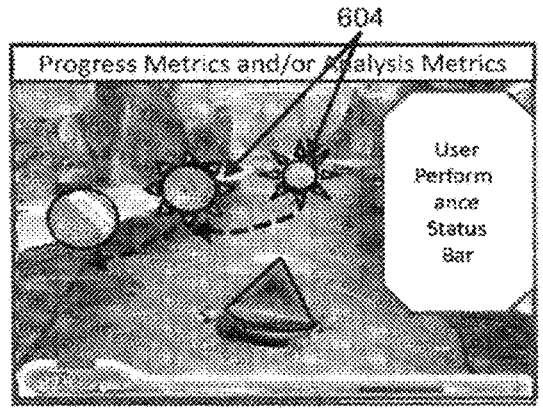
Figure 6D:
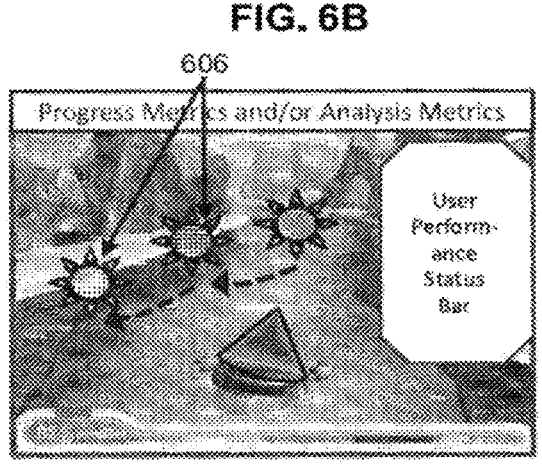
Figure 7A:
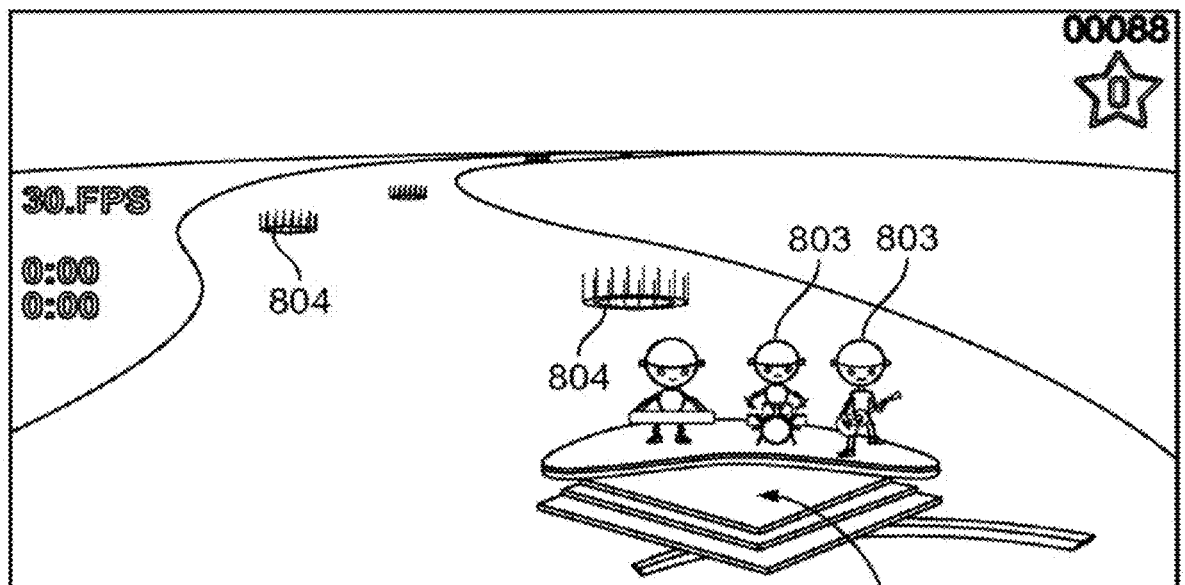
FIGS. 7A-7U, 8A-8Y, 9A-9V, 10A-10Z, and 11A-11H show non-limiting examples of the dynamics of tasks and interferences that can be presented via user interfaces, according to the principles herein.
Figure 7B:
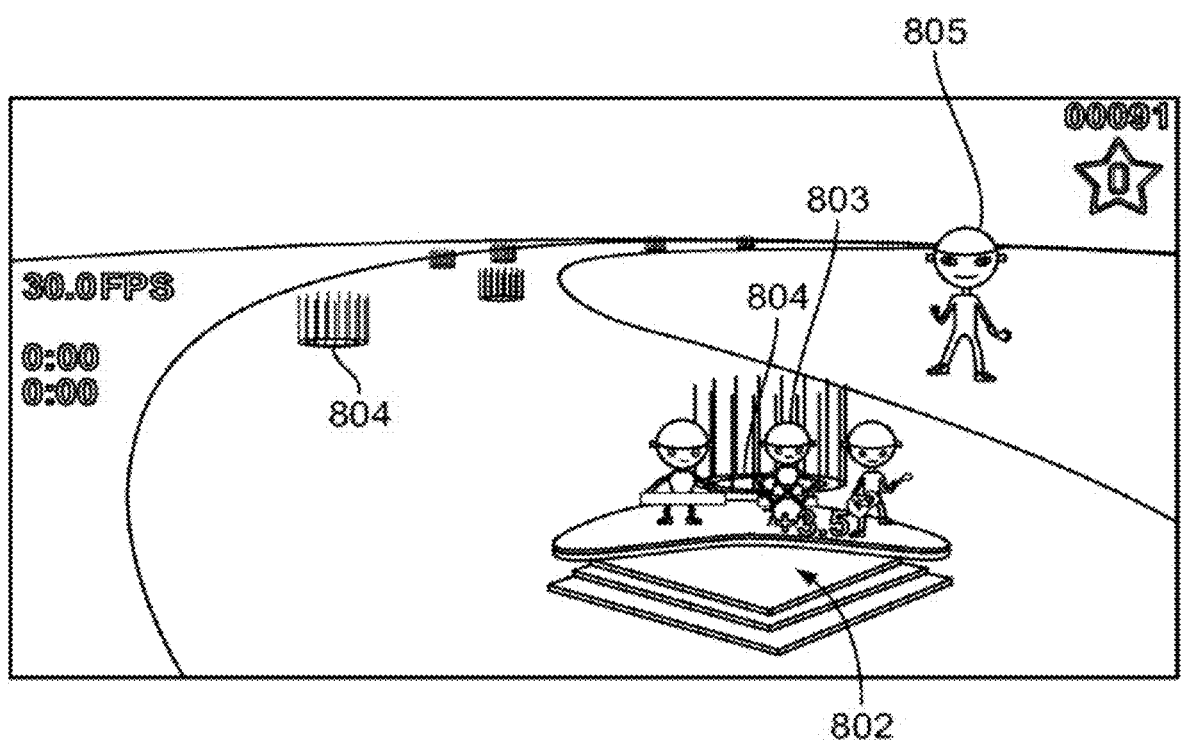
Figure 7C:
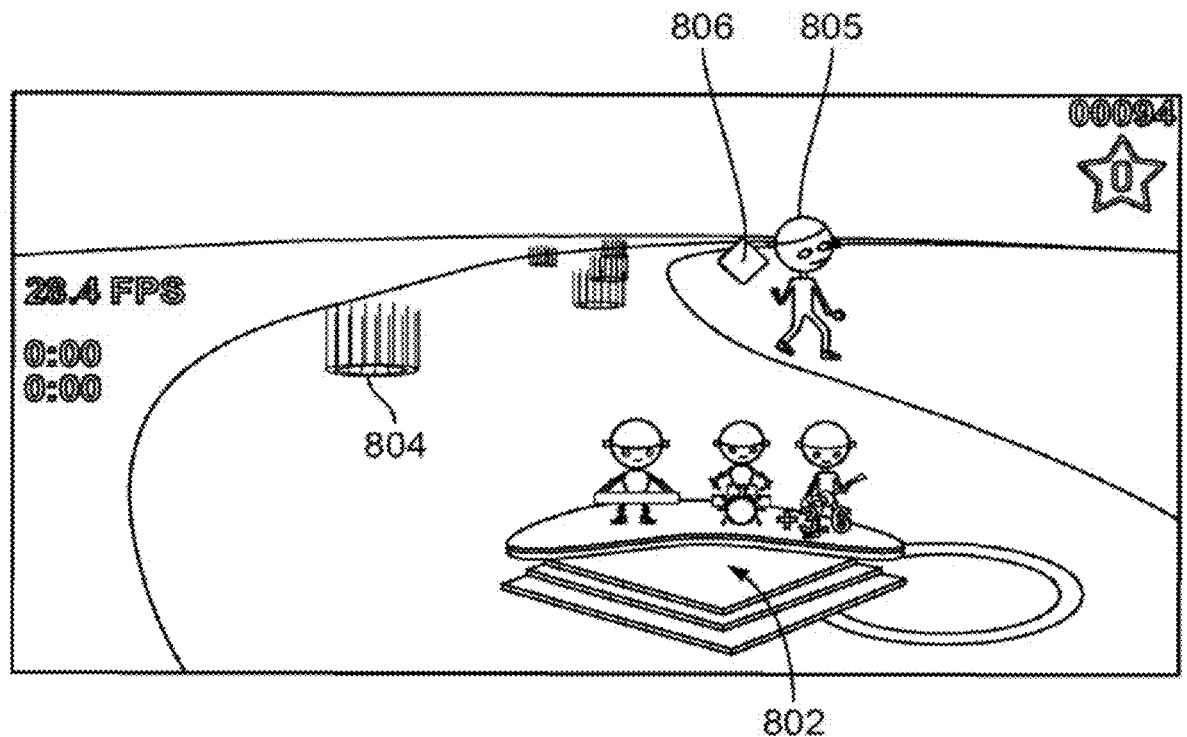
Figure 7D:
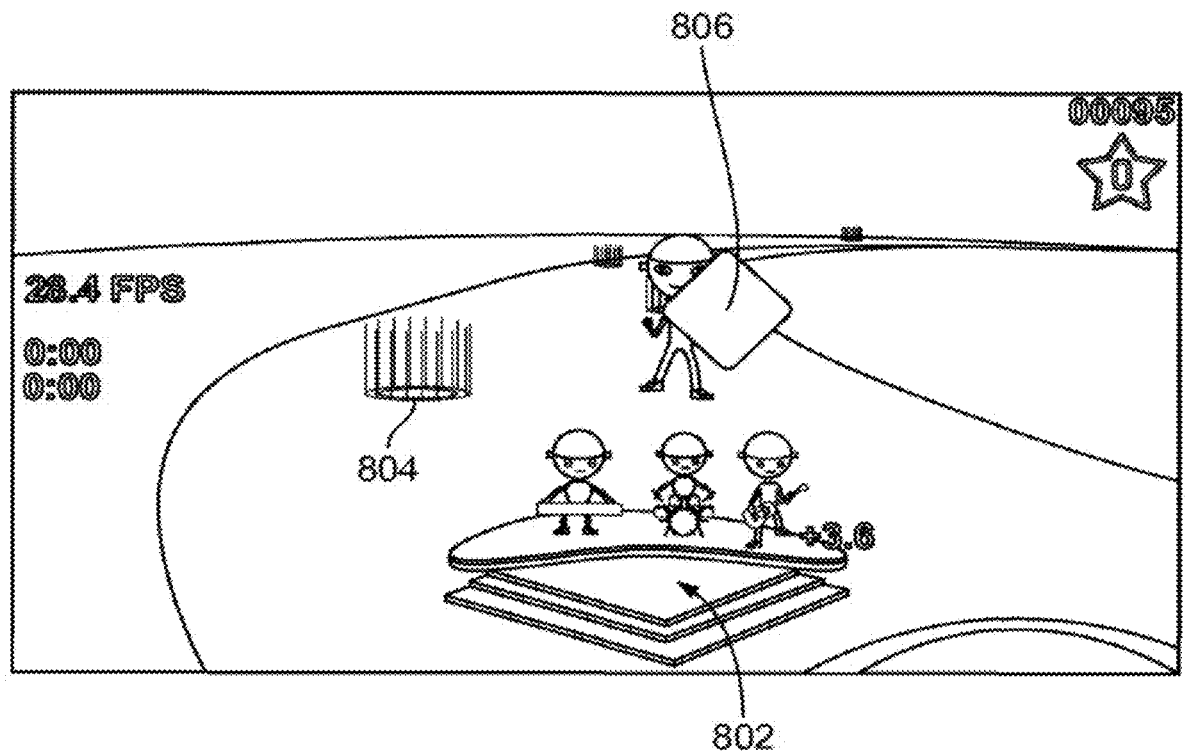
Figure 7E:
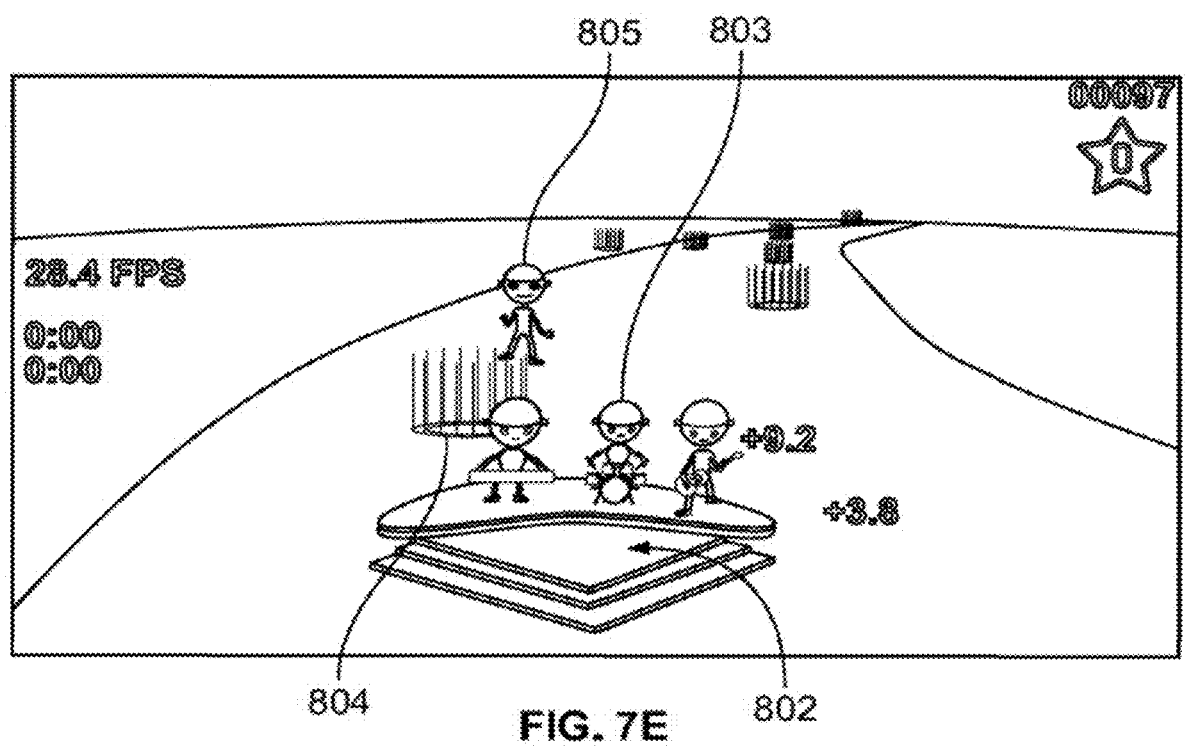
Figure 7F:
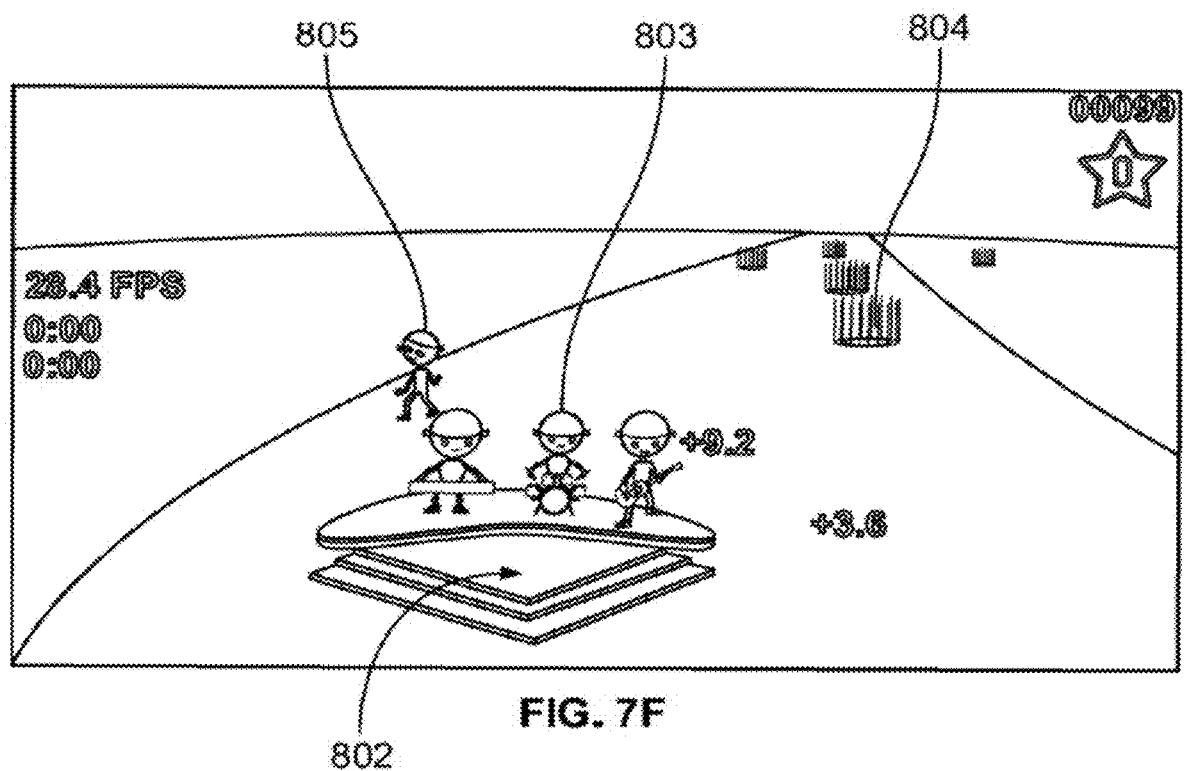
Figure 7G:
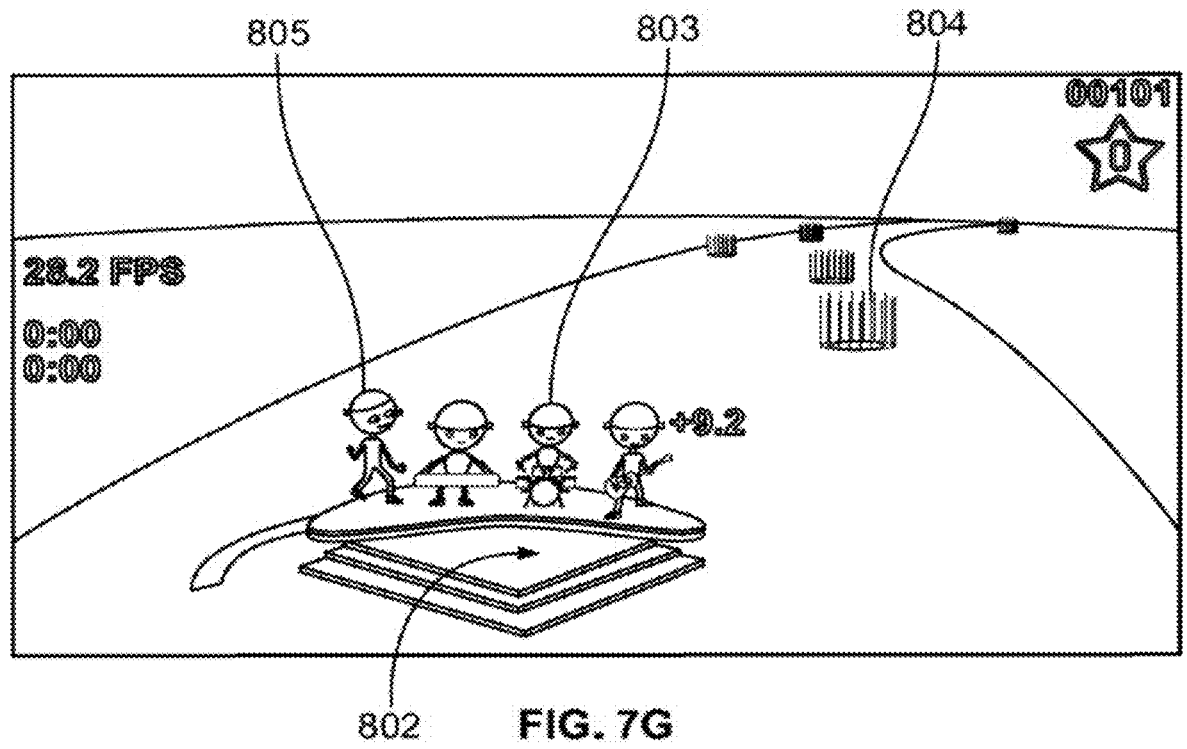
Figure 7H:
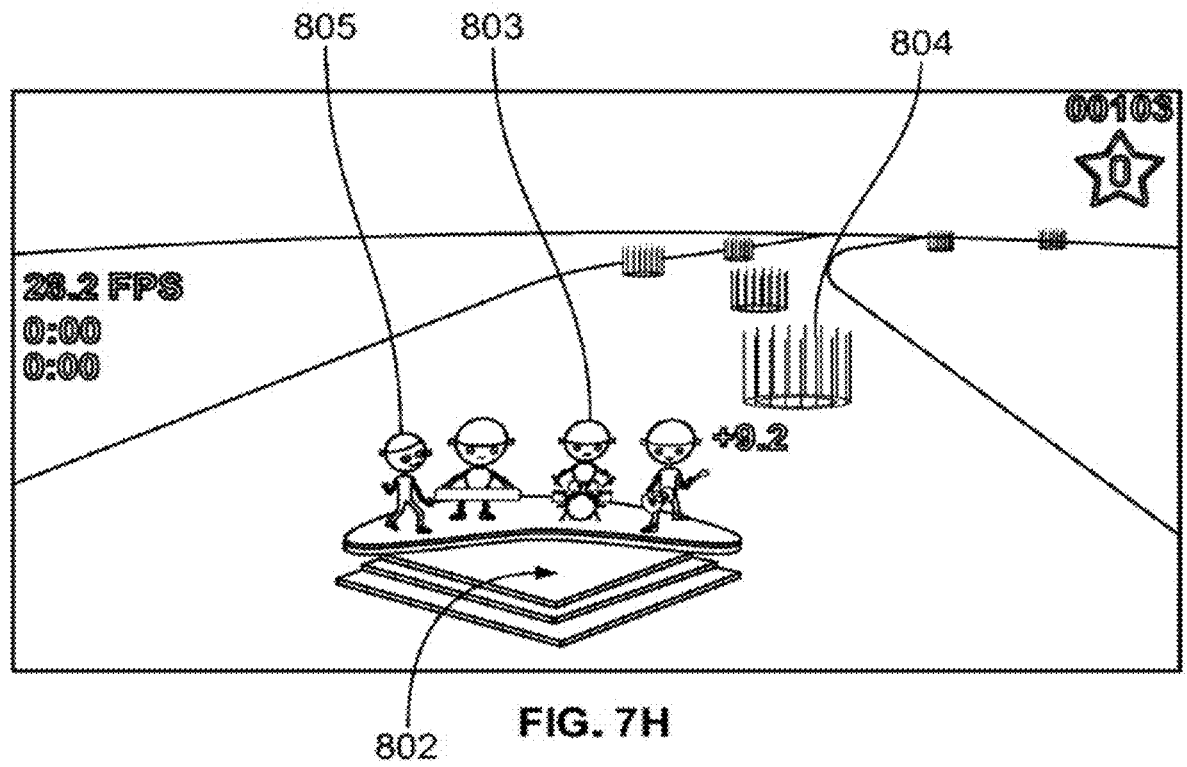
Figure 7I:
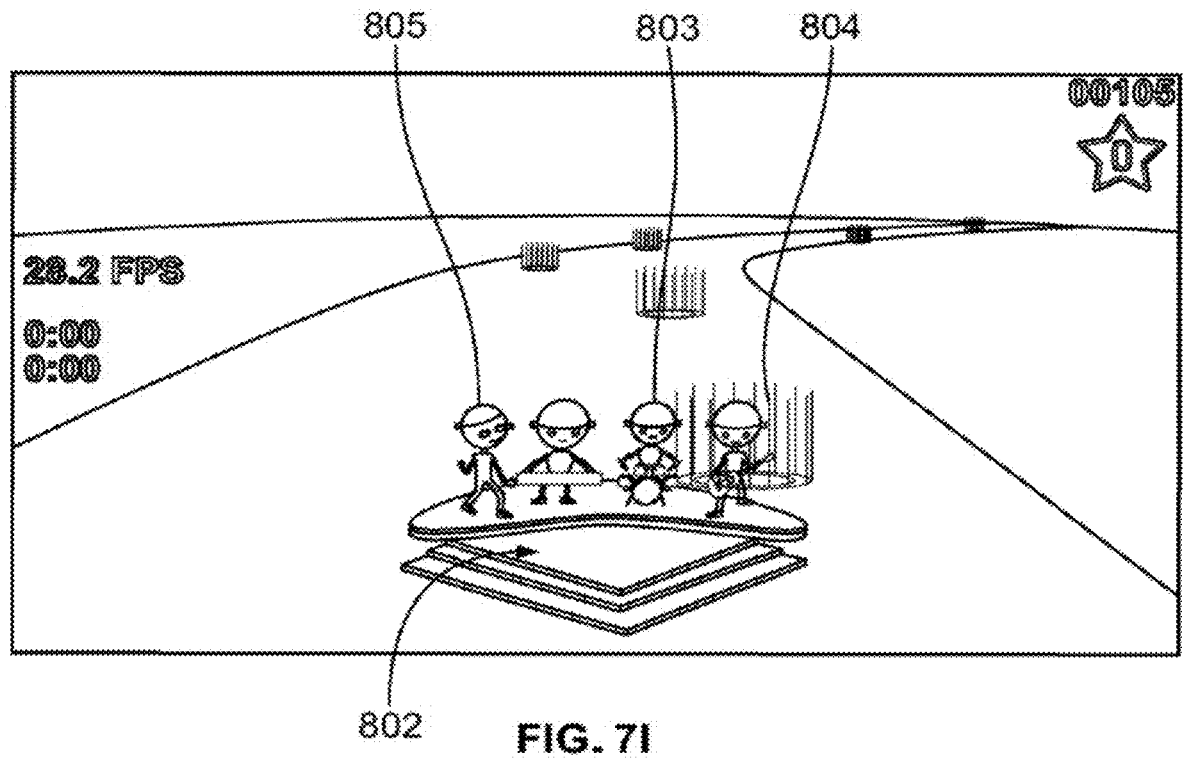
Figure 7J:
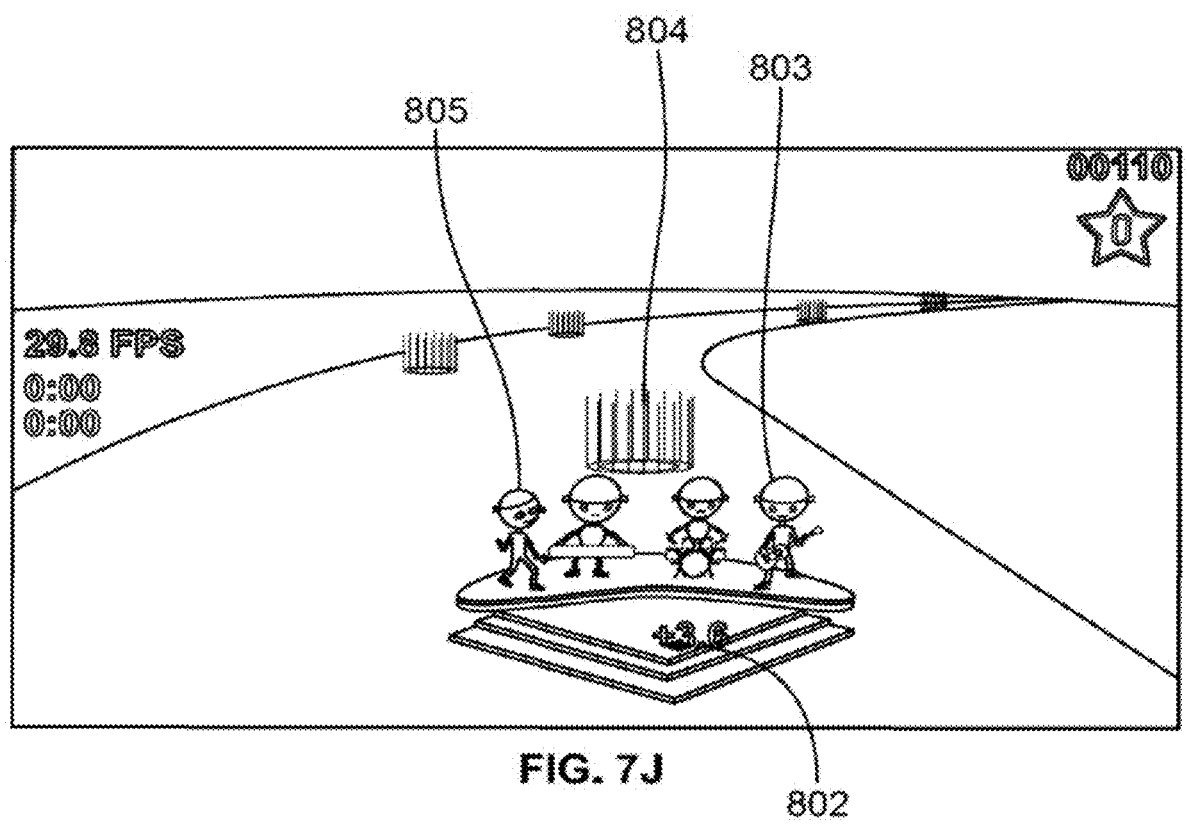
Figure 7K:
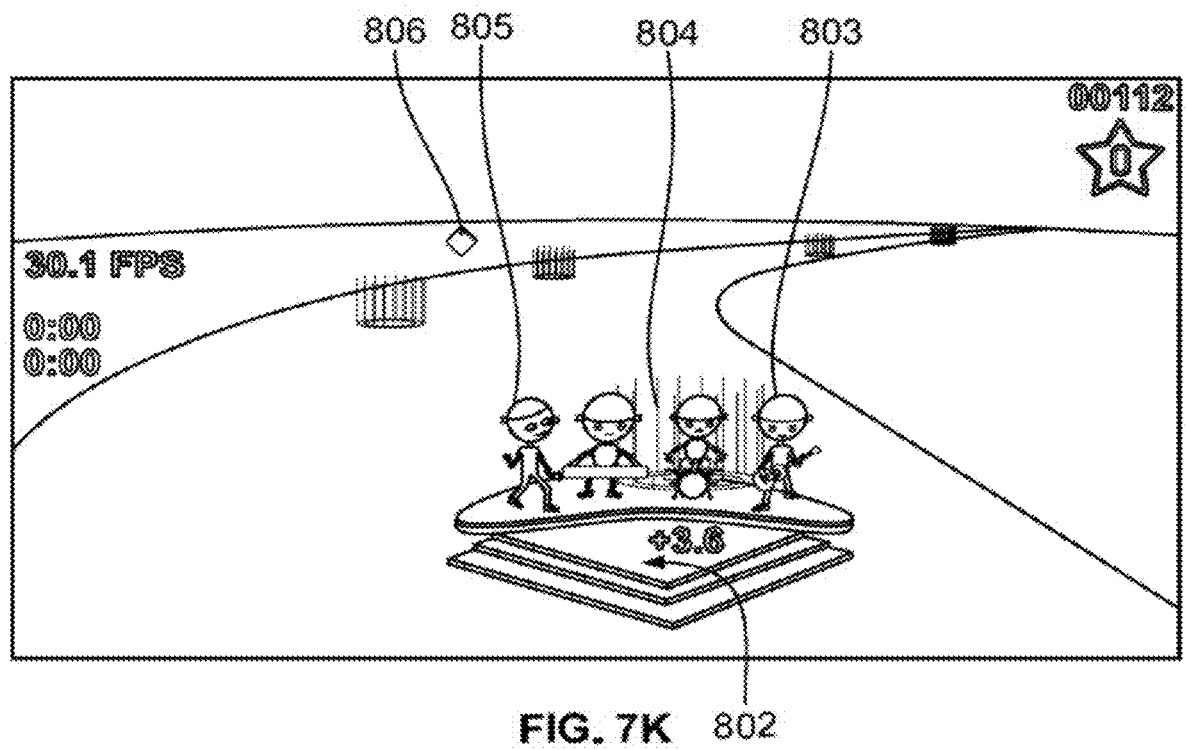
Figure 7L:
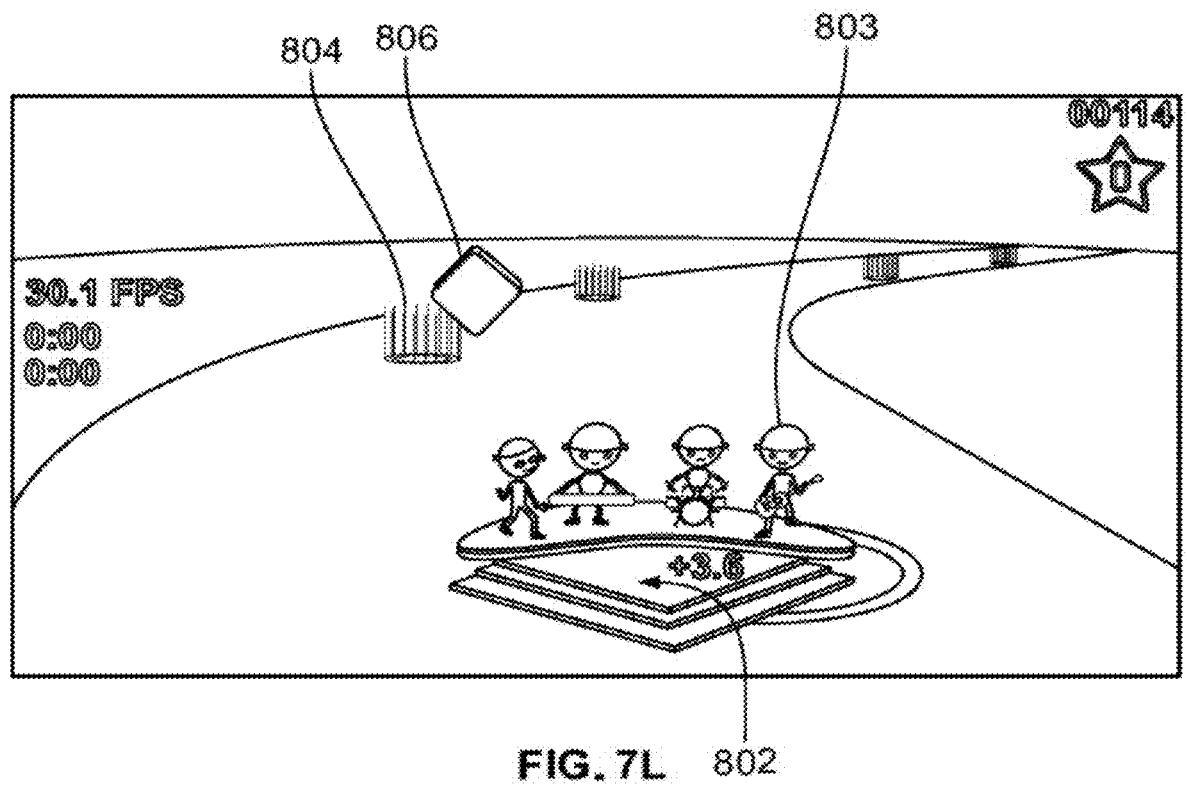
Figure 7M:
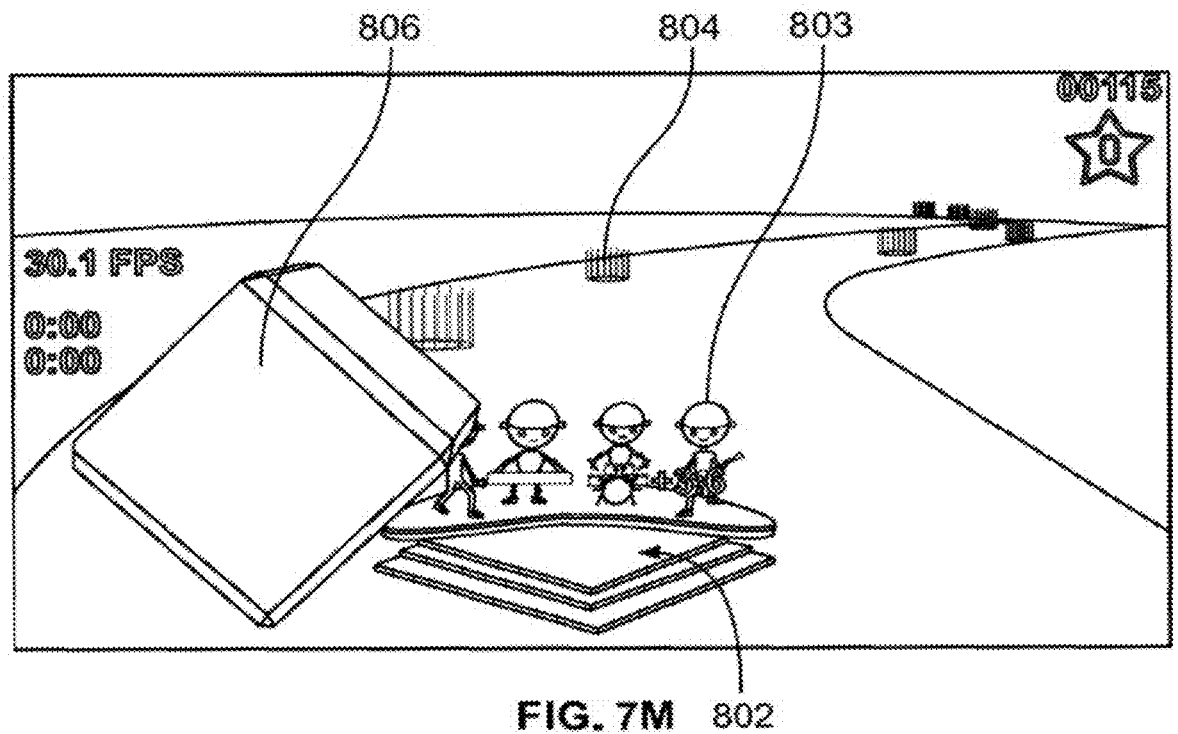
Figure 7N:
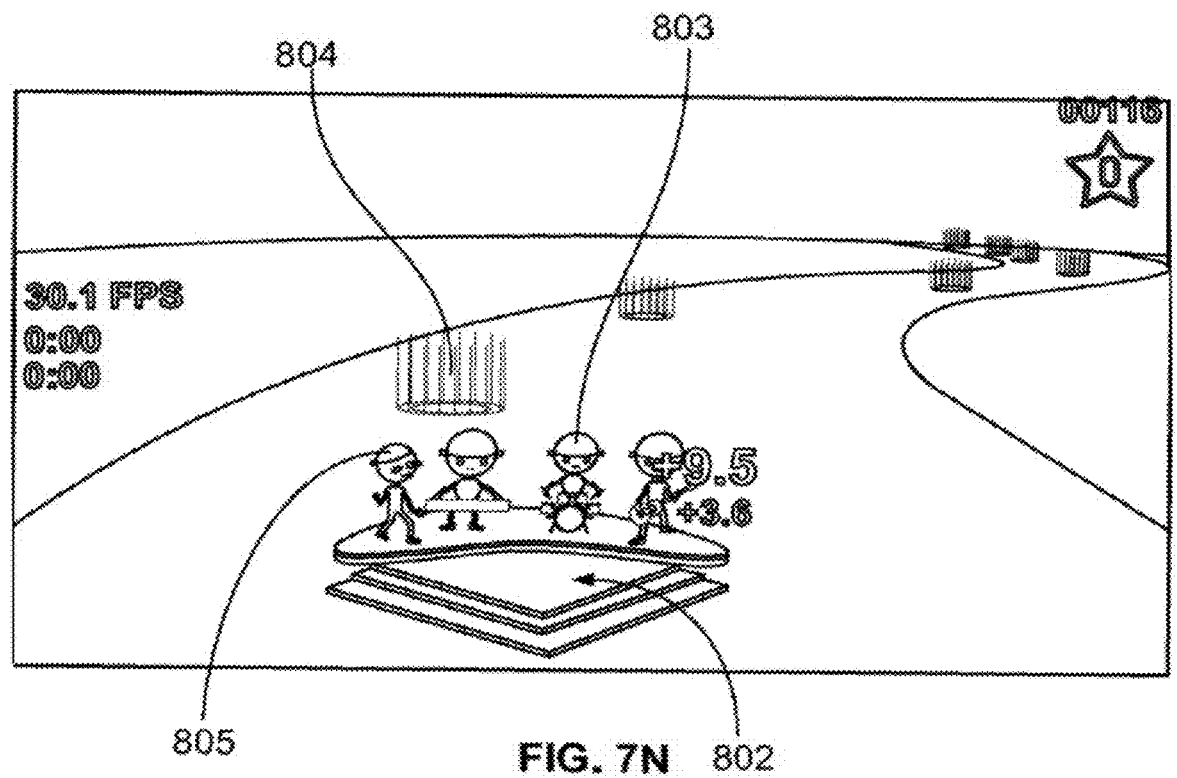
Figure 7O:
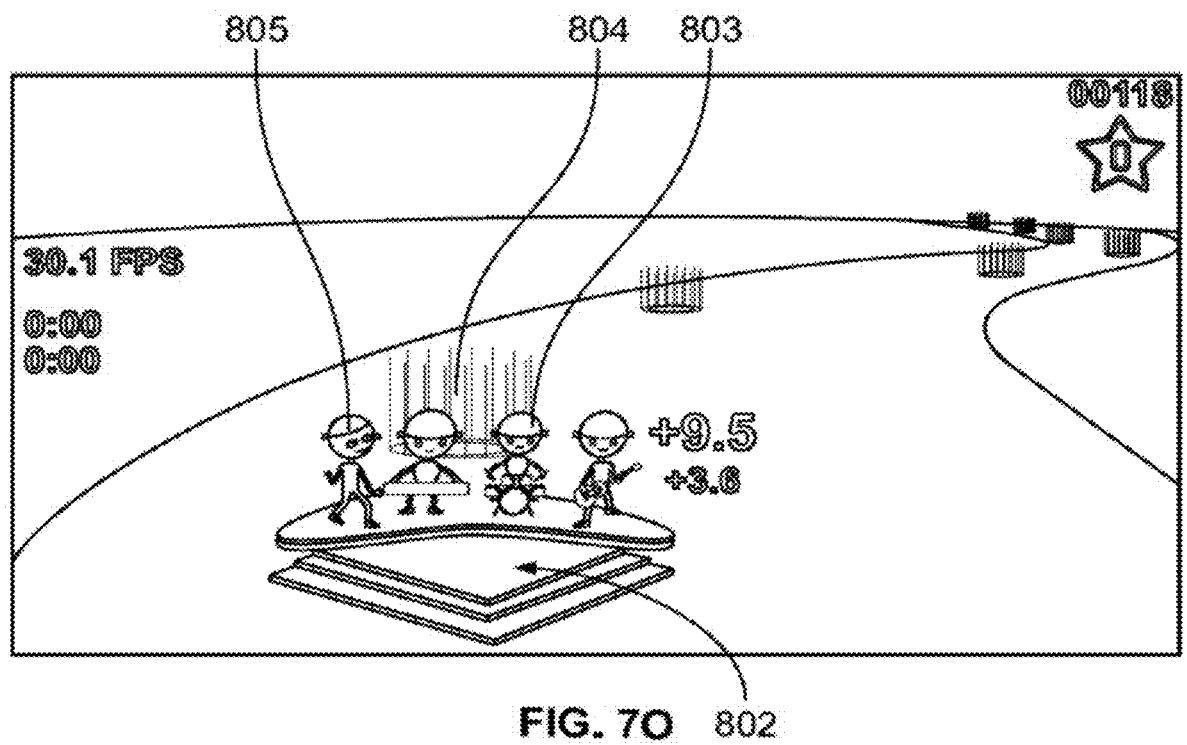
Figure 7P:
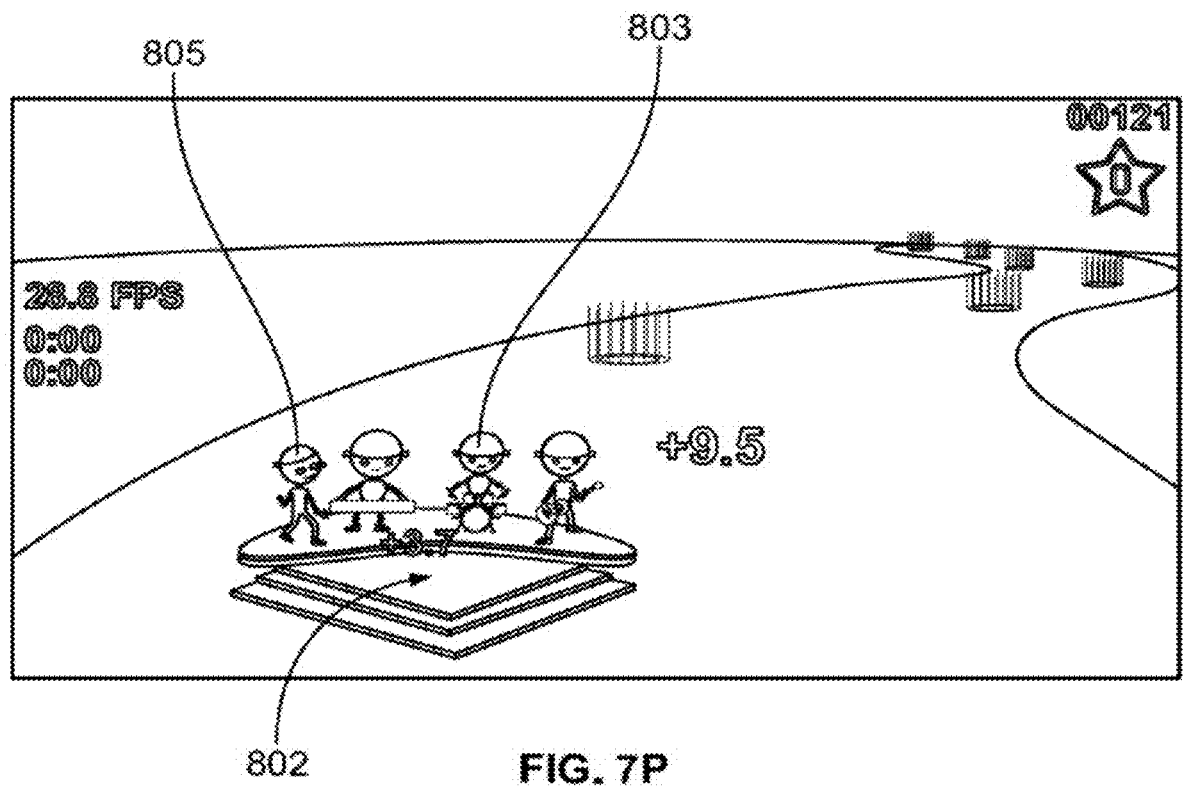
Figure 7Q:
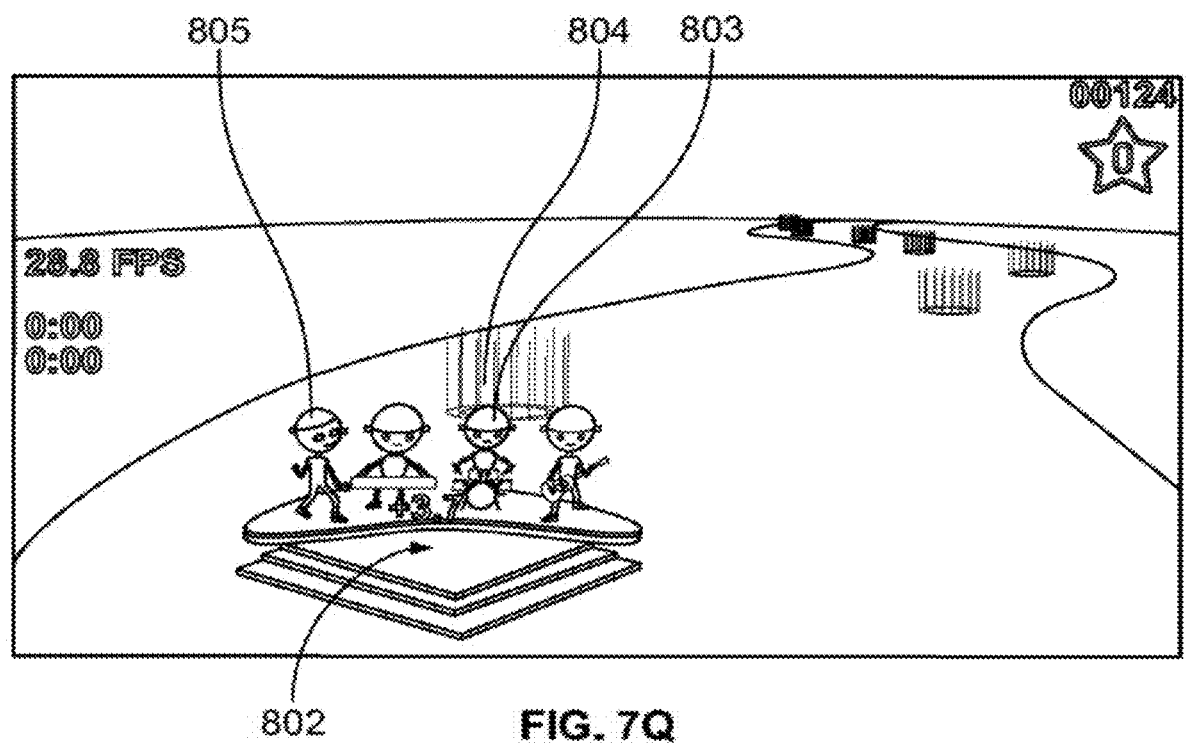
Figure 7R:
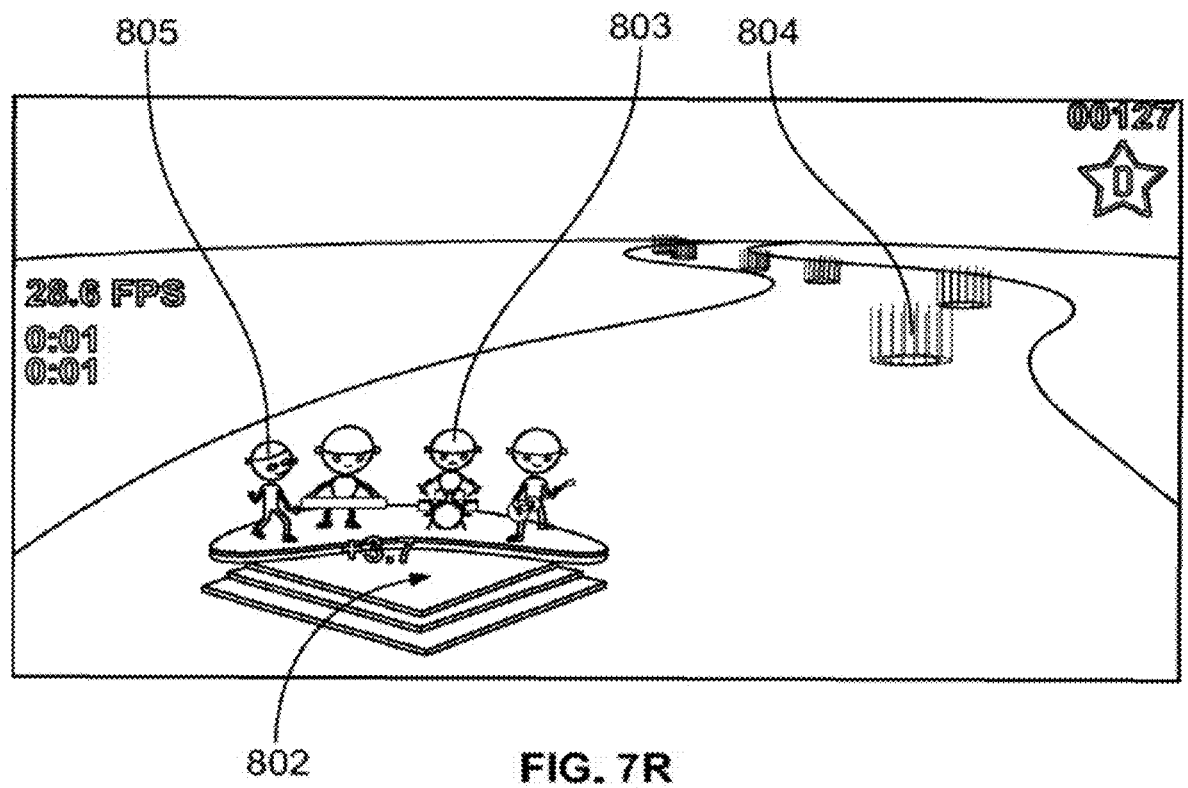
Figure 7S:
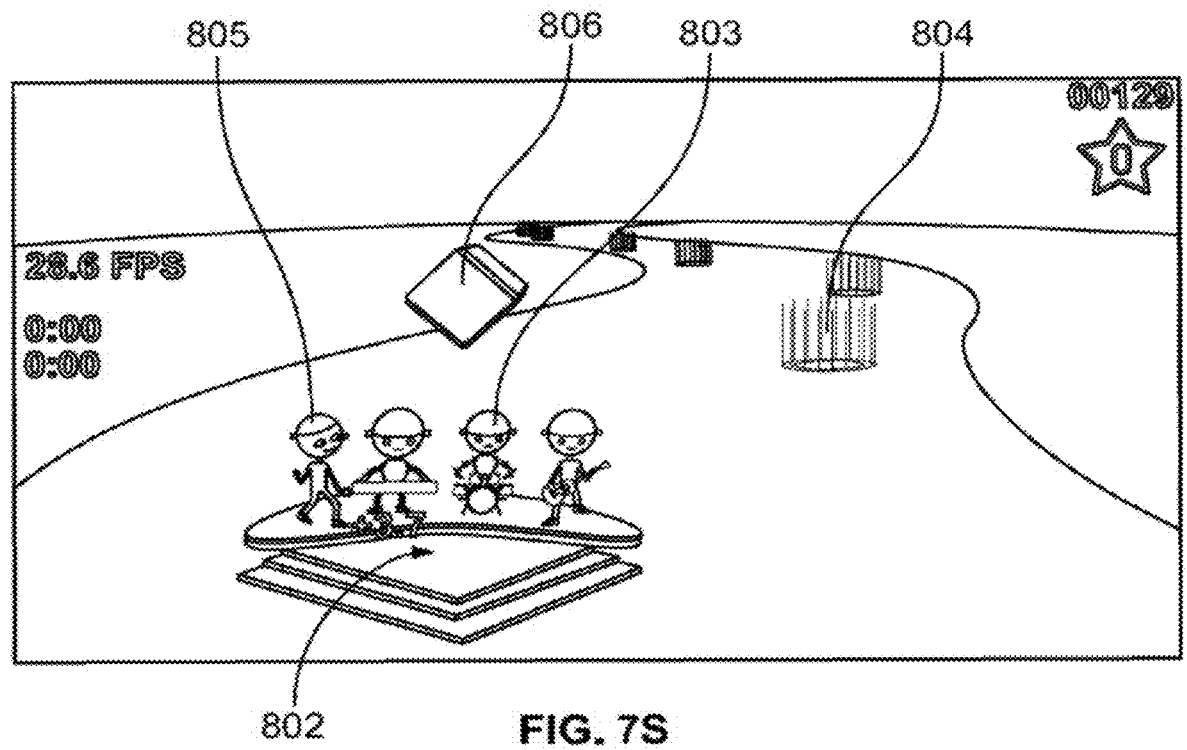
Figure 7T:
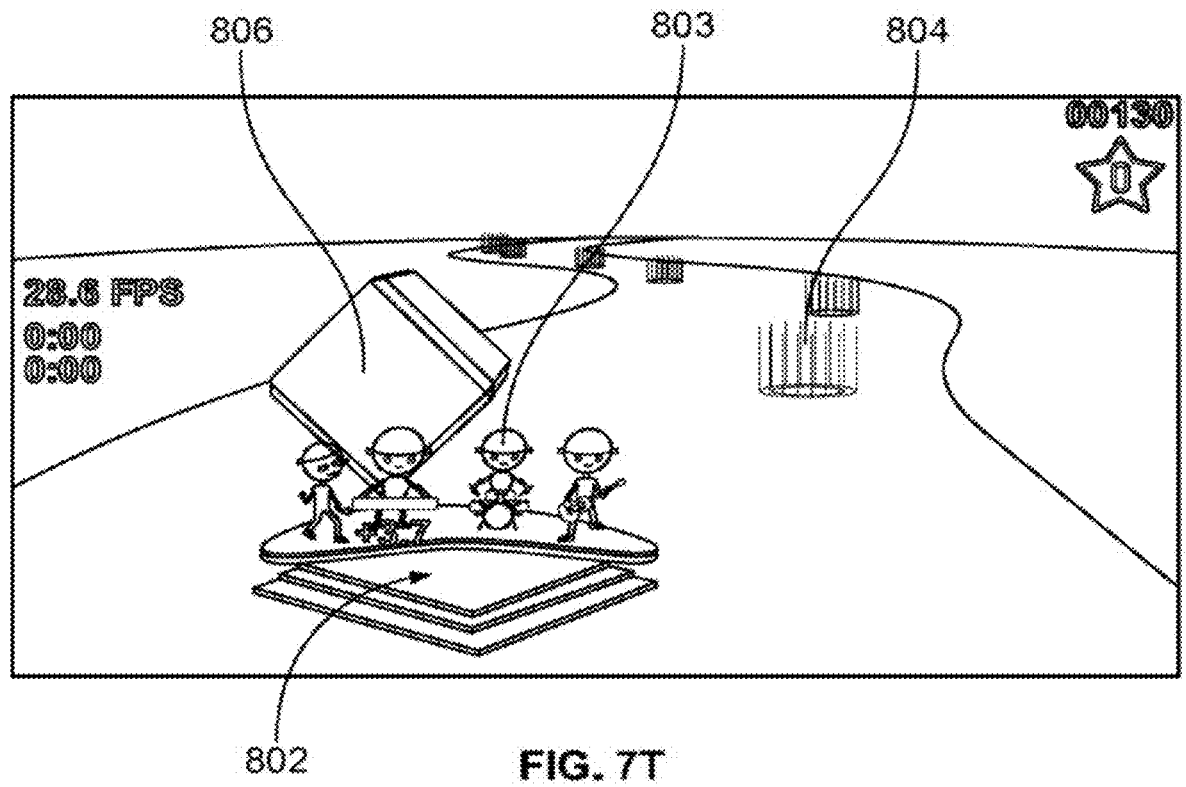
Figure 7U:
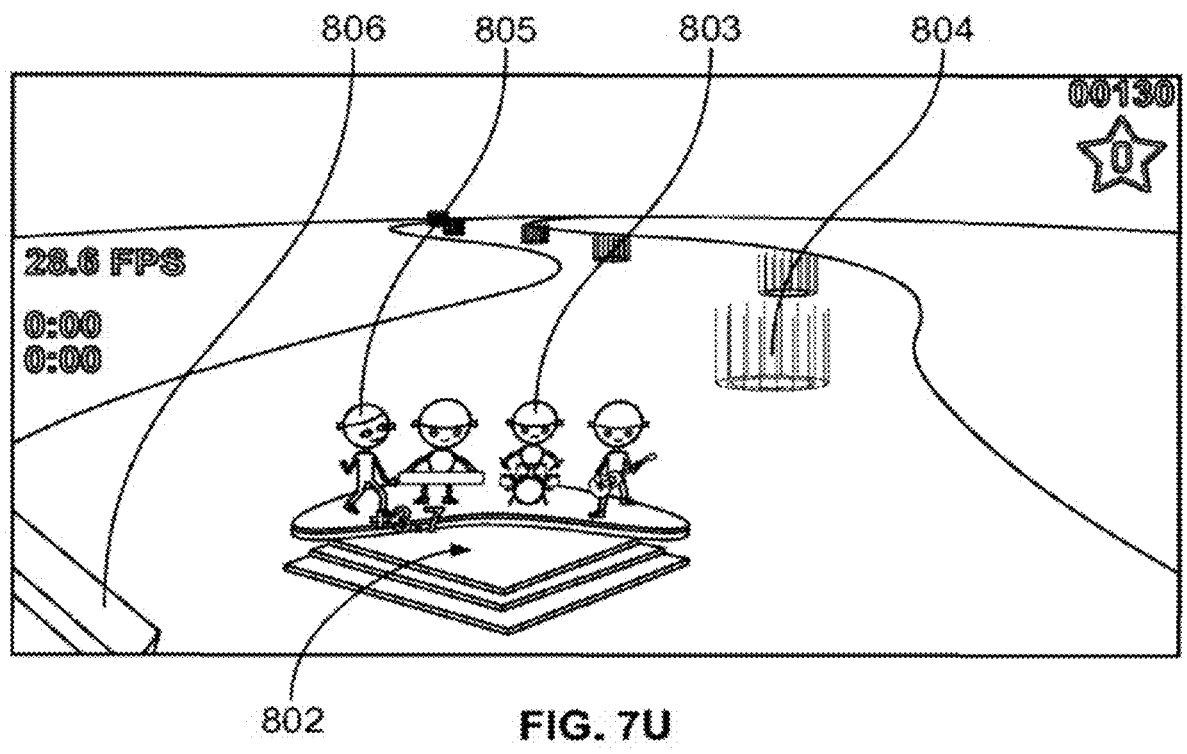

FIGS. 6A-6D show examples of the features of object(s) (targets or non-targets) that can be rendered as time-varying characteristics to an example user interface, according to the principles herein. FIG. 6A shows an example where the modification to the time-varying characteristics of an aspect of the object 600 rendered to the user interface is a dynamic change in position and/or speed of the object 600 relative to environment rendered in the graphical user interface. FIG. 6B shows an example where the modification to the time-varying characteristics of an aspect of the object 602 rendered to the user interface is a dynamic change in size and/or direction of trajectory/motion, and/or orientation of the object 602 relative to the environment rendered in the graphical user interface. FIG. 6C shows an example where the modification to the time-varying characteristics of an aspect of the object 604 rendered to the user interface is a dynamic change in shape or other type of the object 604 relative to the environment rendered in the graphical user interface. In this non-limiting example, the time-varying characteristic of object 604 is effected using morphing from a first type of object (a star object) to a second type of object (a round object). In another non-limiting example, the time-varying characteristic of object 604 is effected by rendering a blendshape as a proportionate combination of a first type of object and a second type of object. FIG. 6C shows an example where the modification to the time-varying characteristics of an aspect of the object 604 rendered to the user interface is a dynamic change in shape or other type of the object 604 rendered in the graphical user interface (in this non-limiting example, from a star object to a round object). FIG. 6D shows an example where the modification to the time-varying characteristics of an aspect of the object 606 rendered to the user interface is a dynamic change in pattern, or color, or visual feature of the object 606 relative to environment rendered in the graphical user interface (in this non-limiting example, from a star object having a first pattern to a round object having a second pattern). In another non-limiting example, the time-varying characteristic of object can be a rate of change of a facial expression depicted on or relative to the object. In any example herein, the foregoing time-varying characteristic can be applied to an object including the computerized adjustable element to modify a cognitive or emotional load of the individual's interaction with the apparatus (e.g., computing device or cognitive platform).

FIGS. 7A-7U and 8A-8Y show non-limiting examples of the dynamics of tasks and interferences that can be generated via user interfaces, according to the principles herein. In this example, the task is a visuomotor navigation task, and the interference is target discrimination (as a secondary task). The computerized adjustable element is rendered as a base vehicle 802 including at least one avatar object 803. The example system is programmed to instruct the individual to perform the visuomotor task and target discrimination (with identification of a specific type of target object as the discrimination task). As shown in FIGS. 7A-7U and 8A-8Y, the individual is required to perform the navigation task by controlling the motion of the avatar vehicle 802 along a path that coincides with the milestone objects 804. FIGS. 7A-7U and 8A-8Y show a non-limiting exemplary implementation where the individual is expected to actuate an apparatus or computing device (including a sensing device) to cause the avatar vehicle 802 to coincide with the milestone object 804 as the response in the navigation task, with scoring based on the success of the individual at crossing paths with (e.g., hitting) the milestone objects 804. In another example, the individual is expected to actuate an apparatus or computing device (or other sensing device) to cause the avatar 802 to miss the milestone object 804, with scoring based on the success of the individual at avoiding the milestone objects 804. FIGS. 7A-7U and 8A-8Y also show the dynamics of a non-target object 806 and a target object 808, where the time-varying characteristic is the trajectory of motion of the objects, and the objects differ by color but not shape. The interference is a secondary task requiring the individual to indicate the individual's discrimination of the objects (target vs. non-target), such as but not limited to by tapping or other indication.

FIGS. 7A-7U and 8A-8Y also show the dynamics of a modification of the computerized adjustable element based on the individual's degree of success in performing the task and/or interference. In the example of FIG. 7B to 7F, an additional avatar object 805 is shown to propagate over to and be positioned on the base vehicle 802 to join the other avatar objects 803 in response to (i) the individual's success at the primary task (e.g., success at steering the base vehicle 802 to coincide with the milestone objects 804 in a visuomotor task), or (ii) the individual's success at the secondary task (e.g., target discrimination as an interference), or (iii) some combination of (i) and (ii). That is, computerized adjustable element is adjusted/modified to add avatar object 807 as an indication of the degree of success of the individual in performing the task and/or interference through a certain stage (e.g., a first time interval T-1) of performing the task and/or interference. In the example of FIG. 8A to 8F, yet another avatar object 807 is shown propagating over to and being positioned on the base vehicle 802 to join the other avatar objects 803 and 803 in response to (i) the individual's success at the primary task (e.g., success at steering the base vehicle 802 to coincide with the milestone objects 804 in a visuomotor task), or (ii) the individual's success at the secondary task (e.g., target discrimination as an interference), or (iii) some combination of (i) and (ii). That is, computerized adjustable element is further adjusted/modified to add another avatar object as yet another indication of the degree of success of the individual in performing the task and/or interference through another stage (e.g., second time interval T-2 (different from T-1)) of performing the task and/or interference.

Figure 8A:
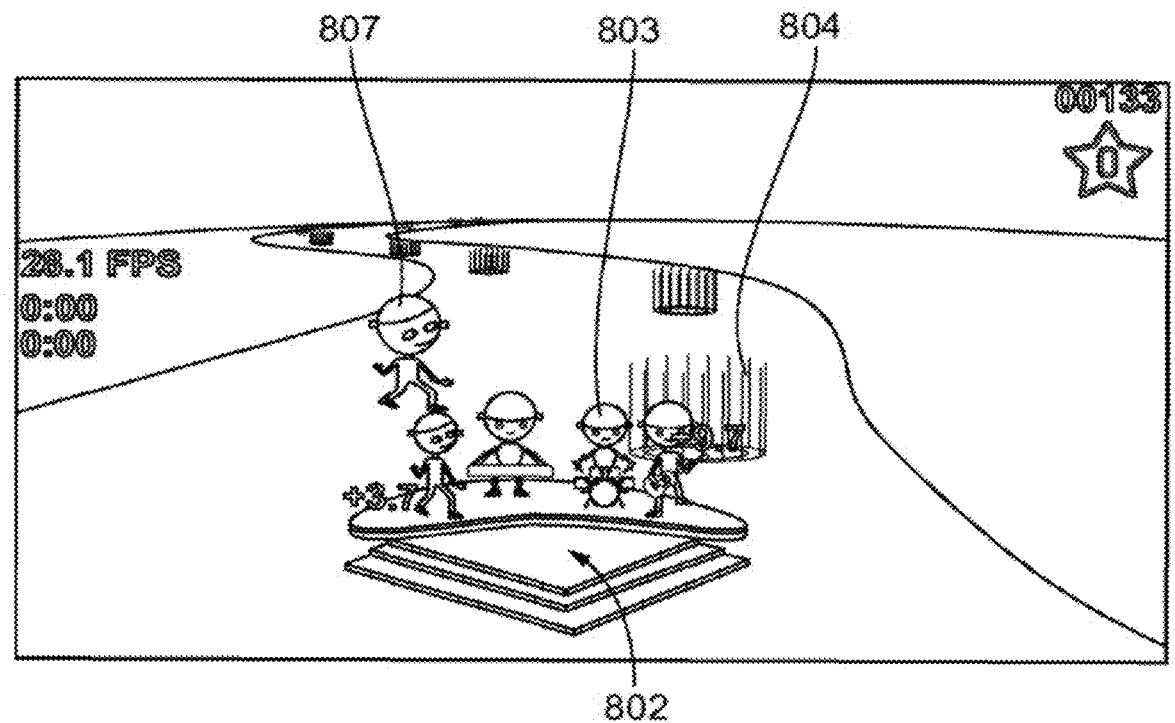
Figure 8B:
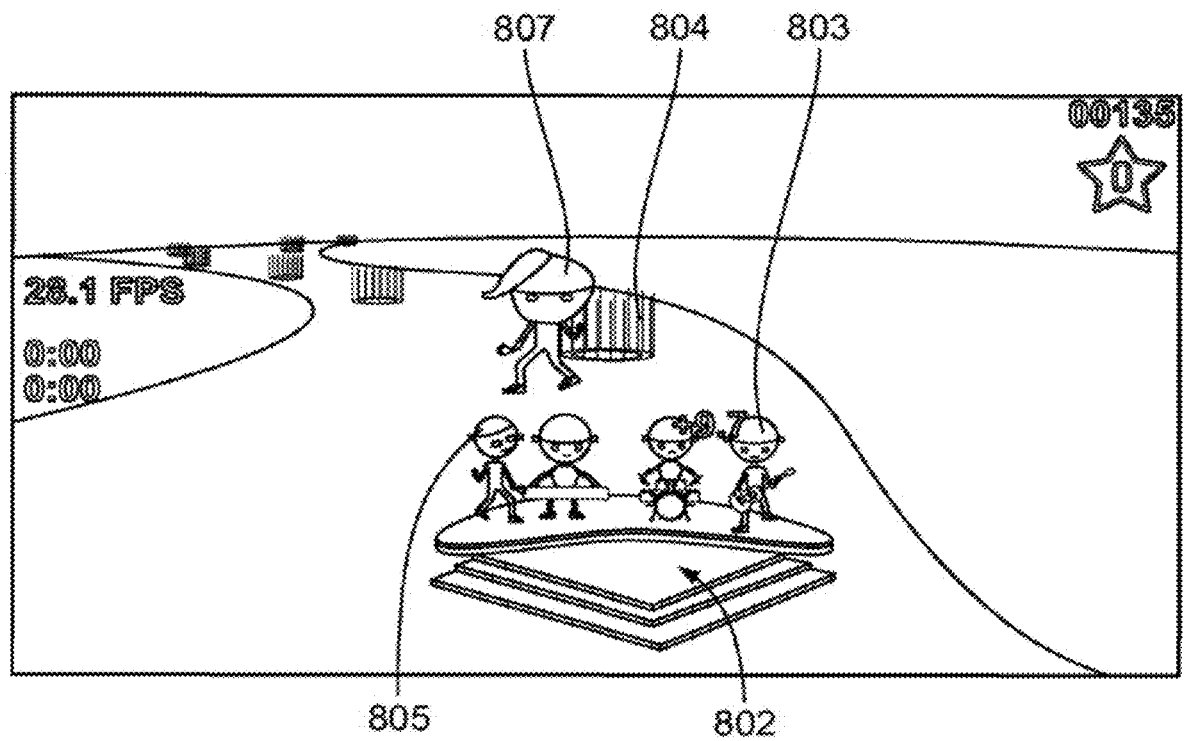
Figure 8C:
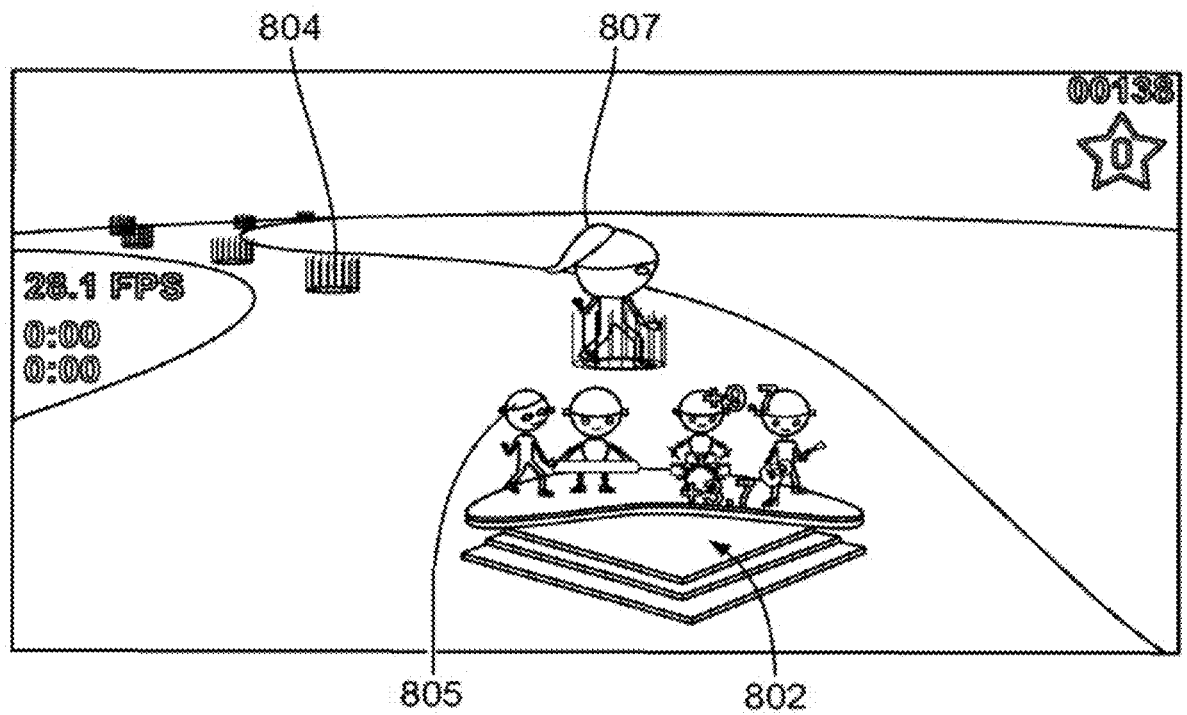
Figure 8D:
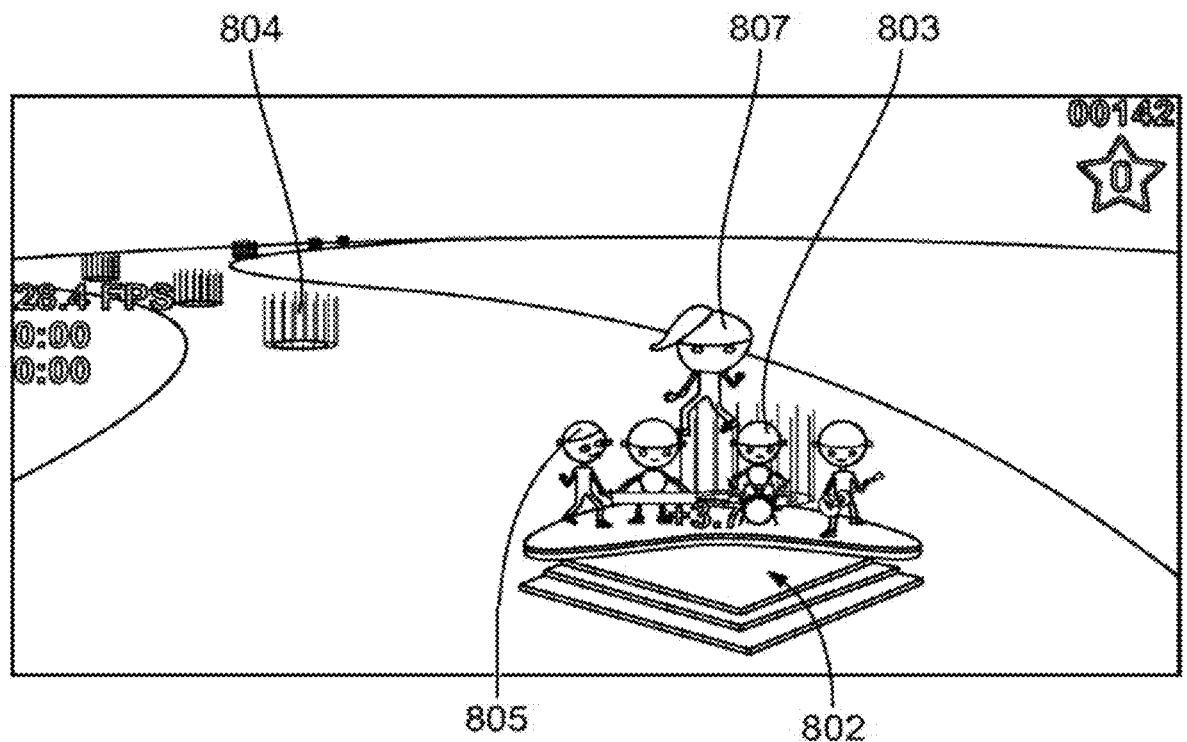
Figure 8E:
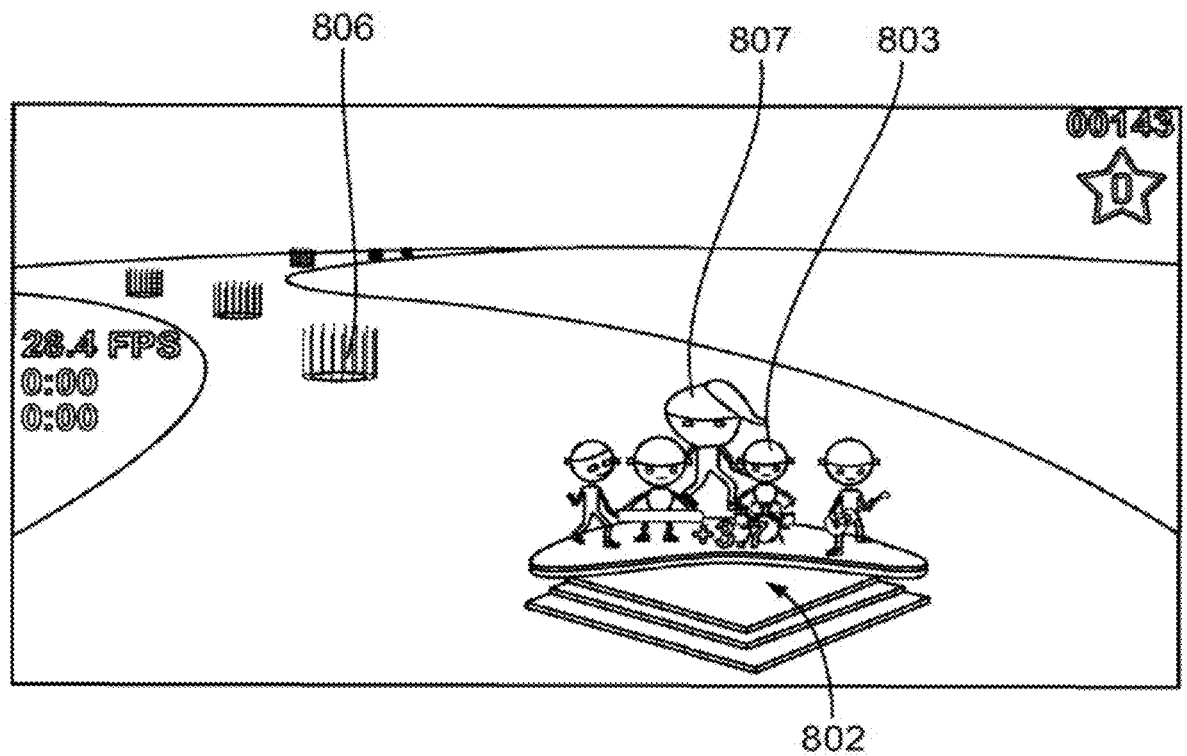
Figure 8F:
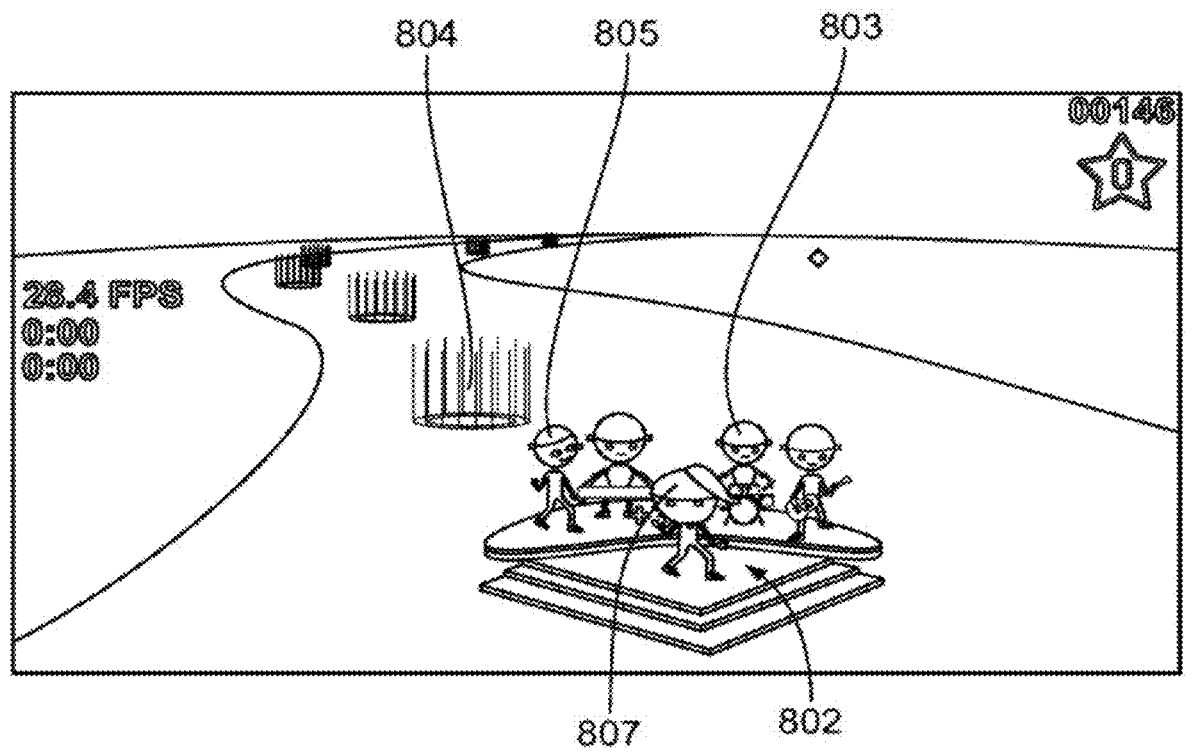
Figure 8G:
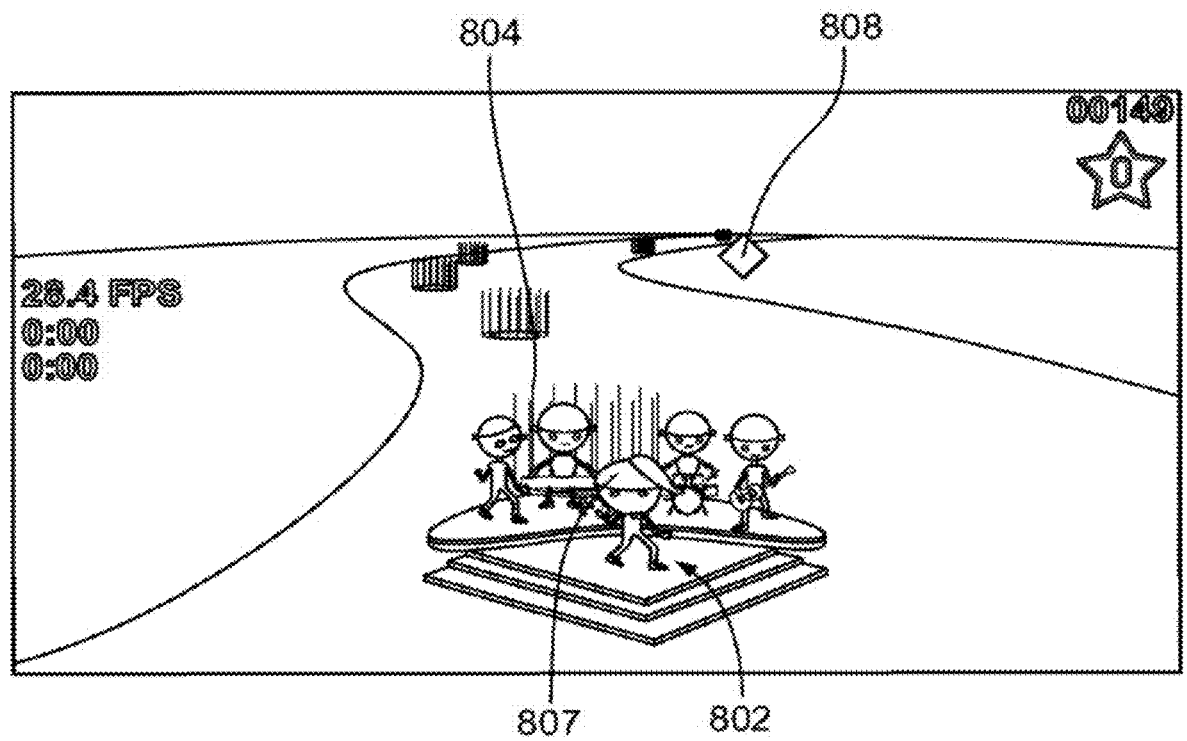
Figure 8H:
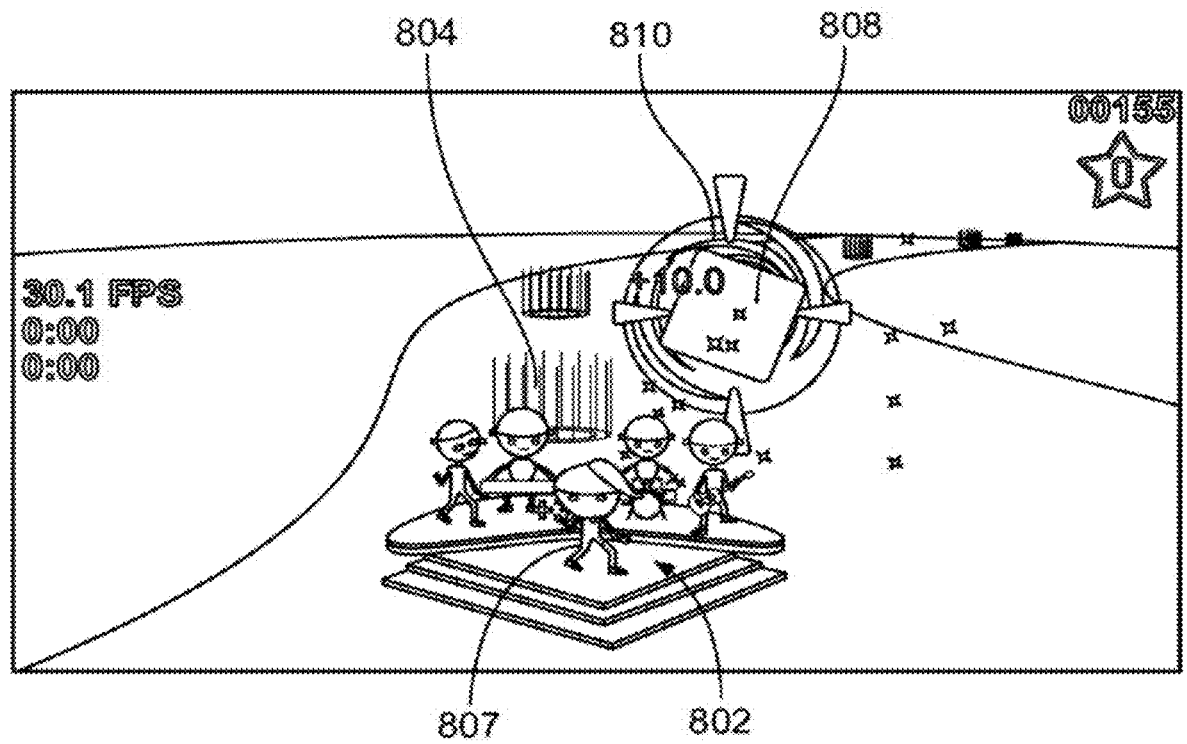
Figure 8I:
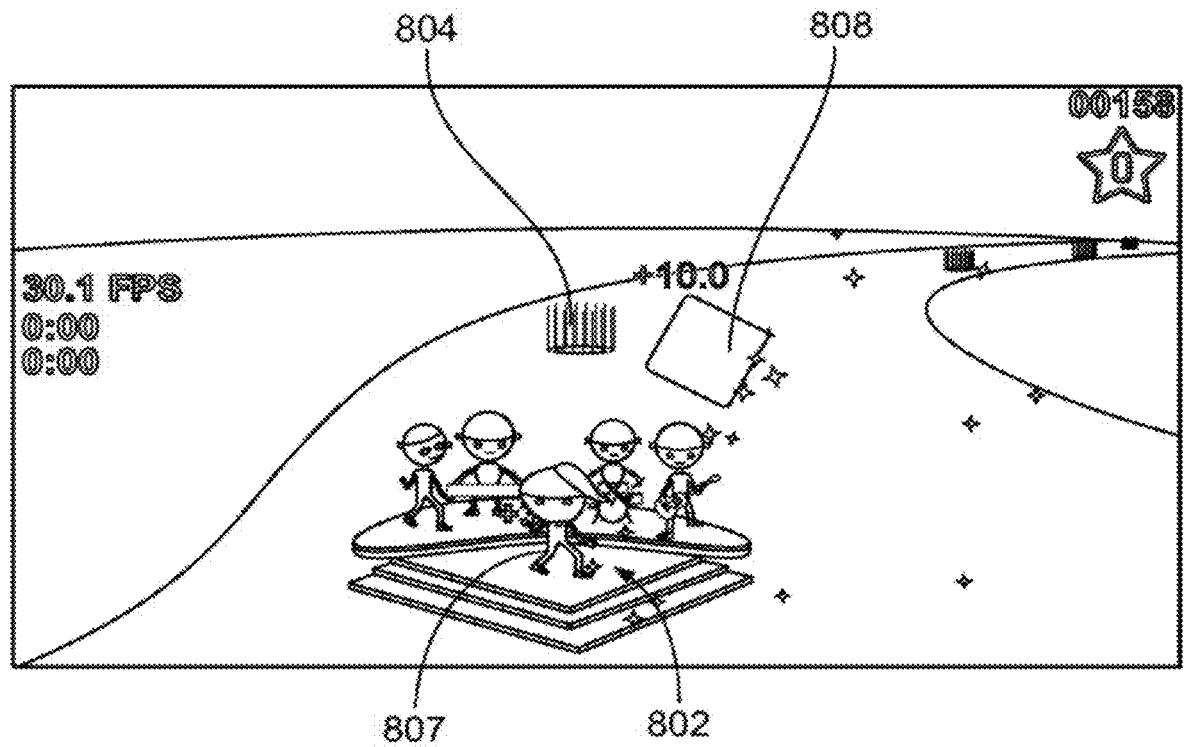
Figure 8J:
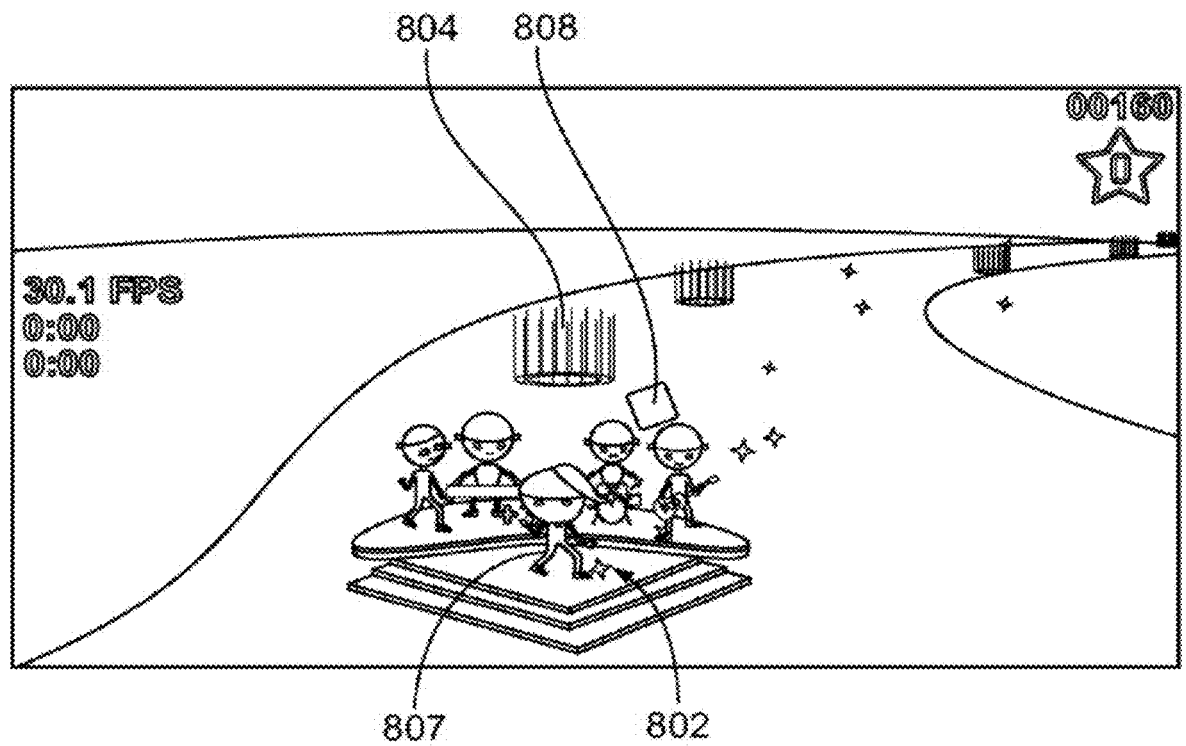
Figure 8K:
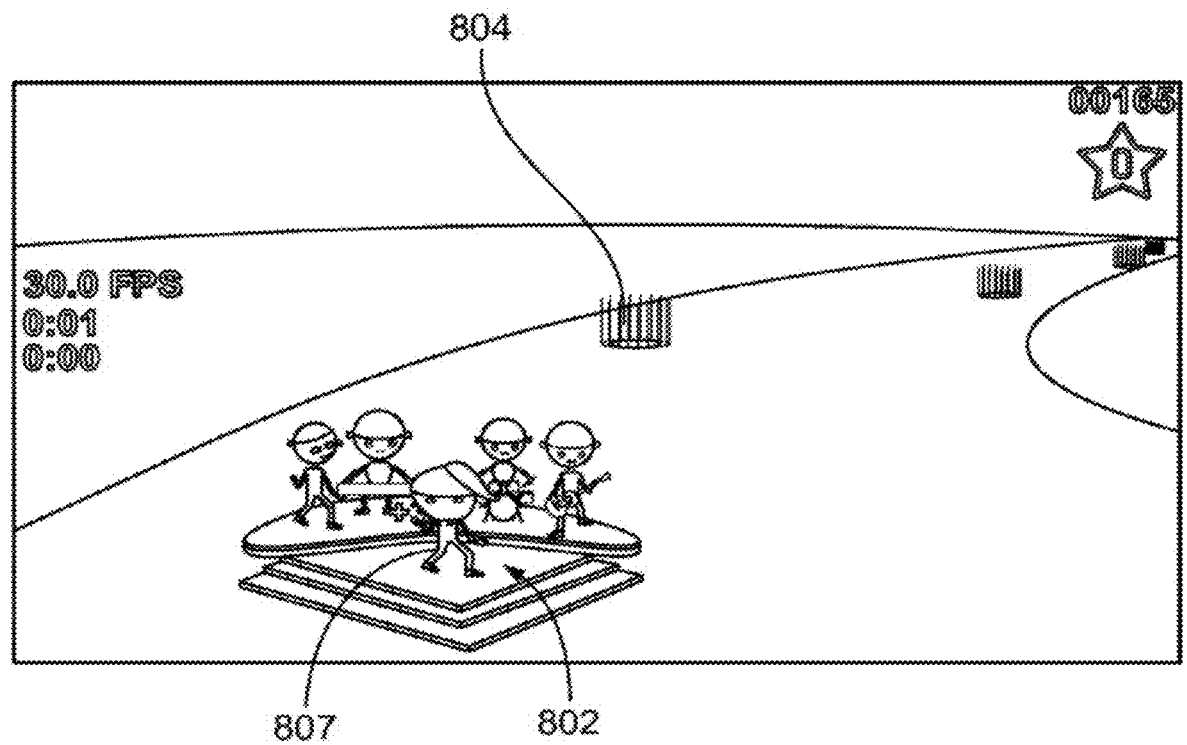
Figure 8L:
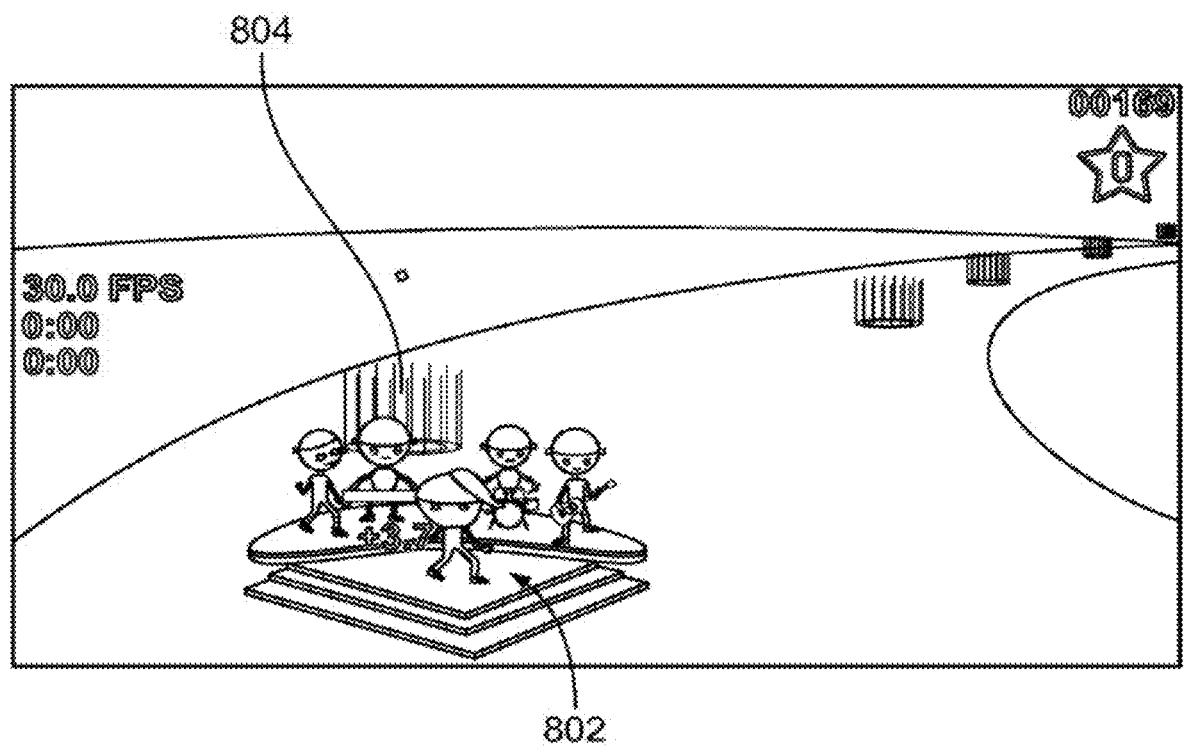
Figure 8M:
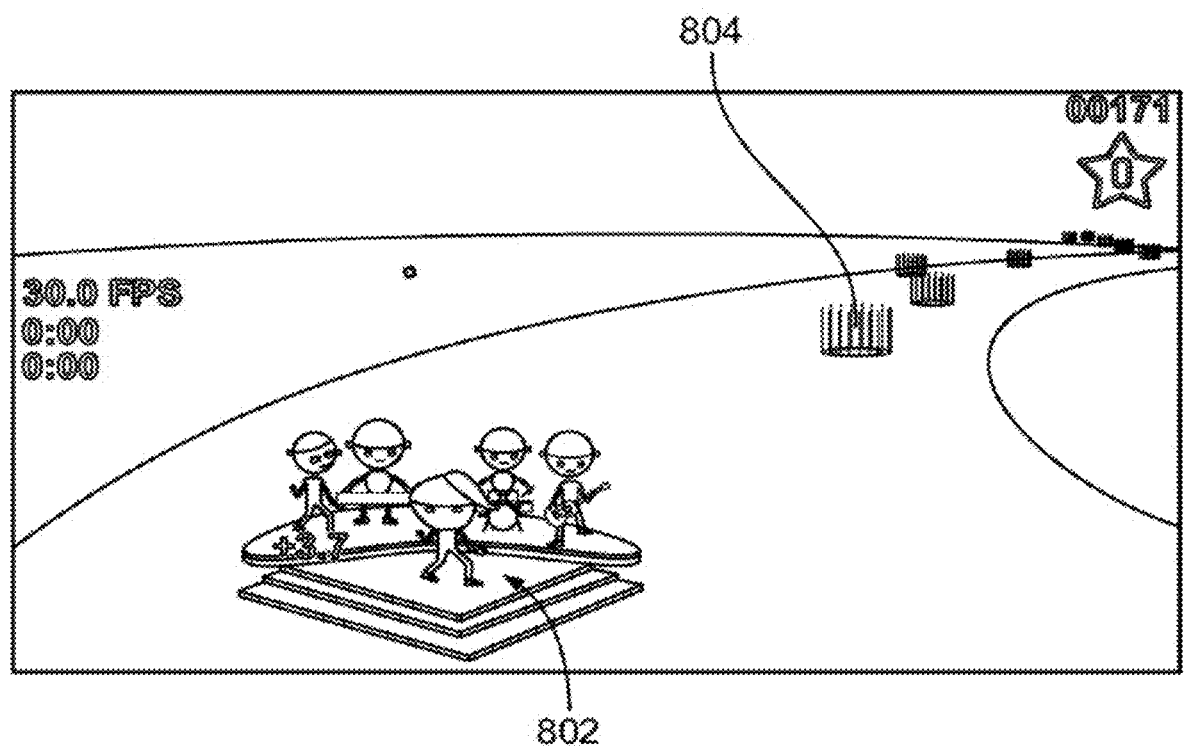
Figure 8N:
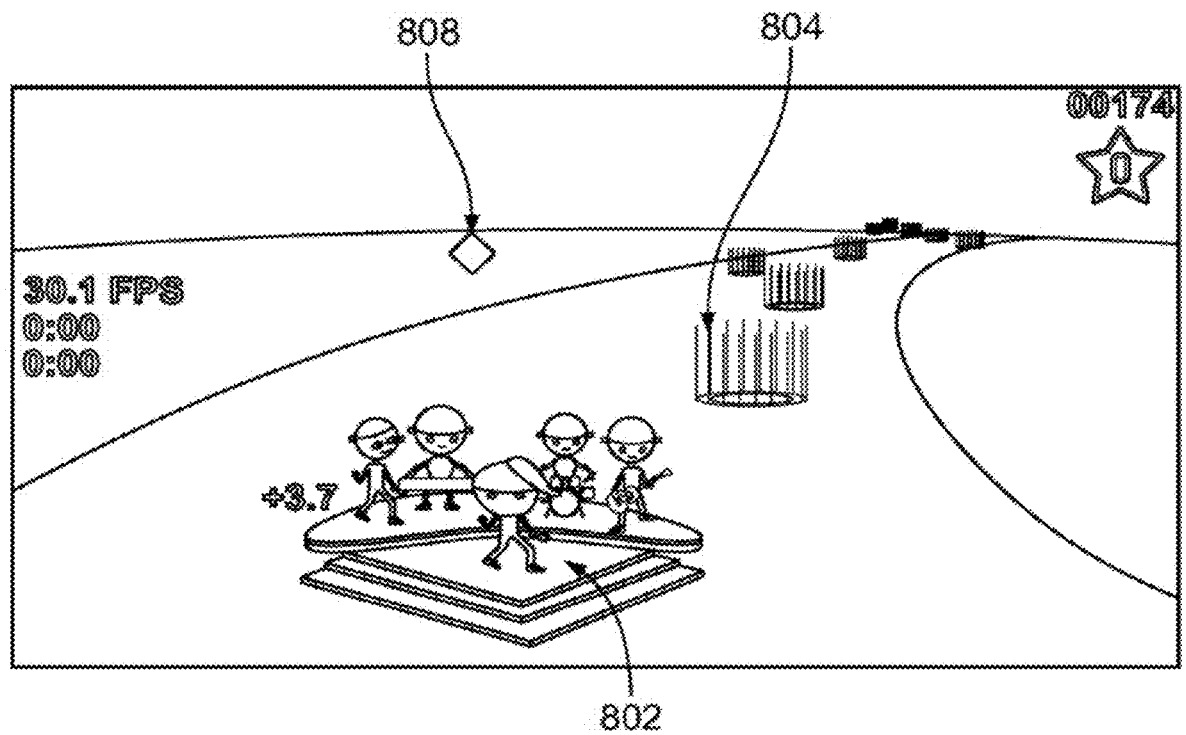
Figure 8O:
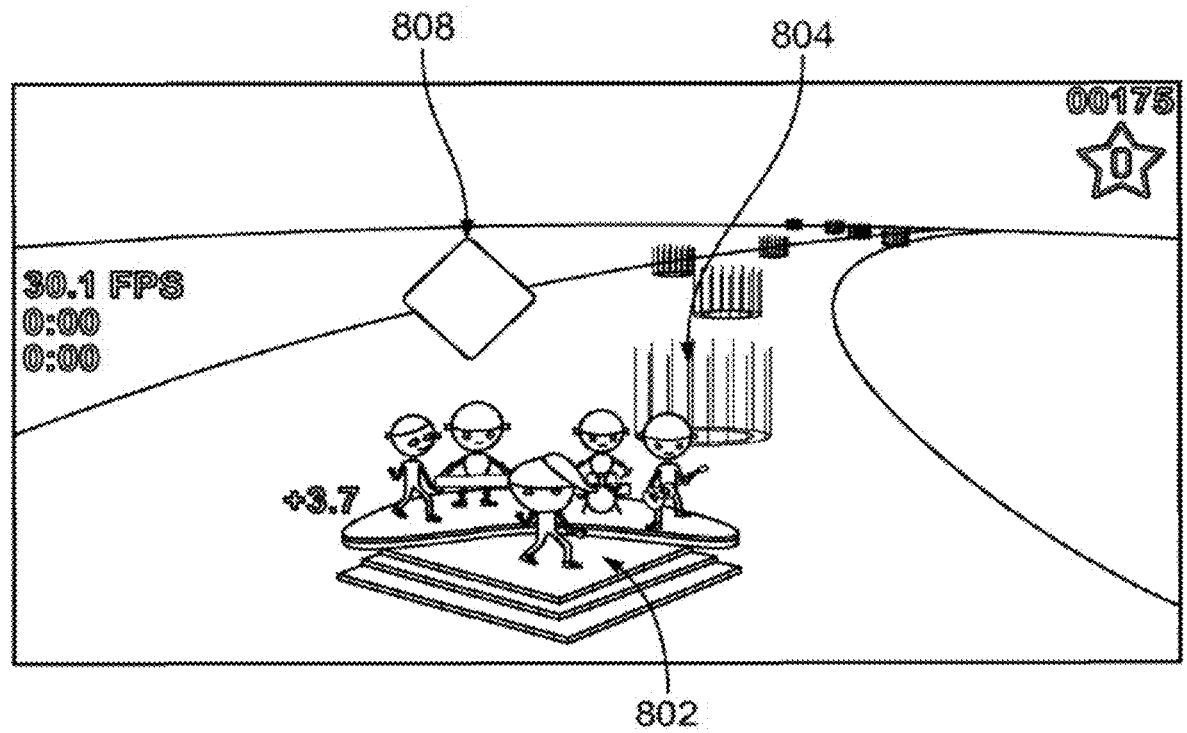
Figure 8P:
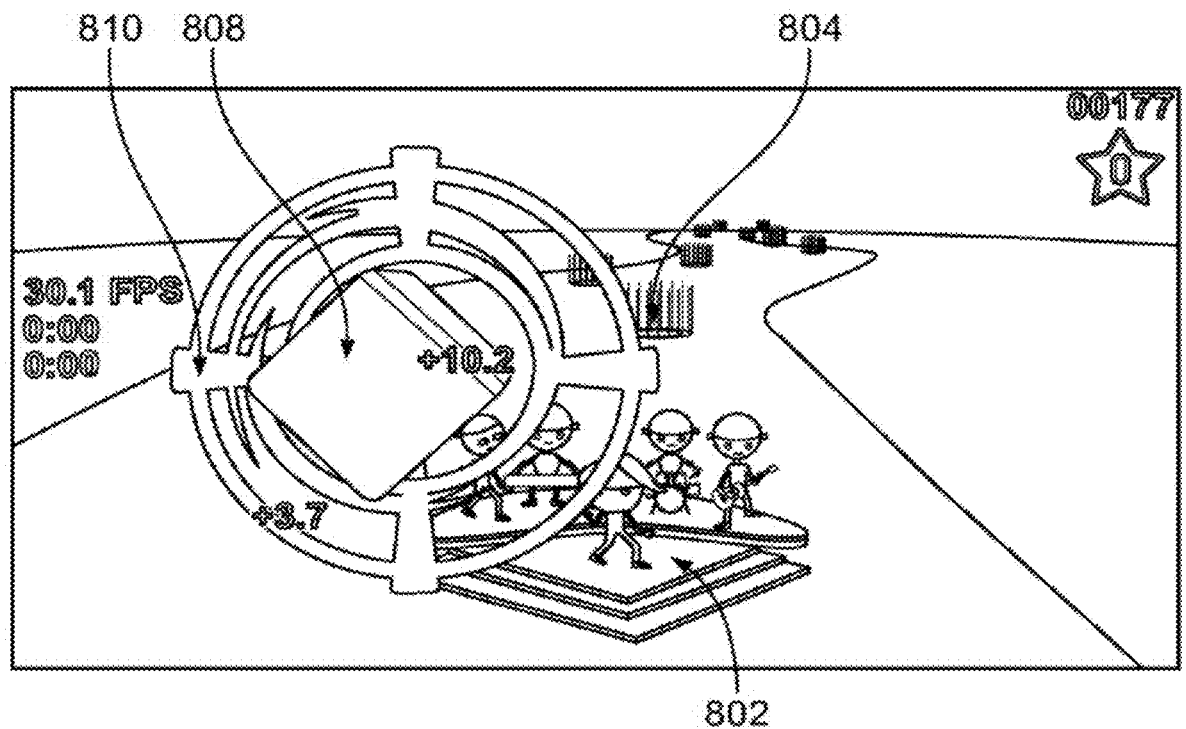
Figure 8Q:
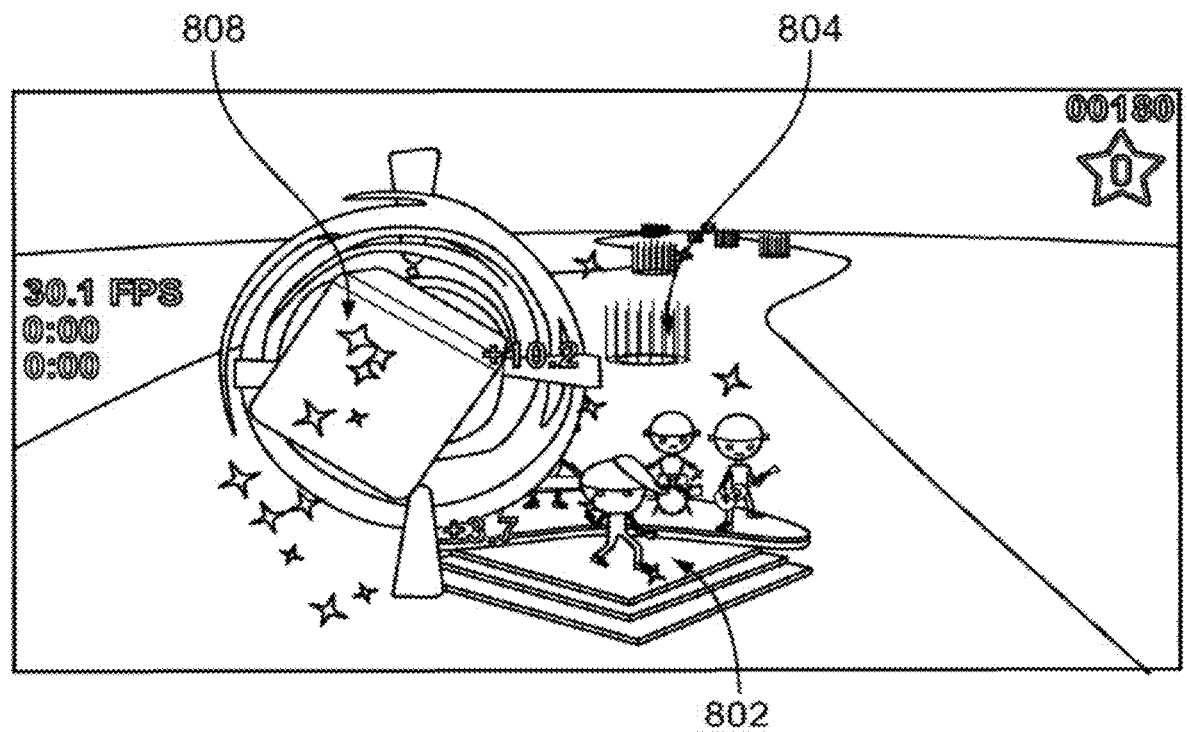
Figure 8R:
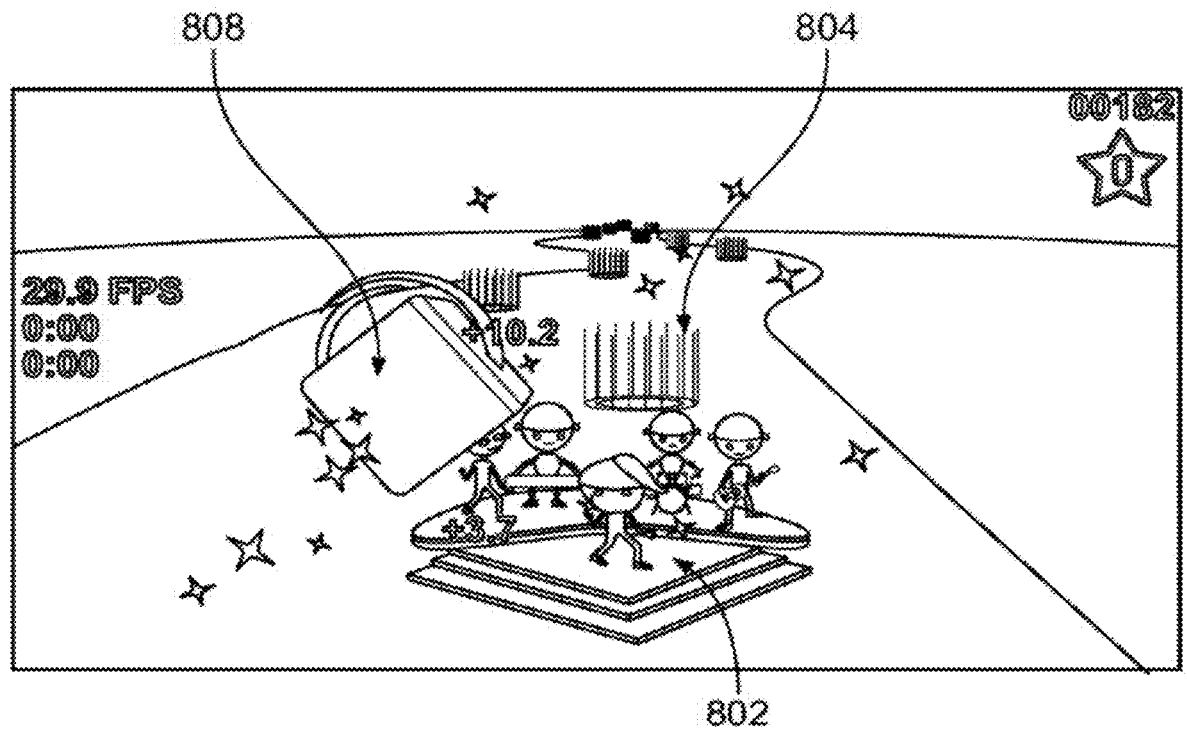
Figure 8S:
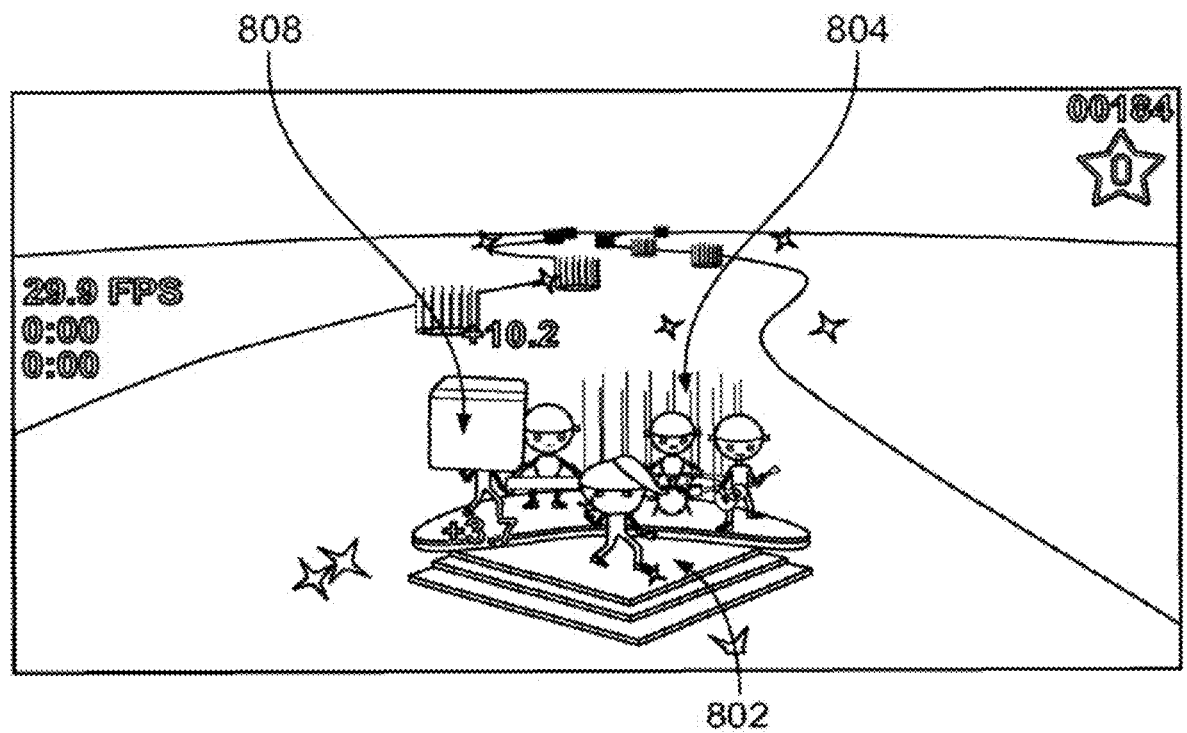
Figure 8T:
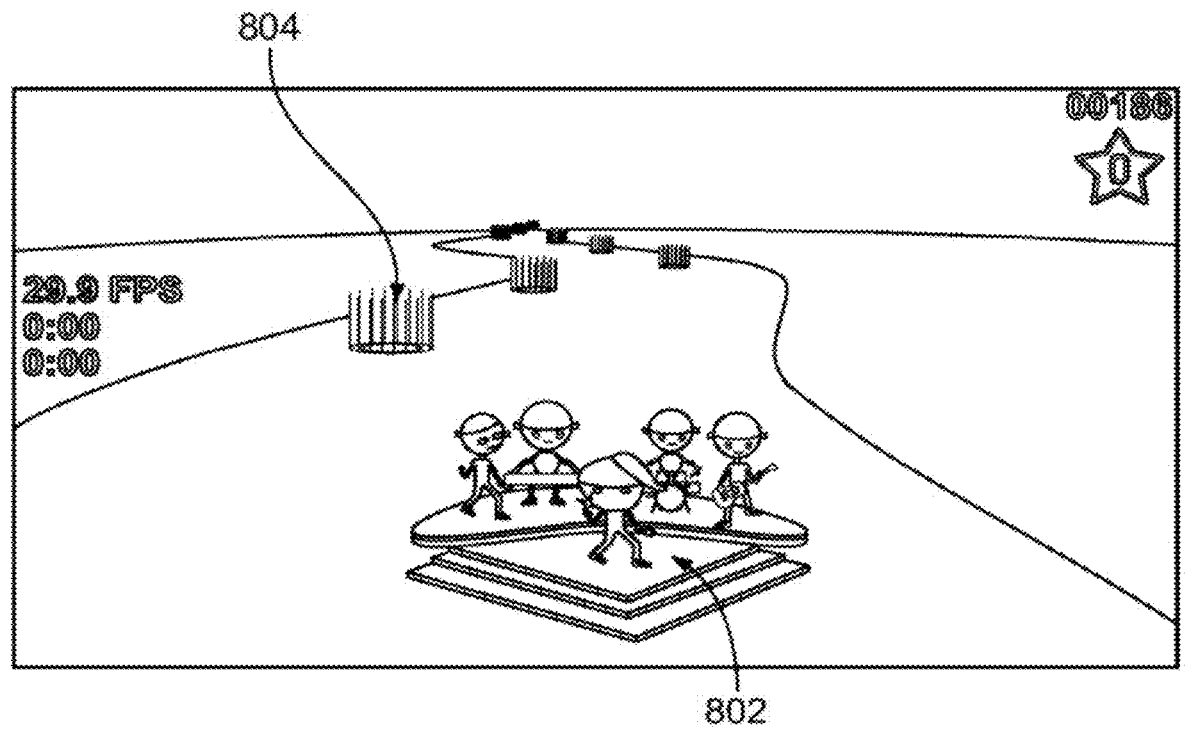
Figure 8U:
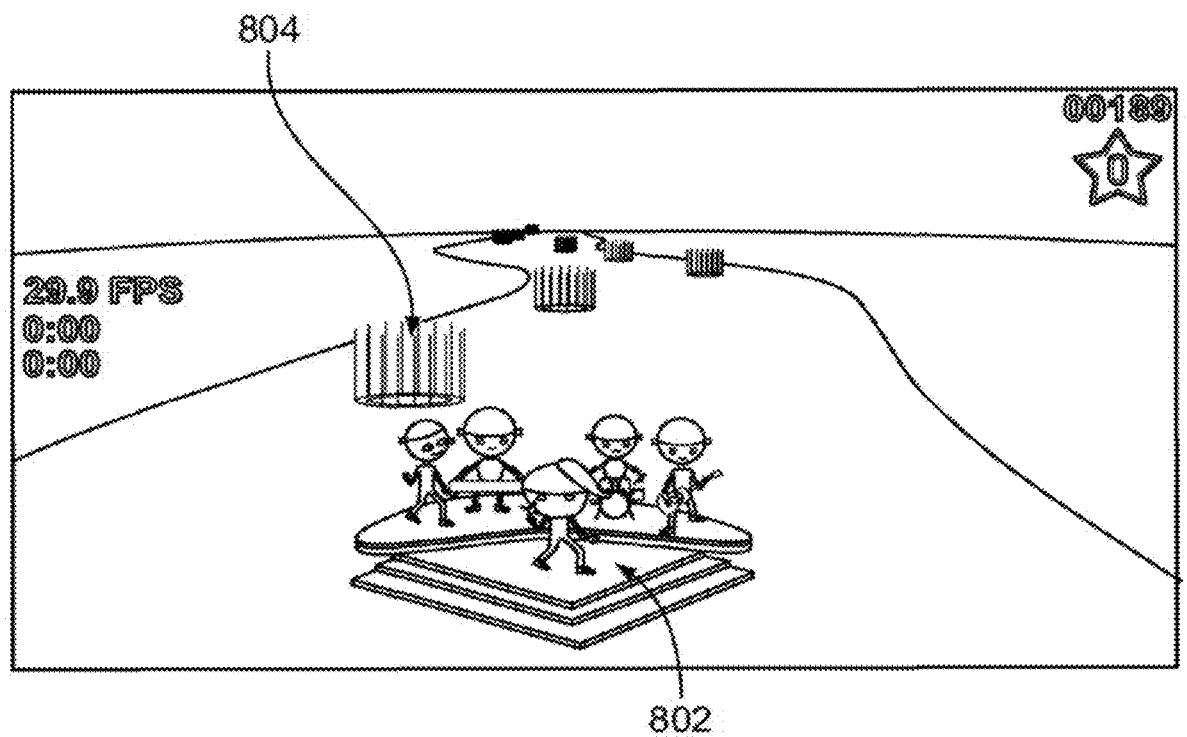
Figure 8V:
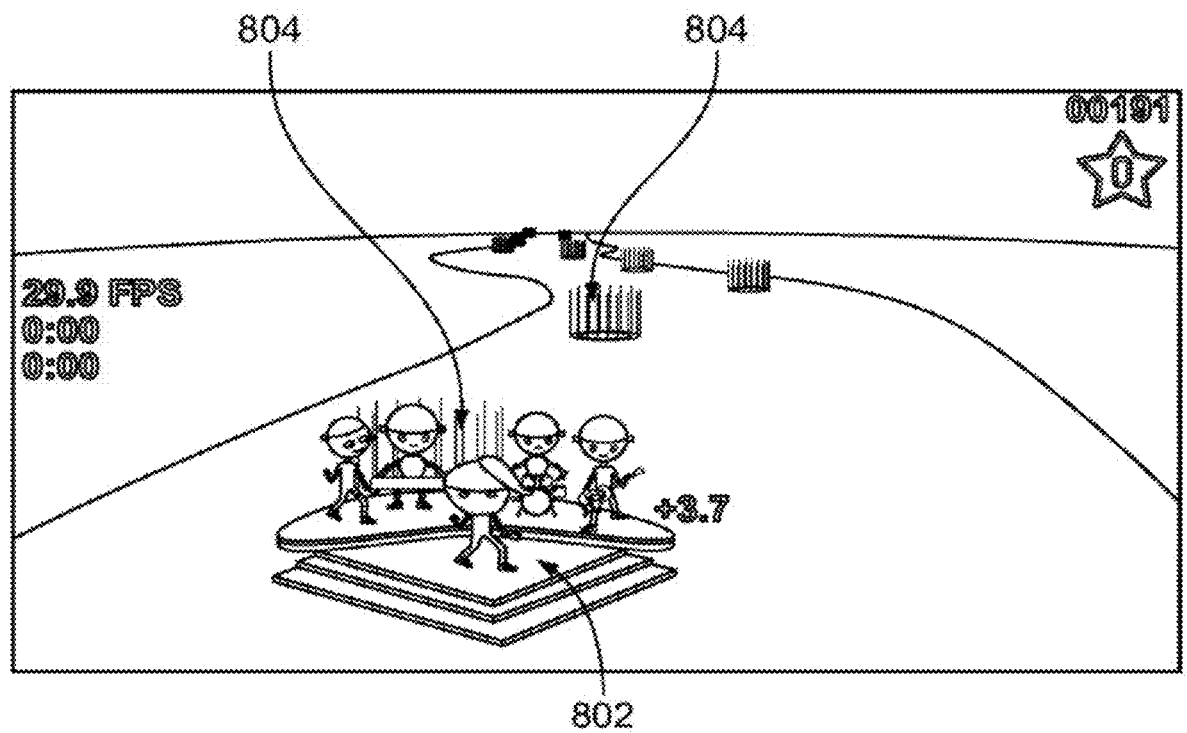
Figure 8W:
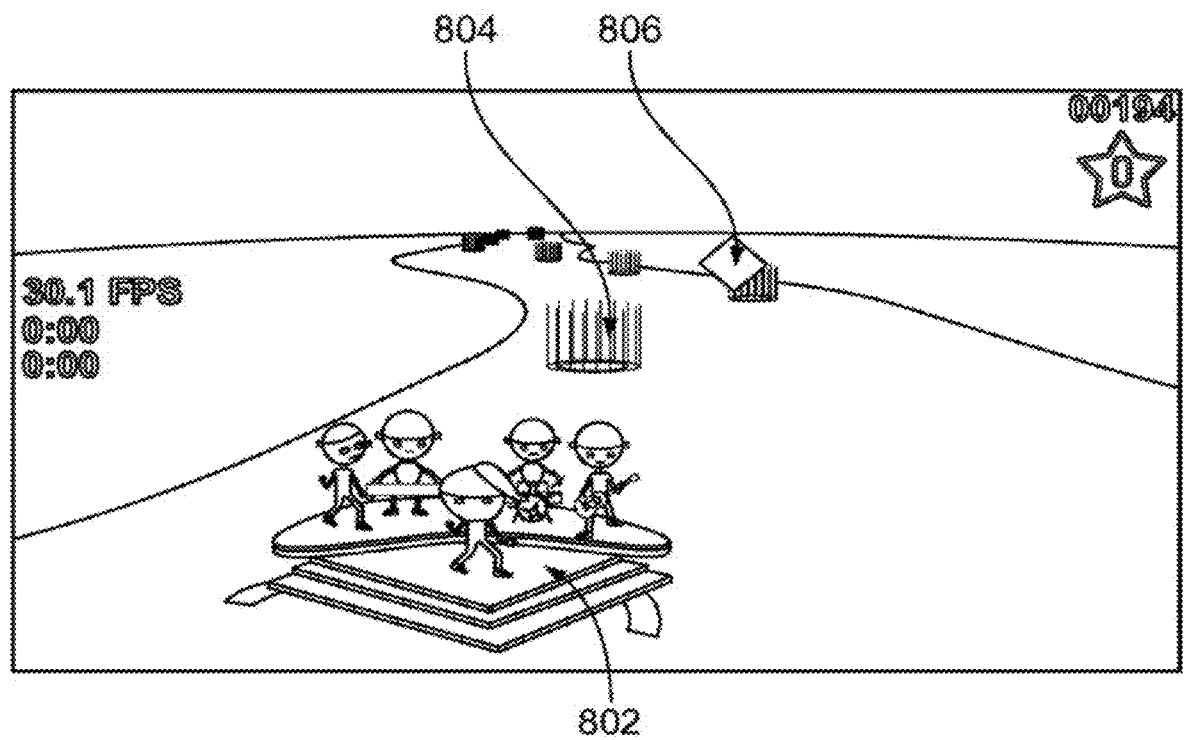
Figure 8X:
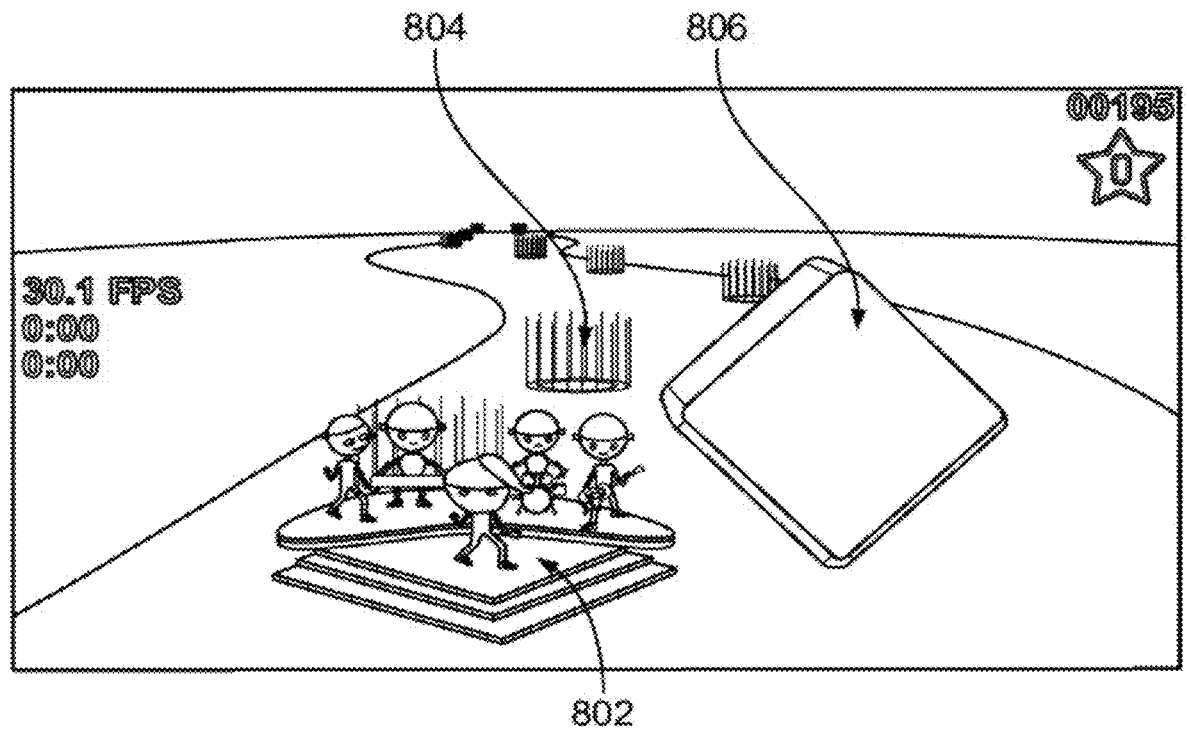
Figure 8Y:
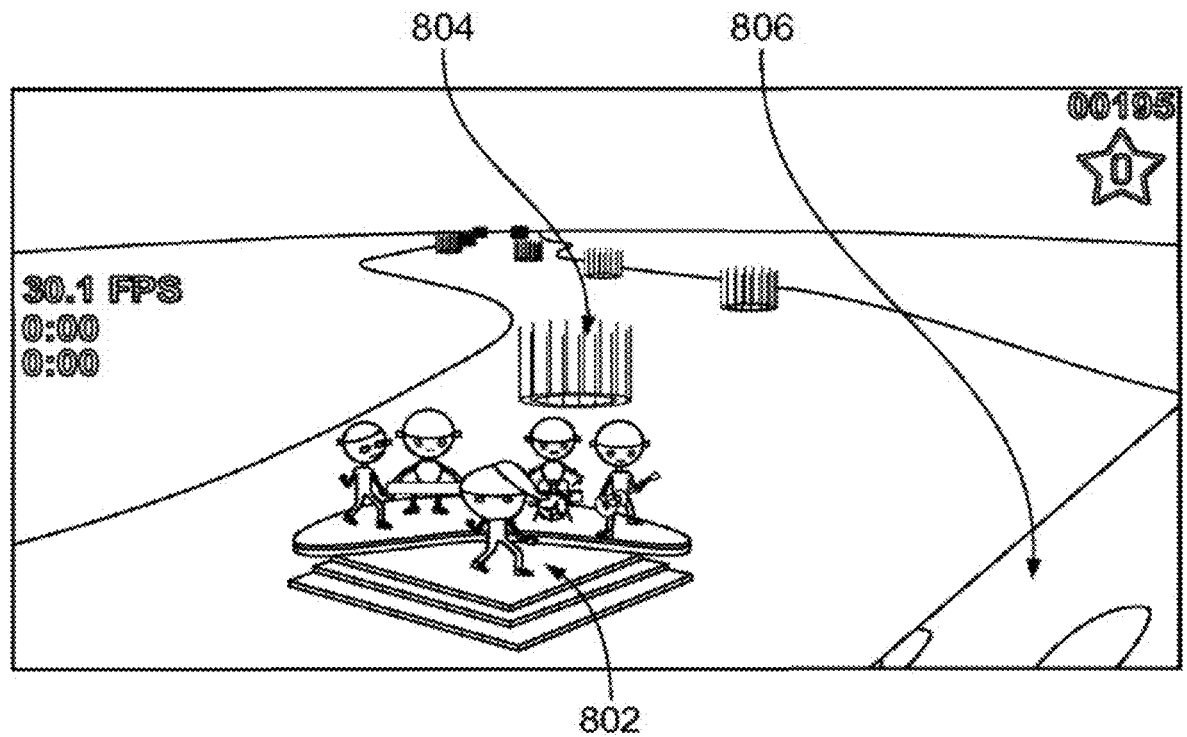

In the non-limiting examples of FIGS. 8H, 8P, and 8Q, the individual's success at selecting a target object 808 is indicated using circles 810 around the target object 808.

In the example of FIGS. 7A-7U and 8A-8Y, one or more processors, i.e., the processing unit of the exemplary system, method, and apparatus are configured to receive data indicative of the individual's physical actions to cause the avatar 802 to navigate the path. For example, the individual may be required to perform physical actions to "steer" the avatar, e.g., by changing the rotational orientation or otherwise moving a computing device. Such action can cause a gyroscope or accelerometer or other motion or position sensor device to detect the movement, thereby providing measurement data indicative of the individual's degree of success in performing the navigation task.

In the examples of FIGS. 7A-7U and 8A-8Y, the one or more processors of the exemplary system, method, and apparatus are configured to receive data indicative of the individual's physical actions to perform the target discrimination. For example, the individual may be instructed prior to a trial or other session to tap, or make another physical indication, in response to a display of a target object having the specified color (target object 808), and not to tap to make the physical indication in response to display of a non-target object 806. In FIGS. 7A-7U and 8A-8Y, the target discrimination acts as an interference (i.e., a secondary task) to the primary navigation task, in an interference processing multitasking implementation. As described hereinabove, the exemplary systems, methods, and apparatus can cause the processing unit to render a display feature (e.g., display feature 500) to display the instructions to the individual as to the expected performance (i.e., which object to respond to in the target discrimination task, and what is expected in the performance of the navigation tasks). As also described hereinabove, the processing unit of the example system, method, and apparatus can be configured to (i) receive the data indicative of the measure of the degree and type of the individual's response to the primary task substantially simultaneously as the data indicative of the measure of the individual's response to the interference is collected, or (ii) to selectively receive data indicative of the measure of the individual's response to the specified object as a target stimulus (i.e., an interruptor (target object)) substantially simultaneously (i.e., at substantially the same time) as the data indicative of the measure of the degree and type of the individual's response to the task is collected and to selectively not collect the measure of the individual's response to the non-target stimulus (i.e., a distraction (non-target object)) substantially simultaneously (i.e., at substantially the same time) as the data indicative of the measure of the degree and type of the individual's response to the primary task is collected.

In FIGS. 7A-7U and 8A-8Y, modifications to the computerized adjustable element, e.g., the type or number of avatar objects added to the avatar vehicle 802, is configured to signals to the individual that analysis of the data indicative of the individual's responses to the navigation task and/or target discrimination interference indicate satisfactory performance. In this example, the modifications to the computerized adjustable element, e.g., the type or number of avatar objects added to the avatar vehicle 802 is an example of a change in the type of rewards presented to the individual as an indication of satisfactory performance. Many other types of reward elements can be used, and the rate and type of reward elements displayed can be changed and modulated as a time-varying element.

Figure 9A:
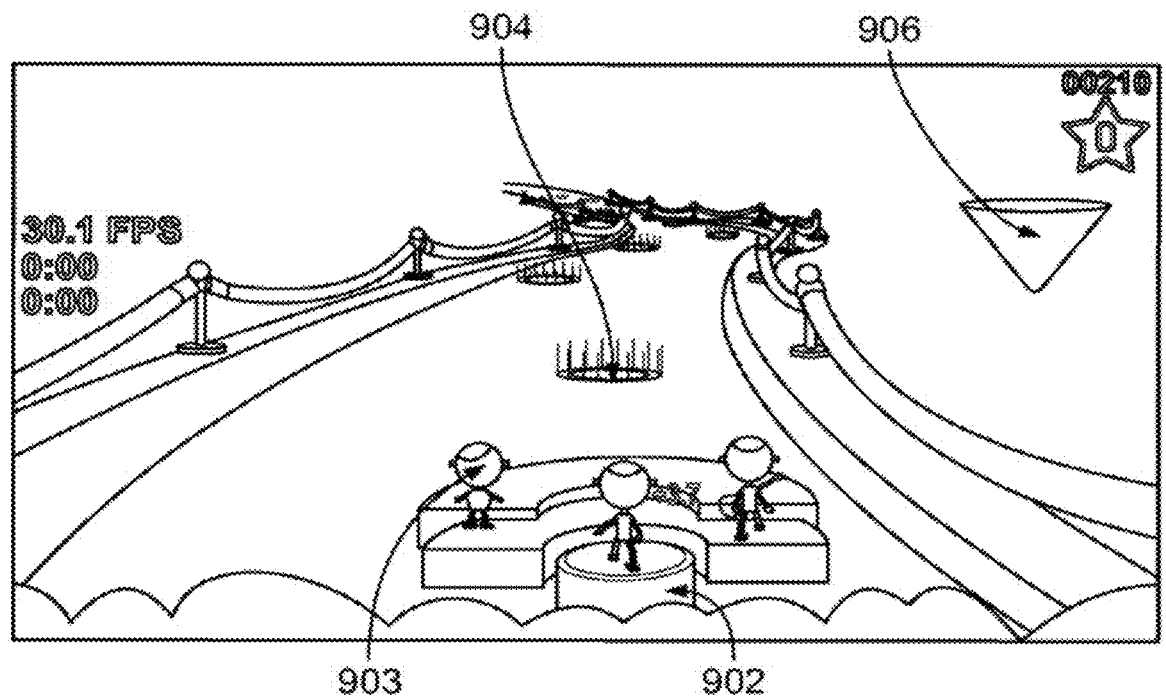
Figure 9B:
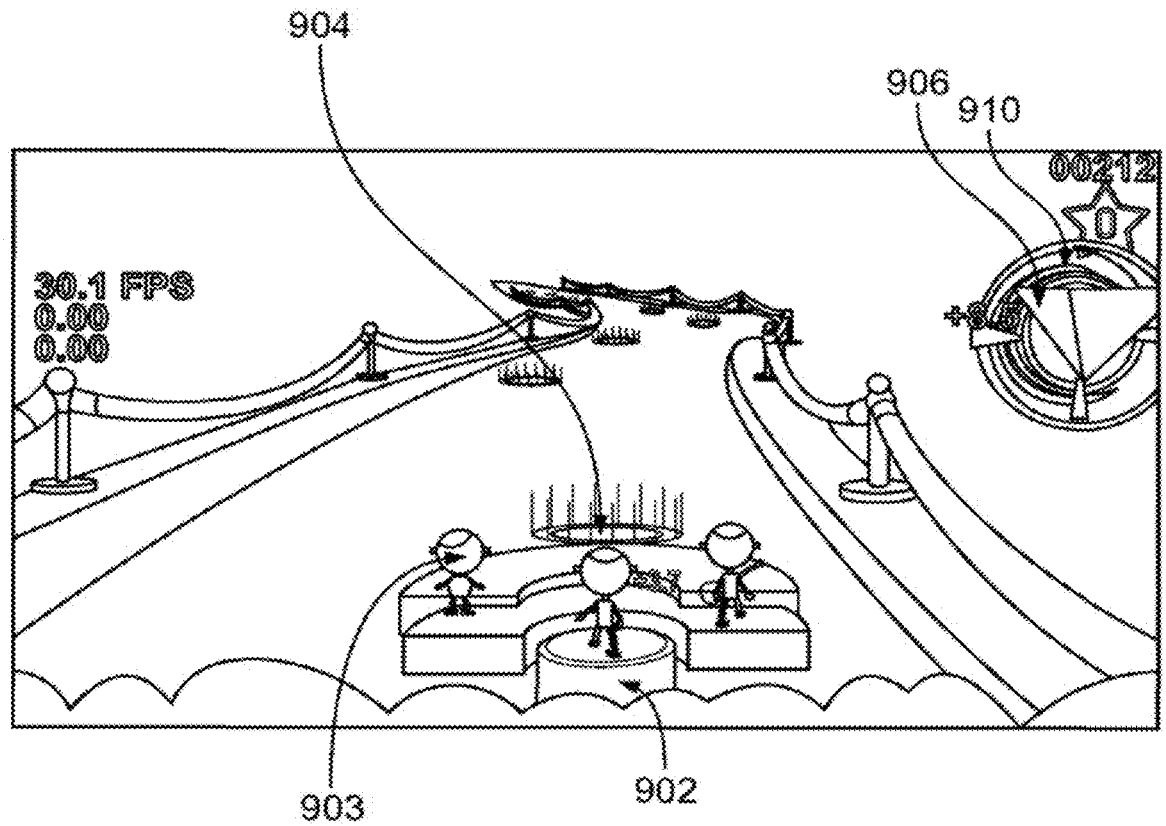
Figure 9C:
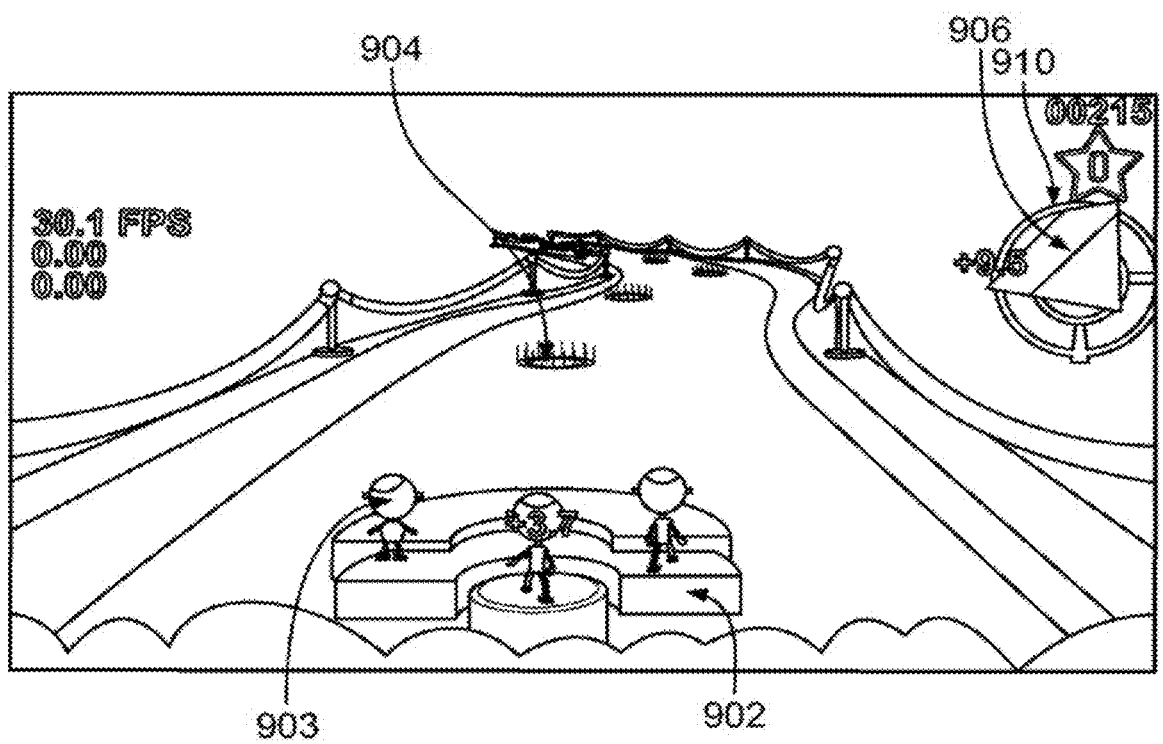
Figure 9D:
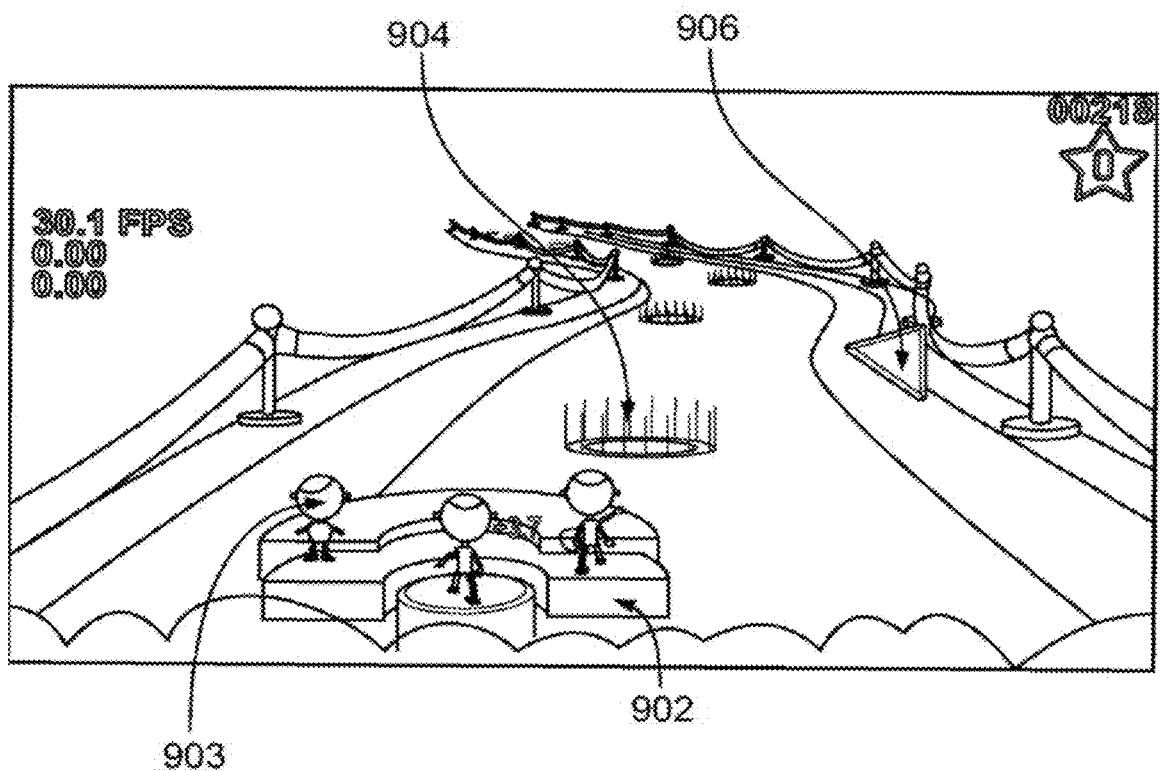
Figure 9E:
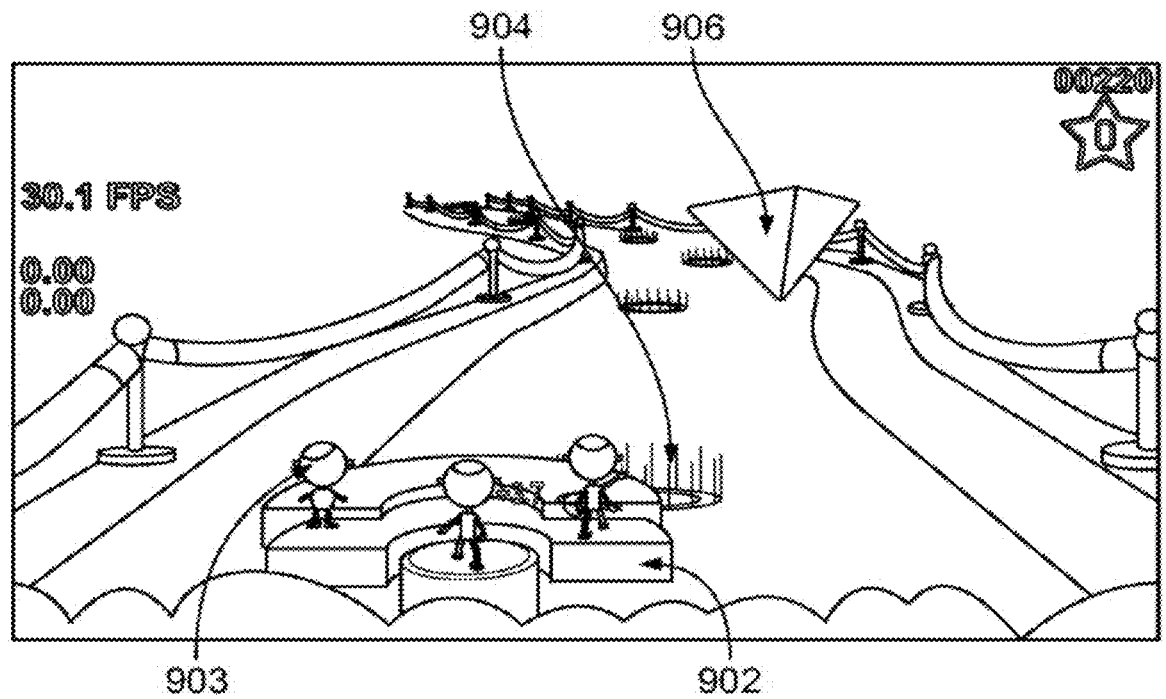
Figure 9F:
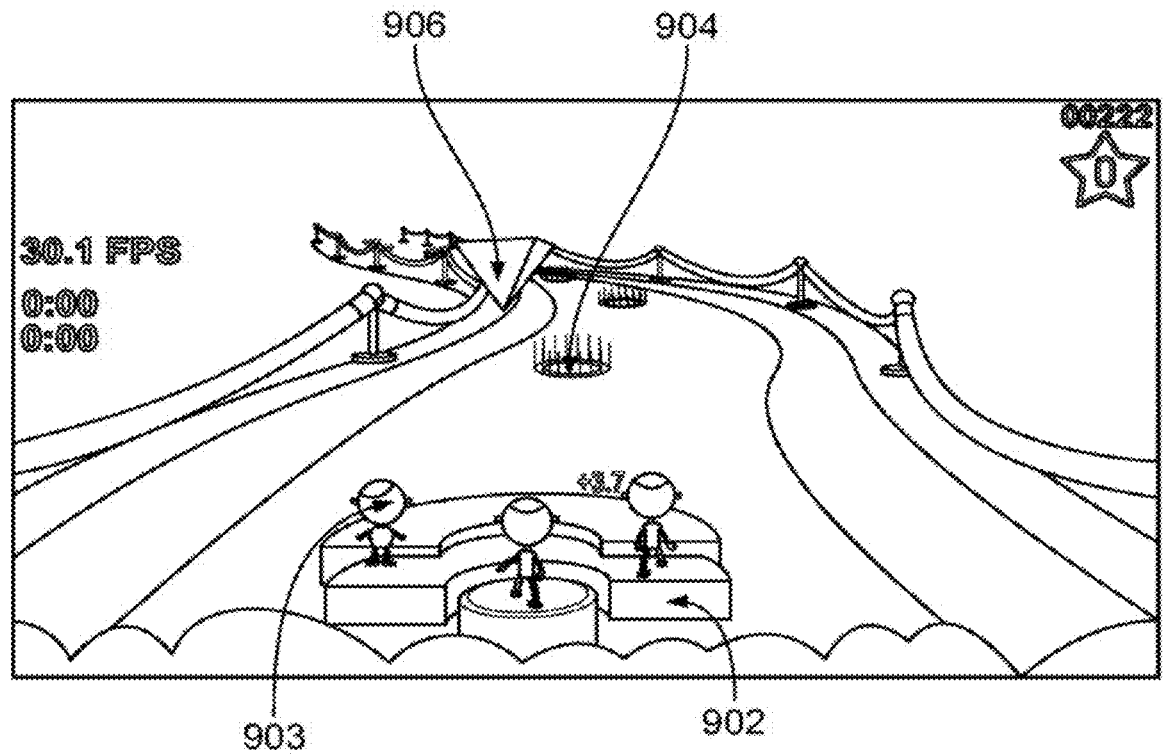
Figure 9G:
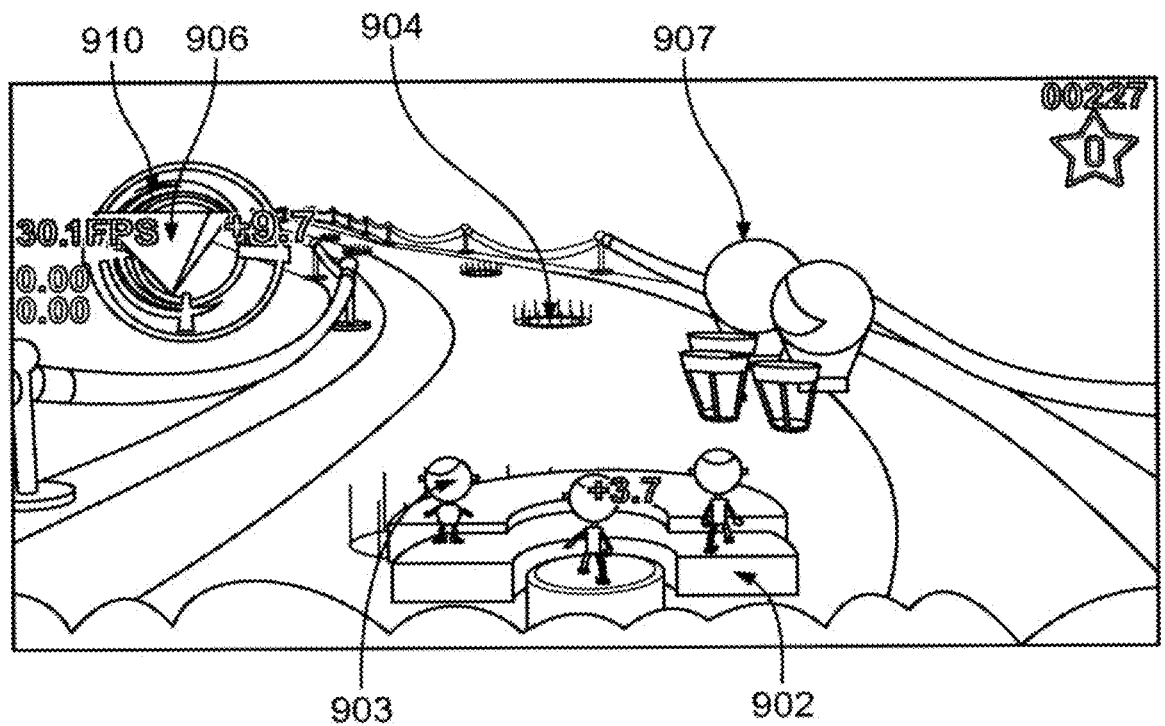
Figure 9H:
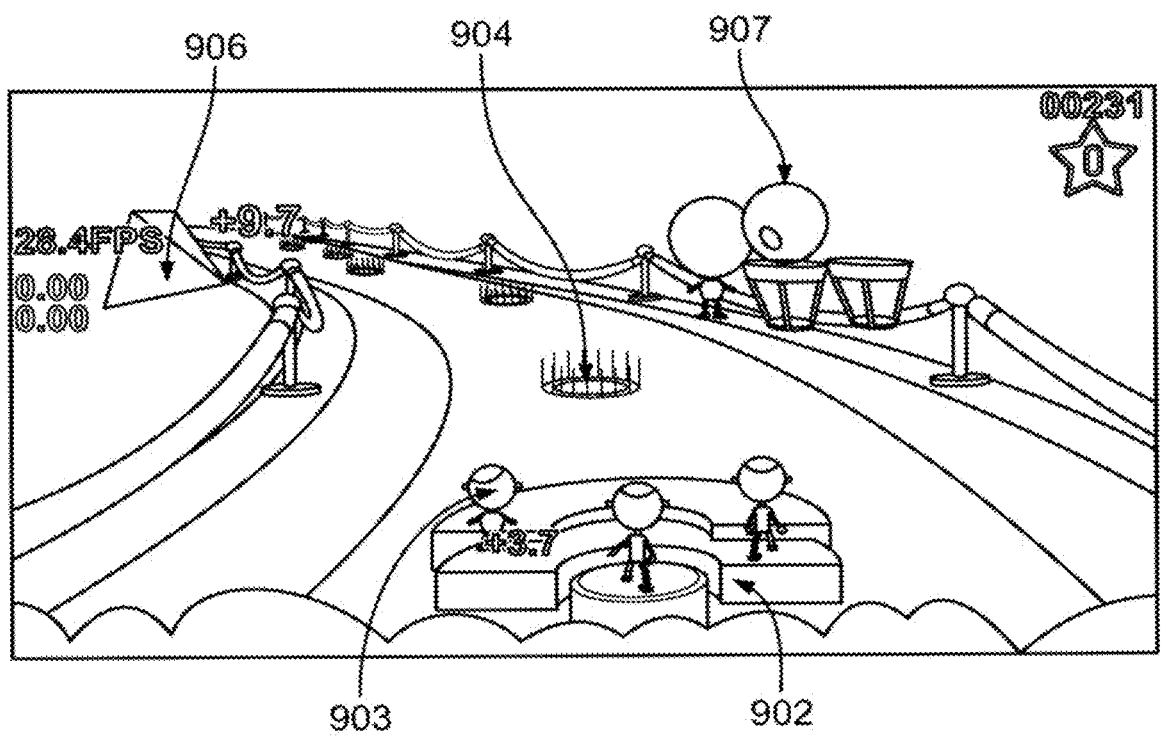
Figure 9I:
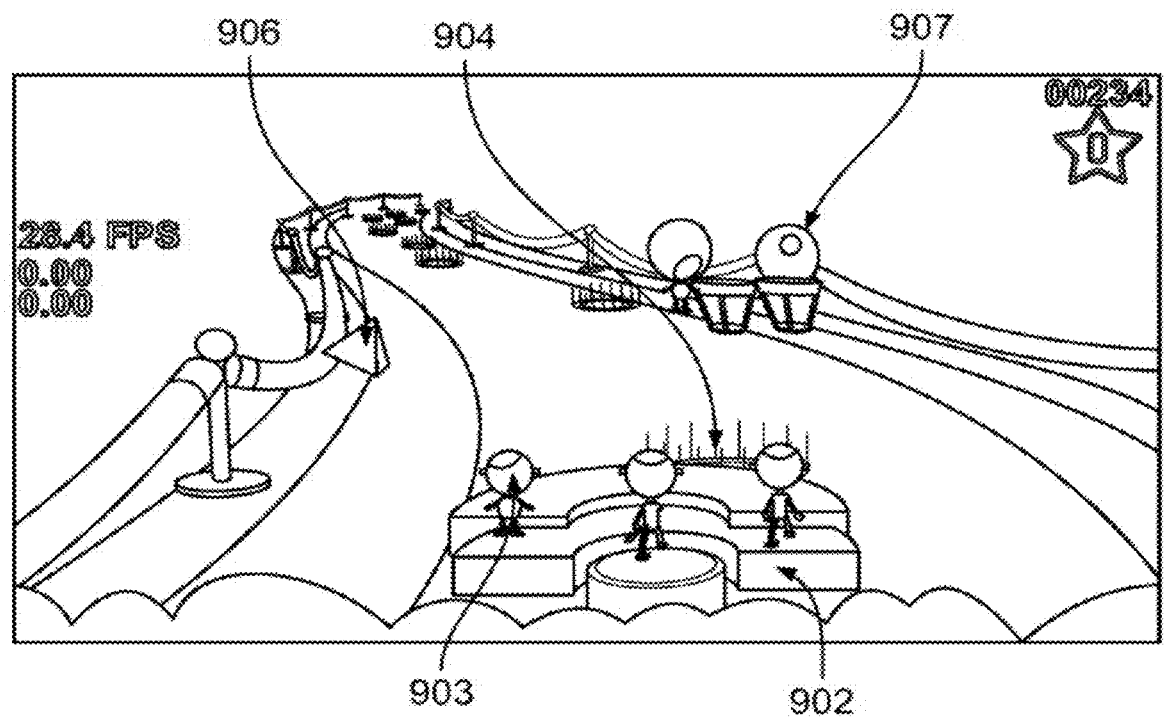
Figure 9J:
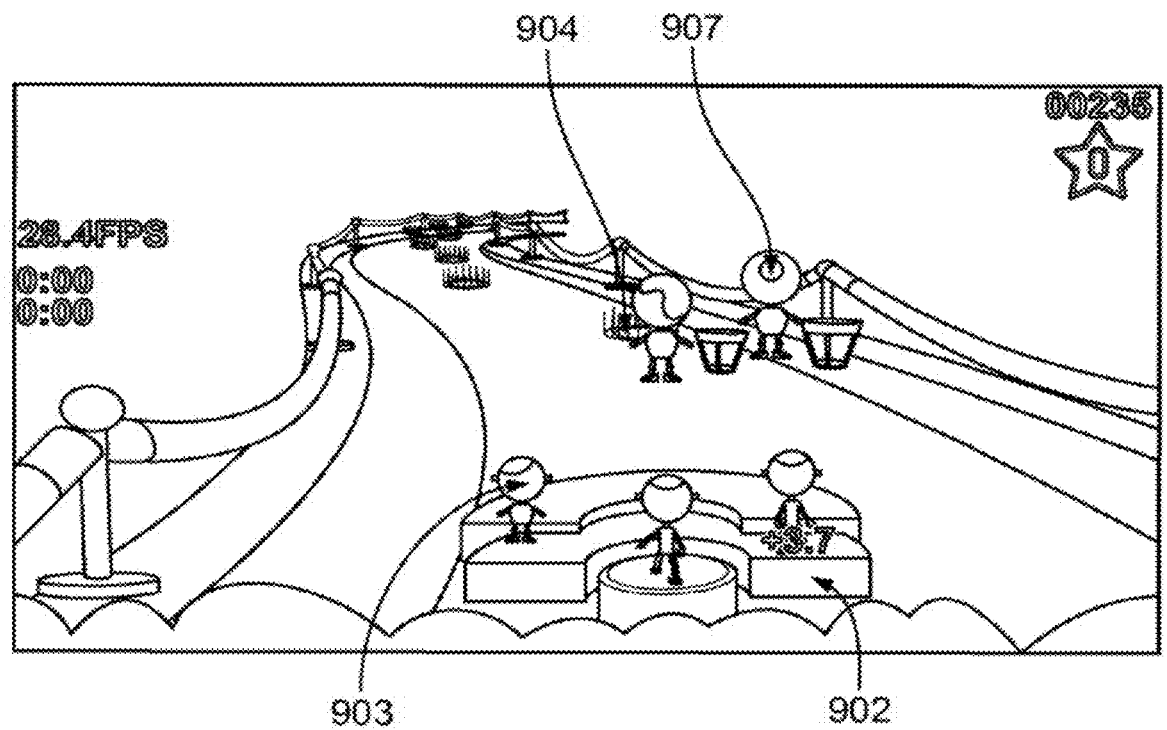
Figure 9K:
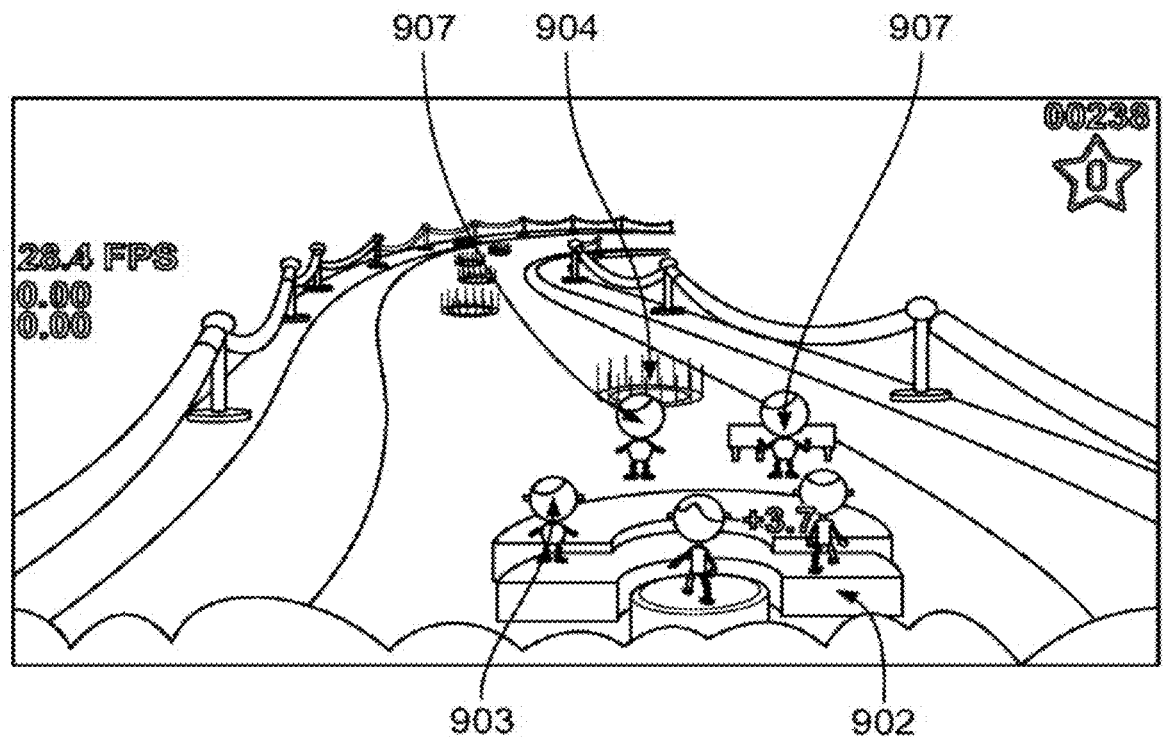
Figure 9L:
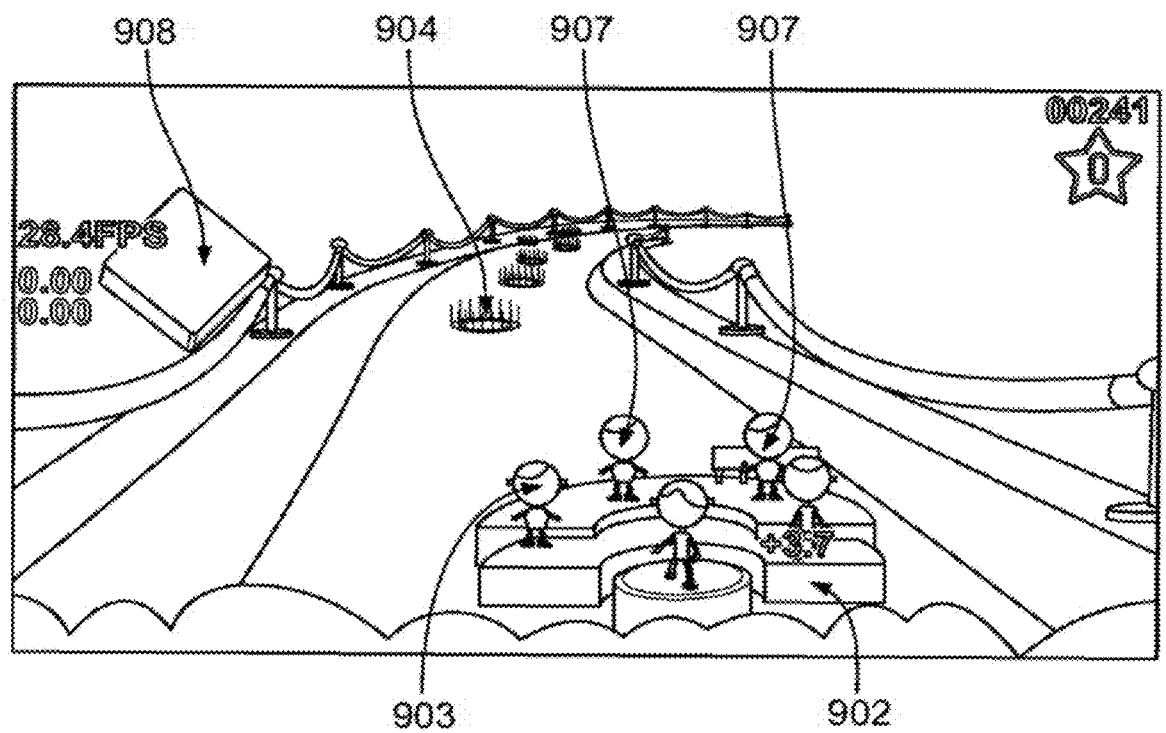
Figure 9M:
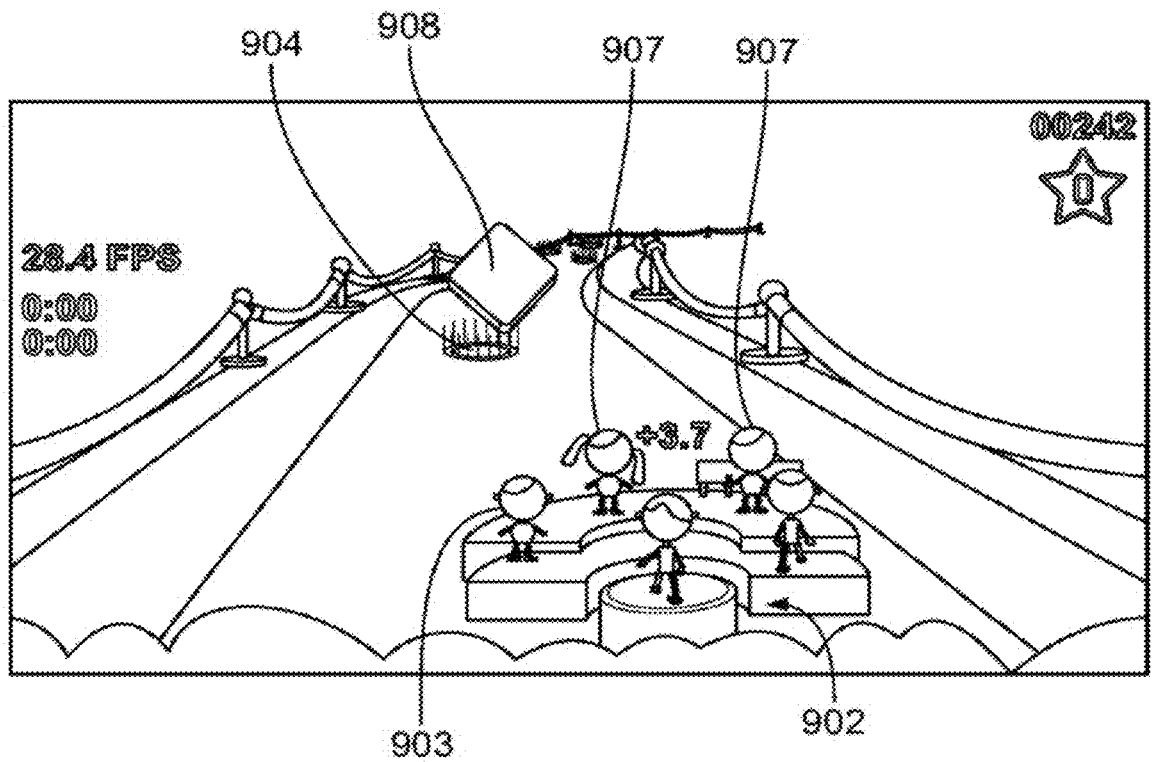
Figure 9N:
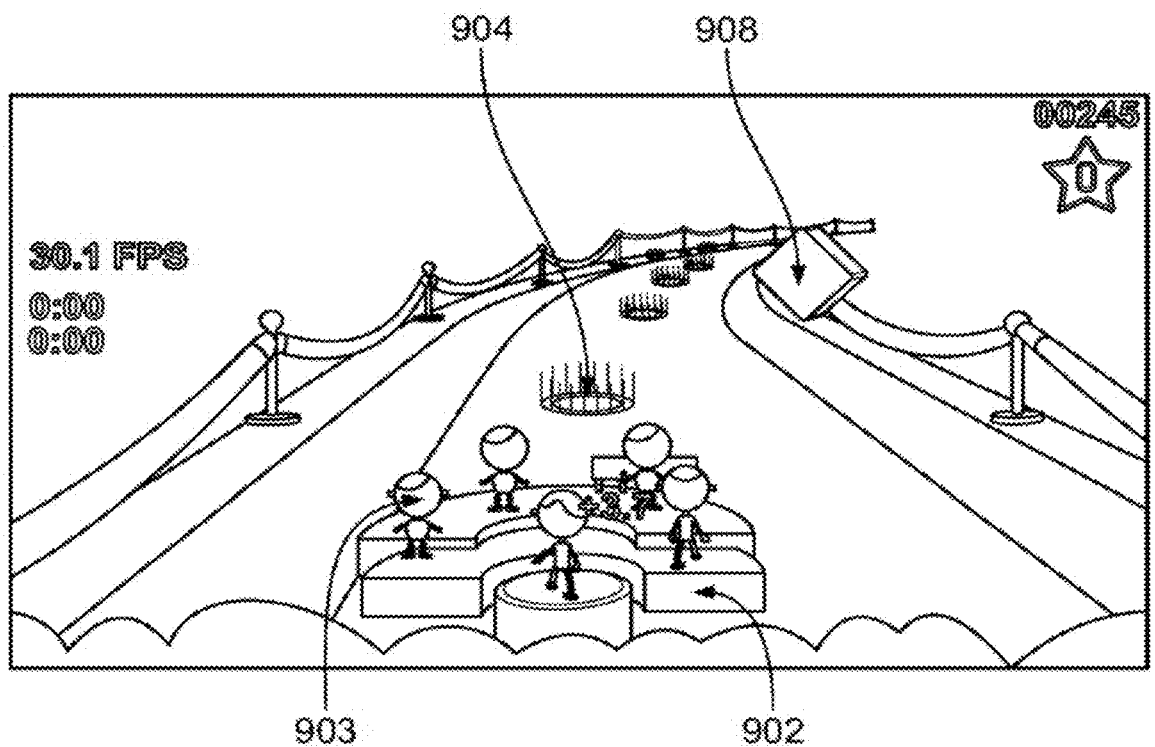
Figure 9O:
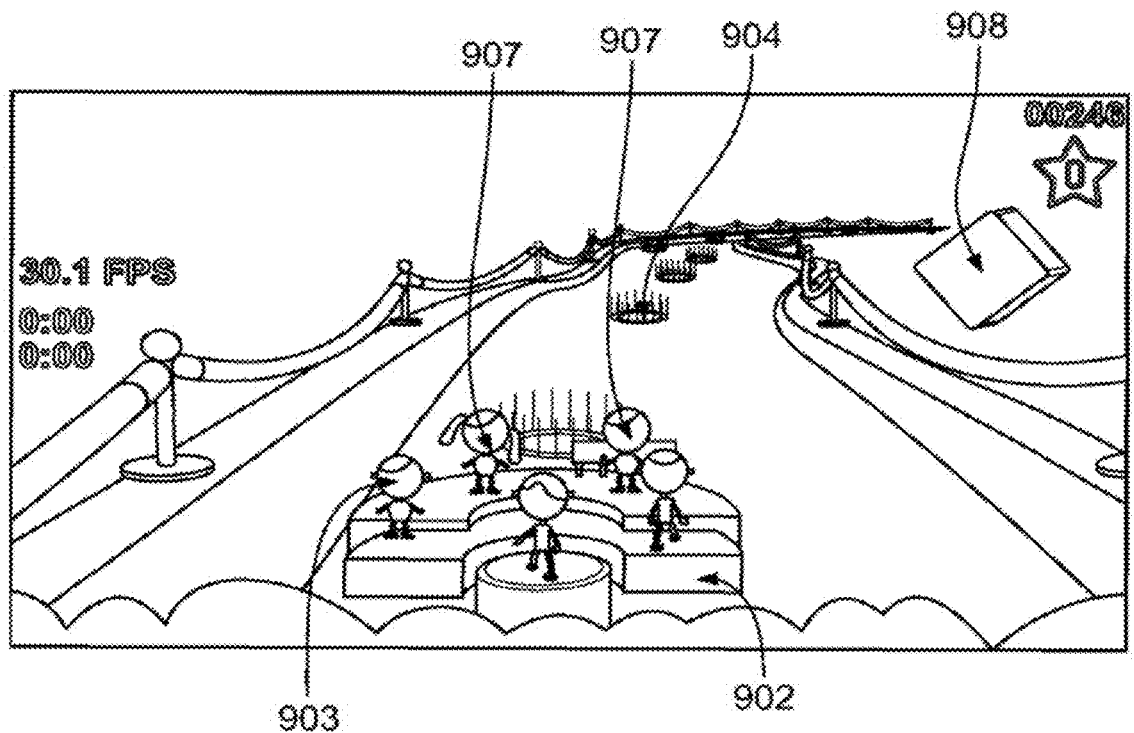
Figure 9P:
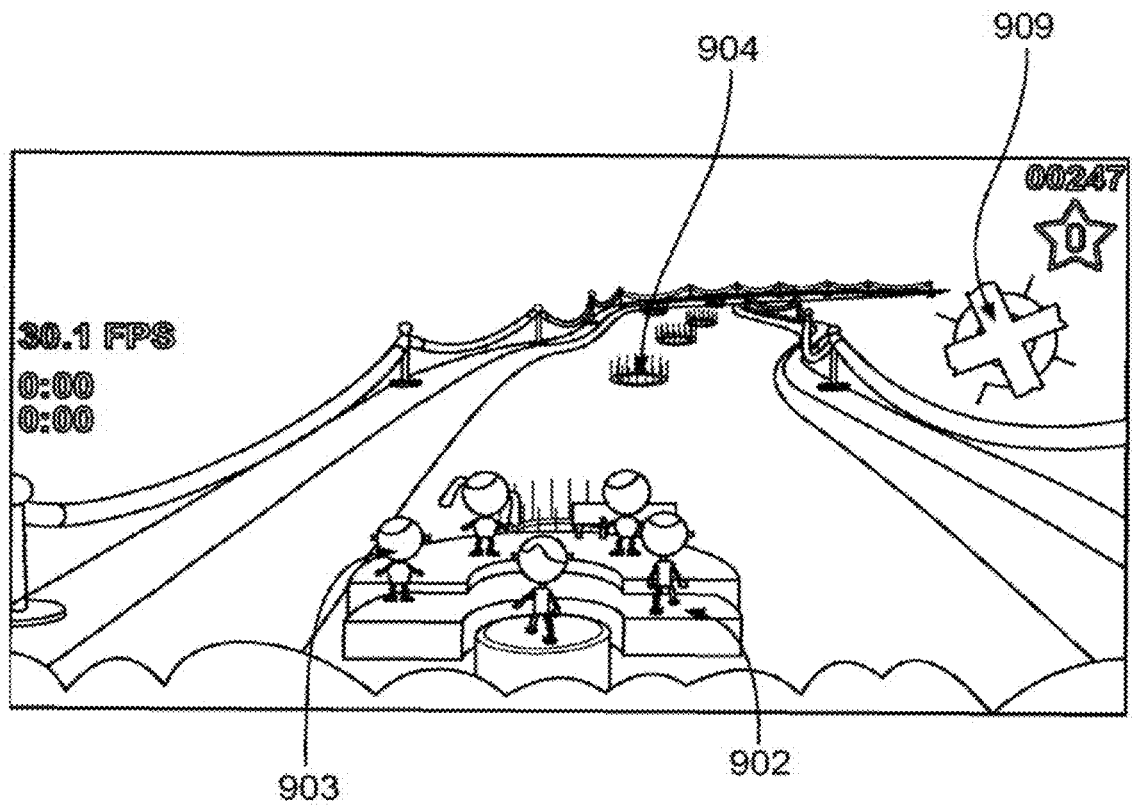
Figure 9Q:
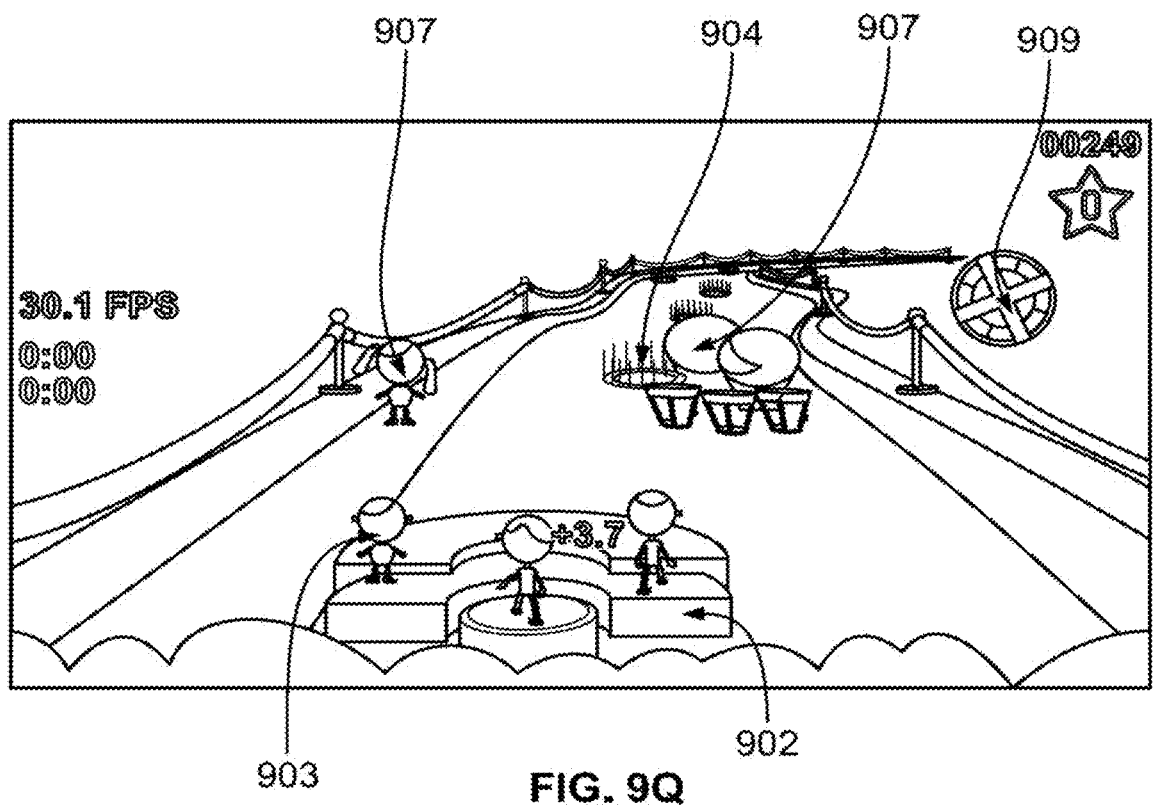
Figure 9R:
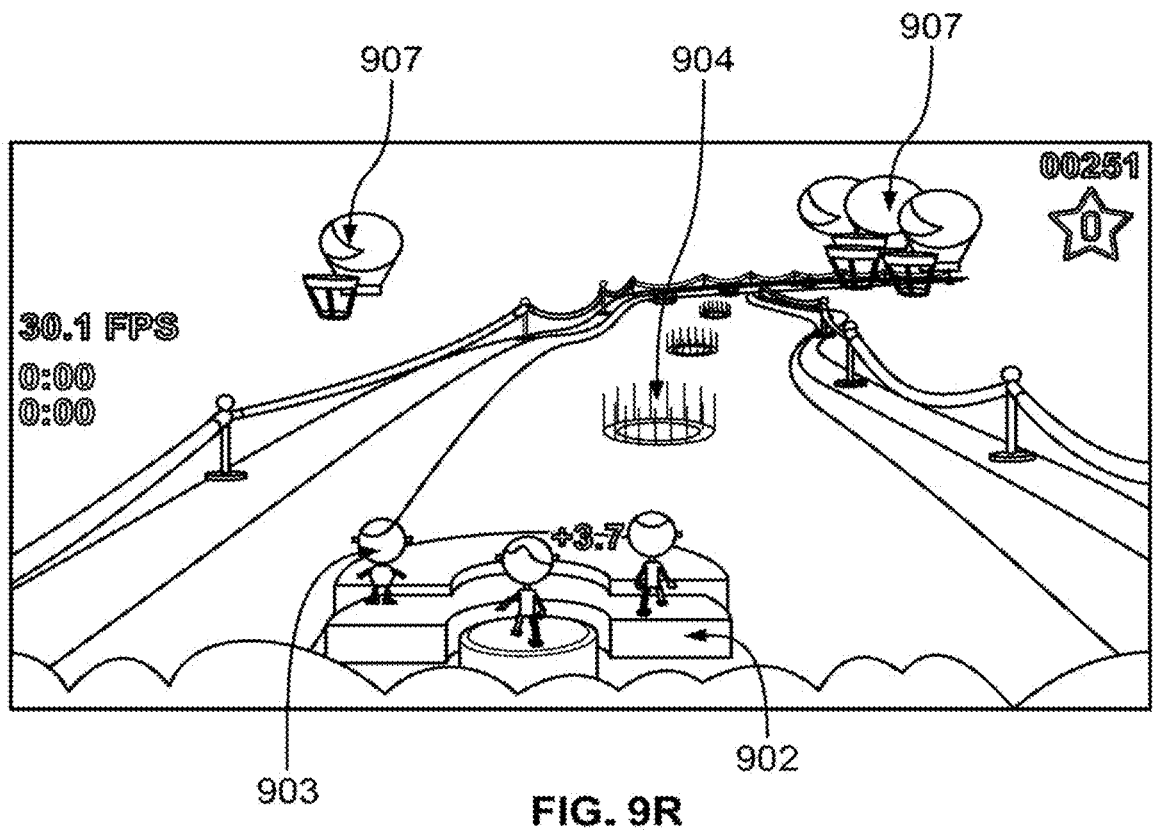
Figure 9S:
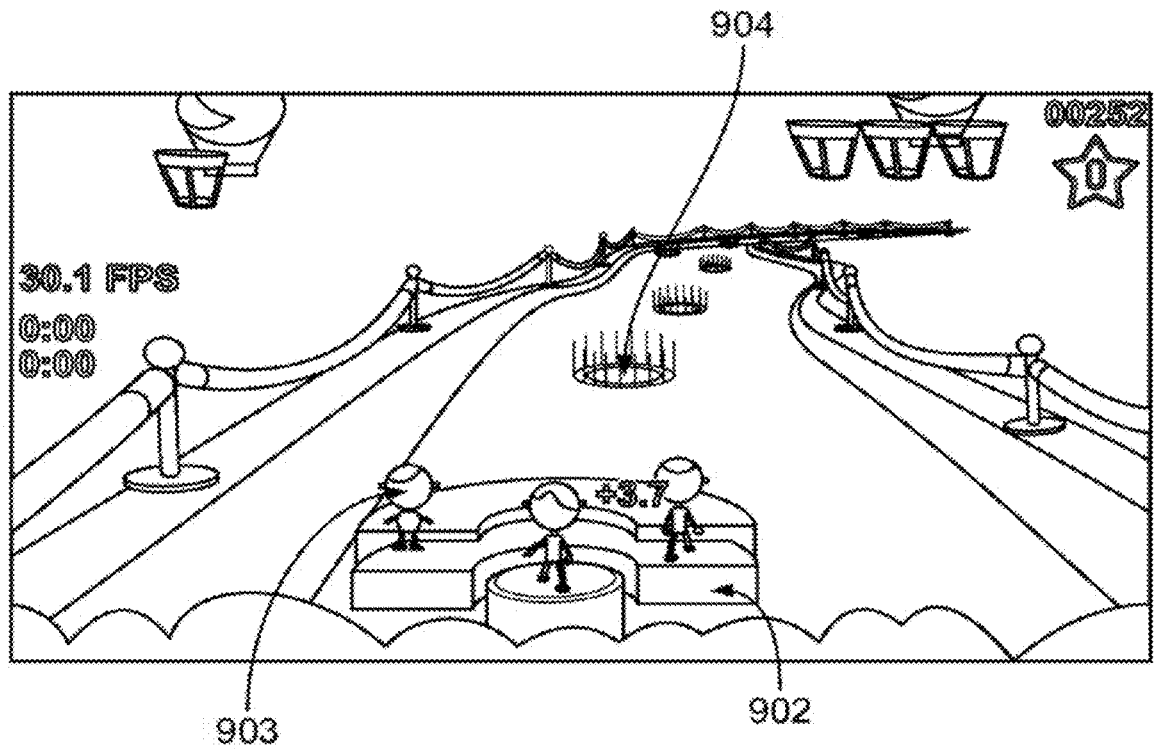
Figure 9T:
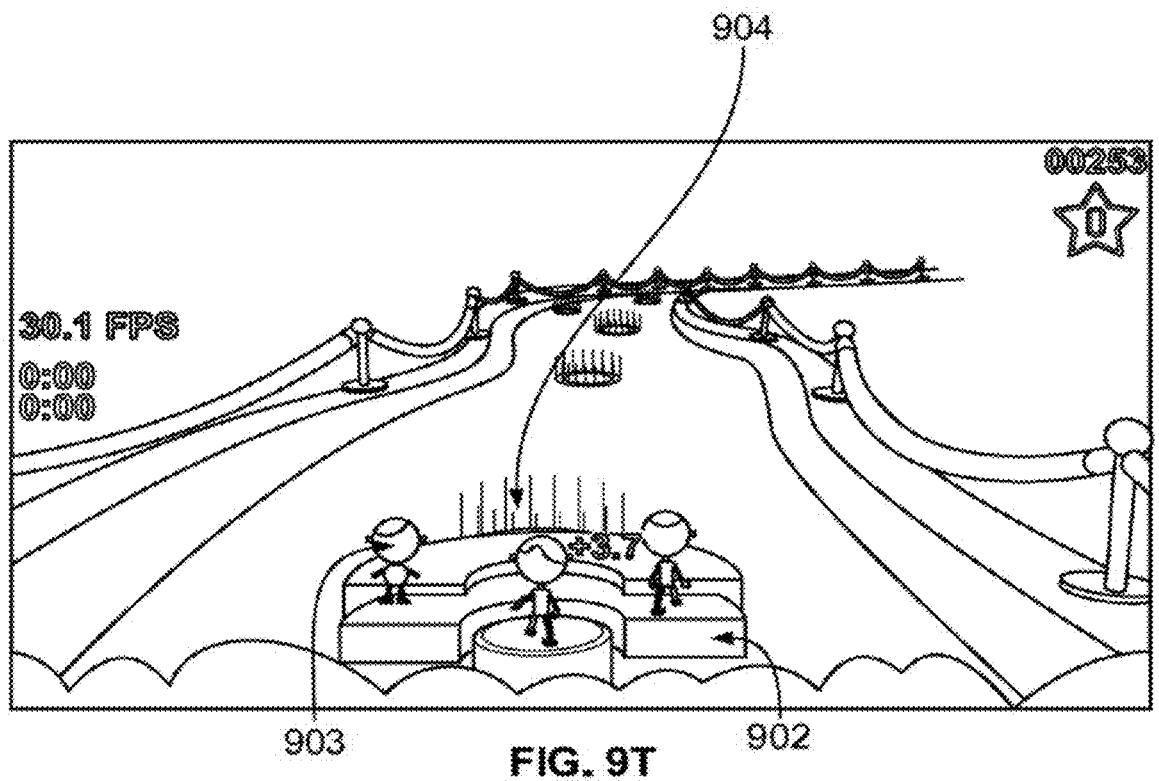
Figure 9U:
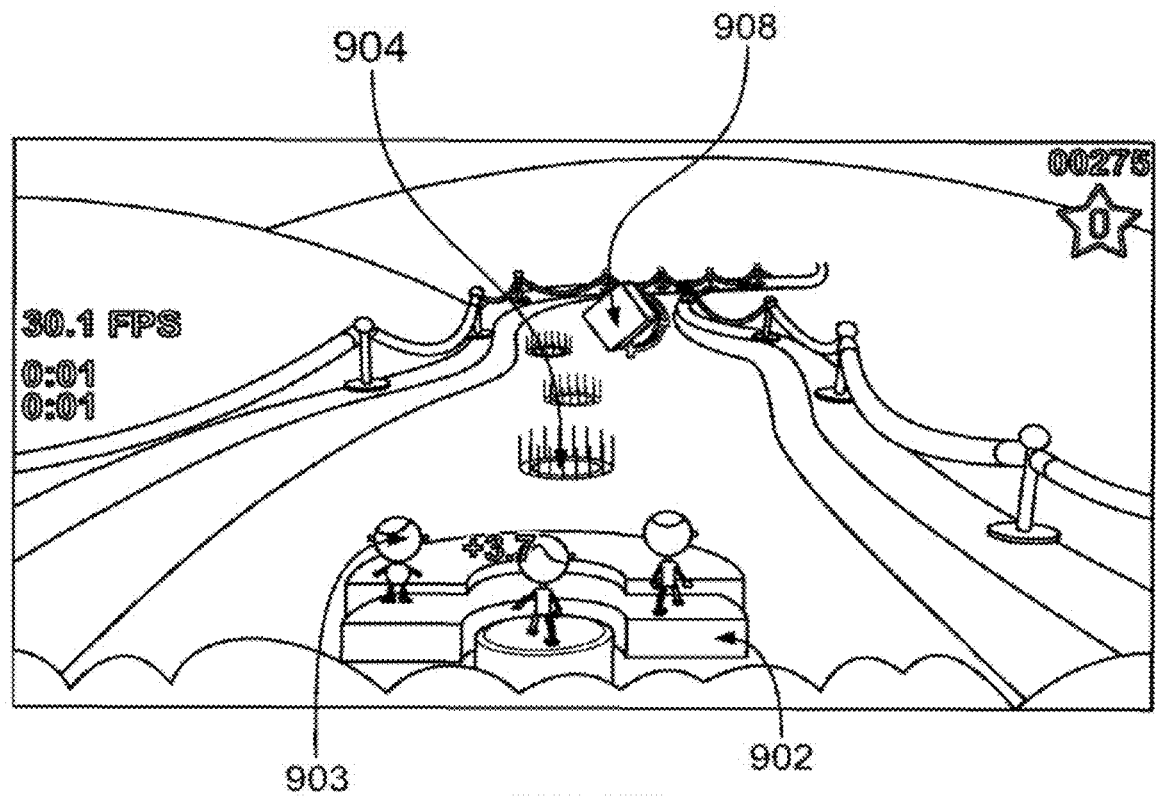
Figure 9V:
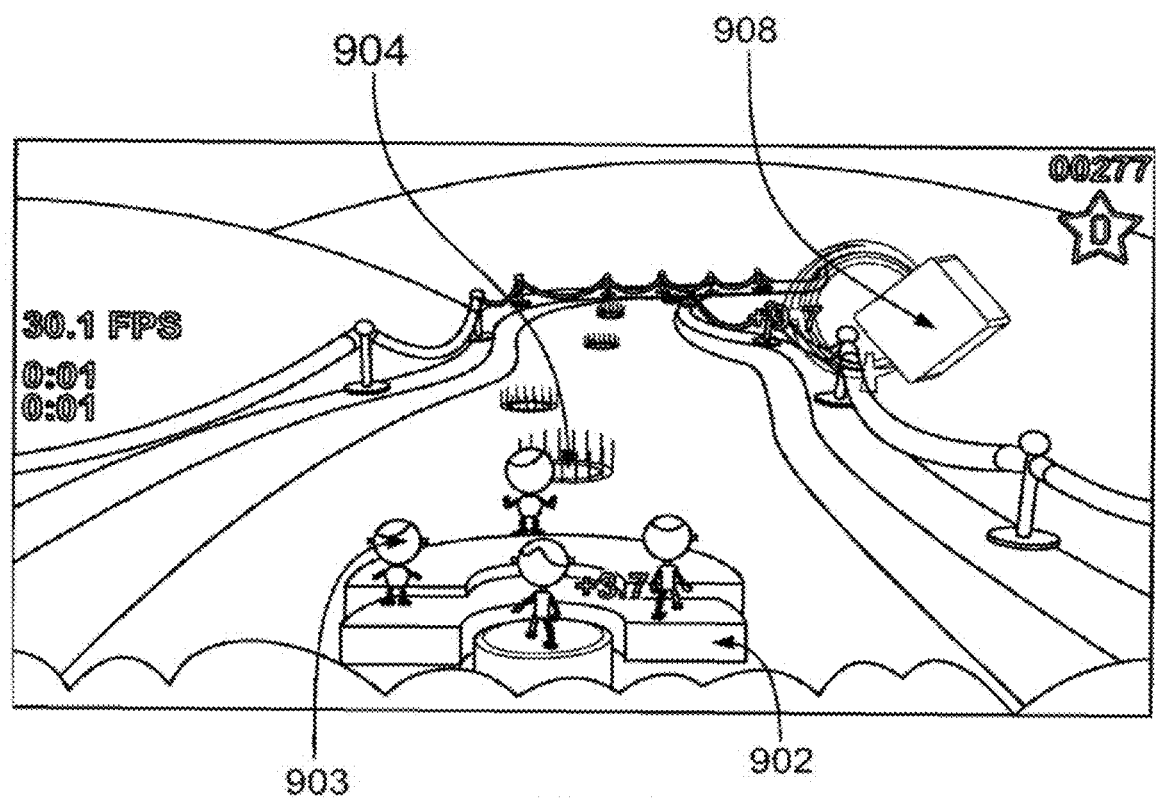

FIGS. 9A-9V show another non-limiting example of the dynamics of tasks and interferences that can be rendered at user interfaces, according to the principles herein. In this example, the task is a visuomotor navigation task, and the interference is target discrimination (as a secondary task). As shown in FIGS. 9A-9V, the individual is required to perform the navigation task by controlling the motion of the avatar vehicle 902 along a path that coincides with the milestone objects 904. FIGS. 9A-9V show a non-limiting exemplary implementation where the individual is expected to actuate an apparatus or computing device (or other sensing device) to cause the avatar vehicle 902 to coincide with the milestone object 904 as the response in the navigation task, with scoring based on the success of the individual at crossing paths with the milestone objects 904. FIGS. 9A-9V also show the dynamics of a target object 906 and a non-target object 908, where the time-varying characteristic is the trajectory of motion of the object, and the objects differ by shape but not color. The interference is a secondary task requiring the individual to indicate the individual's discrimination of the objects (target vs. non-target), such as but not limited to by tapping or other indication. FIGS. 9A-9V also show the dynamics of a modification of the computerized adjustable element based on the individual's degree of success in performing the task and/or interference. In the example of FIGS. 9G-9K, additional avatar objects 907 are shown propagating over to and being positioned on the base vehicle 902 to join the other avatar objects 903 in response to (i) the individual's success at the primary task (e.g., success at steering the base vehicle 902 to coincide with the milestone objects 904 in a visuomotor task), or (ii) the individual's success at the secondary task (e.g., target discrimination as an interference), or (iii) some combination of (i) and (ii). That is, computerized adjustable element is adjusted/modified to add avatar object 907 as an indication of the degree of success of the individual in performing the task and/or interference through a certain stage (e.g., a first time interval T-1) of performing the task and/or interference. In the example of FIGS. 9P-9Q, based on the individual providing an indication in response to a non-target 908 (thereby not succeeding at the target discrimination) the user interface renders a warning signal 909, and the avatar objects 907 are shown to be removed from and propagate away from the base vehicle 802 in response to the individual's lack of success at the secondary task (e.g., target discrimination as an interference). That is, computerized adjustable element is adjusted/modified as an indication of the degree of success or lack of success of the individual in performing the task and/or interference through another stage (e.g., second time interval T-2 (different from T-1)) of performing the task and/or interference.

In the non-limiting examples of FIGS. 9B, 9C, and 9G, the individual's success at selecting a target object 906 is indicated using circles 910 around the target object 906.

In the examples of FIGS. 9A-9V, the one or more processors, e.g., the processing unit of the exemplary system, method, and apparatus, are configured to receive data indicative of the individual's physical actions to cause the avatar vehicle 902 to navigate the path. For example, the individual may be required to perform physical actions to "steer" the avatar, e.g., by changing the rotational orientation or otherwise moving a computing device. Such action can cause a gyroscope or accelerometer or other motion or position sensor device to detect the movement, thereby providing measurement data indicative of the individual's degree of success in performing the navigation task.

In the examples of FIGS. 9A-9V, the processing unit of the exemplary system, method, and apparatus is configured to receive data indicative of the individual's physical actions to perform the target discrimination and to identify a specified computerized adjustable element (i.e., a specified facial expression). For example, the individual may be instructed using display feature 500 prior to a trial or other session to tap, or make other physical indication, in response to display of a target object having the specified target object 906, and not to tap to make the physical indication in response to display of a non-target object 908. In FIGS. 9A-9V, the target discrimination acts as an interference (i.e., a secondary task) to the primary navigation task, in an interference processing multi-tasking implementation. As described hereinabove, the exemplary systems, methods, and apparatus can cause the processing unit to render a display feature (e.g., display feature 500) to display the instructions to the individual as to the expected performance (i.e., which object to respond to in the target discrimination task, and what is expected in the performance of the navigation tasks). As also described hereinabove, the processing unit of the exemplary system, method, and apparatus can be configured to (i) receive the data indicative of the measure of the degree and type of the individual's response to the primary task substantially simultaneously as the data indicative of the measure of the individual's response to the computerized adjustable element is collected (for a specified computerized adjustable element), or (ii) to selectively receive data indicative of the measure of the individual's response to the specified computerized adjustable element as a target stimulus (i.e., an interruptor) substantially simultaneously (i.e., at substantially the same time) as the data indicative of the measure of the degree and type of the individual's response to the task is collected and to selectively not collect the measure of the individual's response to the non-specified computerized adjustable element a non-target stimulus (i.e., a distraction) substantially simultaneously (i.e., at substantially the same time) as the data indicative of the measure of the degree and type of the individual's response to the task is collected.

FIGS. 10A-10Z and 11A-11H show another non-limiting example of the dynamics of tasks and interferences that can be rendered at user interfaces, according to the principles herein. In this example, the task is a visuomotor navigation task, and the interference is target discrimination (as a secondary task). As shown in FIGS. 10A-10Z and 11A-11H, the individual is required to perform the navigation task by controlling the motion of the avatar vehicle 1002 along a path that includes two types of the milestone objects (1004-1 and 1004-2). FIGS. 10A-10Z and 11A-11H show a non-limiting exemplary implementation at a higher difficulty level in which the individual is expected to actuate an apparatus or computing device (or other sensing device) to cause the avatar vehicle 1002, as the response in the navigation task, to coincide with the milestone object 1004-1 (i.e., to cross paths with) and to avoid (i.e., not to cross paths with) the milestone objects 1004-2, with scoring based on the success of the individual at crossing paths with the milestone objects 1004-1 and/or avoiding crossing paths with the milestone objects 1004-2. FIGS. 10A-10Z and 11A-11H also show the dynamics of non-target objects 1006 and target objects 1008, where the time-varying characteristic is the trajectory of motion of the object, and the objects differ by both shape and color. The interference is a secondary task requiring the individual to indicate the individual's discrimination of the objects (target vs. non-target), such as but not limited to by tapping or other indication. FIGS. 10A-10Z and 11A-11H also show the dynamics of a modification of the computerized adjustable element based on the individual's degree of success in performing the task and/or interference.

Figure 10A:
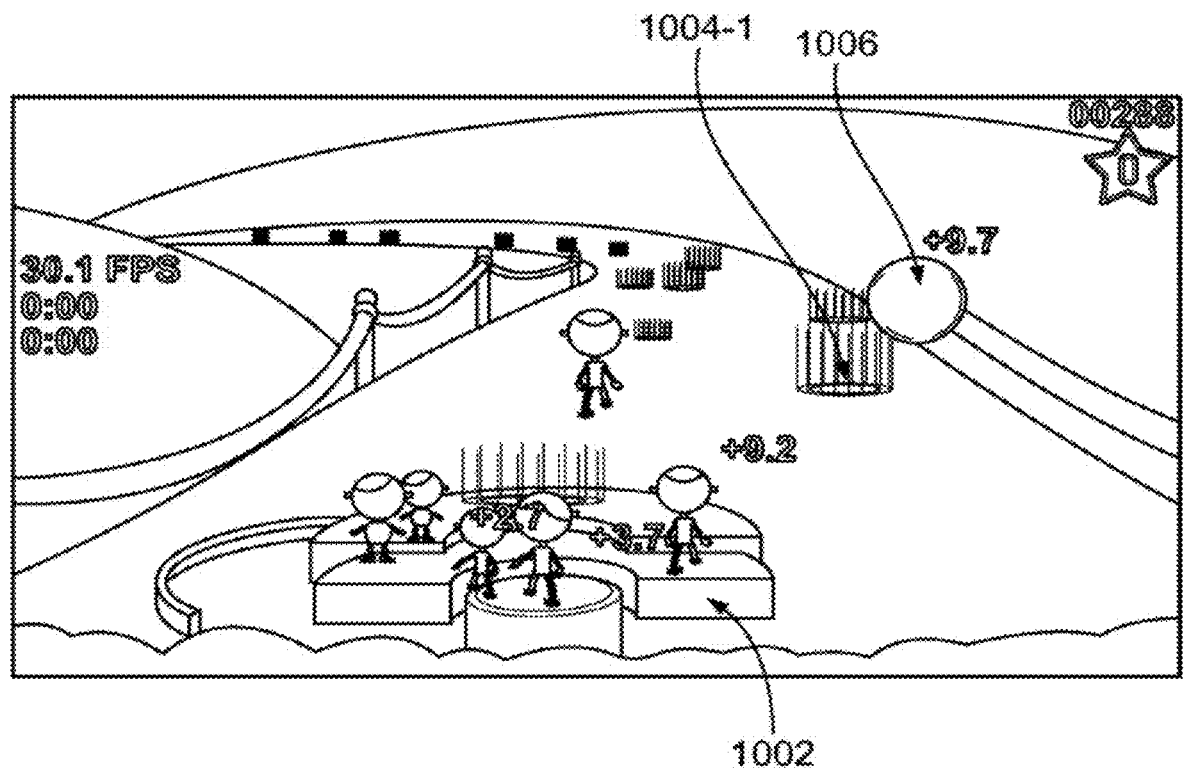
Figure 10B:
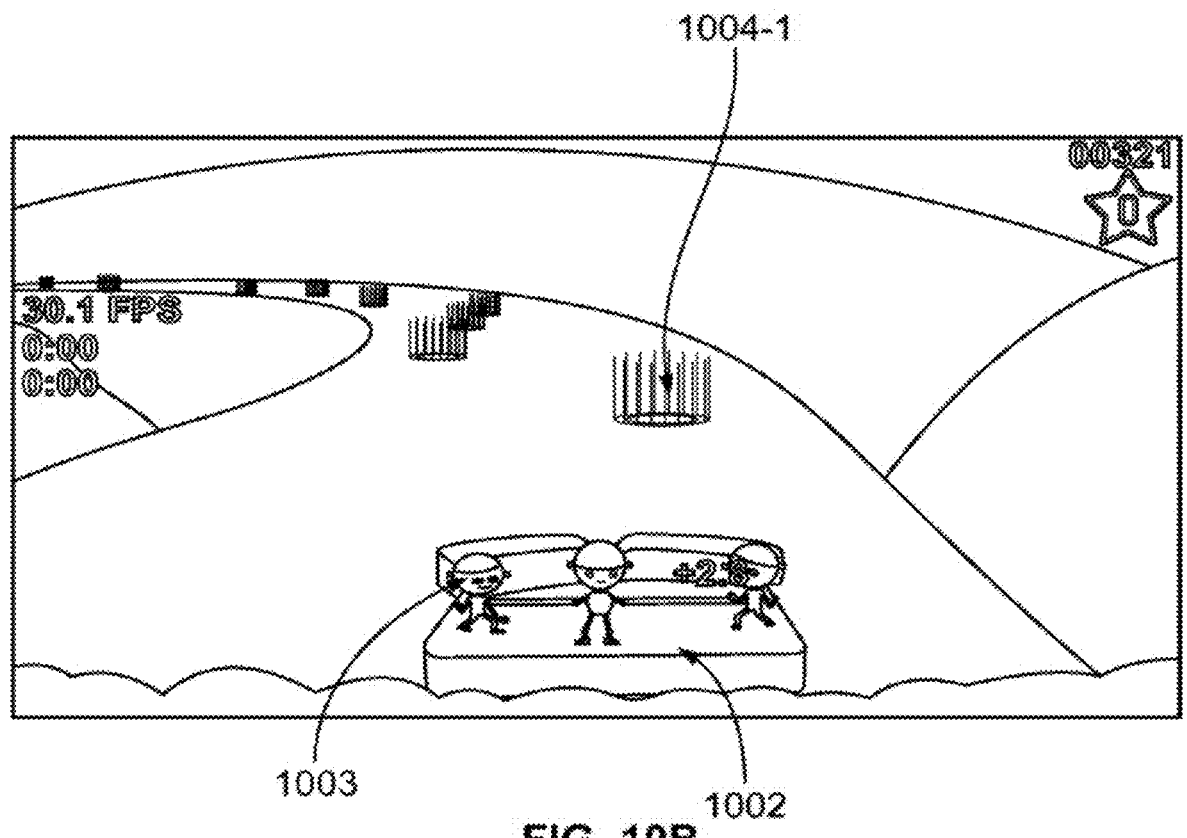
Figure 10C:
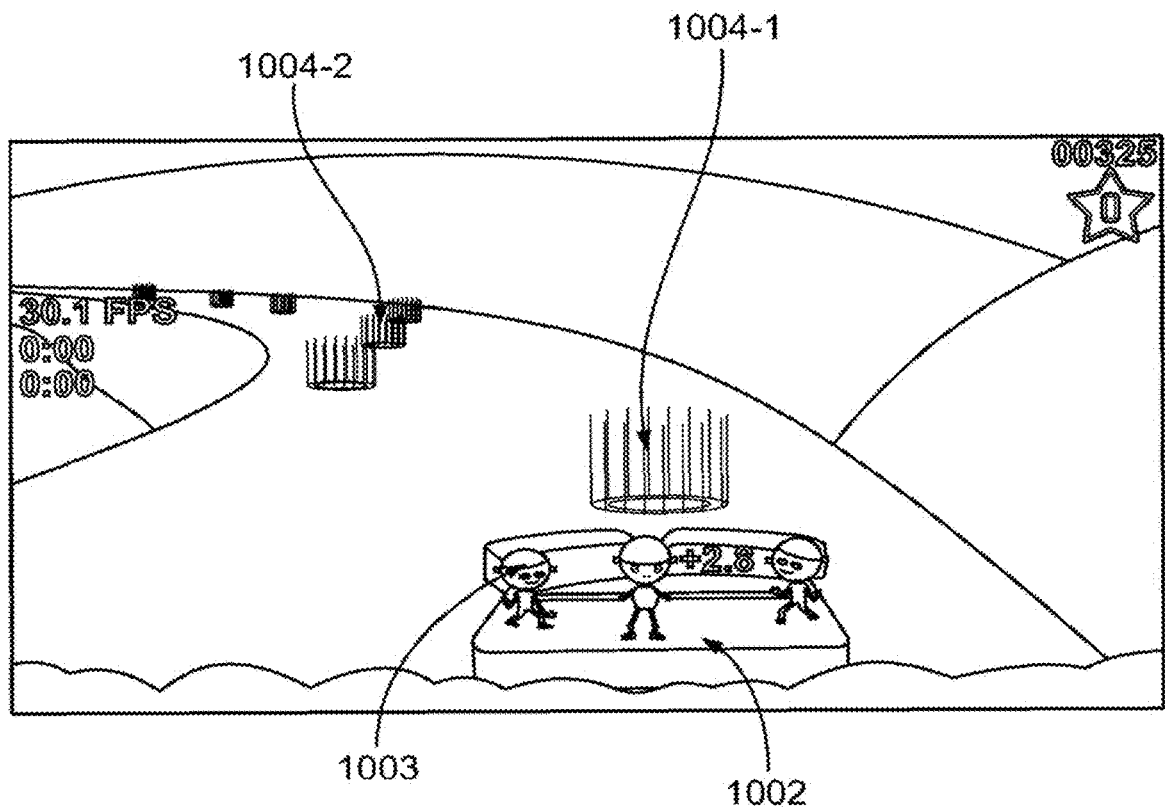
Figure 10D:
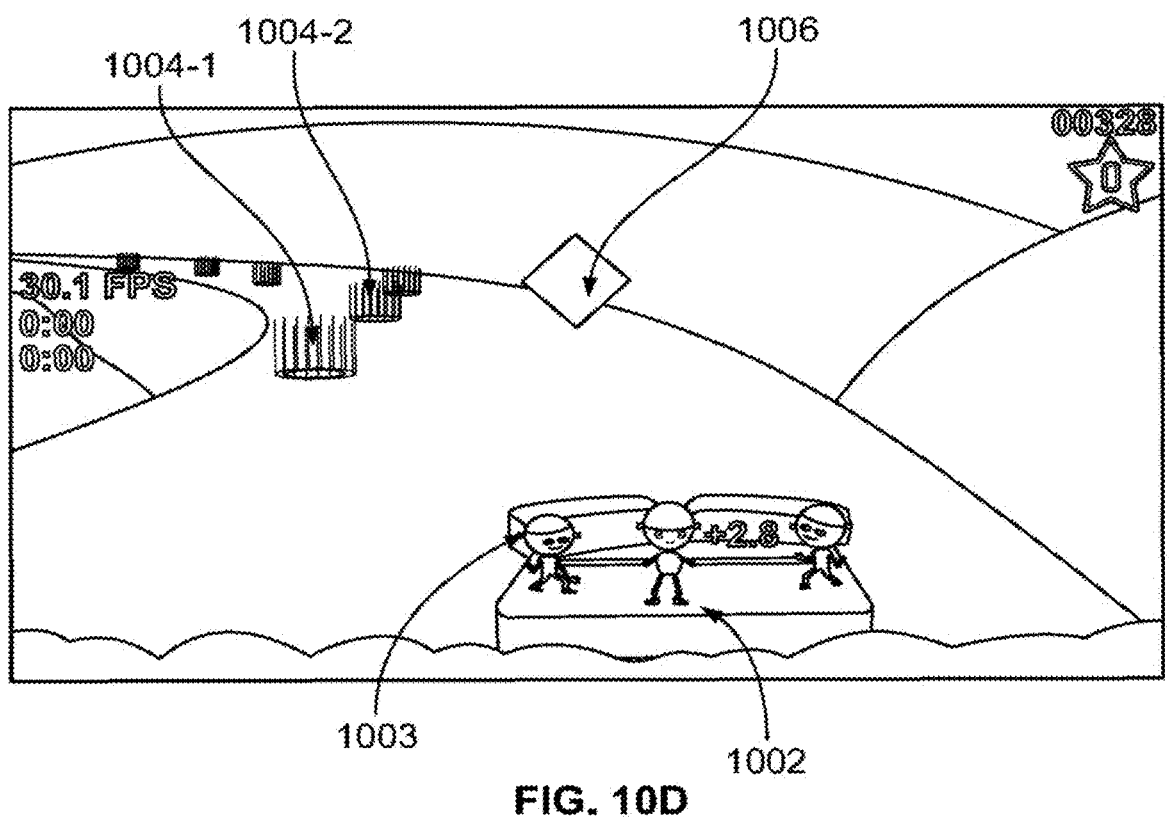
Figure 10E:
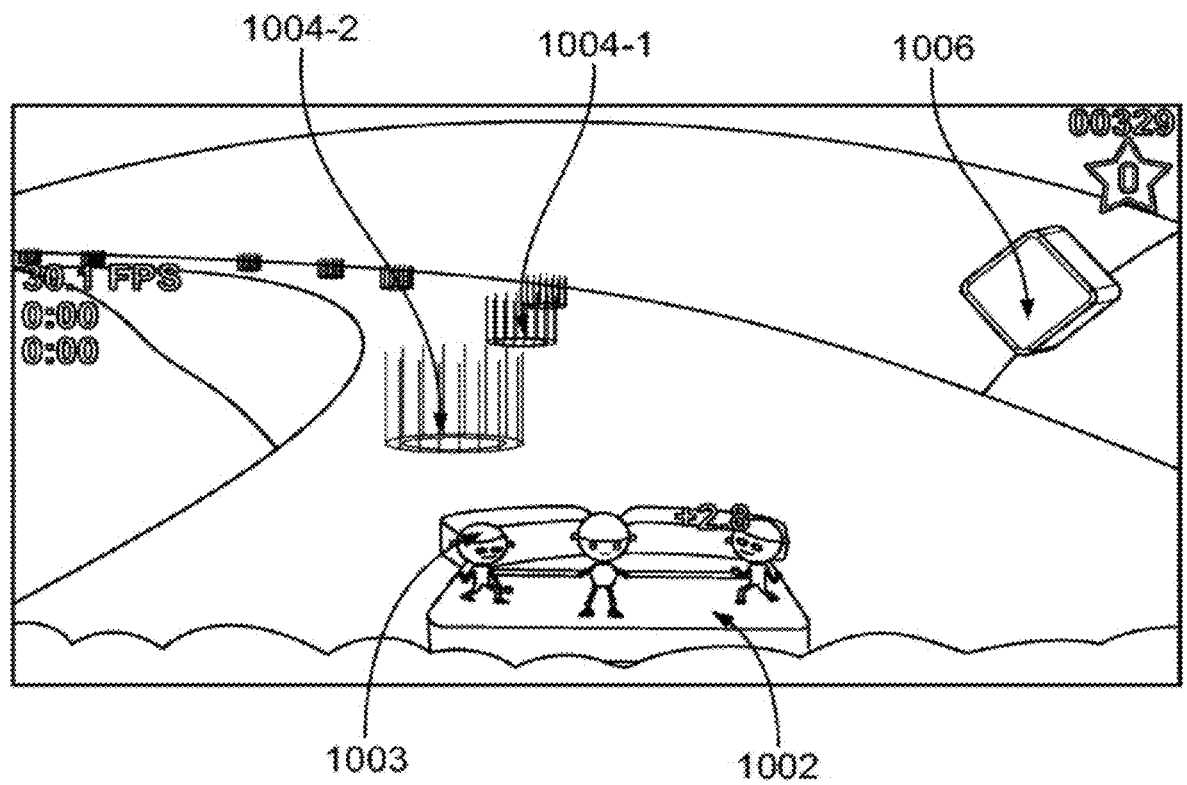
Figure 10F:
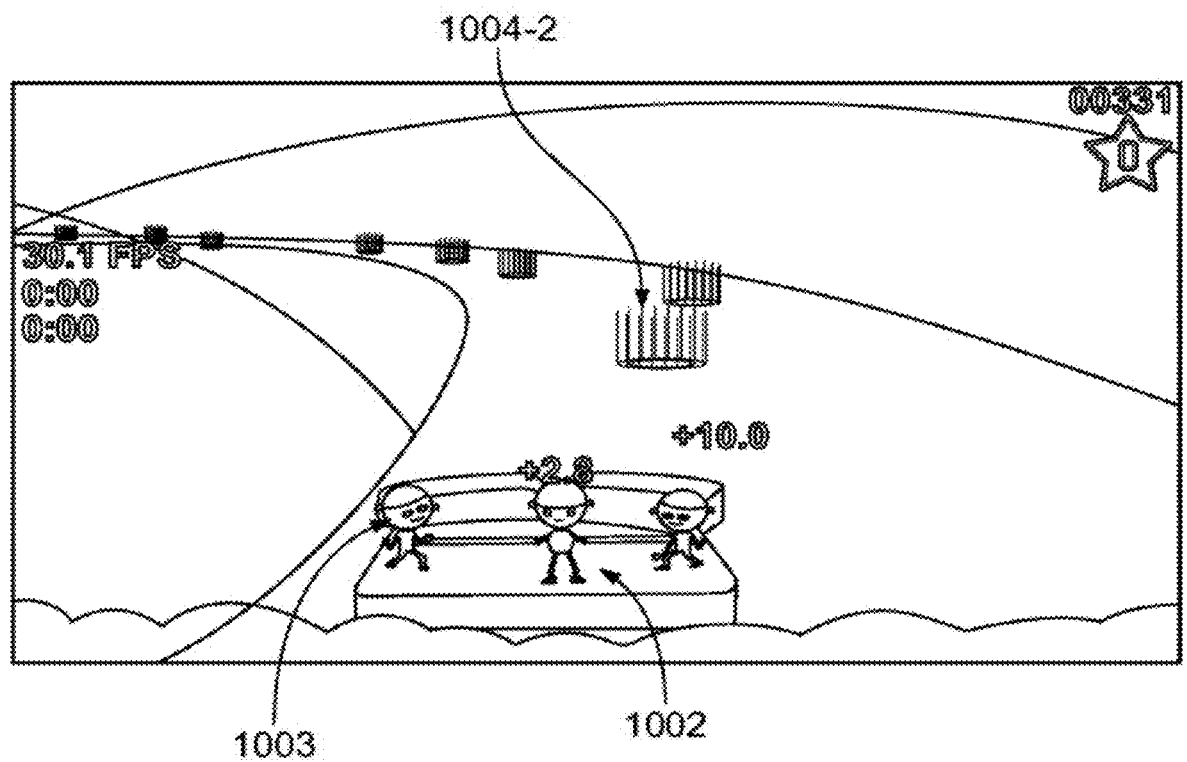
Figure 10G:
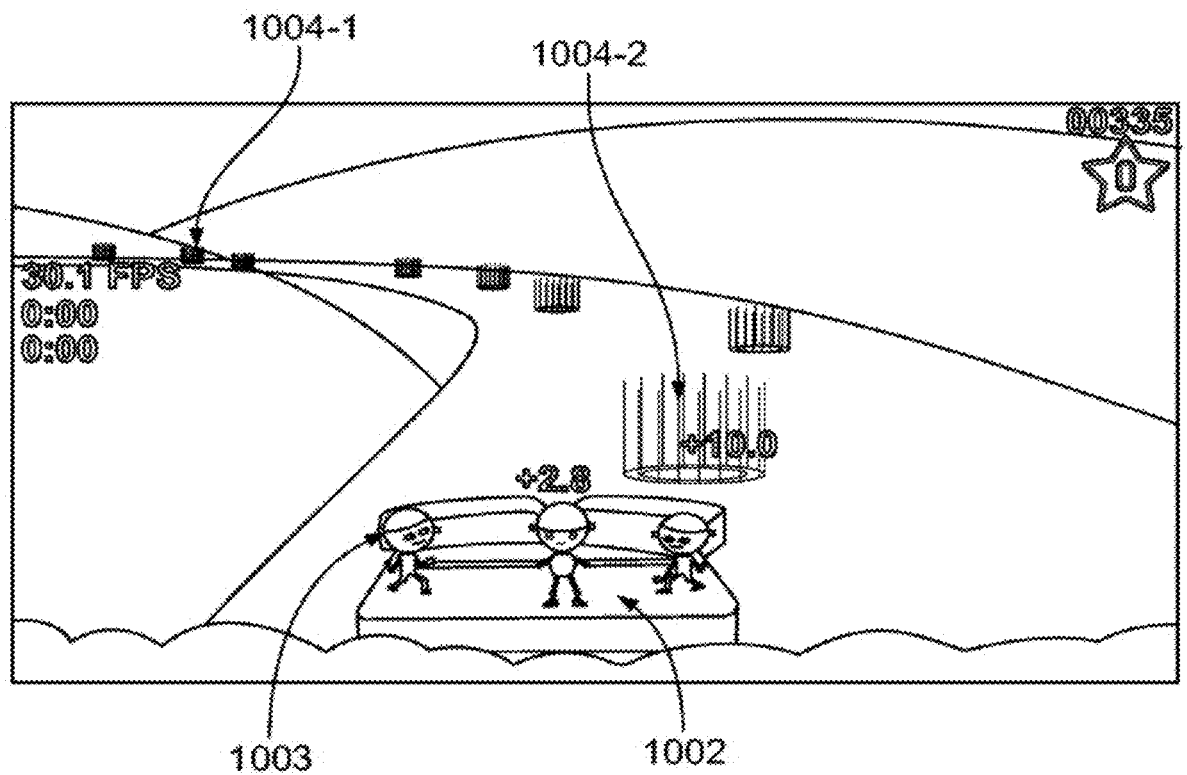
Figure 10H:
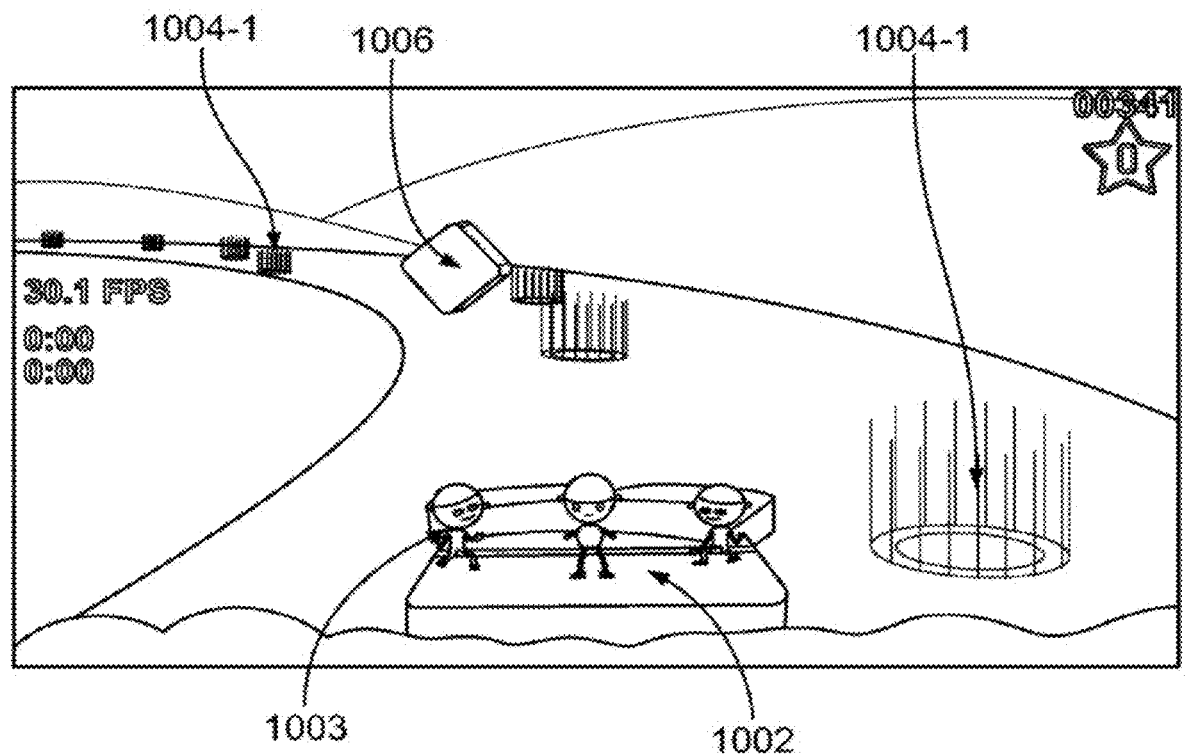
Figure 10I:
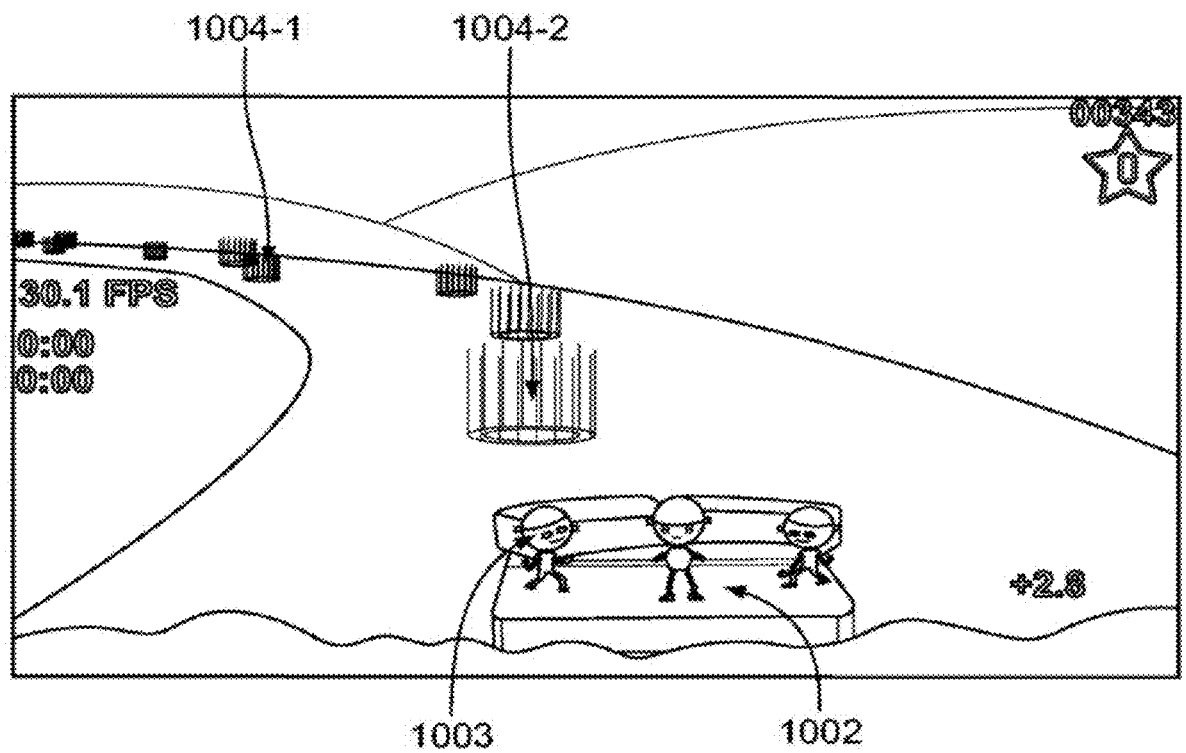
Figure 10J:
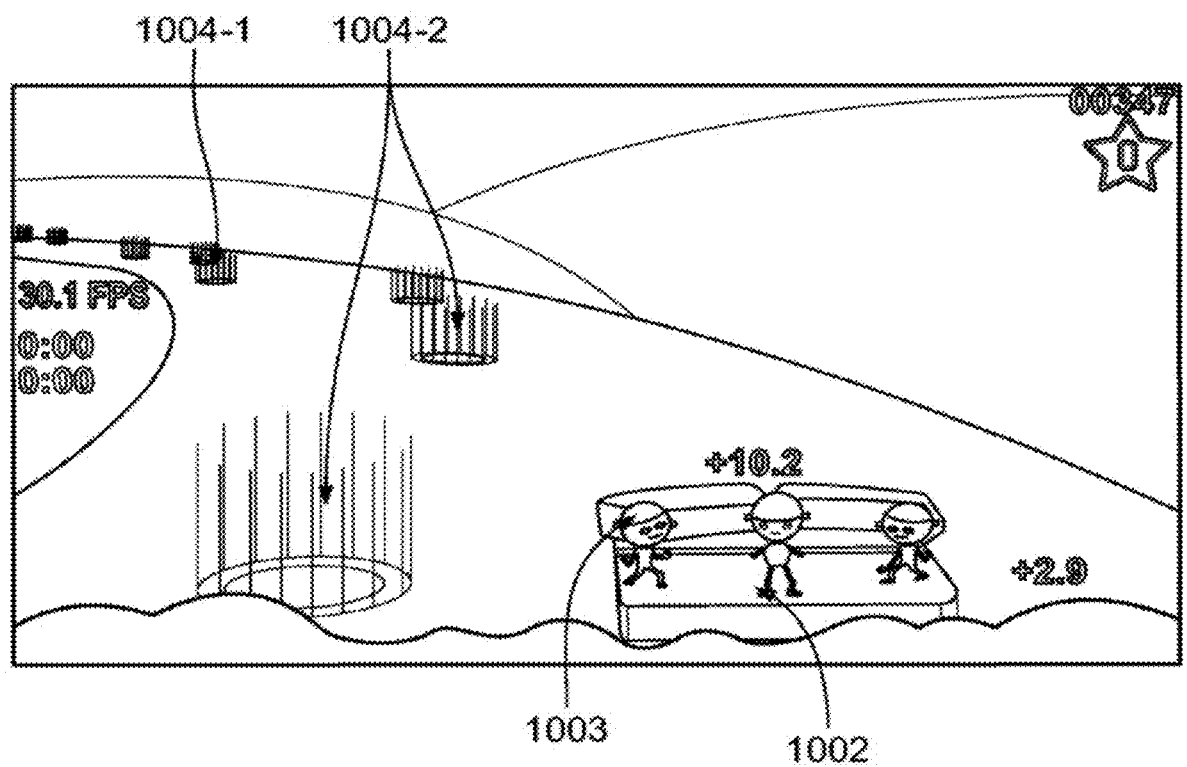
Figure 10K:
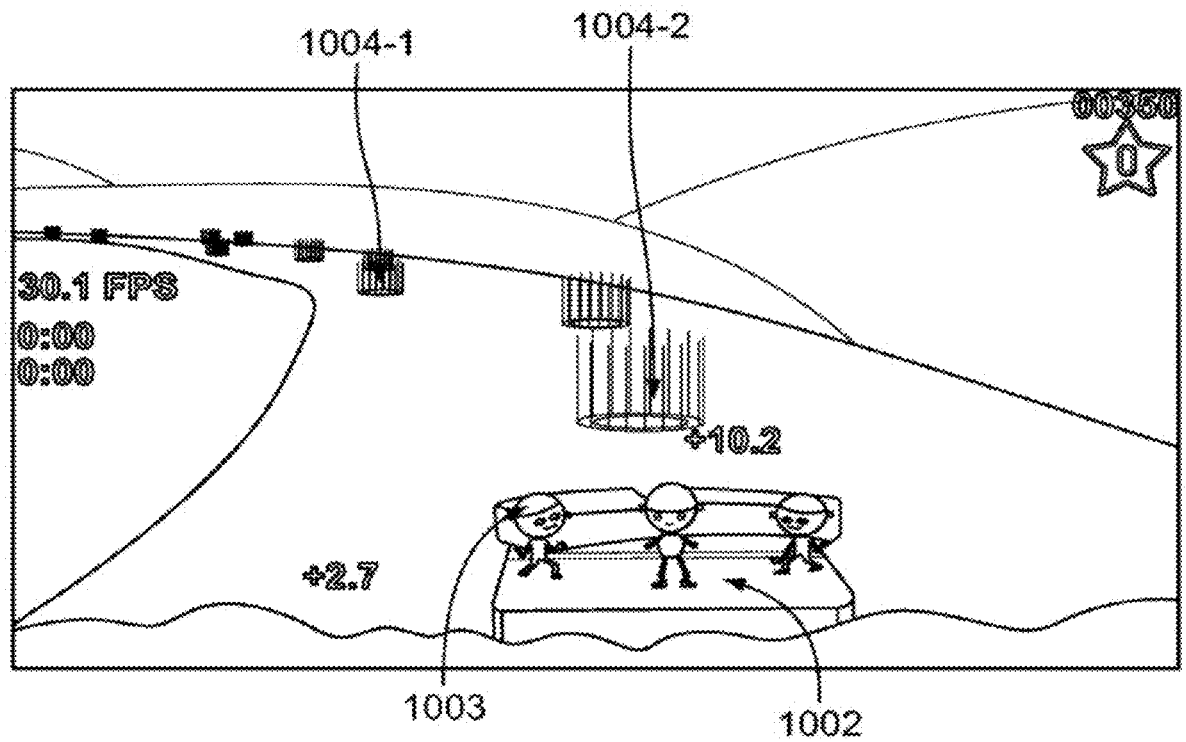
Figure 10L:
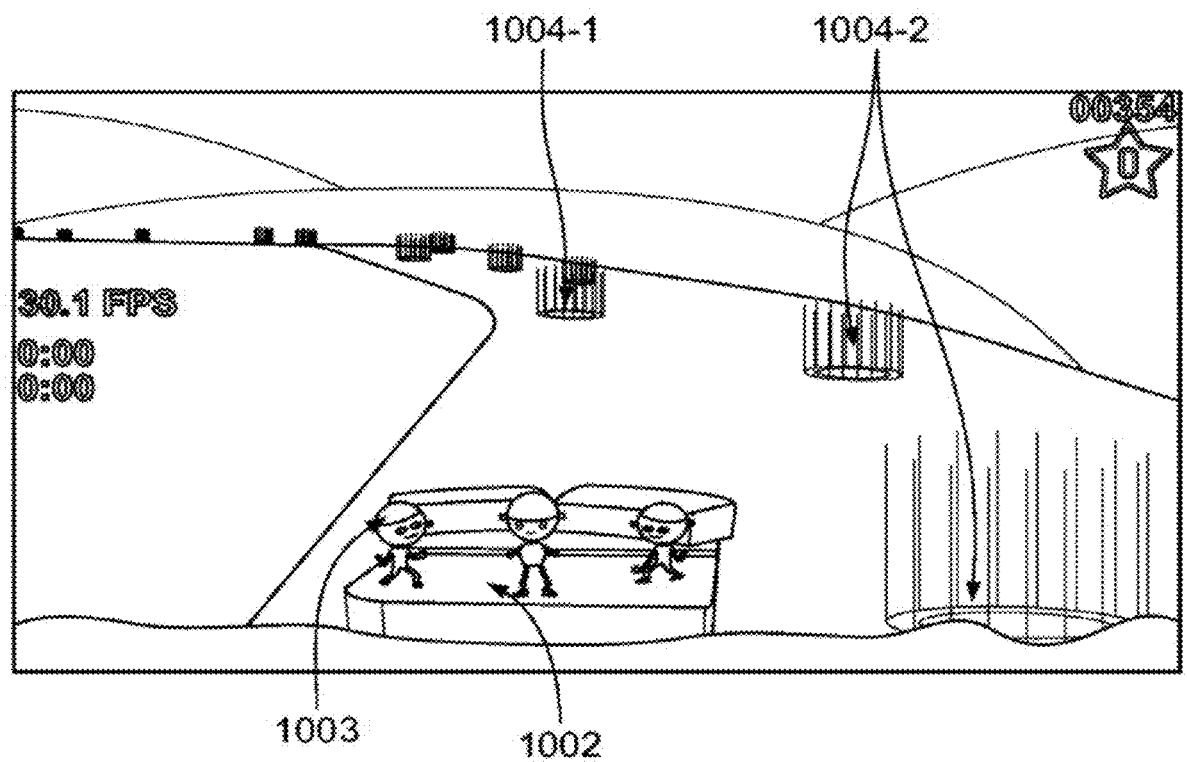
Figure 10M:
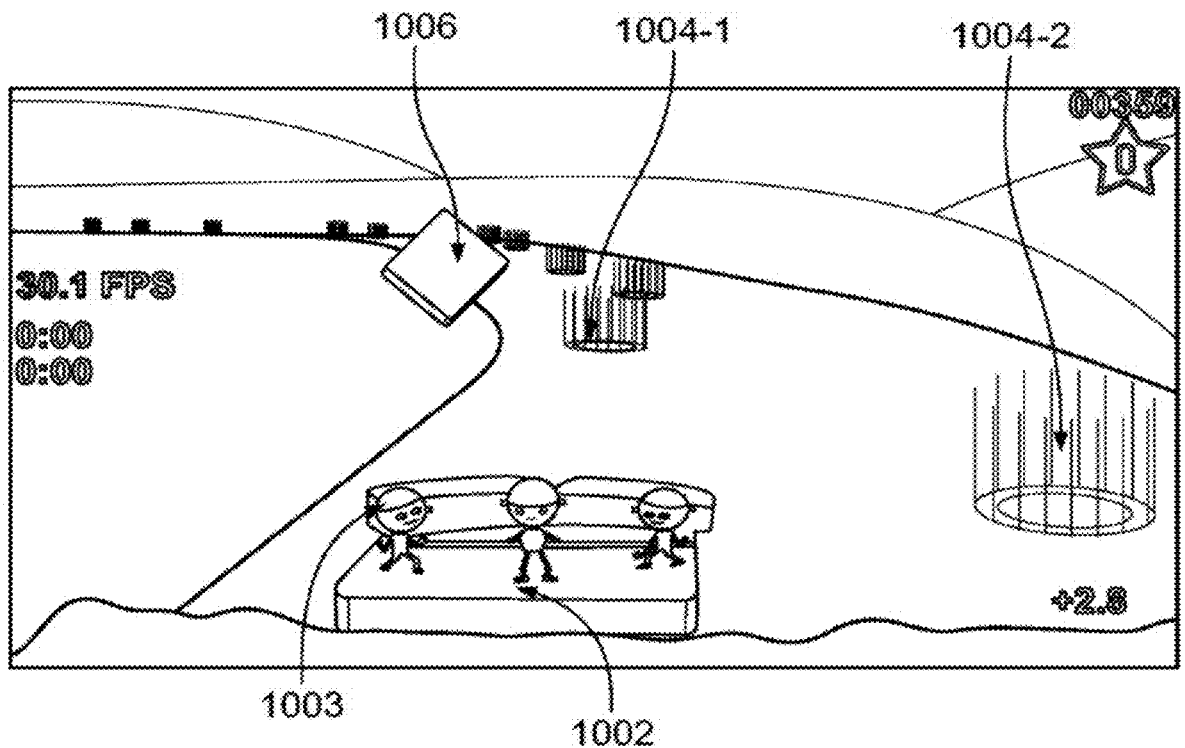
Figure 10N:
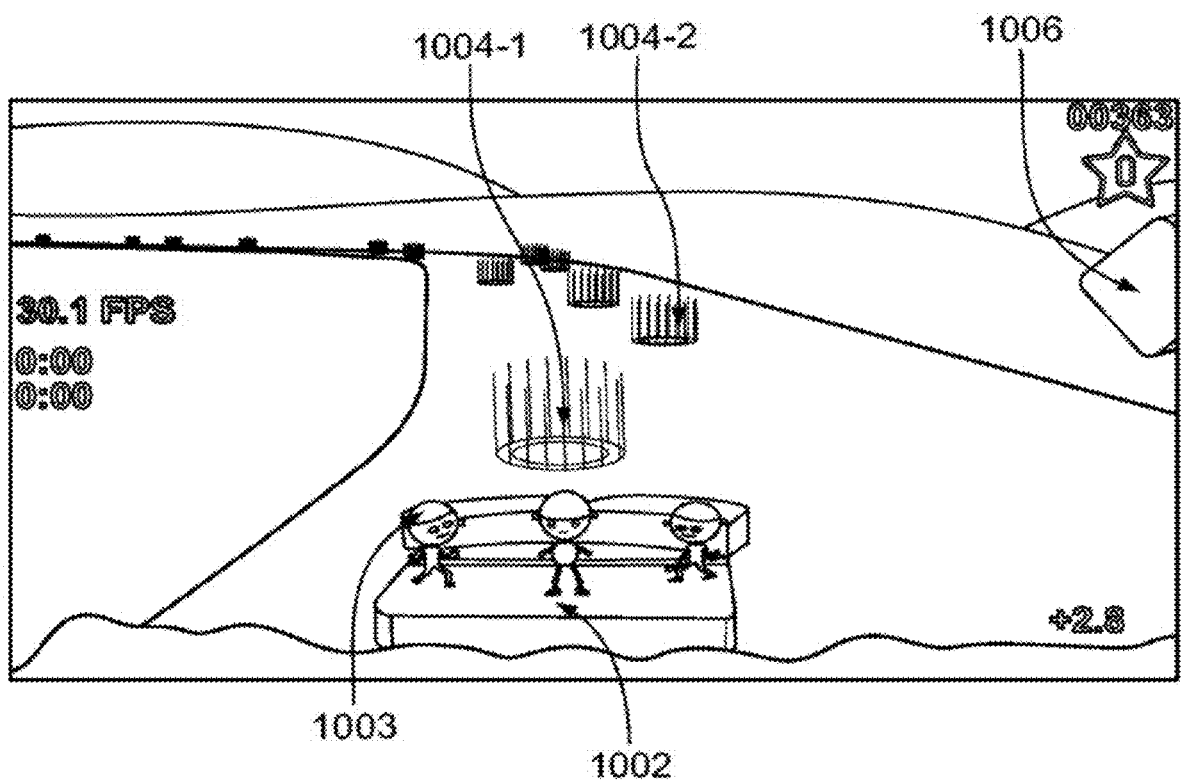
Figure 10O:
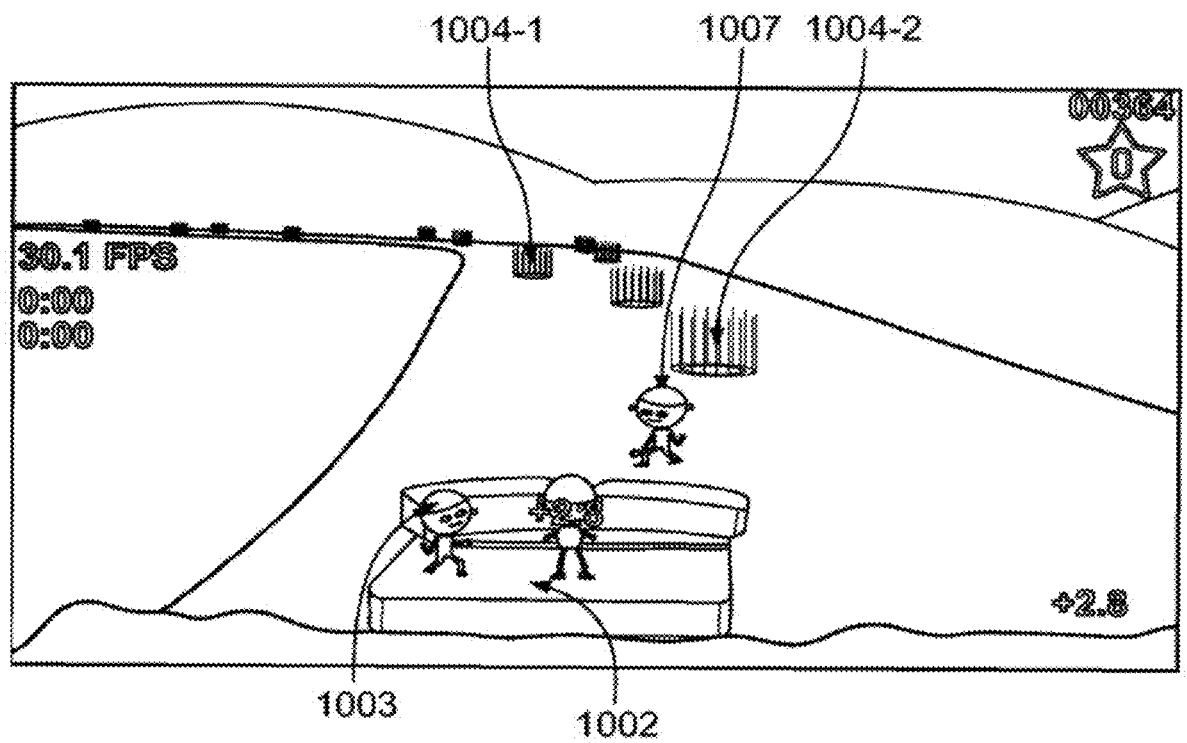
Figure 10P:
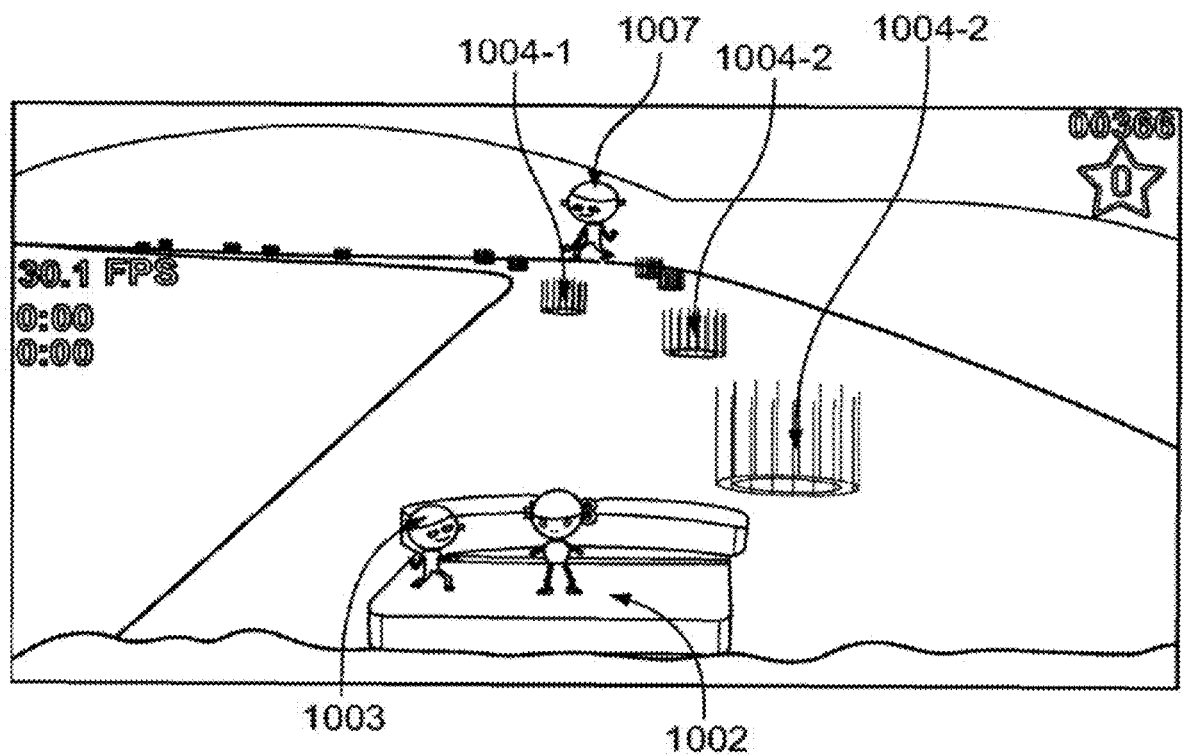
Figure 10Q:
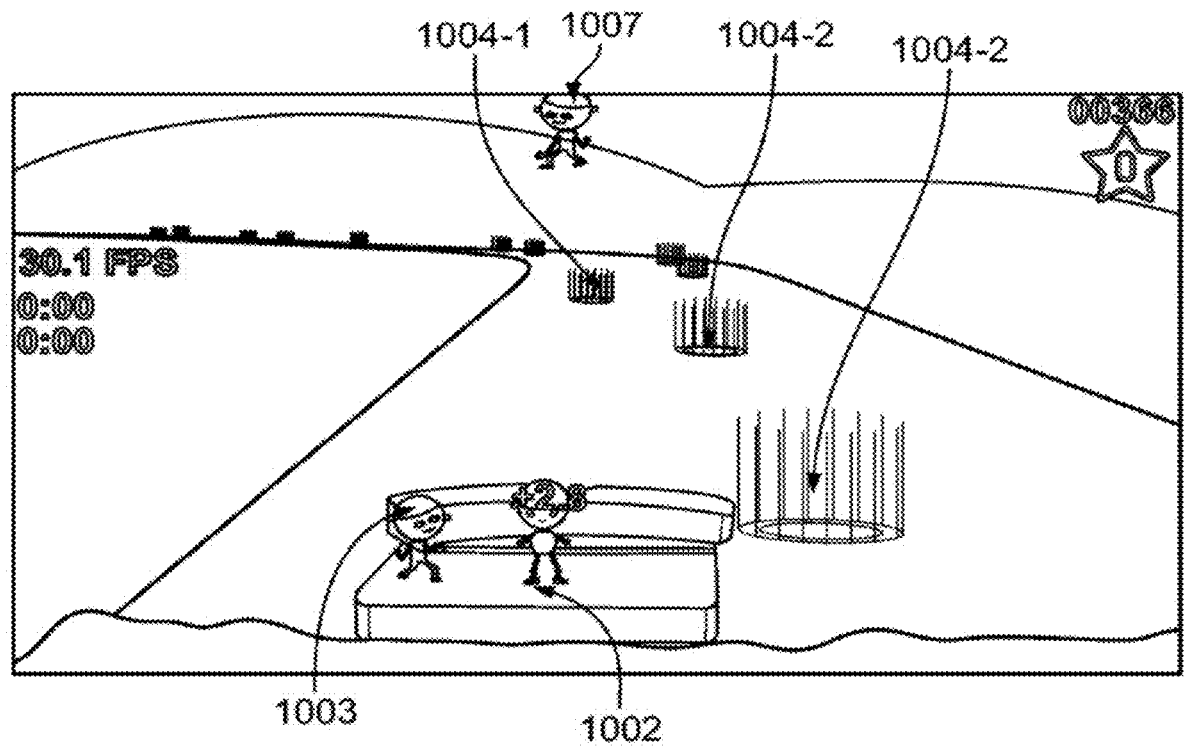
Figure 10R:
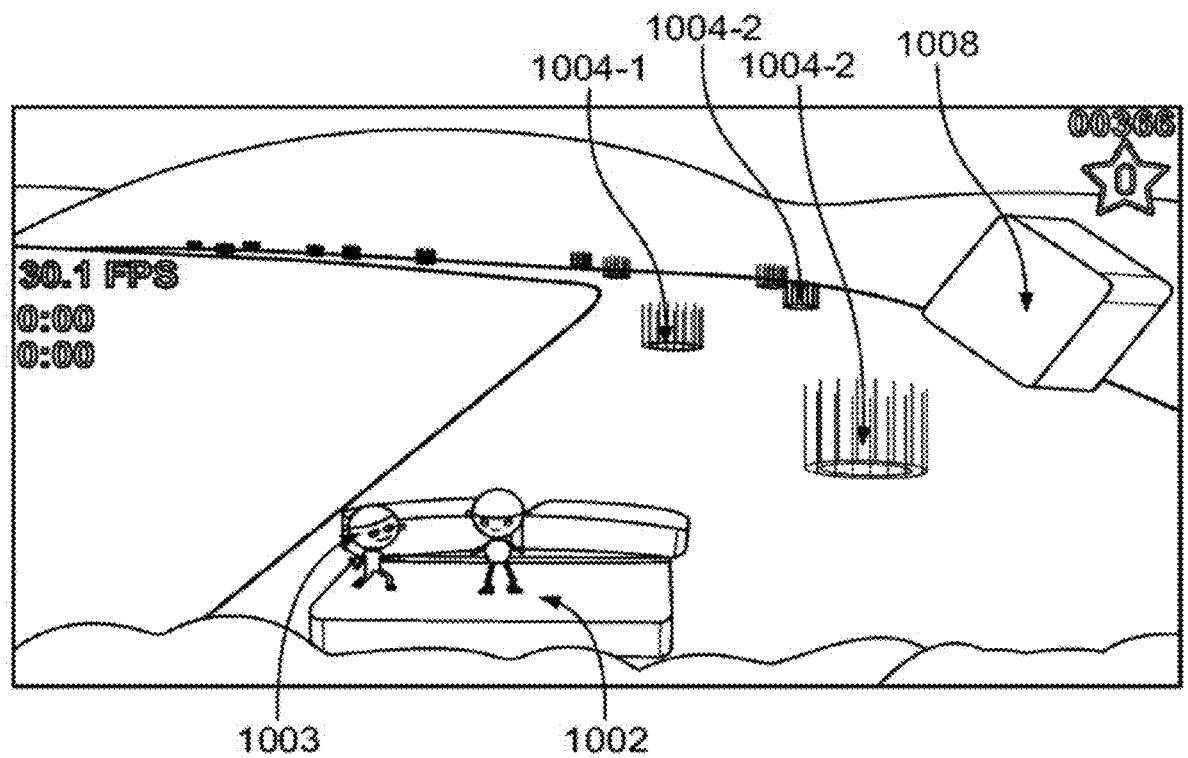
Figure 10S:
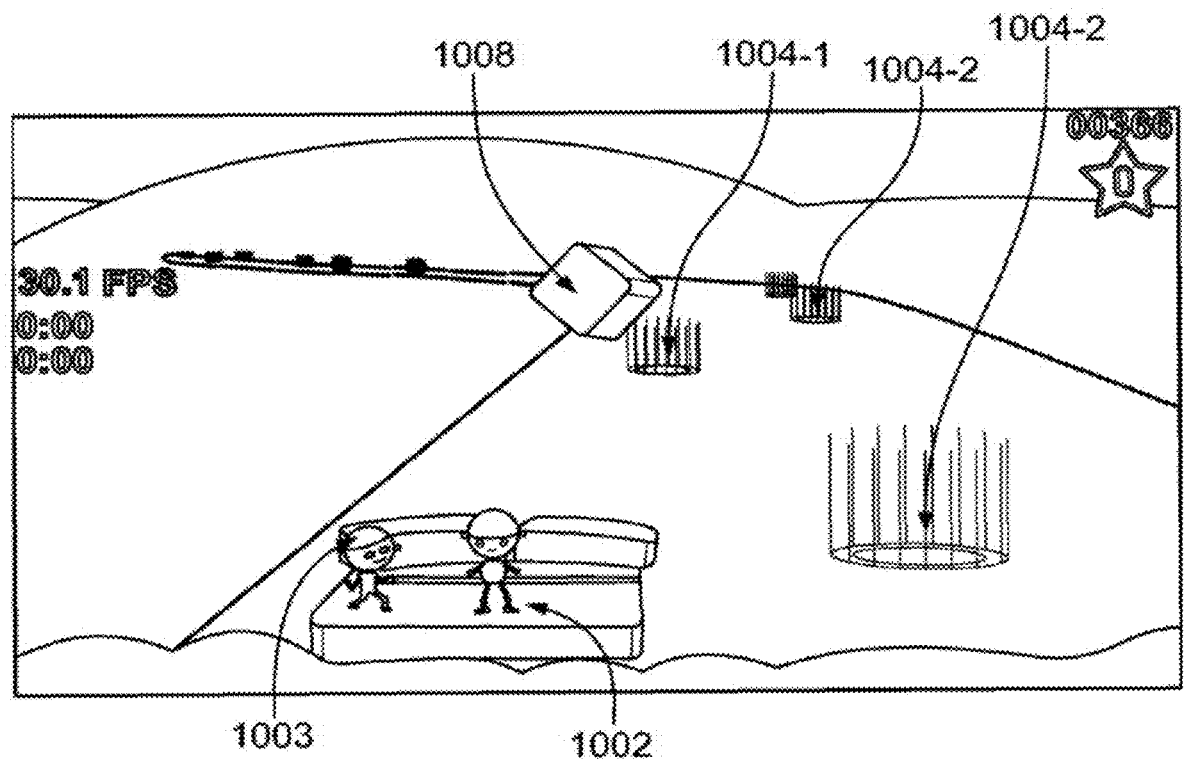
Figure 10T:
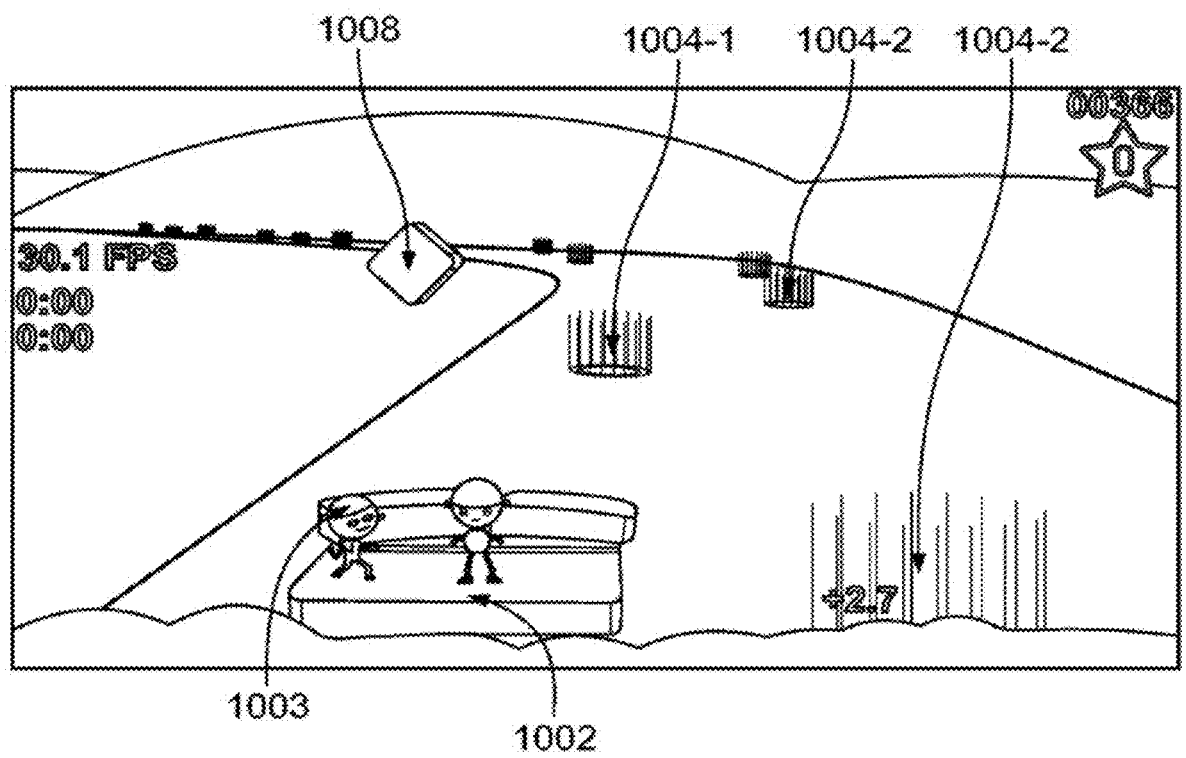
Figure 10U:
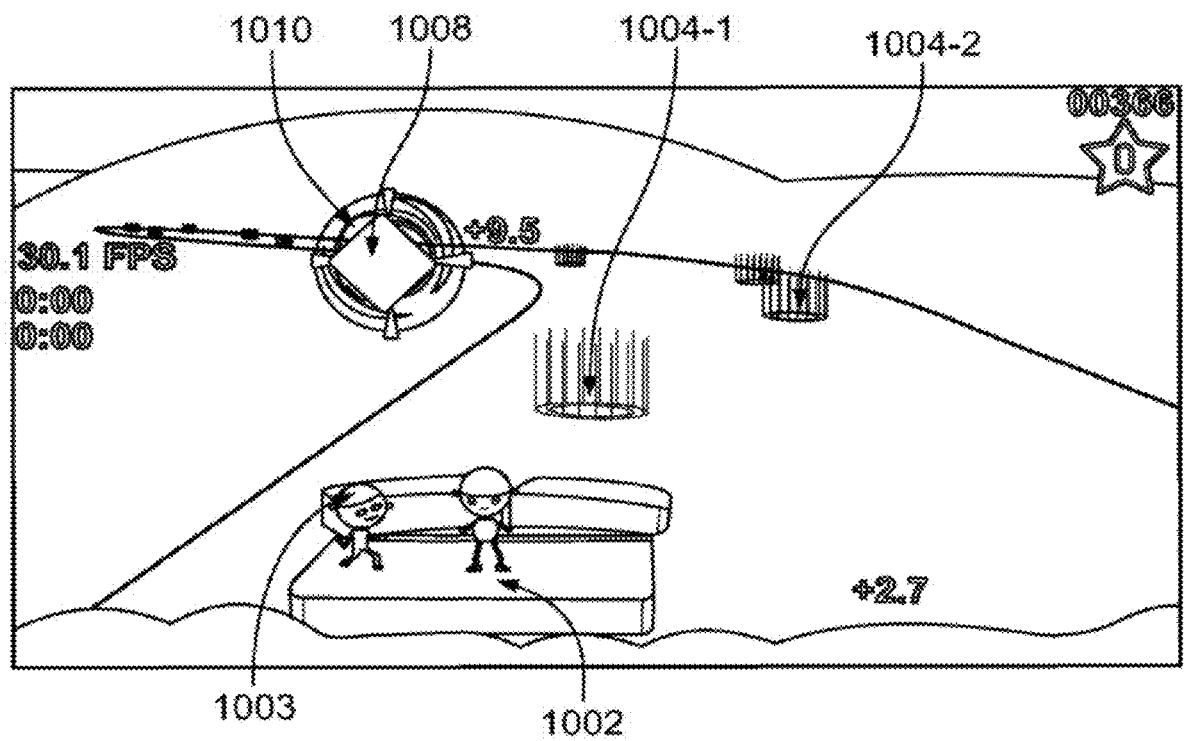

In the example of FIGS. 100-10Q, avatar object 1007 is shown as being removed from and propagated away from the base vehicle 1002 in response to (i) the individual's lack of success at the primary task (e.g., steering the base vehicle 1002 to coincide with the milestone objects 1004-2 in the visuomotor task), or (ii) the individual's lack of success at the secondary task (e.g., selecting a non-target object 1006 in the target discrimination as an interference), or (iii) some combination of (i) and (ii). In the example of FIGS. 11A-11G, avatar object 1007 is shown as propagating over to and being positioned on the base vehicle 1002 to re-join the other avatar objects 1003 in response to (i) the individual's success at the primary task (e.g., success at steering the base vehicle 1002 to coincide with the milestone objects 1004 in a visuomotor task), or (ii) the individual's success at the secondary task (e.g., selecting a target object 1008 in the target discrimination as an interference), or (iii) some combination of (i) and (ii). That is, the computerized adjustable element is adjusted/modified to remove avatar object 1007 as an indication of the lack of success of the individual in performing the task and/or interference through a certain stage (e.g., a first time interval T-1) of performing the task and/or interference. The computerized adjustable element is adjusted/modified to add avatar object 1007 as an indication of the degree of success of the individual in performing the task and/or interference through another stage (e.g., second time interval T-2 (different from T-1)) of performing the task and/or interference.

Figure 10V:
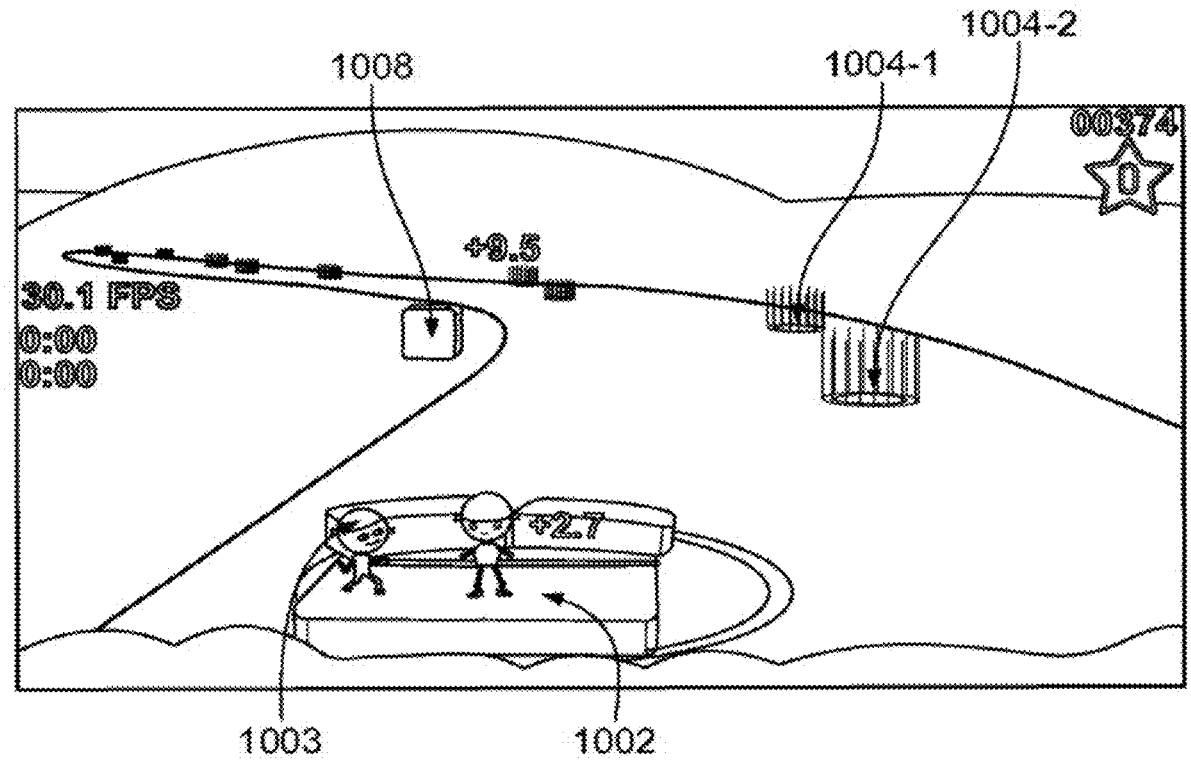
Figure 10W:
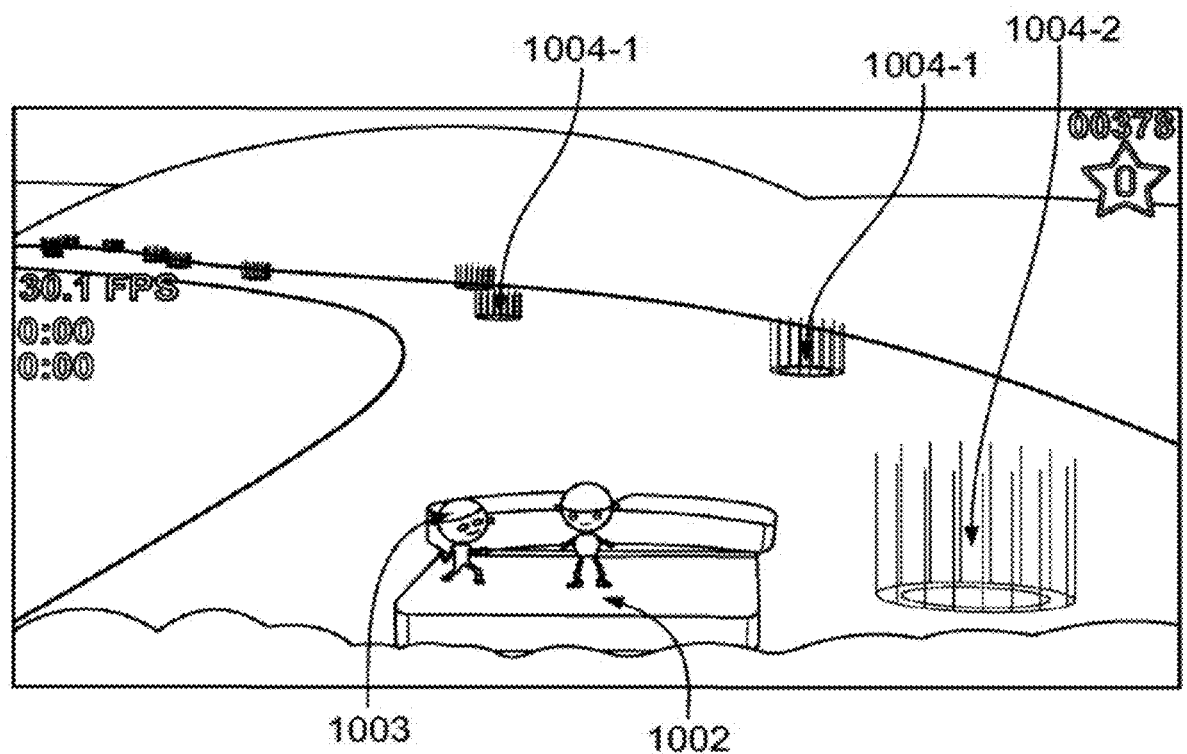
Figure 10X:
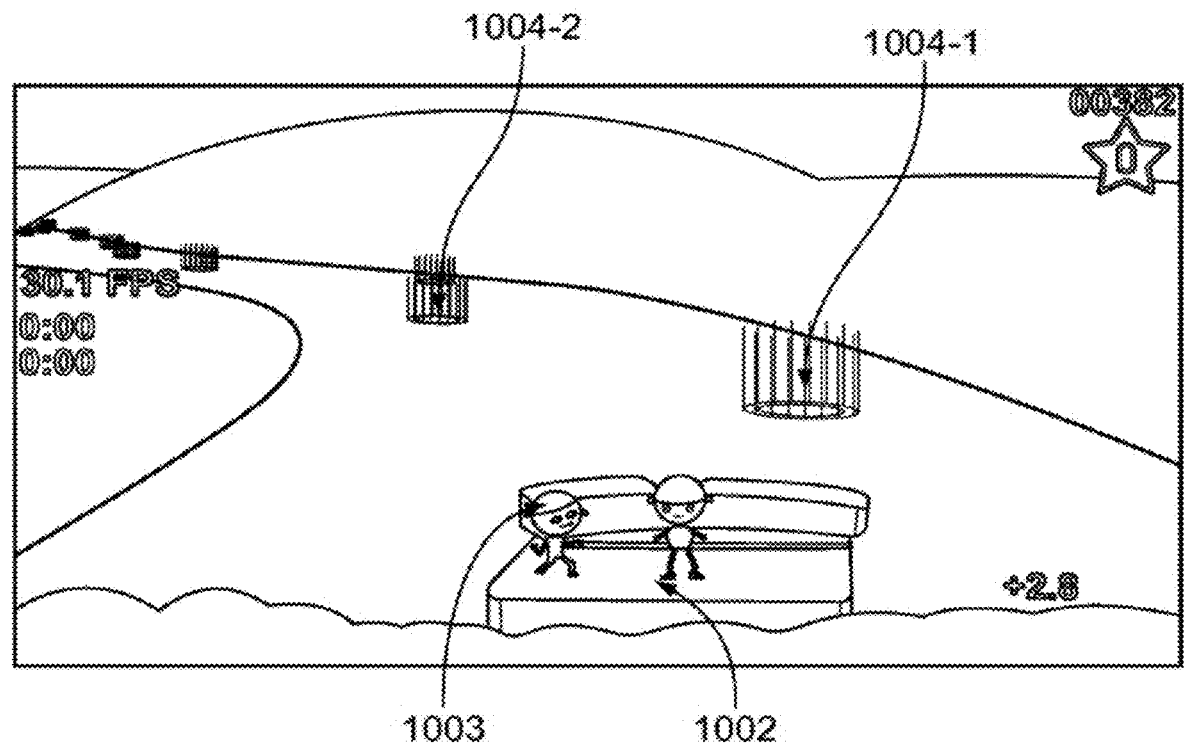
Figure 10Y:
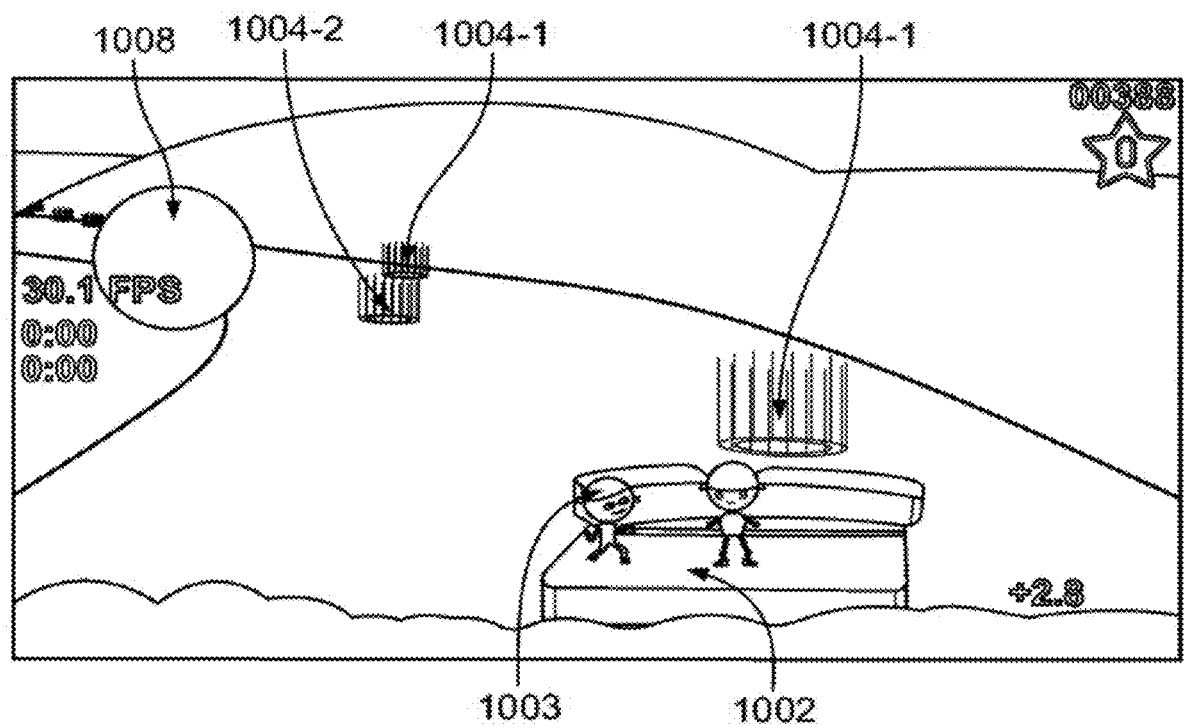
Figure 10Z:
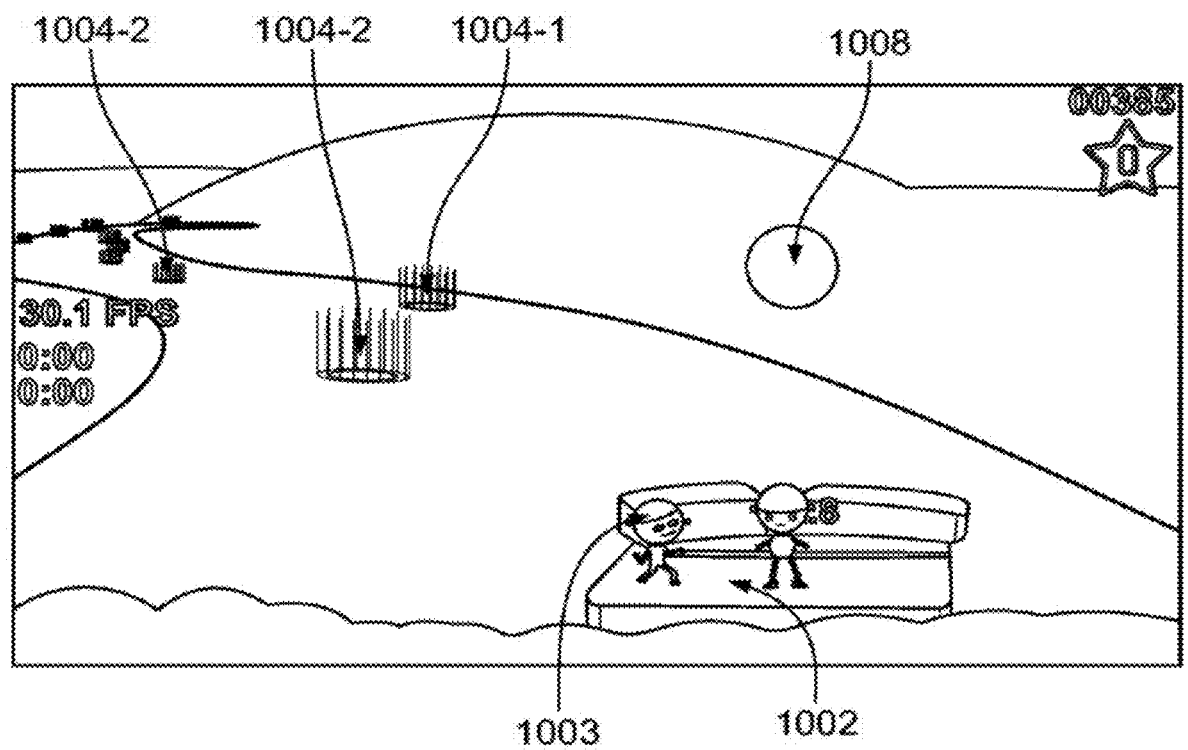
Figure 11A:
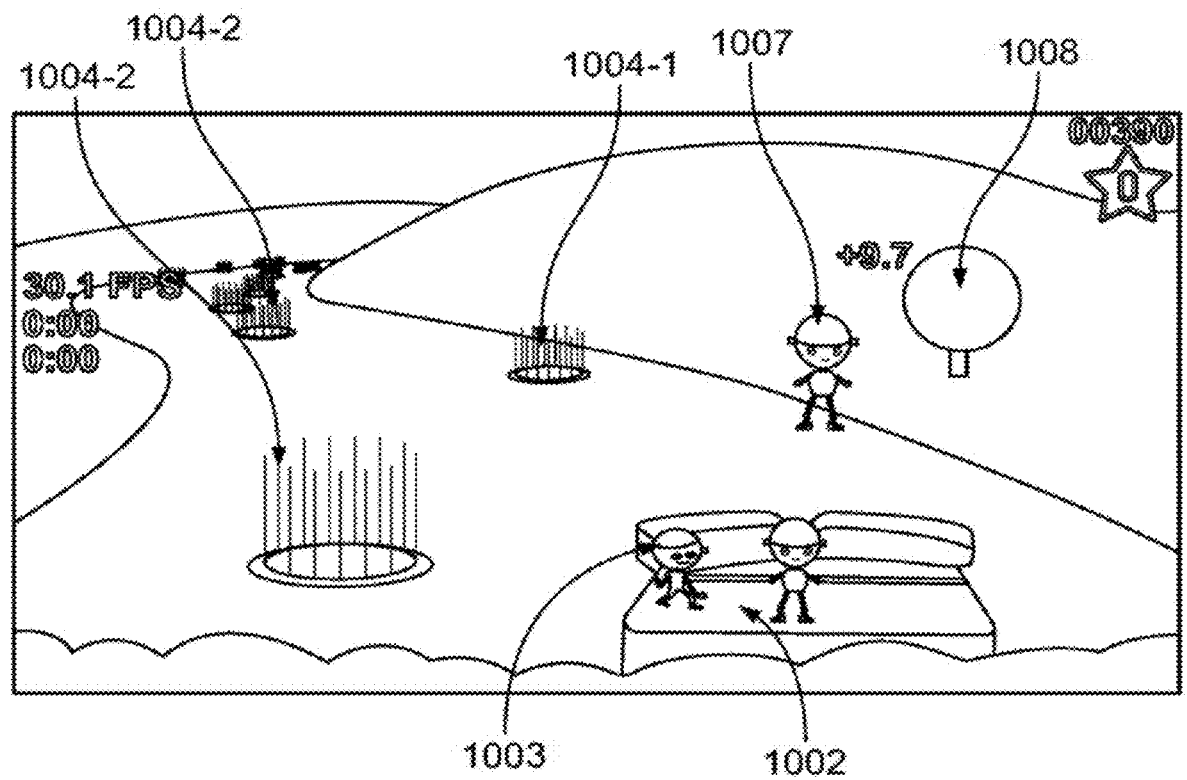
Figure 11B:
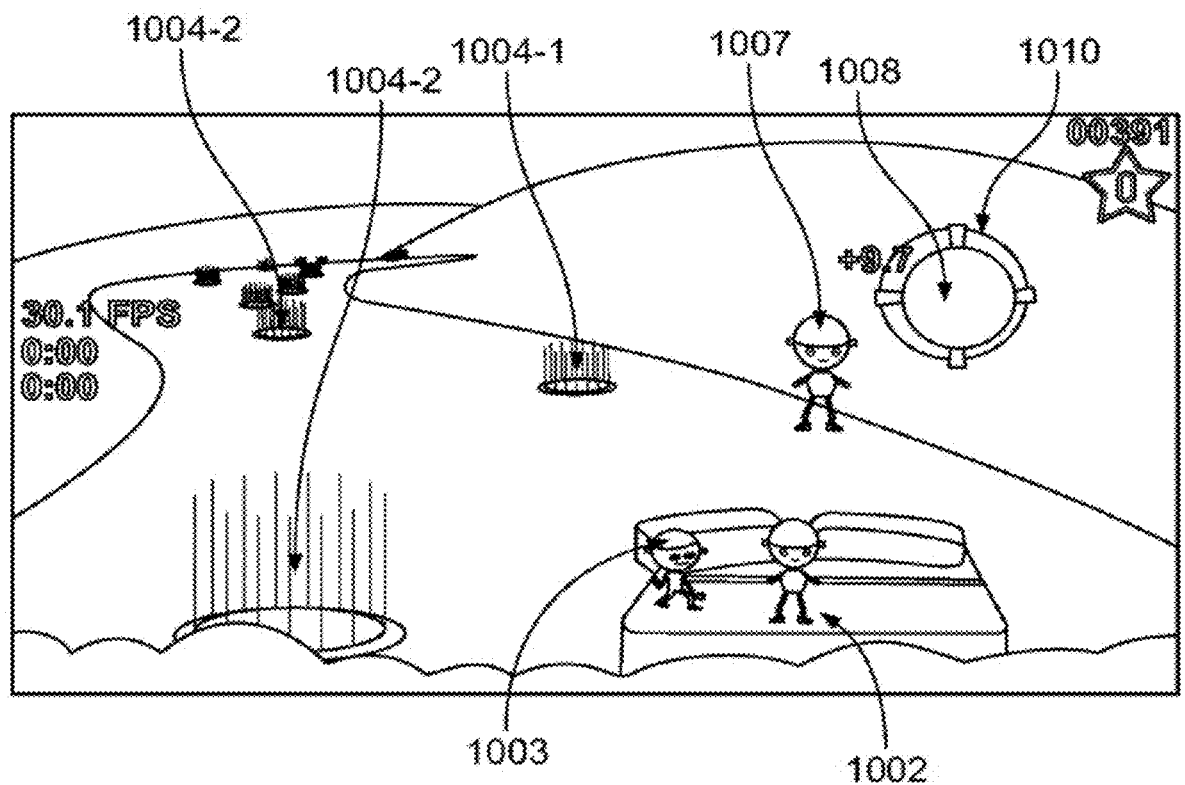
Figure 11C:
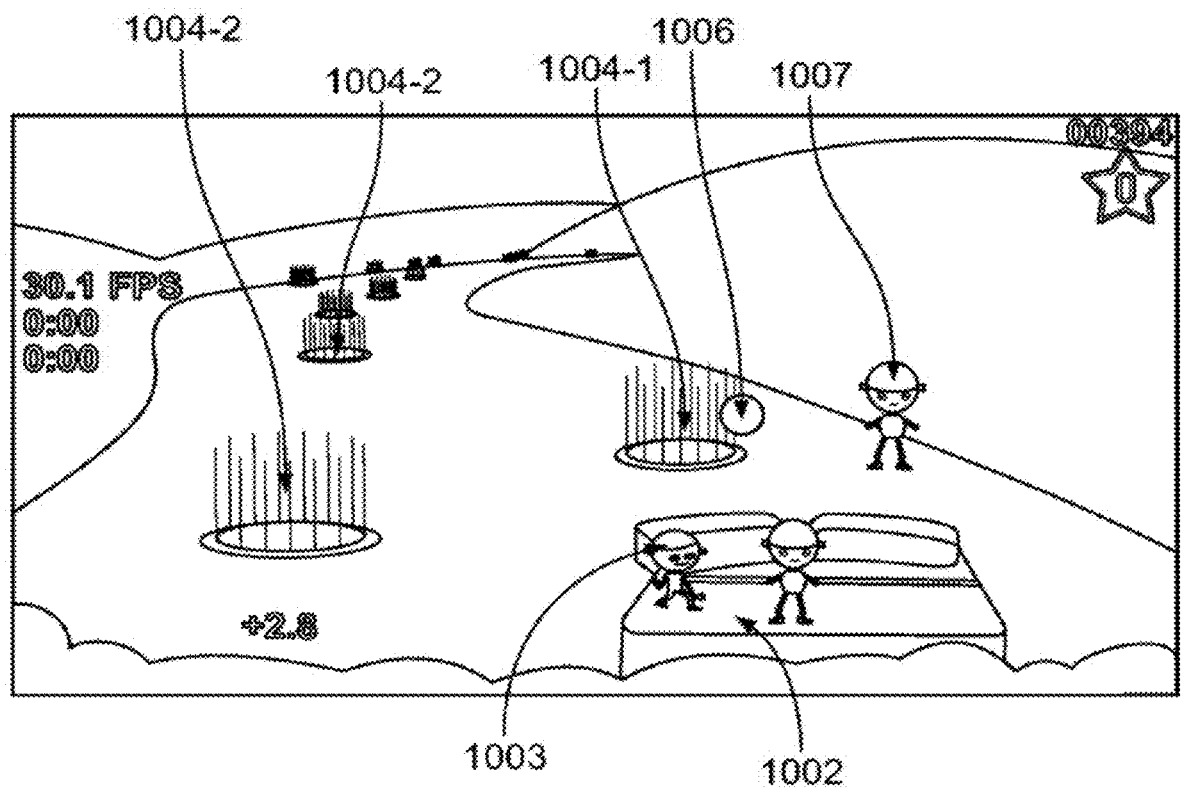
Figure 11D:
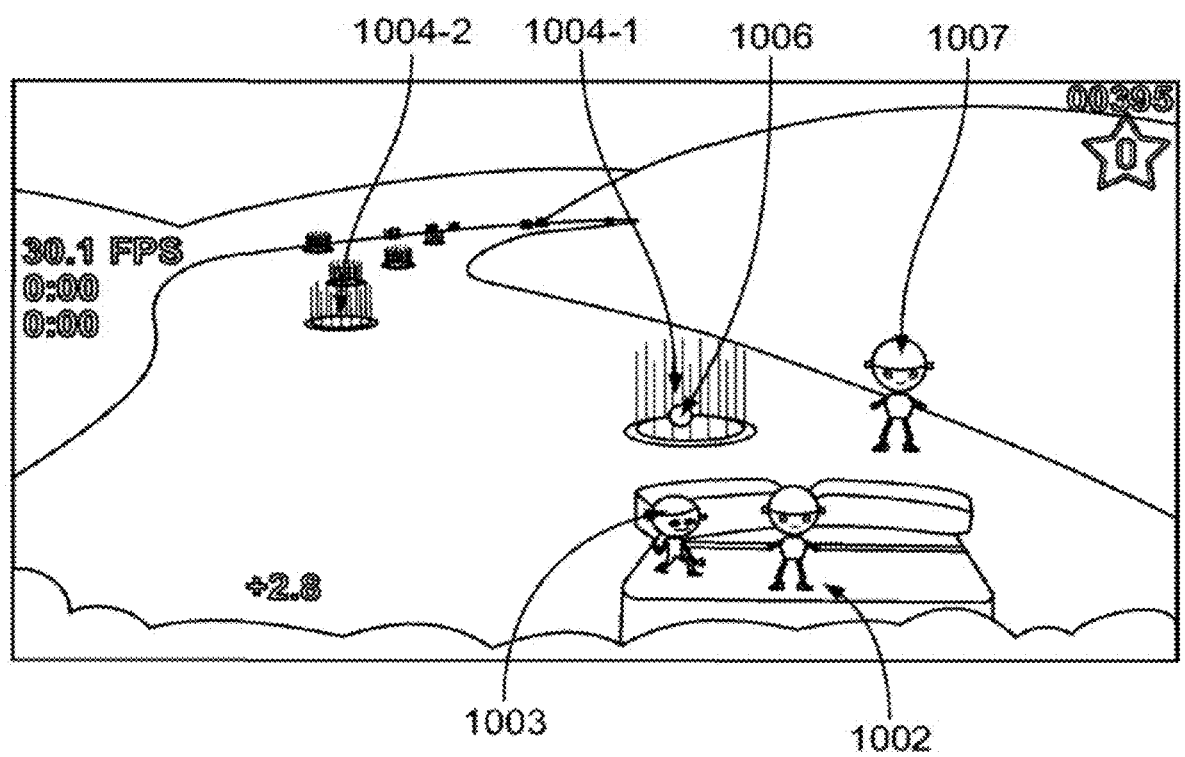
Figure 11E:
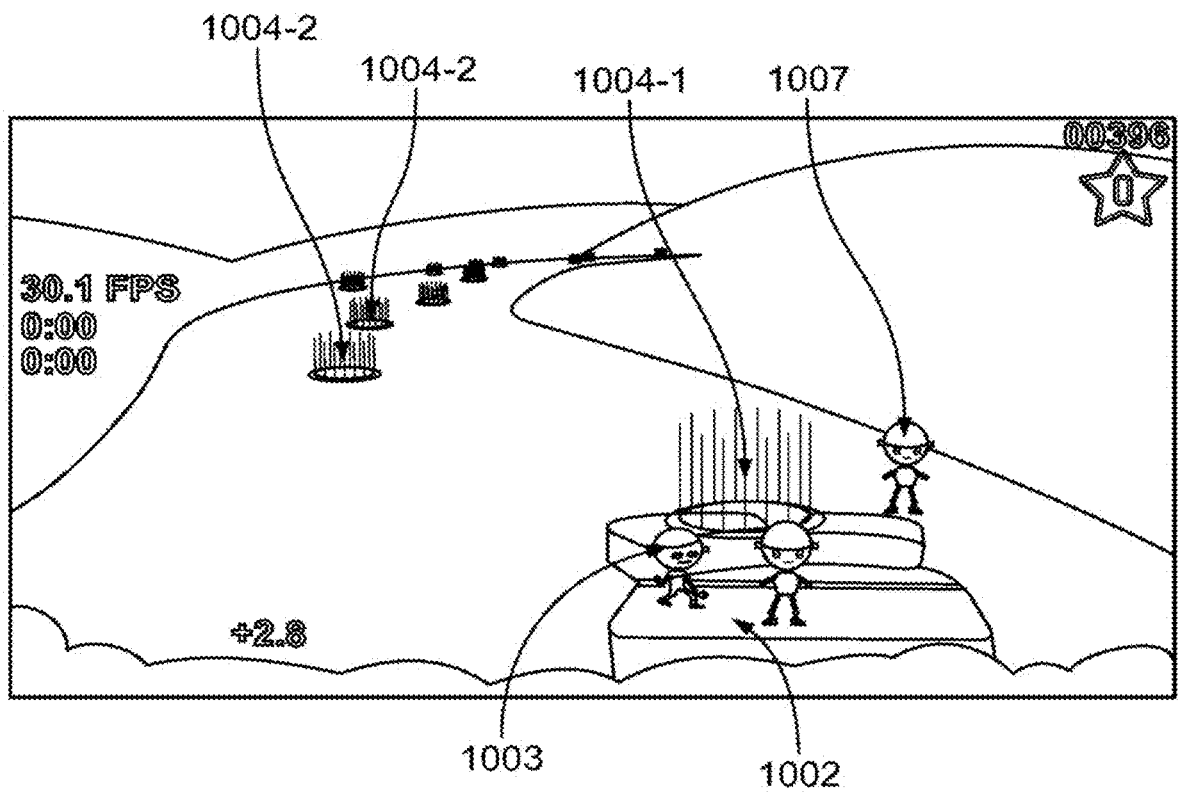
Figure 11F:
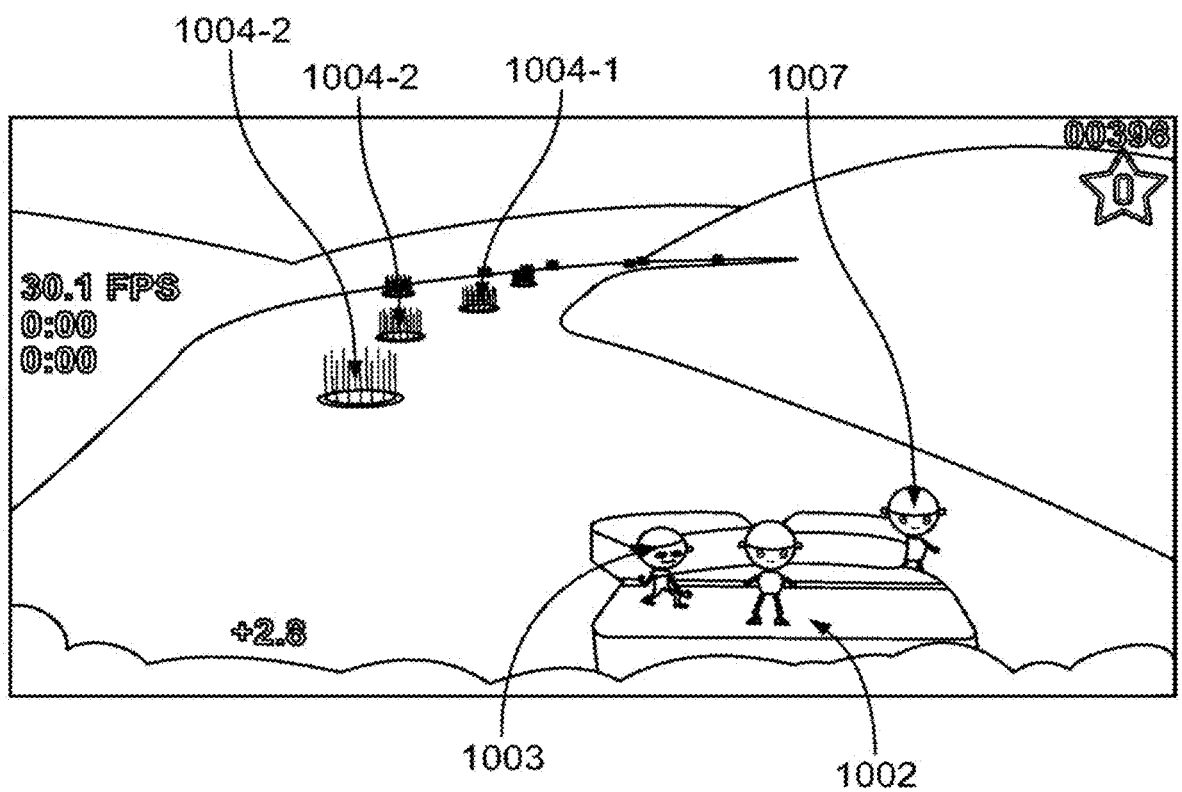
Figure 11G:
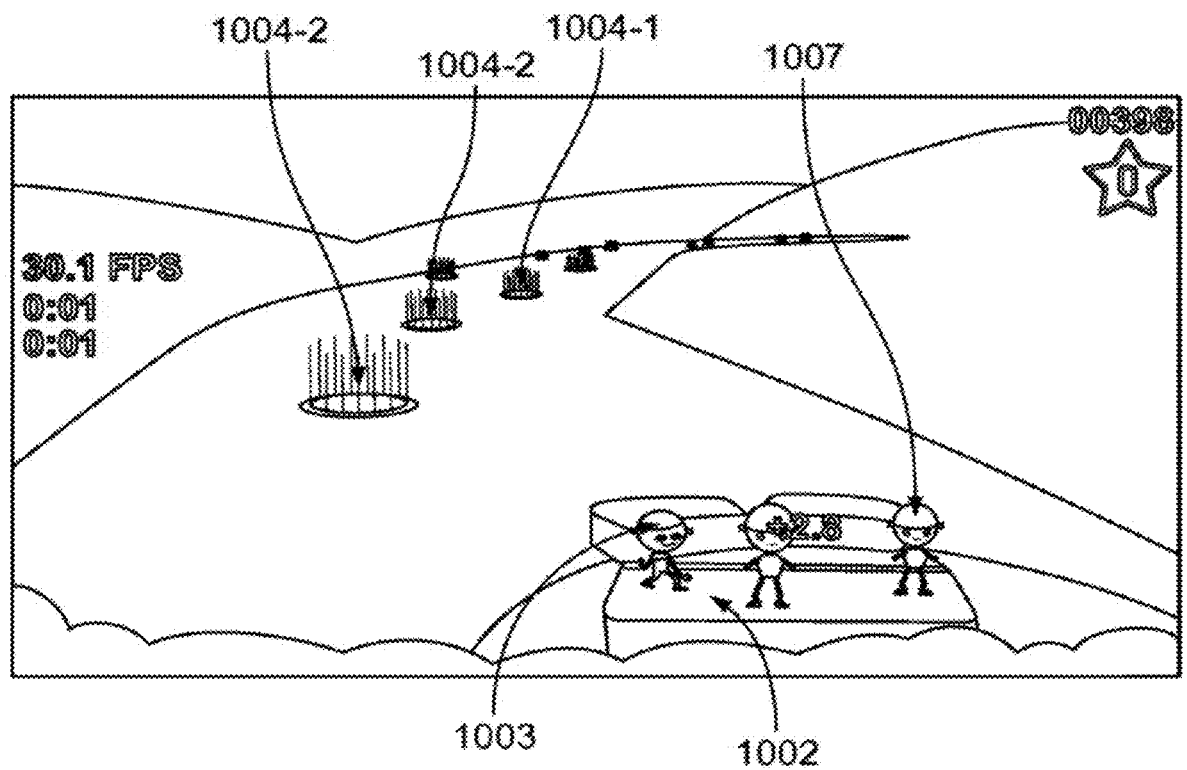
Figure 11H:
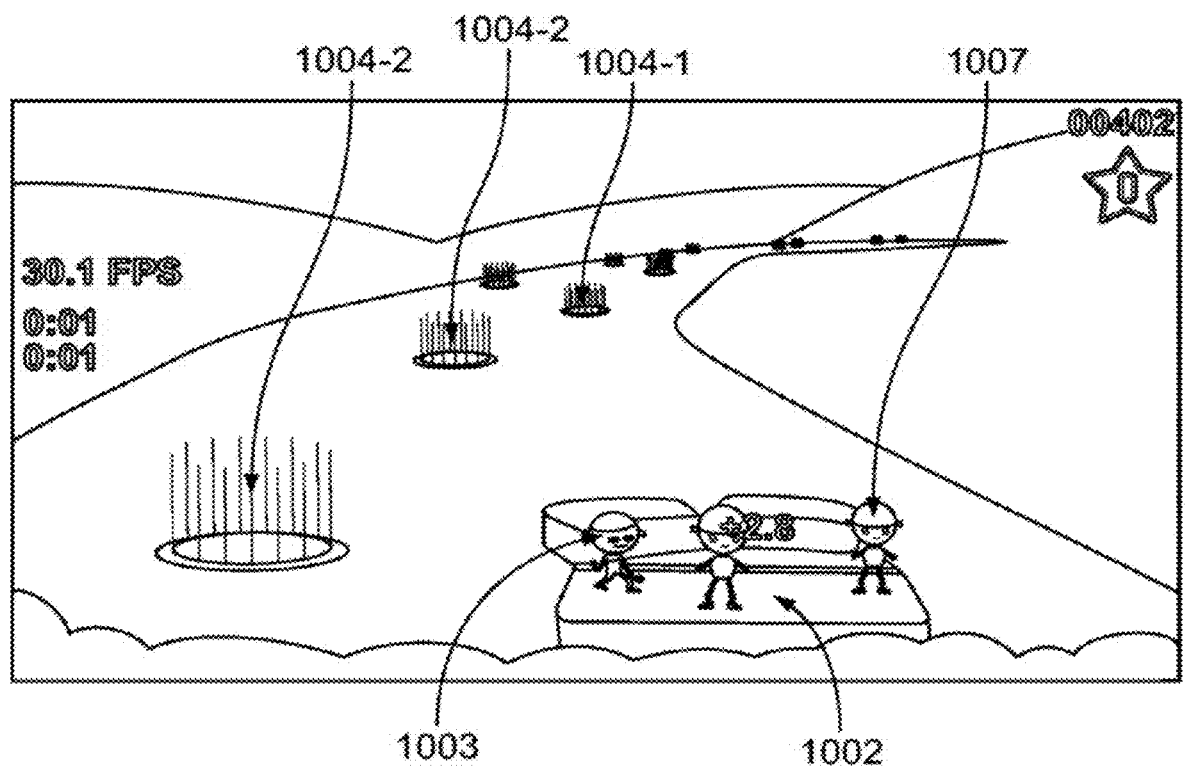

In the non-limiting examples of FIGS. 10V and 11B, the individual's success at selecting a target object 1008 is indicated using circles 1010 around the target object 1008. As shown in the non-limiting example of FIGS. 10A-11H, the difficulty level is also higher since the individual is required to identify and perform actions for selection based on two differing types of target objects (e.g., both a round object of a first color and a cuboid object of a second color are designated as target objects 1008).

In the example of FIGS. 10A through 11H, the processing unit of the exemplary system, method, and apparatus is configured to receive data indicative of the individual's physical actions to cause the avatar vehicle 1002 to navigate the path. For example, the individual may be required to perform physical actions to "steer" the avatar, e.g., by changing the rotational orientation or otherwise moving a computing device. Such action can cause a gyroscope or accelerometer or other motion or position sensor device to detect the movement, thereby providing measurement data indicative of the individual's degree of success in performing the navigation task.

In the example of FIGS. 10A through 11H, the processing unit of the exemplary system, method, and apparatus is configured to receive data indicative of the individual's physical actions to perform the target discrimination and to identify a specified computerized adjustable element (i.e., a specified facial expression). For example, the individual may be instructed using display feature 500 prior to a trial or other session to tap, or make other physical indication, in response to display of a target object having the specified target object 1008, and not to tap to make the physical indication in response to display of a non-target object 1006. In FIGS. 10A through 11H, the target discrimination acts as an interference (i.e., a secondary task) to the primary navigation task, in an interference processing multi-tasking implementation. As described hereinabove, the exemplary systems, methods, and apparatus can cause the processing unit to render a display feature (e.g., display feature 500) to display the instructions to the individual as to the expected performance (i.e., which object to respond to in the target discrimination task, and what is expected in the performance of the navigation tasks). As also described hereinabove, the processing unit of the example system, method, and apparatus can be configured to (i) receive the data indicative of the measure of the degree and type of the individual's response to the primary task substantially simultaneously as the data indicative of the measure of the individual's response to the computerized adjustable element is collected (for a specified computerized adjustable element), or (ii) to selectively receive data indicative of the measure of the individual's response to the specified computerized adjustable element as a target stimulus (i.e., an interruptor) substantially simultaneously (i.e., at substantially the same time) as the data indicative of the measure of the degree and type of the individual's response to the task is collected and to selectively not collect the measure of the individual's response to the non-specified computerized adjustable element a non-target stimulus (i.e., a distraction) substantially simultaneously (i.e., at substantially the same time) as the data indicative of the measure of the degree and type of the individual's response to the task is collected.

While the examples of FIG. 7A through 11H depict the computerized adjustable elements as musical bands, with band members being added or subtracted from the base vehicle 1002, the computerized adjustable elements can be rendered as any other type of modifiable objects.

In the examples of FIGS. 5A-11H, the exemplary systems, methods, and apparatus can be configured to modulate a sound or the music that accompanies at least a portion of the presentation of the tasks and/or interferences (either or both with computerized adjustable element) for user interactions. Modulating the sound or the music can include gradually or discretely modifying or otherwise controlling one or more parameters of the sound or the music, such as but not limited to the volume, the frequency, the beat, the tempo, the pitch, the melody, the harmony, the rhythm, the pattern, the spectrum, the envelope, the energy, or the overtones of the sound or the music. The sound or the music can be modulated based on the individual's degree of success in responding to the task and/or the interference, as an additional progress indicator of success in performance of the task and/or the interference in a trial and/or over a session. As non-limiting examples, one or more parameters of the sound or the music, such as but not limited to the tempo and/or volume, can be modified (e.g., heightened or increased) as an auditory indication to the individual of increased degree of success on providing the responses to the task and/or the interference.

In an example, adjusting the difficulty of the one or more of the task and/or the interference includes adjusting one or more of a sound, music, message of encouragement, and/or imposing a delay in rendering of the task and/or the interference.

In various examples, the degree of non-linearity of the accumulation of belief for an individual's decision making (i.e., as to whether to execute a response) can be modulated based on adjusting the time-varying characteristics of the task and/or interference. As a non-limiting example, when the time-varying characteristic is a trajectory, speed, orientation, type and/or size of the object (target or non-target), the amount of information available to an individual to develop a belief (in order to make decision as to whether to execute a response) can be made smaller initially, e.g., where the object caused to be more difficult to discriminate by being rendered as farther away or smaller, and can be made to increase at differing rates (nonlinearly) depending on how quickly more information is made available to the individual to develop belief (e.g., as the object is rendered to appear to get larger, change orientation, move slower, or move closer in the environment). Other non-limiting example time-varying characteristics of the task and/or interference that can be adjusted to modulate the degree of non-linearity of the accumulation of belief include one or more of a rate of change of a facial expression, at least one color of an object, the type of the object (including whether there is one or two or more differing types of target objects), a rate of morphing of a first type of object to change to a second type of object, and a blendshape of computerized adjustable elements.

The data indicative of the individual's response to the task and the response of the individual to the at least one computerized adjustable element is used to generate at least one performance metric comprising at least one quantified indicator of cognitive abilities of the individual. In a non-limiting example, the performance metric can include the computed interference cost.

The difficulty levels (including the difficulty of the task and/or interference, and of the computerized adjustable element) of a subsequent session can be set based on the performance metric generated for the individual's performance from a previous session, and can be optimized to modify an individual's performance metric (e.g., to lower or optimize the interference cost).

In a non-limiting example, the difficulty of a task and/or interference may be adapted with each different stimulus that is presented as a computerized adjustable element.

In another non-limiting example, the exemplary system, method, and apparatus described herein can be configured to adapt a difficulty level of a task and/or interference (including the computerized adjustable element) one or more times in fixed time intervals or in other set schedule, such as but not limited to each second, in 10 second intervals, every 30 seconds, or on frequencies of once per second, 2 times per second, or more (such as but not limited to 30 times per second).

In an example, the difficulty level of a task or interference can be adapted by changing the time-varying characteristics, such as but not limited to a speed of an object, a rate of change of a facial expression, a direction of trajectory of an object, a change of orientation of an object, at least one color of an object, a type of an object, or a size of an object, or changing a sequence or balance of presentation of a target stimulus versus a non-target stimulus.

In a non-limiting example of a visuomotor task (a type of navigation task), one or more of navigation speed, shape of the course (changing frequency of turns, changing turning radius), and number or size of obstacles can be changed to modify the difficulty of a navigation game level, with the difficulty level increasing with increasing speed and/or increasing numbers and/or sizes of obstacles (including types of milestone objects (e.g., some milestone objects to avoid or some milestone objects with which to cross/coincide).

In a non-limiting example, the difficulty level of a task and/or interference of a subsequent level can also be changed in real-time as feedback, e.g., the difficulty of a subsequent level can be increased or decreased in relation to the data indicative of the performance of the task.

Figure 12A:
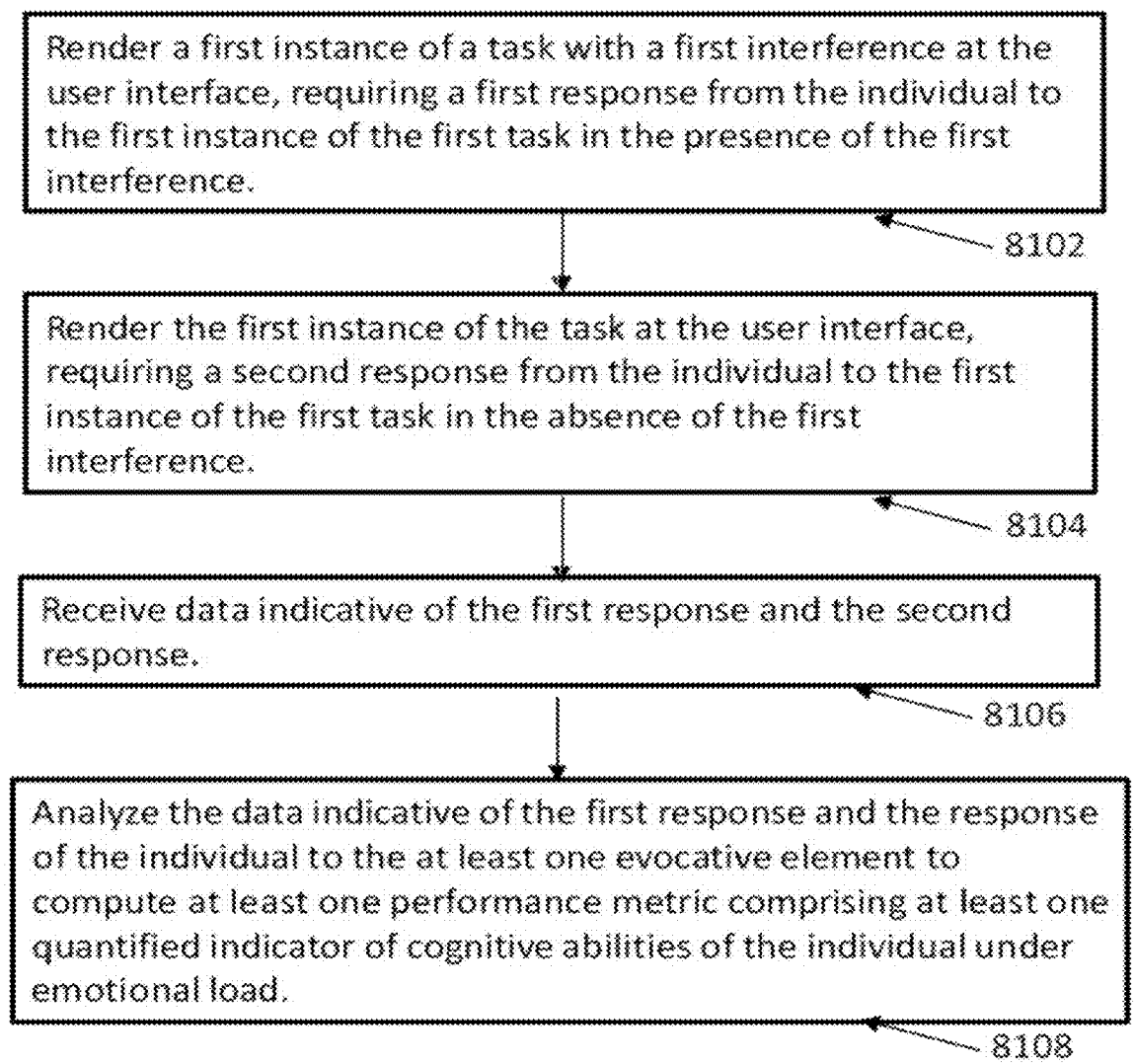

FIG. 12A shows a flowchart of a non-limiting exemplary method that can be implemented using a platform product that includes one or more processors, e.g., at least one processing unit. In block 8102, the at least one processing unit is configured to generate a user interface, and to present via the user interface a first instance of a task with a first interference at the user interface, requiring a first response from the individual to the first instance of the first task in the presence of the first interference. In block 8104, the at least one processing unit generates at least one user interface to render the first instance of the task, requiring a second response from the individual to the first instance of the first task in the absence of the first interference. For example, the at least one processing unit generates at least one graphical user interface to present a computerized stimuli or interaction (CSI) or other interactive elements to the user, or cause an actuating component of the platform product to effect auditory, tactile, or vibrational computerized elements (including CSIs) to effect the stimulus or other interaction with a user. The first instance of the first task and/or the first interference can include the at least one computerized adjustable element. The processing unit is configured to measure data indicative of the response of the individual to the at least one computerized adjustable element (where the data includes at least one measure of cognitive capabilities of the individual). The apparatus is configured to measure substantially simultaneously the first response from the individual to the first instance of the first task and the response from the individual to the first interference (as a secondary task). In block 8106, the at least one processing unit causes a component of the program product to receive data indicative of the first response and the second response. For example, the at least one processing unit causes a component of the program product to receive data indicative of at least one user response based on the user interaction with the CSI or other interactive element (such as but not limited to cData). In an example where at least one graphical user interface is generated to present the computerized stimuli or interaction (CSI) or other interactive elements to the user, the at least one processing unit can be programmed to cause the graphical user interface to receive the data indicative of at least one user response (including the first response and the second response). In block 8108, the at least one processing unit causes a component of the program product to analyze the data indicative of the first response and the second response to compute at least one performance metric comprising at least one quantified indicator of cognitive abilities of the individual. For example, the at least one processing unit also can be used to: analyze the differences in the individual's performance based on determining the differences between the user's responses (including the first response and the second response), and/or adjust the difficulty level of the computerized stimuli or interaction (CSI) or other interactive elements based on the individual's performance determined in the analysis, and/or provide an output or other feedback from the platform product indicative of the individual's performance, and/or cognitive assessment, and/or response to cognitive treatment. In some examples, the results of the analysis may be used to modify the difficulty level or other property of the computerized stimuli or interaction (CSI) or other interactive elements.

FIG. 12B shows a flowchart of a non-limiting exemplary method that can be implemented using a platform product that includes one or more processors, e.g., at least one processing unit. In block 8142, the at least one processing unit is configured to present via the user interface a first instance of a task with an interference at the user interface, requiring a first response from the individual to the first instance of the task in the presence of the interference. In block 8144, the at least one processing unit is configured to present via the user interface the first instance of the task, requiring a second response from the individual to the first instance of the task in the absence of the interference, where at least one of the first instance of the task and the interference comprises a computerized adjustable element that is adjusted in real time as an indication of a degree of success of the performance of at least one of the task or the interference. In block 8146, the at least one processing unit is configured to cause a component of the program product to measure substantially simultaneously the first response from the individual to the first instance of the task and the response from the individual to the interference. In block 8148, the at least one processing unit is configured to cause a component of the program product to receive data indicative of the first response and the second response. For example, the at least one processing unit causes a component of the program product to receive data indicative of at least one user response based on the user interaction with the CSI or other interactive element (such as but not limited to cData). In an example where at least one graphical user interface is generated to present the computerized stimuli or interaction (CSI) or other interactive elements to the user, the at least one processing unit can be programmed to cause the graphical user interface to receive the data indicative of at least one user response (including the first response and the second response). In block 8150, the at least one processing unit is configured to cause a component of the program product to analyze the data indicative of the first response and the second response to generate at least one performance metric comprising at least one quantified indicator of cognitive abilities of the individual. For example, the at least one processing unit also can be used to: analyze the differences in the individual's performance based on determining the differences between the user's responses (including the first response and the second response), and/or adjust the difficulty level of the computerized stimuli or interaction (CSI) or other interactive elements based on the individual's performance determined in the analysis, and/or provide an output or other feedback from the platform product indicative of the individual's performance, and/or cognitive assessment, and/or response to cognitive treatment. In some examples, the results of the analysis may be used to modify the difficulty level or other property of the computerized stimuli or interaction (CSI) or other interactive elements.

Figure 12C:
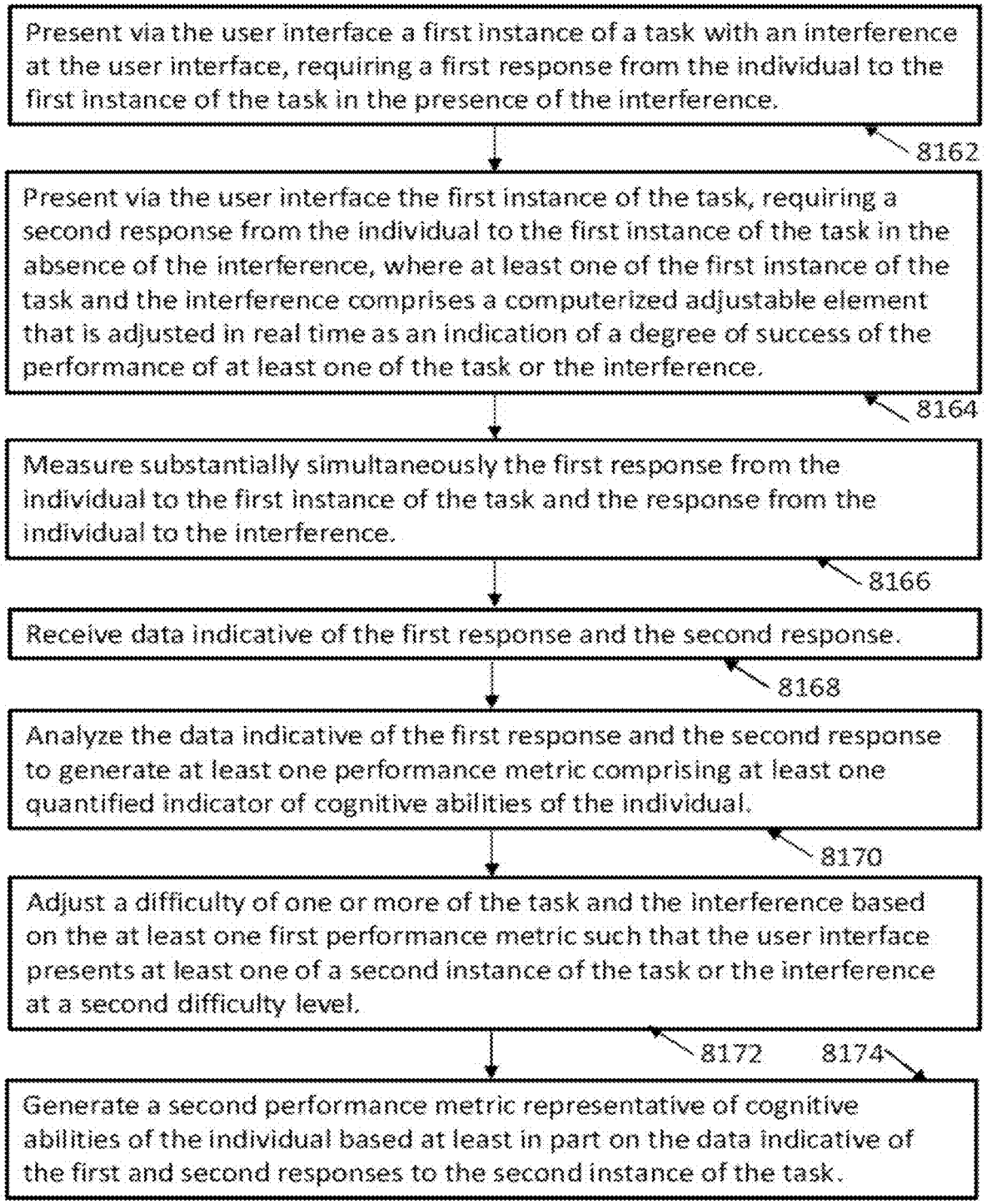

FIG. 12C shows a flowchart of a non-limiting exemplary method that can be implemented using a platform product that includes one or more processors, e.g., at least one processing unit. In block 8162, the at least one processing unit is configured to present via the user interface a first instance of a task with an interference at the user interface, requiring a first response from the individual to the first instance of the task in the presence of the interference. In block 8164, the at least one processing unit is configured to present via the user interface the first instance of the task, requiring a second response from the individual to the first instance of the task in the absence of the interference, where at least one of the first instance of the task and the interference comprises a computerized adjustable element that is adjusted in real time as an indication of a degree of success of the performance of at least one of the task or the interference. In block 8166, the at least one processing unit is configured to cause a component of the program product to measure substantially simultaneously the first response from the individual to the first instance of the task and the response from the individual to the interference. In block 8168, the at least one processing unit is configured to cause a component of the program product to receive data indicative of the first response and the second response. For example, the at least one processing unit causes a component of the program product to receive data indicative of at least one user response based on the user interaction with the CSI or other interactive element (such as but not limited to cData). In an example where at least one graphical user interface is generated to present the computerized stimuli or interaction (CSI) or other interactive elements to the user, the at least one processing unit can be programmed to cause the graphical user interface to receive the data indicative of at least one user response (including the first response and the second response). In block 8170, the at least one processing unit is configured to cause a component of the program product to analyze the data indicative of the first response and the second response to generate at least one performance metric comprising at least one quantified indicator of cognitive abilities of the individual. In block 8172, the at least one processing unit is configured to adjust a difficulty of one or more of the task and the interference based on the at least one first performance metric such that the user interface presents at least one of a second instance of the task or the interference at a second difficulty level. The at least one processing unit may be configured to cause a component of the program product to present, in an iterative manner, the second instance of the task with the interference and in the absence of the interference, and to measure the first response to the second instance of the task with the interference and the second response to the second instance of the task in the absence of the interference. In block 8174, the at least one processing unit is configured to generate a second performance metric representative of cognitive abilities of the individual based at least in part on the data indicative of the first and second responses to the second instance of the task. In an example, the at least one processing unit can be used to: analyze the differences in the individual's performance based on determining the differences between the user's responses (including the first response and the second response), and/or adjust the difficulty level of the computerized stimuli or interaction (CSI) or other interactive elements based on the individual's performance determined in the analysis, and/or provide an output or other feedback from the platform product indicative of the individual's performance, and/or cognitive assessment, and/or response to cognitive treatment. In some examples, the results of the analysis may be used to modify the difficulty level or other property of the computerized stimuli or interaction (CSI) or other interactive elements.

Figure 13:
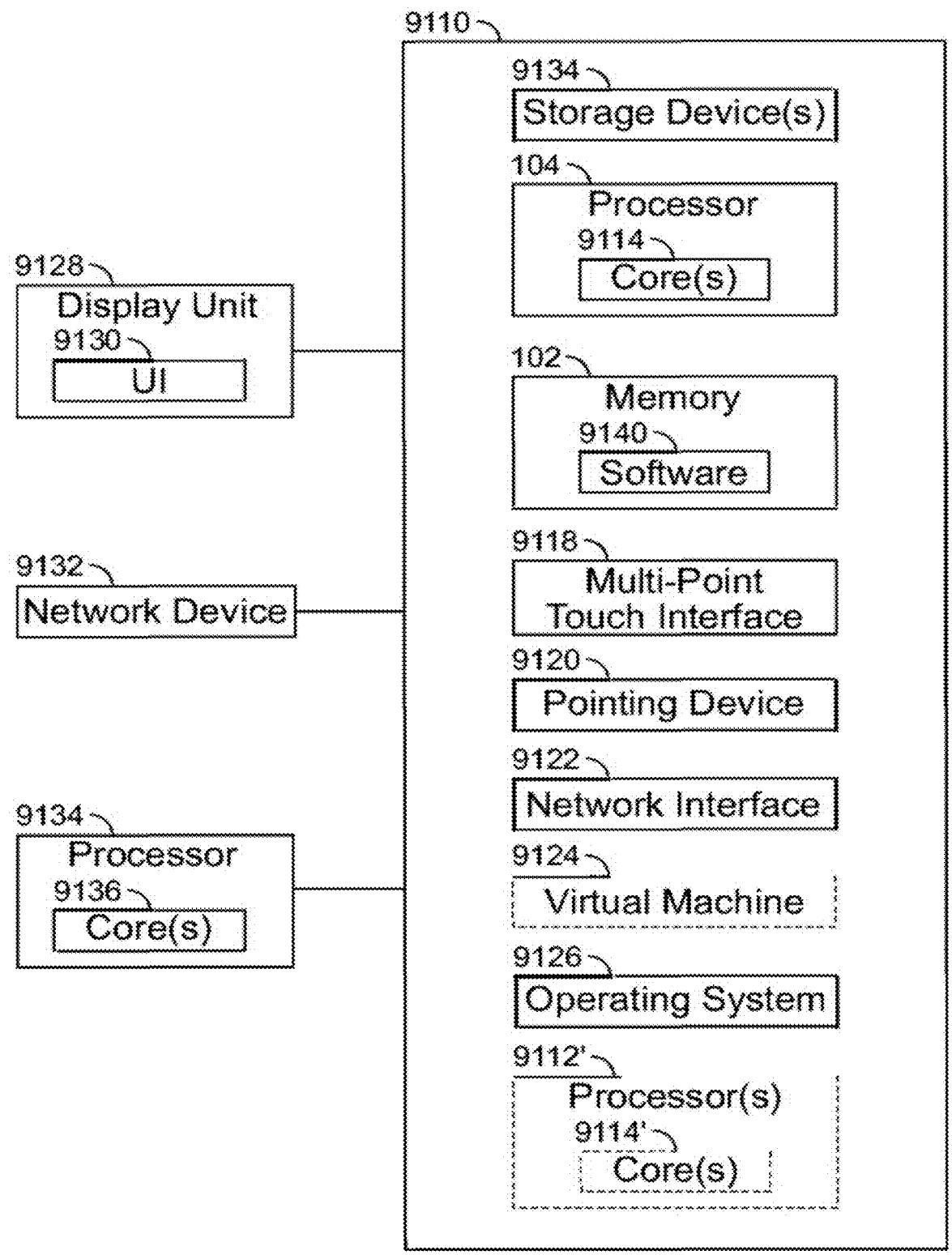
FIG. 13 shows the architecture of an exemplary computer system, according to the principles herein.

FIG. 13 is a block diagram of an exemplary computing device 9110 that can be used as a computing component according to the principles herein. In any example herein, computing device 9110 can be configured as a console that receives user input to implement the computing component, including to apply the signal detection metrics in computer-implemented adaptive response-deadline procedures. For clarity, FIG. 13 also refers back to and provides greater detail regarding various elements of the exemplary system of FIG. 1 and the exemplary computing device of FIG. 2. The computing device 9110 can include one or more non-transitory computer-readable media for storing one or more computer-executable instructions or software for implementing examples. The non-transitory computer-readable media can include, but are not limited to, one or more types of hardware memory, non-transitory tangible media (for example, one or more magnetic storage disks, one or more optical disks, one or more flash drives), and the like. For example, memory 102 included in the computing device 9110 can store computer-readable and computer-executable instructions or software for performing the operations disclosed herein. For example, the memory 102 can store a software application 9140 which is configured to perform various of the disclosed operations (e.g., analyze cognitive platform measurement data and response data (including response to the computerized adjustable element), compute a performance metric (including an interference cost), or perform other computation as described herein). The computing device 9110 also includes configurable and/or programmable processor 104 and an associated core 9114, and optionally, one or more additional configurable and/or programmable processing devices, e.g., processor(s) 9112' and associated core(s) 9114' (for example, in the case of computational devices having multiple processors/cores), for executing computer-readable and computer-executable instructions or software stored in the memory 102 and other programs for controlling system hardware. Processor 104 and processor(s) 9112' can each be a single core processor or multiple core (9114 and 9114') processor.

Virtualization can be employed in the computing device 9110 so that infrastructure and resources in the console can be shared dynamically. A virtual machine 9124 can be provided to handle a process running on multiple processors so that the process appears to be using only one computing resource rather than multiple computing resources. Multiple virtual machines can also be used with one processor.

Memory 102 can include a computational device memory or random-access memory, such as DRAM, SRAM, EDO RAM, and the like. Memory 102 can include other types of memory as well, or combinations thereof.

A user can interact with the computing device 9110 through a visual display unit 9128, such as a computer monitor, which can display one or more user interfaces (UI) 9130 that can be provided in accordance with example systems and methods. The computing device 9110 can include other I/O devices for receiving input from a user, for example, a keyboard or any suitable multi-point touch interface 9118, a pointing device 9120 (e.g., a mouse). The keyboard 9118 and the pointing device 9120 can be coupled to the visual display unit 9128. The computing device 9110 can include other suitable conventional I/O peripherals.

The computing device 9110 can also include one or more storage devices 9134, such as a hard-drive, CD-ROM, or other computer readable media, for storing data and computer-readable instructions and/or software that perform operations disclosed herein. Example storage device 9134 can also store one or more databases for storing any suitable information required to implement example systems and methods. The databases can be updated manually or automatically at any suitable time to add, delete, and/or update one or more items in the databases.

The computing device 9110 can include a network interface 9122 configured to interface via one or more network devices 9132 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 9122 can include a built-in network adapter, network interface card, PCMCIA network card, card bus network adapter, wireless network adapter, USB network adapter, modem or any other device suitable for interfacing the computing device 9110 to any type of network capable of communication and performing the operations described herein. Moreover, the computing device 9110 can be any computational device, such as a workstation, desktop computer, server, laptop, handheld computer, tablet computer, or other form of computing or telecommunications device that is capable of communication and that has sufficient processor power and memory capacity to perform the operations described herein.

The computing device 9110 can run any operating system 9126, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the console and performing the operations described herein. In some examples, the operating system 9126 can be run in native mode or emulated mode. In an example, the operating system 9126 can be run on one or more cloud machine instances.

Examples of the systems, methods and operations described herein can be implemented in digital electronic circuitry, or in computer software, firmware, or hardware, including the structures disclosed in this specification and their structural equivalents, or in combinations of one or more thereof. Examples of the systems, methods and operations described herein can be implemented as one or more computer programs, i.e., one or more modules of computer program instructions, encoded on computer storage medium for execution by, or to control the operation of, data processing apparatus. The program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, application or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing on one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), for example. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, for displaying information to the user and a keyboard and a pointing device, e.g., a mouse, a stylus, touch screen or a trackball, by which the user can provide input to the computer. Other kinds of devices can be used to provide for interaction with a user as well. For example, feedback (i.e., output) provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

In some examples, a system, method or operation herein can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Example computing system 400 can include clients and servers. A client and server are generally remote from each other and typically interact through a communication network. The relationship of client and server arises by virtue of computer programs running on the respective computers and having a client-server relationship to each other. In some embodiments, a server transmits data to a client device (e.g., for purposes of displaying data to and receiving user input from a user interacting with the client device). Data generated at the client device (e.g., a result of the user interaction) can be received from the client device at the server.

CONCLUSION

The above-described embodiments can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system for adaptive analysis of user-activity data, comprising:
    an input device comprising one or more sensors configured to measure a physical action of a user temporally and spatially and receive an input in response to the physical action of the user;
    one or more processors communicatively coupled with the input device to receive an input signal indicative of the physical action of the user; and
    a non-transitory computer readable medium communicatively coupled with the one or more processors and having processor-executable instructions stored thereon to cause the one or more processors to perform one or more operations,
    wherein upon execution of the processor-executable instructions by the one or more processors, the one or more processors are configured to:
        generate a graphical user interface comprising an instance of a cognitive platform or application;
        present, via the graphical user interface, one or more computerized stimuli or interaction configured to prompt a user-generated input associated with at least one task, wherein the at least one task comprises a time-varying task having a response deadline and wherein the at least one task comprises a targeting task;
        receive, via the input device and in response to the one or more computerized stimuli or interaction, one or more user-generated inputs associated with the at least one task,
        wherein receiving the one or more user-generated inputs comprises selectively discriminating between windows of response of the user to target versus non-target stimuli by selectively controlling a state of the one or more sensors of the input device to measure the physical action of the user temporally and spatially;
        present, via the graphical user interface, at least one computerized adjustable element configured as a performance indicator associated with the at least one task and comprising at least one evocative element,
        wherein the at least one evocative element comprises an image of a face that represents or correlates with an expression of a specific emotion or a combination of emotions,
        wherein the at least one evocative element is modified in real time to adjust a level of valence of the at least one evocative element;
        render or modify at least one graphical element of the at least one computerized adjustable element via the graphical user interface in response to the one or more user-generated inputs associated with the at least one task;
        analyze the one or more user-generated inputs associated with the at least one task in response to the one or more computerized stimuli or interaction and the at least one computerized adjustable element to generate at least one performance metric,
        wherein the at least one performance metric comprises a quantified indicator of a cognitive or emotional load of the instance of the cognitive platform or application on the user,
        wherein analyzing the one or more user-generated inputs comprises analyzing a degree to which a performance level of the user at the at least one task is affected in the presence of the at least one computerized adjustable element; and
        modify at least one interaction sequence for the one or more computerized stimuli or interaction in response to the at least one performance metric.

2. The system of claim 1 wherein the one or more processors are further configured to modify, via the graphical user interface, the at least one graphical element of the at least one computerized adjustable element or the at least one task in response to the at least one performance metric.

3. The system of claim 2 wherein the one or more processors are further configured to analyze one or more user-generated input in response to the one or more modified computerized stimuli or interaction or the at least one modified graphical element of the at least one computerized adjustable element to determine a measure of change in one or more specific metrics.

4. The system of claim 3 wherein the measure of change in the one or more specific metrics comprises a quantified indicator of a measure of change in the cognitive load or the emotional load of the instance of the cognitive platform or application on the user.

5. The system of claim 1 wherein the one or more processors are further configured to compute a psychometric curve of expected user performance on a task across stimulus or difficulty levels.

6. The system of claim 3 wherein the one or more processors are further configured to modify, via the graphical user interface, the at least one task based on a comparison of the at least one performance metric with normative data or a computer model to select a set of metrics in the one or more specific metrics to target for changing in a specific order.

7. A processor-implemented method for adaptive analysis of user-activity data, comprising:
generating, with one or more processors via a display device, a graphical user interface comprising an instance of a cognitive platform or application;
presenting, with the one or more processors via the graphical user interface, one or more computerized stimuli or interaction being configured to prompt one or more user-generated inputs associated with at least one task from a user, wherein the at least one task comprises a time-varying task having a response deadline and wherein the at least one task comprises a targeting task;
presenting, with the one or more processors via the graphical user interface, at least one computerized adjustable element in response to the one or more user-generated inputs, wherein the at least one computerized adjustable element comprises a real-time performance indicator for the at least one task, wherein the at least one computerized adjustable element comprises at least one evocative element,
wherein the at least one evocative element comprises an image of a face that represents or correlates with an expression of a specific emotion or a combination of emotions;
receiving, with the one or more processors via an input device comprising one or more sensors configured to measure a physical action of a user temporally and spatially, the one or more user-generated inputs in response to the one or more computerized stimuli or interaction and the at least one computerized adjustable element,
wherein receiving the one or more user-generated inputs comprises selectively discriminating between windows of response of the user to target versus non-target stimuli by selectively controlling a state of the one or more sensors of the input device to measure the physical action of the user temporally and spatially;
analyzing, with the one or more processors, the one or more user-generated inputs to generate at least one performance metric, wherein the at least one performance metric comprises a quantified indicator of a cognitive or emotional load of the instance of the cognitive platform or application on the user;
modifying, with the one or more processors, the one or more computerized stimuli or interaction or the at least one computerized adjustable element in response to the at least one performance metric, wherein modifying the at least one computerized adjustable element comprises adjusting a level of valence of the at least one evocative element; and
analyzing, with the one or more processors, one or more subsequent user-generated inputs to determine a measure of change in the at least one performance metric in response to modifying the one or more computerized stimuli or interaction or the at least one computerized adjustable element,
wherein analyzing the one or more subsequent user-generated inputs comprises analyzing a degree to which a performance level of the user at the at least one task is affected in the presence of the at least one computerized adjustable element,
wherein modifying the one or more computerized stimuli or interaction or the at least one computerized adjustable element comprises modifying at least one interaction sequence for the at least one task.

8. The method of claim 7 further comprising adaptively modifying, with the one or more processors, at least one graphical element of the at least one computerized adjustable element to increase or decrease a degree of ego depletion for the user in response to the at least one performance metric.

9. The method of claim 7 further comprising computing, with the one or more processors, a psychometric curve of user performance according to the at least one performance metric.

10. The method of claim 7 further comprising adaptively modifying, with the one or more processors, the one or more computerized stimuli or interaction to increase or decrease the cognitive or emotional load of the instance of the cognitive platform or application on the user.

11. The method of claim 7 further comprising adaptively modifying, with the one or more processors, the at least one computerized adjustable element to increase or decrease the cognitive or emotional load of the instance of the cognitive platform or application on the user.

12. The method of claim 7 further comprising analyzing, with the one or more processors, the at least one performance metric to determine a quantified measure corresponding to a mood state or cognitive or affective bias in the user.

13. The method of claim 7 further comprising adaptively modifying, with the one or more processors, the at least one computerized adjustable element until the at least one performance metric is greater than or equal to a target value.

14. A non-transitory computer readable medium having processor-executable instructions stored thereon that, when executed, cause one or more processors to perform one or more operations comprising:
generating a graphical user interface comprising an instance of a cognitive platform or application;
presenting via the graphical user interface one or more computerized stimuli or interaction configured to prompt one or more user-generated inputs associated with at least one task from a user, wherein the at least one task comprises a time-varying task having a response deadline and wherein the at least one task comprises a targeting task;
receiving, via at least one input device comprising one or more sensors configured to measure a physical action of the user temporally and spatially in response to the one or more computerized stimuli or interaction, the one or more user-generated inputs associated with the at least one task,
wherein receiving the one or more user-generated inputs comprises selectively discriminating between windows of response of the user to target versus non-target stimuli by selectively controlling a state of the one or more sensors of the at least one input device to measure the physical action of the user temporally and spatially;

presenting, via the graphical user interface, at least one computerized adjustable element configured as a performance indicator and comprising at least one evocative element, wherein the at least one evocative element comprises an image of a face that represents or correlates with an expression of a specific emotion or a combination of emotions, wherein the at least one computerized adjustable element is rendered or modified in real time in response to the one or more user-generated inputs, wherein the at least one evocative element is modified in real time to adjust a level of valence of the at least one evocative element;

analyzing the one or more user-generated inputs in response to the one or more computerized stimuli or interaction and the at least one computerized adjustable element to generate at least one performance metric, wherein the at least one performance metric comprises a quantified indicator of cognitive or emotional load for the instance of the cognitive platform or application on the user, wherein analyzing the one or more user-generated inputs comprises analyzing a degree to which a performance level of the user at the at least one task is affected in the presence of the at least one computerized adjustable element; and modifying at least one interaction sequence for the one or more computerized stimuli or interaction in response to the at least one performance metric.

15. The system of claim 1 wherein the one or more processors are further configured to modify, via the graphical user interface, a trajectory, a response window or a difficulty level of the one or more computerized stimuli or interaction in response to the at least one performance metric.

16. The method of claim 7 further comprising adaptively modifying, with the one or more processors, a trajectory, a response window or a difficulty level of the one or more computerized stimuli or interaction in response to the at least one performance metric.

* * * * *